US010294489B2

(12) United States Patent
Meksem et al.

(10) Patent No.: US 10,294,489 B2
(45) Date of Patent: May 21, 2019

(54) SOYBEAN RESISTANT TO CYST NEMATODES

(71) Applicants: Board of Trustees of Southern Illinois University, Carbondale, IL (US); The Curators of the University of Missouri, Columbia, MO (US)

(72) Inventors: Khalid Meksem, Carbondale, IL (US); Shiming Liu, Carbondale, IL (US); Pramod Kaitheri Kandoth, Columbia, MO (US); Melissa G. Mitchum, Columbia, MO (US); David Lightfoot, Carbondale, IL (US)

(73) Assignees: BOARD OF TRUSTEES OF SOUTHERN ILLINOIS UNIVERSITY, Carbondale, IL (US); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 560 days.

(21) Appl. No.: 14/218,669

(22) Filed: Mar. 18, 2014

(65) Prior Publication Data

US 2014/0380522 A1 Dec. 25, 2014

Related U.S. Application Data

(60) Provisional application No. 61/799,912, filed on Mar. 15, 2013.

(51) Int. Cl.

| | |
|---|---|
| ***C12N 15/82*** | (2006.01) |
| ***A01H 1/04*** | (2006.01) |
| ***A01H 5/10*** | (2018.01) |
| ***C07K 14/415*** | (2006.01) |

(52) U.S. Cl.

CPC .......... *C12N 15/8285* (2013.01); *A01H 1/04* (2013.01); *A01H 5/10* (2013.01); *C07K 14/415* (2013.01); *Y02A 40/164* (2018.01)

(58) Field of Classification Search

None

See application file for complete search history.

(56) References Cited

U.S. PATENT DOCUMENTS

| | | | |
|---|---|---|---|
| 4,582,788 | A | 4/1986 | Erlich |
| 4,683,194 | A | 7/1987 | Saiki et al. |
| 4,683,202 | A | 7/1987 | Mullis |
| 5,210,015 | A | 5/1993 | Gelfand |
| 5,217,863 | A | 6/1993 | Cotton et al. |
| 5,378,619 | A | 1/1995 | Rogers |
| 5,468,613 | A | 11/1995 | Erlich et al. |
| 5,595,890 | A | 1/1997 | Newton et al. |
| 5,616,464 | A | 4/1997 | Albagli et al. |
| 5,762,876 | A | 6/1998 | Lincoln et al. |
| 5,800,944 | A | 9/1998 | Blonsky et al. |
| 5,876,930 | A | 3/1999 | Livak et al. |
| 5,945,283 | A | 8/1999 | Kwok et al. |
| 6,004,744 | A | 12/1999 | Goelet et al. |
| 6,013,431 | A | 1/2000 | Soderlund et al. |
| 6,030,787 | A | 2/2000 | Livak et al. |
| 6,054,635 | A | 4/2000 | Bestwick et al. |
| 6,090,558 | A | 7/2000 | Butler et al. |
| 6,207,367 | B1 | 3/2001 | Helentja et al. |
| 6,503,710 | B2 | 1/2003 | Gut et al. |
| 6,613,509 | B1 | 9/2003 | Chen |
| 6,664,387 | B2 | 12/2003 | Chung |
| 6,799,122 | B2 | 9/2004 | Benson |
| 6,913,879 | B1 | 7/2005 | Schena |
| 6,996,476 | B2 | 2/2006 | Najarian |
| 7,238,476 | B2 | 7/2007 | McKeown et al. |
| 7,250,252 | B2 | 7/2007 | Katz et al. |
| 7,270,981 | B2 | 9/2007 | Armes et al. |
| 7,282,355 | B2 | 10/2007 | Shi |
| 7,297,485 | B2 | 11/2007 | Bornarth et al. |
| 7,312,039 | B2 | 12/2007 | Barany et al. |
| 2005/0204780 | A1 | 9/2005 | Moridaira et al. |
| 2005/0216545 | A1 | 9/2005 | Aldrich et al. |
| 2005/0218305 | A1 | 10/2005 | Tsukamoto et al. |
| 2008/0083042 | A1 | 4/2008 | Butruille et al. |
| 2008/0282431 | A1 | 11/2008 | Dasgupta et al. |
| 2008/0313776 | A1 | 12/2008 | Li |
| 2011/0083234 | A1* | 4/2011 | Nguyen .................. A01H 1/00 800/301 |

(Continued)

FOREIGN PATENT DOCUMENTS

| | | |
|---|---|---|
| EP | 0050424 | 4/1982 |
| EP | 0084796 | 8/1983 |
| EP | 0201184 | 12/1986 |

(Continued)

OTHER PUBLICATIONS

Fourgoux-Nicol et al (1999, Plant Molecular Biology 40: 857-872).*

Kandoth et al (the Soybean Rhg1 Locus for Resistance to the Soybean Cyst Nematode Heterodera glycines Regulates the Expression of a Large Number of Stress- and Defense-Related Genes in Degenerating Feeding Cells. Plant Physiology, vol. 155, pp. 1960-1975, Apr. 2011).*

Holden et al (the use of 35S and Tnos expression elements in the measurement of genetically engineered plant materials. Anal Bioanal Chem. 396:2175-2187, 2010).*

Barkley et al., Application of Tilling and EcoTilling as Reverse Genetic Approaches to Elucidate the Function of Genes in Plants and Animals, Current Genomics, 2008, pp. 212-226, vol. 9.

Benfey et al., The cauliflower Mosaic Virus 35S Promoter: Combinatorial Regulation of Transcription in Plants, Science, 1990, pp. 959-966, vol. 250.

(Continued)

*Primary Examiner* — Medina A Ibrahim

*Assistant Examiner* — Wayne Zhonh

(74) *Attorney, Agent, or Firm* — Dentons US LLP

(57) ABSTRACT

A transgenic soybean plant or parts thereof, resistant to soybean cyst nematodes, transformed to express Glyma18g02570, Glyma18g02580, or Glyma18g02590, or a variant thereof. Also provided is a method of making such a plant. Also provided is an artificial DNA construct encoding Glyma18g02570, Glyma18g02580, or Glyma18g02590, or a variant thereof.

19 Claims, 5 Drawing Sheets

Specification includes a Sequence Listing.

(56) References Cited

U.S. PATENT DOCUMENTS

2013/0305410 A1* 11/2013 Bent .................. C12N 15/8285 800/279

FOREIGN PATENT DOCUMENTS

| | | |
|---|---|---|
| EP | 0237362 | 9/1987 |
| EP | 0258017 | 3/1988 |
| JP | 2002238564 | 2/2001 |
| WO | WO 2000/037662 | 6/2000 |

OTHER PUBLICATIONS

Borevitz et al., Large-Scale Identification of Single-Feature Polymorphisms in Complex Genomes, Genome Research, 2003, pp. 513-523, vol. 13.
Brown et al., A High-Throughput Automated Technique for Counting Females of Heterodera glycines using a Fluorescence-Based Imaging System, J. Nematology, 2010, pp. 201-206, vol. 42, No. 3.
Cook et al., Copy Number Variation of Multiple Genes at Rhg1 Mediates Nematode Resistance in Soybean, Science, 2012, pp. 1206-1209, vol. 338.
Cooper et al., Tilling to detect induced mutation in soybean, BMC Plant Biology, 2008, 10 pages.
Cui et al., Detecting single-feature polymorphisms using oligonucleotide arrays and robustified projection pursuit, Bioinformatics, 2005, pp. 3852-3858, vol. 21, No. 20.
Dillon et al., RNAi as an Experimental and Therapeutic Tool to Study and Regulate Physiological and Disease Processes, Annu. Rev. Physiol., 2005, pp. 147-173, vol. 67.
Dykxhoorn et al., The Silent Revolution: RNA Interference as Basic Biology, Research Tool, and Therapeutic, Annu. Rev. Med., 2005, pp. 401-423, vol. 56.
Elhai et al., Conjugal Transfer of DNA to Cyanobacteria, Methods in Enzymology, 1988, pp. 747-754, vol. 167.
Ghadessy et al., Directed evolution of polymerase function by compartmentalized self-replication, PNAS, 2001, pp. 4552-4557, vol. 98 No. 8.
Helene et al., Control of Gene Expression by Triple Helix-Forming Oligonucleotides, Ann. NY Acad. Sci., 1992, pp, 27-36, vol. 660.
Holtorf et al., Promoter subfragments of the sugar beet V-type H+-ATPase subunit c isoform drive the expression of transgenes in the moss Physcomitrella patens, Plant Cell Rep., 2002, pp. 341-346, vol. 21.
Horstmann et al., Quantitative promoter analysis in *Physcomitrella patens*: a set of plant vectors activating gene expression within three orders of magnitude, BMC Biotechnology, 2004, vol. 4, 13 pages.
Jost et al., Isolation and characterisation of three moss-derived beta-tubulin promoters suitable for recombinant expression, Curr Gener, 2005, pp. 111-120, vol. 47.
Kandoth et al., The Soybean Rhg1 Locus for Resistance to the Soybean Cyst Nematode *Heterodera glycines* Regulates the Expression of a Large Number of Stress- and Defense-Related Genes in Degenerating Feeding Cells, Plant Physiology, 2011, pp. 1960-1975, vol. 155.
Lee et al., Aptamer therapeutics advance, Curr Opinion in Chemical Biology, 2006, pp. 282-289, vol. 10.
Link et al., Beyond toothpicks: new methods for isolating mutant bacteria, Nature, 2007, pp. 680-688, vol. 5.
Liu et al., Soybean cyst nematode resistance in soybean is independent of the Rhg4 locus LRR-RLK gene, Funct Intergr Genomics, 2011, pp. 539-549, vol. 11.
Maher, L. James, III, DNA Triple-Helix Formation: An Approach to Artificial Gene Repressors?, BioEssays, 1992, pp. 807-815, vol. 14, No. 12.
Malik et al., A constitutive gene expression system derived from the tCUP cryptic promoter elements, Theor Appl Genet, 2002, pp. 505-514, vol. 105.
Meksem et al., High-throughput genotyping for a polymorphism linked to soybean cyst nematode resistance gene RHG4 by using Taqman probes, Molecular Breeding, 2001, pp. 63-71, 2001.
Mullis et al., Specific Enzymatic Amplification of DNA In Vitro: The Polymerase Chain Reaction, Symposia on Quantitative Biology, 1986, pp. 263-273, vol. 51.
Pushparaj et al., Short Intefering RNA (siRNA) as a Novel Therapeutic, Clinical and Experimental Pharmacology and Physiology, 2006, pp. 504-510, vol. 33.
Reynolds et al., Rational siRNA design for RNA interference, Nature Biotechnology, 2004, pp. 326-330, vol. 22, No. 3.
Sagner et al., Rapid filter assay for the detection of DNA polymerase activity: direct identification of the gene for the DNA polymerase from *Thermus aquaticus*, 1991, pp. 119-123, vol. 97.
Saidi et al., Controlled expression of recombinant proteins in *Physcomitrella patens* by a conditional heat-shock promoter: a tool for plant research and biotechnology, Plant Molecular Biology, 2005, pp. 697-711, vol. 59.
Stavolone et al., Cestrum yellow leaf curling virus (CmYLCV) promoter: a new strong constitutive promoter for heterologous gene expression in a wide variety of crops, Plant Molecular Biology, 2003, pp. 703-713, vol. 53.
Studier, F. William, Protein production by auto-induction in high-density shaking cultures, Protein Expression & Purification, 2005, pp. 207-234, vol. 41.
Weise et al., Use of *Physcomitrella patens* actin 5' regions for high transgene expression: importance of 5' introns, 2006, pp. 337-345, vol. 70.
You et al., Use of Bacterial Quorum-Sensing Components to Regulate Gene Expression in Plants, Plant Physiology, 2006, pp. 1205-1212, vol. 140.
Zeidler et al., Tetracycline-regulated reporter gene expression in the moss *Physcomitrella patens*, 1996, pp. 199-205, vol. 30.
Zhang et al., The Development of an Efficient Multipurpose Bean Pod Mottle Virus Viral Vector Set for Foreign Gene Expression and RNA Silencing, Plant Physiology, 2010, pp. 52-65, vol. 153.
Liu, S., et al., "The Soybean GmSNAP18 Gene Underlies Two Types of Resistance to Soybean Cyst Nematode"; Nature Communications; Published Mar. 27, 2017; pp. 1-11.
Kandoth, P. K., et al., "Systematic Mutagenesis of Serine Hydroxymethyltransferase Reveals an Essential Role in Nematode Resistance", Plant Physiology; vol. 175, pp. 1-11, Nov. 2017.

* cited by examiner

| Haplotype | PI Name | 39 | 203 | 208 | 251 | 261 | 263 | 285 | 286 | 287 | 288 | 289 | SNAP Genotype | Rhg4 genotype | SCN infection phenotype |
|---|---|---|---|---|---|---|---|---|---|---|---|---|---|---|---|
| I | Forrest | A | Q | E | T | T | L | E | Y | E | V | I | R | R | R |
| | Peking | | Q | E | T | T | L | E | Y | E | V | I | R | R | R |
| | PI437654 | | Q | E | T | T | L | E | Y | E | V | I | R | R | R |
| | PI89772 | | Q | E | T | T | L | E | Y | E | V | I | R | R | R |
| | PI90763 | | Q | E | T | A | L | E | Y | E | V | I | R | R | R |
| | | | | | | | | | | | | | | | |
| II | PI88788 | A | K | D | T | T | L | Q | H | E | A | I | R | R | R |
| | PI548316 | G | K | D | T | T | L | Q | H | E | A | I | R | R | R |
| | PI209332 | A | K | D | S | T | L | Q | H | E | A | I | R | S | R |
| | | | | | | | | | | | | | | | |
| III | Williams 82 | A | Q | D | T | T | L | E | D | D | - | L | S | S | S |
| | PI603428C | A | Q | D | T | T | L | E | D | D | - | L | S | S | S |
| | Essex | A | Q | D | T | T | L | E | D | D | - | L | S | S | S |

SOYBEAN RESISTANT TO CYST NEMATODES

CROSS-REFERENCE TO RELATED APPLICATIONS

The present application claims the benefit of U.S. Provisional Application No. 61/799,912 filed 15 Mar. 2013, which is incorporated herein by reference in its entirety.

STATEMENT REGARDING FEDERALLY SPONSORED RESEARCH OR DEVELOPMENT

This invention was made with government support under grant number 0820642 awarded by National Science Foundation Plant Genome Research Program and DBI-0845196 awarded by National Science Foundation. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

BACKGROUND OF THE INVENTION

Soybean (*Glycine max* (L.) Merr.) is a major crop that provides a sustainable source of protein and oil worldwide. Soybean cyst nematode (SCN), *Heterodera glycines* Ichinohe, is a major constraint to soybean production. This nematode causes more than $1 billion in yield losses annually in the United States alone, making it the most economically important pathogen of soybeans. Although planting of resistant cultivars forms the core management strategy for this pathogen, nothing is known about the nature of resistance. Moreover, the increase in virulent populations of this parasite on most known resistance sources necessitates the development of novel approaches for control.

SUMMARY OF THE INVENTION

Disclosed herein are methods of transforming a soybean plant using artificial DNA constructs to increase resistance to soybean cyst nematode (SCN).

One aspect provides a transgenic soybean resistant to SCN, or a seed, plant part, or progeny thereof. In some embodiments, the soybean plant can be transformed with an artificial DNA construct. In some embodiments, the DNA construct includes, as operably associated components in the 5' to 3' direction of transcription, a promoter that functions in a soybean. In some embodiments, the DNA construct also includes a transcribable nucleic acid molecule.

In some embodiments, the transcribable nucleic acid molecule includes a nucleotide sequence selected from the group consisting of SEQ ID NO: 1 (Glyma18g02570), SEQ ID NO: 2 (Glyma18g02580), and SEQ ID NO: 3 (Glyma18g02590). In some embodiments, the transcribable nucleic acid molecule includes a nucleotide sequence at least 95% identical to a nucleotide sequence selected from the group consisting of SEQ ID NO: 1, SEQ ID NO: 2, and SEQ ID NO: 3 encoding a polypeptide having Glyma18g02570, Glyma18g02580, or Glyma18g02590 activity, respectively.

In some embodiments, the transcribable nucleic acid molecule includes a nucleotide sequence encoding a polypeptide comprising SEQ ID NO: 4 (Glyma18g02570), SEQ ID NO: 5 (Glyma18g02580), SEQ ID NO: 6 (Glyma18g02590), and SEQ ID NO: 7 (Forrest SNAP A111D mutant). In some embodiments, the transcribable nucleic acid molecule includes a nucleotide sequence encoding a polypeptide having an amino acid sequence at least 95% identical a polypeptide comprising SEQ ID NO: 4, SEQ ID NO: 5, SEQ ID NO: 6, and SEQ ID NO: 7 having Glyma18g02570, Glyma18g02580, Glyma18g02590, or SNAP activity, respectively.

In some embodiments, the transcribable nucleic acid molecule includes a nucleotide sequence that hybridizes under stringent conditions to a nucleic acid sequence of SEQ ID NO: 1, SEQ ID NO: 2, or SEQ ID NO: 3. In some embodiments, the polynucleotide encodes a polypeptide having Glyma18g02570, Glyma18g02580, or Glyma18g02590 activity. In some embodiments, stringent conditions include incubation at 65° C. in a solution including 6×SSC (0.9 M sodium chloride and 0.09 M sodium citrate). In some embodiments, the transcribable nucleic acid molecule includes a nucleotide sequence which is the reverse complement of nucleotide sequences disclosed herein.

In some embodiments, the DNA construct also includes a transcriptional termination sequence. In some embodiments, the transgenic soybean exhibits increased SCN resistance compared to a control not expressing the transcribable nucleic acid molecule.

In some embodiments, the nucleotide sequence can be at least 95% identical to SEQ ID NO: 3 having one of more mutations selected from the group consisting of C163225G, G164968T, A164972AGGT, C164974A, C163208A, G164965C, G164968C, A164972AGGC, and C164974A. In some embodiments, the encoded polypeptide includes an amino acid sequence at least 95% identical to SEQ ID NO: 6 having one of more mutations selected from the group consisting of D208E, D286Y, D287E, −288V, L289I, Q203K, E285Q, D286H, D287E, −288A, L289I, and A111D.

In some embodiments, the encoded polypeptide includes an amino acid sequence at least 95% identical to SEQ ID NO: 6, a mutation of A111D, and Glyma18g02590 polypeptide activity. In some embodiments, the transcribable nucleic acid molecule is expressed in epidermis, vascular tissue, meristem, cambium, cortex, pith, leaf, sheath, root, flower, developing ovule or seed.

In some embodiments, the promoter includes an inducible promoter or a tissue-specific promoter. In some embodiments, the promoter includes a nematode-inducible promoter. In some embodiments, the promoter is selected from the group consisting of factor EF1α gene promoter; rice tungro bacilliform virus (RTBV) gene promoter; cestrum yellow leaf curling virus (CmYLCV) promoter; tCUP cryptic promoter system; T6P-3 promoter; S-adenosyl-L-methionine synthetase promoter; Raspberry E4 gene promoter; cauliflower mosaic virus 35S promoter; figwort mosaic virus promoter; conditional heat-shock promoter; promoter subfragments of sugar beet V-type H+-ATPase subunit c isoform; and beta-tubulin promoter.

In some embodiments, increased SCN resistance comprises at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, at least about 600%, at least about 700%, at least about 800%, at least about 900%, or at least about 1000% decrease in susceptibility to SCN as compared to a non-transformed control.

In some embodiments, the transcribable nucleic acid molecule includes a nucleotide sequence selected from the group consisting of SEQ ID NO: 1, SEQ ID NO: 2, and SEQ ID NO: 3. In some embodiments, the transcribable nucleic acid molecule includes a nucleotide sequence at least 95% identical to SEQ ID NO: 1, SEQ ID NO: 2, or SEQ ID NO: 3, and encodes a polypeptide having Glyma18g02570, Glyma18g02580, or Glyma18g02590 activity, respectively. In some embodiments, the transcribable nucleic acid molecule encodes a polypeptide including SEQ ID NO: 4, SEQ ID NO: 5, SEQ ID NO: 6, or SEQ ID NO: 7. In some embodiments, the transcribable nucleic acid molecule encodes a polypeptide including an amino acid sequence at least 95% identical to SEQ ID NO: 4, SEQ ID NO: 5, SEQ ID NO: 6, or SEQ ID NO: 7 and having Glyma18g02570, Glyma18g02580, Glyma18g02590, or SNAP activity, respectively.

In some embodiments, the transgenic progeny, seed, or part comprises the transcribable nucleic acid molecule.

One aspect provides a soybean plant including in its genome at least one introgressed allele locus associated with an SCN resistant phenotype. In some embodiments, the locus can be in a genomic region flanked by at least two loci selected from TABLE 6. In some embodiments, the soybean plant also includes in its genome one or more polymorphic loci including alleles or combinations of alleles that are not found in an SCN resistant variety and that are linked to said locus associated with an SCN resistant phenotype, or a progeny plant therefrom. In some embodiments, the at least one allele locus is selected from the group consisting of Glyma18g02570, Glyma18g02580, and Glyma18g02590.

One aspect provides a method of producing a soybean plant as disclosed herein including crossing a first soybean plant lacking a locus associated with an SCN resistant phenotype with a second soybean plant. In some embodiments, the second soybean plant includes an allele of at least one polymorphic nucleic acid associated with an SCN resistant phenotype located in a genomic region flanked by at least two loci selected from TABLE 6. In some embodiments, the second soybean plant also includes at least one additional polymorphic locus located outside of said region that is not present in the first soybean plant, to obtain a population of soybean plants segregating for the polymorphic locus associated with an SCN resistant phenotype and said additional polymorphic locus.

In some embodiments, the method also includes detecting said polymorphic locus in at least one soybean plant from said population of soybean plants. In some embodiments, the method also includes selecting a soybean plant including the locus associated with an SCN resistant phenotype that lacks the additional polymorphic locus, thereby obtaining a soybean plant including in its genome at least one introgressed allele of a polymorphic nucleic acid associated with an SCN resistant phenotype. In some embodiments, the first soybean plant includes germplasm capable of conferring agronomically elite characteristics to a progeny plant of the first soybean plant and the second soybean plant.

One aspect provides an artificial DNA construct including, as operably associated components in the 5' to 3' direction of transcription, a promoter that functions in a soybean.

In some embodiments, the DNA construct also includes a transcribable nucleic acid molecule. In some embodiments, the transcribable nucleic acid molecule includes a nucleotide sequence selected from the group consisting of SEQ ID NO: 1, SEQ ID NO: 2, and SEQ ID NO: 3, or a nucleotide sequence at least 95% identical thereto encoding a polypeptide having Glyma18g02570, Glyma18g02580, or Glyma18g02590 activity, respectively. In some embodiments, the transcribable nucleic acid molecule includes a nucleotide sequence encoding a polypeptide including SEQ ID NO: 4, SEQ ID NO: 5, SEQ ID NO: 6, or SEQ ID NO: 7, or an amino acid sequence at least 95% identical thereto having Glyma18g02570, Glyma18g02580, Glyma18g02590, or SNAP activity, respectively. In some embodiments, the transcribable nucleic acid molecule includes a nucleotide sequence that hybridizes under stringent conditions to a nucleic acid sequence of SEQ ID NO: 1, SEQ ID NO: 2, or SEQ ID NO: 3. In some embodiments, the polynucleotide encodes a polypeptide having Glyma18g02570, Glyma18g02580, or Glyma18g02590 activity. In some embodiments, said stringent conditions include incubation at 65° C. in a solution including 6×SSC (0.9 M sodium chloride and 0.09 M sodium citrate). In some embodiments, the transcribable nucleic acid molecule includes a nucleotide sequence which is the reverse complement of nucleotide sequences disclosed herein.

In some embodiments, DNA construct also includes a transcriptional termination sequence.

One aspect provides a method of increasing SCN resistance of a soybean including transforming a soybean plant with an artificial DNA construct disclosed herein.

DESCRIPTION OF THE DRAWINGS

Those of skill in the art will understand that the drawings, described below, are for illustrative purposes only. The drawings are not intended to limit the scope of the present teachings in any way.

FIG. 1A shows high-density genetic maps of the Rhg1 locus developed using two recombinant inbred line populations, developed from crosses between a resistant line "Forrest" (F) and a susceptible line "Essex" (E) or "Williams 82" (W), showing recombinant lines WxF6034 (I, SCN-susceptible), ExF3126 (II, SCN-resistant) and ExF4361 (III, SCN-resistant). Black horizontal lines represent approximately 370 kb of the Rhg1 chromosomal interval. Arrows designate DNA marker positions and names. Numbers above the black horizontal line denote marker position relative to marker RLK (an LRR-RLK gene at the Rhg1 locus; assigned position '0'). Arrows with one asterisk designate the physical position of each tested DNA marker within the Rhg1 locus using published DNA sequence of Williams 82 as a reference. Arrows with no asterisk represent the DNA markers with Forrest alleles found in recombinants WxF6034, ExF3126 and ExF4361. Arrows with two asterisks represent the DNA markers with heterozygote alleles (Forrest allele with Essex allele). The arrow with three asterisks represents DNA marker 600 having polymorphisms between Essex and Forrest, and between Essex and Williams 82, but not between Forrest and Williams 82. FIG. 1B shows the genomic DNA gene model for the SNAP gene. The gene is 4,223 bp from start codon to stop codon and contains nine exons (light-grey boxes) and eight introns (solid black lines). Numbers above the light-grey boxes and solid black line indicate the length (bp) of each exon or intron, while the numbers under the dotted lines indicate the nucleotide position relative to the first nucleotide of the start codon. FIG. 1C shows a comparison of the predicted SNAP protein sequences between Forrest and Essex with the amino acid differences (Y206D, E207D, V288- and I289L) highlighted (SEQ ID NO: 8). FIG. 1D shows the predicted armadillo/beta-catenin-like repeat sequence (marker 570) (SEQ ID NO: 4). FIG. 1E shows the predicted amino acid transporter sequence (marker 580) (SEQ ID NO: 5).

FIG. 3A and FIG. 3B show the virus-induced gene-silencing (VIGS) phenotype of Glyma18g02590-VIGS-AS bombarded plants at 16 days post-inoculation. FIG. 3C and FIG. 3D show the VIGS phenotype of Glyma18g02590-VIGS-AS rub-inoculated plants at 16 days post-inoculation.

DETAILED DESCRIPTION OF THE INVENTION

Figure 1:
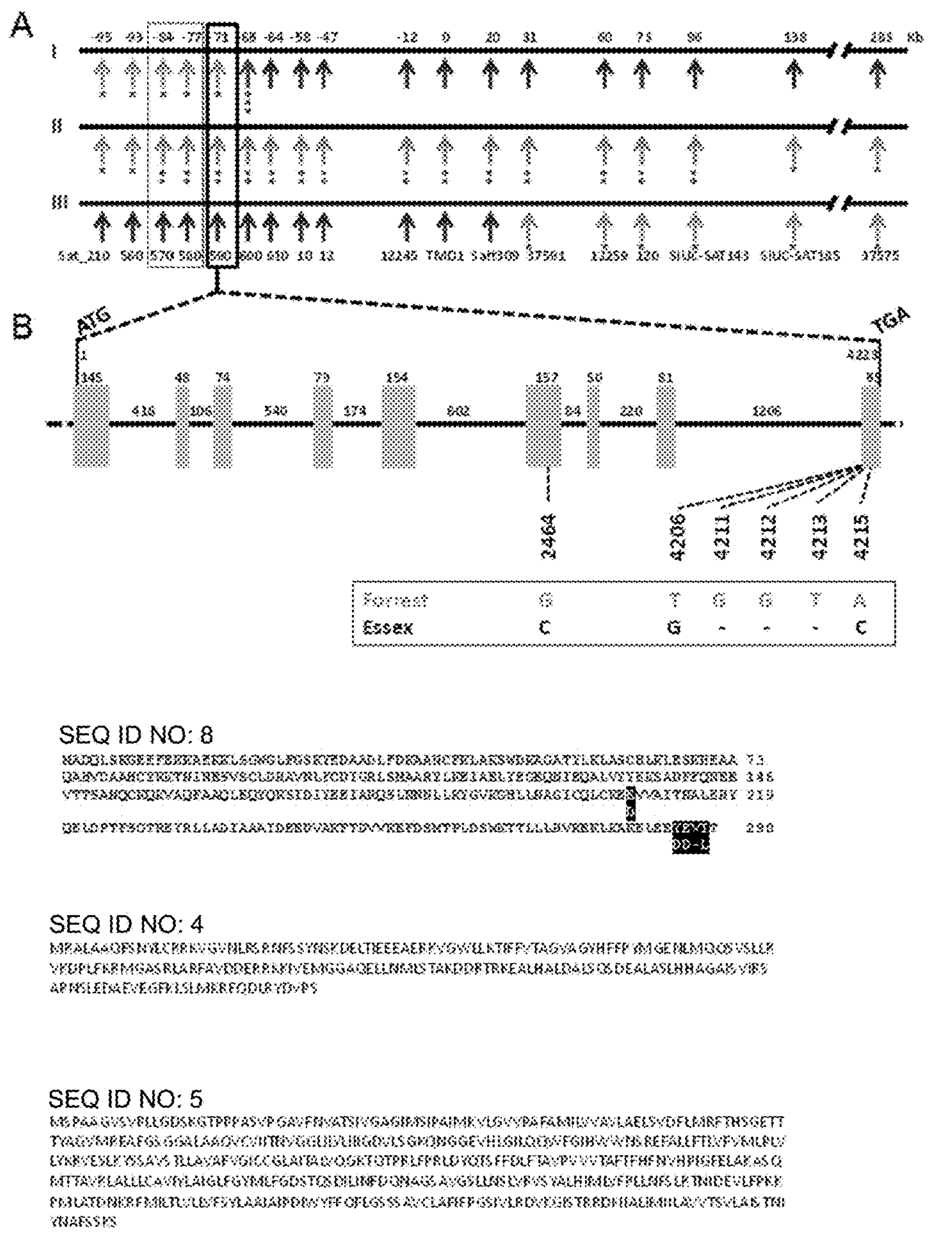
FIG. 1 is a series of drawings and a sequence listing illustrating the positional cloning of the Rhg1 gene.

The present disclosure is based, at least in part, on the discovery that three genes mapped to the Rhg1 (for resistance to *Heterodera glycines* 1) locus confer resistance to SCN.

Reported herein is the map-based cloning of three genes at the Rhg1 locus, a major quantitative trait locus conferring resistance to this pathogen. Results herein indicate that three genes that can confer SCN-resistance at the Rhg1 locus include Glyma18g02570 (an armadillo/beta-catenin-like repeat), Glyma18g02580 (an amino acid transporter), or Glyma18g02590 (a SNAP-like protein).

According to the approach described herein, a soybean cell or plant can be transformed so as to provide for SCN resistance. In some embodiments, a soybean host cell or plant can be transformed with a nucleic acid molecule encoding a polypeptide having activity of Glyma18g02570, Glyma18g02580, or Glyma18g02590. A nucleic acid encoding a polypeptide having Glyma18g02570, Glyma18g02580, or Glyma18g02590 activity can confer SCN resistance.

Since the discovery of the genes involved in resistance to SCN, others have published data providing confirmation that the three genes are involved in the resistance to SCN. Proof of principle data includes the following additional evidence that the Rhg1 locus confers SCN-resistance in soybean. It has since been shown that upregulation of genes at nematode feeding sites in near-isogenic lines of resistant and susceptible soybean cultivars differ at the Rhg1 locus (Kandoth et al., Plant Physiology, 155:1960-1975, 2011). These results show that expression of Glyma18g02580 and Glyma18g02590 increased in resistant cells as described herein (see e.g., TABLE 1). The effect of copy number variation of multiple genes at the Rhg1 locus was shown for nematode resistance in soybean (Cook et al., Science, 338 (6111):1206-1209, 2012).

TABLE 1

Glyma18g02580 and Glyma18g02590 gene expression in SCN-resistant cells.

| Gene | Description | Fold increase (R:S) |
|---|---|---|
| Glyma18g02580.1 | Amino acid transporter | 4.08 |
| Glyma18g02590.1 | NSF soluble attachment protein | 1.50 |

TRANSFORMED ORGANISM

Provided herein is a soybean plant genetically engineered to be SCN-resistant. The host genetically engineered to resist SCN can be any soybean plant or cell.

Assays to assess SCN resistance are well known in the art (see e.g., Examples). Therefore, except as otherwise noted herein, plant SCN resistance can be carried out in accordance with such assays.

One aspect of the current invention is therefore directed to the aforementioned plants, and parts thereof, and methods for using these plants and plant parts. Plant parts include, but are not limited to, pollen, an ovule, and a cell. The invention further provides tissue cultures of regenerable cells of these plants, which cultures regenerate soybean plants capable of expressing all the physiological and morphological characteristics of the starting variety. Such regenerable cells may include embryos, meristematic cells, pollen, leaves, roots, root tips or flowers, or protoplasts or callus derived therefrom. Also provided by the invention are soybean plants regenerated from such a tissue culture, wherein the plants are capable of expressing all the physiological and morphological characteristics of the starting plant variety from which the regenerable cells were obtained.

Such SCN-resistant plants can have a commercially significant yield, for example, a yield of at least 90% to at least 110% (e.g., at least 95%, 100%, 105%) of a soybean check line. Plants are provided comprising the Glyma18g02570, Glyma18g02580, or Glyma18g02590 alleles and SCN resistance and a grain yield of at least about 90%, 94%, 98%, 100%, 105% or about 110% of these lines.

In various embodiments, a nucleic acid sequence encoding a polypeptide having Glyma18g02570, Glyma18g02580, or Glyma18g02590 activity is engineered in a host plant (e.g., a soybean plant) so as to result in an SCN-resistant phenotype. A nucleic acid sequence encoding a polypeptide having Glyma18g02570, Glyma18g02580, or Glyma18g02590 activity can be endogenous or exogenous to the host plant. Transformation of a plant to express a polypeptide having Glyma18g02570, Glyma18g02580, or Glyma18g02590 activity can convey SCN resistance to a host lacking such phenotype. Transformation of a plant to express a polypeptide having Glyma18g02570, Glyma18g02580, or Glyma18g02590 activity can increase SCN resistance to a host already possessing such phenotype.

In some embodiments, a host plant transformed to express a polypeptide having Glyma18g02570, Glyma18g02580, or Glyma18g02590 activity can exhibit at least about 10% decrease in susceptibility to SCN. For example, a host plant transformed to express a polypeptide having Glyma18g02570, Glyma18g02580, or Glyma18g02590 activity can exhibit at least about 20%, at least about 30%, at least about 40%, at least about 50%, at least about 60%, at least about 70%, at least about 80%, at least about 90%, or at least about 100% decrease in susceptibility to SCN as compared to a non-transformed control. As another example, a host plant transformed to express a polypeptide having Glyma18g02570, Glyma18g02580, or Glyma18g02590 activity can exhibit at least about 100%, at least about 200%, at least about 300%, at least about 400%, at least about 500%, at least about 600%, at least about 700%, at least about 800%, at least about 900%, or at least about 1000% decrease in susceptibility to SCN as compared to a non-transformed control.

Genes of particular interest for engineering a soybean plant to exhibit SCN resistance include Glyma18g02570 (SEQ ID NO: 1), Glyma18g02580 (SEQ ID NO: 2), or Glyma18g02590 (SEQ ID NO: 3). As described herein, Glyma18g02570, Glyma18g02580, or Glyma18g02590 have been mapped to the Rhg1 locus and can confer SCN-resistance.

A transformed host soybean plant can comprise a nucleotide sequence of SEQ ID NO: 1 (Glyma18g02570), SEQ ID NO: 2 (Glyma18g02580), or SEQ ID NO: 3 (Glyma18g02590). A transformed host soybean plant can comprise a nucleotide sequence having at least about 80% sequence identity to SEQ ID NO: 1 (Glyma18g02570), SEQ ID NO: 2 (Glyma18g02580), or SEQ ID NO: 3 (Glyma18g02590), wherein the nucleotide sequence encodes a polypeptide having Glyma18g02570, Glyma18g02580, or Glyma18g02590 activity, respectively, or the transformed soybean exhibits SCN resistance. For example, a transformed host soybean plant can comprise a nucleotide sequence having at least about 85%, at least about 90%, at least about 95%, or at least about 99% sequence identity to SEQ ID NO: 1 (Glyma18g02570), SEQ ID NO: 2 (Glyma18g02580), or SEQ ID NO: 3 (Glyma18g02590), wherein the nucleotide sequence encodes a polypeptide having Glyma18g02570, Glyma18g02580, or Glyma18g02590 activity, respectively, or the transformed soybean exhibits SCN resistance.

A nucleotide sequence described herein can include one or mutations affecting the activity of a Glyma18g02570, Glyma18g02580, or Glyma18g02590 polypeptide or host SCN resistance. For example, a nucleotide sequence of SEQ ID NO: 1 (Glyma18g02570), SEQ ID NO: 2 (Glyma18g02580), or SEQ ID NO: 3 (Glymal18g02590) can have one or more mutations affecting the activity of a Glyma18g02570, Glyma18g02580, or Glyma18g02590 polypeptide or host SCN resistance. For example, a nucleotide sequence variant (e.g., at least 80%, 85%, 90%, 95, or 99% identity) of SEQ ID NO: 3 (Glyma18g02590) can have one or more of the following mutations: C163225G, G164968T, A164972AGGT, C164974A, C163208A, G164965C, G164968C, A164972AGGC, or C164974A. As another example, the SNAP gene (Glyma18g02590; e.g., SEQ ID NO: 3) in Forrest or Peking backgrounds can include one or more of the following mutations: C163225G, G164968T, A164972AGGT, or C164974A. As another example, the SNAP gene (Glyma18g02590; e.g., SEQ ID NO: 3) in a PI88788 background can include one or more of the following mutations: C163208A, G164965C, G164968C, A164972AGGC, or C164974A.

A transformed host soybean plant can comprise a nucleotide sequence encoding a polypeptide of SEQ ID NO: 4 (Glyma18g02570), SEQ ID NO: 5 (Glyma18g02580), SEQ ID NO: 6 (Glyma18g02590), or SEQ ID NO: 7 (Forrest SNAP A111D mutant). A transformed host soybean plant can comprise a nucleotide sequence encoding a polypeptide having at least about 80% sequence identity to SEQ ID NO: 4 (Glyma18g02570), SEQ ID NO: 5 (Glyma18g02580), SEQ ID NO: 6 (Glyma18g02590), or SEQ ID NO: 7 (Forrest SNAP A111D mutant), wherein the polypeptide has Glyma18g02570, Glyma18g02580, Glyma18g02590, or SNAP activity, respectively, or the transformed soybean exhibits SCN resistance. For example, a transformed host soybean plant can comprise a nucleotide sequence encoding a polypeptide having at least about 85%, at least about 90%, at least about 95%, or at least about 99% sequence identity to SEQ ID NO: 4 (Glyma18g02570), SEQ ID NO: 5 (Glyma18g02580), SEQ ID NO: 6 (Glyma18g02590), or SEQ ID NO: 7 (Forrest SNAP A111D mutant), wherein the nucleotide sequence encodes a polypeptide having Glyma18g02570, Glyma18g02580, Glyma18g02590, or SNAP activity, respectively, or the transformed soybean exhibits SCN resistance.

A polypeptide sequence described herein can include one or mutations affecting the activity of a Glyma18g02570, Glyma18g02580, or Glyma18g02590 polypeptide or host SCN resistance. For example, an encoded or expressed polypeptide of SEQ ID NO: 4 (Glyma18g02570), SEQ ID NO: 5 (Glyma18g02580), SEQ ID NO: 6 (Glyma18g02590), or SEQ ID NO: 7 (Forrest SNAP A111D mutant) can have one or more mutations affecting the activity of the polypeptide or host SCN resistance. For example, an encoded or expressed polypeptide variant (e.g., at least 80%, 85%, 90%, 95, or 99% identity) of SEQ ID NO: 3 (Glyma18g02590) can have one or more of the following mutations: D208E, D286Y, D287E, -288V, L289I, Q203K, E285Q, D286H, D287E, -288A, L289I, or A111D. As another example, the SNAP-like protein (SEQ ID NO: 6, encoded by, e.g., Glyma18g02590, SEQ ID NO: 3) in Forrest or Peking backgrounds can include one or more of the following mutations: D208E, D286Y, D287E, -288V, L289I, or A111D. As another example, the SNAP-like protein (SEQ ID NO: 6, encoded by, e.g., Glyma18g02590, SEQ ID NO: 3) in a PI88788 background can include one or more of the following mutations: Q203K, E285Q, D286H, D287E, -288A, L289I, or A111D.

As another example, a transformed soybean can comprise a nucleotide sequence that hybridizes under stringent conditions to a Glyma18g02570, Glyma18g02580, or Glyma18g02590 polynucleotide (e.g., SEQ ID NO: 1, SEQ ID NO: 2, or SEQ ID NO: 3, respectively) over the entire length thereof, and which encodes a polypeptide having Glyma18g02570, Glyma18g02580, Glyma18g02590, or SNAP A111D mutant (e.g., SEQ ID NO: 4, SEQ ID NO: 5, SEQ ID NO: 6, or SEQ ID NO: 7, respectively) activity.

As a further example, a transformed soybean can comprise the complement to any of the above sequences.

Variant Sequences

As describe above, a plant can be transformed with a variant of a Glyma18g02570, Glyma18g02580, or Glyma18g02590 polynucleotide (e.g., SEQ ID NO: 1, SEQ ID NO: 2, or SEQ ID NO: 3) or with a polynucleotide encoding a variant of a Glyma18g02570, Glyma18g02580, Glyma18g02590, SNAP A111D mutant (e.g., SEQ ID NO: 4, SEQ ID NO: 5, SEQ ID NO: 6, or SEQ ID NO: 7, respectively) polypeptide. These species SEQ ID NO: 1, SEQ ID NO: 2, or SEQ ID NO: 3, and their corresponding encoded polypeptides, are representative of the genus of variant nucleic acid and polypeptides, respectively, because all variants must possess the specified catalytic activity (e.g., Glyma18g02570, Glyma18g02580, or Glyma18g02590 activity) and must have the percent identity required above to the reference sequence.

Promoters

One or more of the nucleotide sequences discussed above (e.g., Glyma18g02570, Glyma18g02580, or Glyma18g02590 or a variant thereof) can be operably linked to a promoter that can function in a plant, such as soybean. Promoter selection can allow expression of a desired gene product under a variety of conditions.

Promoters can be selected for optimal function in a soybean host cell into which the vector construct will be inserted. Promoters can also be selected on the basis of their regulatory features. Examples of such features include enhancement of transcriptional activity and inducibility.

Numerous promoters functional in a soybean plant will be known to one of skill in the art (see, e.g., Weise et al., Applied Microbiology and Biotechnology, 70(3):337-345, 2006; Saidi et al., Plant Molecular Biology, 59(5):697-711, 2005; Horstmann et al., BMC Biotechnology, 4, 2004; Holtorf et al., Plant Cell Reports, 21(4):341-346, 2002; Zeidler et al., Plant Molecular Biology, 30(1):199-205, 1996). Except as otherwise noted herein, therefore, the processes and compositions of the present disclosure can be carried out in accordance with such known promoters. Examples of promoters than can be used in accord with methods and compositions described herein include, but are not limited to, factor EF1α gene promoter (US App Pub No. 2008/0313776); rice tungro bacilliform virus (RTBV) gene promoter (US App Pub No. 2008/0282431); cestrum yellow leaf curling virus (CmYLCV) promoter (Stavolone et al., Plant Molecular Biology, 53(5):663-673, 2003); tCUP cryptic promoter system (Malik et al., Theoretical and Applied Genetics, 105(4):505-514, 2002); T6P-3 promoter (JP2002238564); S-adenosyl-L-methionine synthetase promoter (WO/2000/037662); Raspberry E4 gene promoter (U.S. Pat. No. 6,054,635); cauliflower mosaic virus 35S promoter (Benfey et al., Science, 250(4983):959-966, 1990); figwort mosaic virus promoter (U.S. Pat. No. 5,378, 619); conditional heat-shock promoter (Saidi et al., Plant Molecular Biology, 59(5):697-711, 2005); promoter subfragments of the sugar beet V-type H+-ATPase subunit c isoform (Holtorf et al., Plant Cell Reports, 21(4):341-346, 2002); beta-tubulin promoter (Jost et al., Current Genetics, 47(2):111-120, 2005); and bacterial quorum-sensing components (You et al., Plant Physiology, 140(4):1205-1212, 2006).

The promoter can be an inducible promoter. For example, the promoter can be induced according to temperature, pH, a hormone, a metabolite (e.g., lactose, mannitol, an amino acid), light (e.g., wavelength specific), osmotic potential (e.g., salt induced), a heavy metal, or an antibiotic. As another example, the promoter can be a nematode-inducible promoter, such as pZF (Kandoth et al. Plant Physiol. 155: 1960-1975 (2011)). Numerous standard inducible promoters will be known to one of skill in the art.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

Constructs

Any of the transcribable polynucleotide molecule sequences described above can be provided in a construct. Constructs of the present invention generally include a promoter functional in the host plant, such as soybean, operably linked to a transcribable polynucleotide molecule encoding a polypeptide with Glyma18g02570, Glyma18g02580, or Glyma18g02590 activity, such as provided in SEQ ID NO: 1, SEQ ID NO: 2, or SEQ ID NO: 3, or variants thereof as discussed above.

Exemplary promoters are discussed above. One or more additional promoters may also be provided in the recombinant construct. These promoters can be operably linked to any of the transcribable polynucleotide molecule sequences described above.

The term "construct" is understood to refer to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. The term "vector" or "vector construct" is understood to refer to any recombinant polynucleotide construct that may be used for the purpose of transformation, i.e., the introduction of heterologous DNA into a host plant, such as a soybean.

In addition, constructs may include, but are not limited to, additional polynucleotide molecules from an untranslated region of the gene of interest. These additional polynucleotide molecules can be derived from a source that is native or heterologous with respect to the other elements present in the construct.

Host cells developed according to the approaches described herein can be evaluated by a number of means known in the art (see, e.g., Studier, Protein Expr Purif, 41(1):207-234, 2005; Gellissen, ed., (2005) Production of Recombinant Proteins: Novel Microbial and Eukaryotic Expression Systems, Wiley-VCH, ISBN-10:3527310363; Baneyx, (2004) Protein Expression Technologies, Taylor & Francis, ISBN-10:0954523253).

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002)

Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Green and Sambrook 2012 Molecular Cloning: A Laboratory Manual, 4th ed., Cold Spring Harbor Laboratory Press, ISBN-10: 1605500569; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see, e.g., Sambrook and Russell, (2006) Condensed Protocols from Molecular Cloning: A Laboratory Manual, Cold Spring Harbor Laboratory Press, ISBN-10:0879697717; Ausubel et al., (2002) Short Protocols in Molecular Biology, 5th ed., Current Protocols, ISBN-10: 0471250929; Sambrook and Russell, (2001) Molecular Cloning: A Laboratory Manual, 3d ed., Cold Spring Harbor Laboratory Press, ISBN-10:0879695773; Elhai, J. and Wolk, C. P., Methods in Enzymology, 167:747-754, 1988).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art. Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al., Nature Reviews, 5(9):680-688, 2007; Sanger et al., Gene, 97(1):119-123, 1991; and Ghadessy et al., Proc Natl Acad Sci USA, 98(8):4552-4557, 2001. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[$Na^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see, e.g., Sambrook and Russell, (2006)).

Host cells can be transformed using a variety of standard techniques known to the art (see, e.g., Sambrook and Russell (2006); Ausubel et al. (2002); Sambrook and Russell, (2001); Elhai, J. and Wolk, C. P., 1988). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see, e.g., Studier, 2005; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (sRNA), short hairpin RNA (shRNA), and micro RNAs (miRNA) (see, e.g., Fanning and Symonds, Handb Exp Pharmacol., 173:289-303G, 2006, describing hammerhead ribozymes and small hairpin RNA; Helene, C., et al., Ann. N.Y. Acad. Sci., 660:27-36, 1992; Maher, Bioassays 14(12):807-15, 1992, describing targeting deoxyribonucleotide sequences; Lee et al., Curr Opin Chem Biol., 10:1-8, 2006, describing aptamers; Reynolds et al., Nature Biotechnology, 22(3):326-330, 2004, describing RNAi; Pushparaj and Melendez, Clin. and Exp. Pharm. and Phys., 33(5-6):504-510, 2006, describing RNAi; Dillon et al., Annual Review of Physiology, 67:147-173, 2005, describing RNAi; Dykxhoorn and Lieberman, Annual Review of Medicine, 56:401-423, 2005, describing RNAi). RNAi molecules are commercially available from a variety of sources (e.g., Ambion, TX; Sigma Aldrich, MO; Invitrogen). Several siRNA molecule design programs using a variety of algorithms are known to the art (see, e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Breeding

It is disclosed herein that a quantitative trait locus (QTL) with major effects for SCN resistance and single nucleotide polymorphism (SNP) markers in the proximity of this locus have been identified that can be used for the introgression of this genomic region to desirable germplasm, such as by marker-assisted selection and/or marker-assisted backcrossing.

The present disclosure provides genetic markers and methods for the introduction of Glyma18g02570, Glyma18g02580, or Glyma18g02590 alleles into agronomically elite soybean plants. The invention therefore allows the creation of plants that combine these Glyma18g02570, Glyma18g02580, or Glyma18g02590 alleles that confer SCN resistance with a commercially significant yield and an agronomically elite genetic background. Using the methods of the invention, loci conferring the SCN phenotype may be introduced into a desired soybean genetic background, for example, in the production of new varieties with commercially significant yield and SCN resistance.

As used herein, the term "population" means a genetically heterogenous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for alleles that affect the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

"Agronomically elite" refers to a genotype that has a culmination of many distinguishable traits such as emergence, vigor, vegetative vigor, disease resistance, seed set, standability, and threshability, which allows a producer to harvest a product of commercial significance.

As used herein, the term "introgressed," when used in reference to a genetic locus, refers to a genetic locus that has been introduced into a new genetic background. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

Marker assisted introgression involves the transfer of a chromosome region defined by one or more markers from one germplasm to a second germplasm. The initial step in that process is the localization of the trait by gene mapping, which is the process of determining the position of a gene relative to other genes and genetic markers through linkage analysis. The basic principle for linkage mapping is that the closer together two genes are on the chromosome, the more likely they are to be inherited together. Briefly, a cross is generally made between two genetically compatible but divergent parents relative to traits under study. Genetic markers can then be used to follow the segregation of traits under study in the progeny from the cross, often a backcross (BC1), $F_2$, or recombinant inbred population.

The term quantitative trait loci, or QTL, is used to describe regions of a genome showing quantitative or additive effects upon a phenotype. The Rhg1 loci, containing Glyma18g02570, Glyma18g02580, or Glyma18g02590 alleles, represent exemplary QTL because Glyma18g02570, Glyma18g02580, or Glyma18g02590 alleles result in SCN resistance. Herein identified are genetic markers for non-transgenic, Glyma18g02570, Glyma18g02580, or Glyma18g02590 alleles that enable breeding of soybean plants comprising the Glyma18g02570, Glyma18g02580, or Glyma18g02590 alleles with agronomically superior plants, and selection of progeny that inherited the mutant Glyma18g02570, Glyma18g02580, or Glyma18g02590 alleles. Thus, the invention allows the use of molecular tools to combine these QTLs with desired agronomic characteristics.

Various embodiments of the present disclosure utilize a QTL or polymorphic nucleic acid marker or allele located in this genomic region. Subregions of this genomic region associated with SCN resistant phenotype can be described as being flanked by markers shown in TABLE 6. Such markers are believed to be associated with the SCN resistant phenotype because of their location and proximity to the major QTL. One or more polymorphic nucleic acids can be used from TABLE 6. For example, at least two, three, four, five, six, seven, eight, nine, ten, or more of such markers can used.

It can be useful to detect in, or determine whether, a soybean plant has an allelic state that is associated with or not associated with an SCN resistant phenotype.

A plant can be identified in which at least one allele at a polymorphic locus associated with an SCN resistant phenotype is detected. For example, a diploid plant in which the allelic state at a polymorphic locus comprises one allele associated with an SCN resistant phenotype and one allele that is not associated with an SCN resistant phenotype (i.e., heterozygous at that locus). In certain embodiments of the invention, it may be useful to cross a plant that is heterozygous at a locus associated with an SCN resistant phenotype with a plant that is similarly heterozygous or that does not contain any allele associated with an SCN resistant phenotype at the locus, to produce progeny a certain percentage of plants that are heterozygous at that locus. Plants homozygous at the locus may then be produced by various breeding methods, such as by self-crossing or dihaploidization.

One of skill in the art will also recognize that it can be useful to identify at a genetic locus a polymorphic nucleic acid marker that is not associated with an SCN resistant phenotype in a plant, such as when introgressing a QTL associated with an SCN resistant phenotype into a genetic background not associated with such a phenotype.

Markers and allelic states disclosed herein are exemplary. From Table 6, one of skill in the art would recognize how to identify soybean plants with other polymorphic nucleic acid markers and allelic states thereof related to SCN resistance consistent with the present disclosure. One of skill the art would also know how to identify the allelic state of other polymorphic nucleic acid markers located in the genomic region(s) or linked to the QTL or other markers identified herein, to determine their association with SCN resistance.

Provided herein are unique soybean germplasms or soybean plants comprising an introgressed genomic region that is associated with an SCR resistant phenotype and method of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., an SCN resistant phenotype germplasm) and both linked and unlinked markers characteristic of the desired genetic background of a second germplasm. Flanking markers that identify a genomic region associated with an SCN resistant phenotype include those in TABLE 6.

Flanking markers that fall on both the telomere proximal end and the centromere proximal end of any of these genomic intervals may be useful in a variety of breeding efforts that include, but are not limited to, introgression of genomic regions associated with an SCN resistant phenotype into a genetic background comprising markers associated with germplasm that ordinarily contains a genotype associated with a non-SCN resistant phenotype. Markers that are linked and either immediately adjacent or adjacent to the identified SCN resistant phenotype QTL that permit introgression of the QTL in the absence of extraneous linked DNA from the source germplasm containing the QTL are provided herewith. Those of skill in the art will appreciate that when seeking to introgress a smaller genomic region comprising a QTL associated with an SCN resistant phenotype described herein, that any of the telomere proximal or centromere proximal markers that are immediately adjacent to a larger genomic region comprising the QTL can be used to introgress that smaller genomic region.

Soybean plants or germplasm comprising an introgressed region that is associated with an SCN resistant phenotype wherein at least 10%, 25%, 50%, 75%, 90%, or 99% of the remaining genomic sequences carry markers characteristic of plant or germplasm that otherwise or ordinarily comprise a genomic region associated with an non-SCN resistant phenotype, are thus provided. Furthermore, soybean plants comprising an introgressed region where closely linked regions adjacent or immediately adjacent to the genomic regions, QTL, and markers provided herewith that comprise genomic sequences carrying markers characteristic of soybean plants or germplasm that otherwise or ordinarily comprise a genomic region associated with the phenotype are also provided.

Genetic markers that can be used in the practice of the present disclosure include, but are not limited to, Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of the present disclosure, polymorphic nucleic acids can be used to detect in a soybean plant a genotype associated with an SCN resistant phenotype, identify a soybean plant with a genotype associated with an SCN resistant phenotype, or to select a soybean plant with a genotype associated with an SCN resistant phenotype. In certain embodiments of methods of the present disclosure, polymorphic nucleic acids can be used to produce a soybean plant that comprises in its genome an introgressed locus associated with an SCN resistant phenotype. In certain embodiments of the invention, polymorphic nucleic acids can be used to breed progeny soybean plants comprising a locus associated with an SCN resistant phenotype.

Certain genetic markers useful in the present invention include "dominant" or "codominant" markers. "Codominant" markers reveal the presence of two or more alleles (two per diploid individual). "Dominant" markers reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Nucleic acid-based analyses for determining the presence or absence of the genetic polymorphism (i.e. for genotyping) can be used in breeding programs for identification, selection, introgression, or the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with an SCN resistant phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For example, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes or non-coding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' to 3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present disclosure can be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers (see e.g., TABLE 6) appear to be useful for tracking and assisting introgression of QTLs.

Research Tools

The Glyma18g02570, Glyma18g02580, or Glyma18g02590 genes can be used to find or characterize related (interactive) genes or identify or further characterize the cascade for SCN resistance. The discovery of a Glyma18g02570, Glyma18g02580, or Glyma18g02590 as part of the resistance signaling pathway against SCN provides novel insight into this complex host-pathogen interaction. Insights reported herein can be used to discern the relationship between Glyma18g02570, Glyma18g02580, or Glyma18g02590 and metabolism.

In some embodiments, the Glyma18g02570, Glyma18g02580, or Glyma18g02590 genes can be used in a genomics, proteomics, bioinformatics, or statistical modeling approach to fish or isolate candidate genes or encoded proteins or other molecules with a direct or indirect function in mediating disease resistance to SCN in soybeans. In some embodiments, the Glyma18g02570, Glyma18g02580, or Glyma18g02590 genes can be used in a genomics, proteomics, bioinformatics, or statistical modeling approach to fish or isolate candidate genes or encoded proteins or other molecules with a direct or indirect function in mediating compatible or incompatible responses of soybeans to SCN (e.g., to a nematode or any intermediate). Thus is provided various methods to find or characterize related (interactive) genes involved with SCN resistance.

Targeting-Induced Local Lesions in Genomes (TILLING) is a method permitting identification of gene-specific mutations. In particular, this process uses traditional mutagenesis and SNP discovery methods for a reverse genetic strategy that takes advantage of a mismatch endonuclease to locate and detect induced mutations in a high-throughput and low cost manner. EcoTILLING, which is a variant of TILLING, examines natural genetic variation in populations to discover SNPs (reviewed in Barkley and Wang, Curr Genomics, 9(4):212-26, 2008).

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to an antibody (e.g., a monoclonal antibody) specific for a transcribable nucleic acid molecule described herein (e.g., SEQ ID NOS: 1-3, or variants thereof) or encoded polypeptides disclosed herein (e.g., SEQ ID NOS: 4-6, or variants thereof). Methods for generating such a monoclonal antibody are known in the art and can be adapted to the methods or compositions described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms “a” and “an” and “the” and similar references used in the context of describing a particular embodiment (especially in the context of certain of the following claims) can be construed to cover both the singular and the plural, unless specifically noted otherwise. In some embodiments, the term “or” as used herein, including the claims, is used to mean “and/or” unless explicitly indicated to refer to alternatives only or the alternatives are mutually exclusive.

The terms “comprise,” “have” and “include” are open-ended linking verbs. Any forms or tenses of one or more of these verbs, such as “comprises,” “comprising,” “has,” “having,” “includes” and “including,” are also open-ended. For example, any method that “comprises,” “has” or “includes” one or more steps is not limited to possessing only those one or more steps and can also cover other unlisted steps. Similarly, any composition or device that “comprises,” “has” or “includes” one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., “such as”) provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Positional Cloning of the Rhg1 Gene

The following example describes the positional cloning of the Rhg1 gene. Three genetic populations segregating for resistance to SCN PA3 (Hgtype 0) were used for mapping. These included an F2:6 recombinant inbred line (RIL) population from a cross between Forrest and Essex (98 individuals; Meksem et al., 2001), and two large F2 populations generated from crosses between Forrest and either Essex (1,755 lines) or Williams 82 (2,060 lines).

To enrich the chromosomal interval carrying the Rhg1 locus with recombinants, SCN phenotyping was conducted according to Brown et al. (2010). Because Forrest SCN-resistance requires both the Rhg1 and Rhg4 loci (Meksem et al., 2001), genotyping was conducted using DNA markers flanking both loci to detect informative recombinants at the Rhg1 locus. The SSR markers, Sat_210 and Satt309 (see, e.g., SoyBase and the Soybean Breeder’s Toolbox at soybase.org), and SIUC-SAT143 were used to identify chromosomal breakpoints at the Rhg1 locus and the Rhg1 genotype of each recombinant. PCR amplifications were performed using DNA from individuals from each of the three genetic populations. To enrich the chromosomal regions carrying the Rhg1 locus with DNA markers, the GenBank published Williams 82 sequences were used to design PCR primers every 5 to 10 kbp of the 370 kbp carrying the Rhg1 locus. DNA from Forrest and Essex were tested with each primer using a modified EcoTILLING protocol to find and map polymorphic sequences at the Rhg1 locus (Meksem et al., 2008; Liu et al., 2011). The identified SNP and InDel DNA markers were integrated into the informative recombinants to identify chromosomal breakpoints and the interval that carried the Rhg1 locus. A high density genetic map was developed for the Rhg1 locus (see e.g., FIG. 1). Comparison of the SNAP gene sequences between Forrest and Essex identified some significant changes including three SNPs (G2464C, T4206G and A4215C) and three InDels (G4211-, G4212- and G4213-) within the exons (see e.g., FIG. 1B).

Example 2

Relationship Between Genes and Resistance to SCN

The following example shows the relationship between the Glyma18g02570 (armadillo/beta-catenin-like repeat), Glyma18g02580 (amino acid transporter) and Glyma18g02590 (SNAP) genes and resistance to SCN. A haplotype map was developed using 4 DNA markers (560, 570, 590 and Satt309) at the Rhg1 locus and 1 DNA marker (Sat_162) plus the Rhg4 GmSHMT gene at the Rhg4 locus, respectively The Forrest genotype was classified resistant (R) and the Essex genotype was classified susceptible (S).

Lines were classified resistant (R) to SCN if female index (FI)≤10% and susceptible (S) if FI>10% (see e.g., TABLE 2).

TABLE 2

Haplotype map of SCN resistance in soybean.

| Plant line | SCN infection phenotype | Rhg1 locus 560 | 570 | 590 | Satt309 | Rhg4 locus GmSHMT | Sat_162 |
|---|---|---|---|---|---|---|---|
| Forrest | R | R | R | R | R | R | R |
| Peking | R | R | R | R | R | R | R |
| PI437654 | R | R | R | R | R | R | R |
| PI89772 | R | R | R | R | R | R | R |
| PI90763 | R | R | R | R | R | R | R |
| PI88788 | R | R | R | R | S | S | R |
| PI546316 | R | R | R | R | S | S | R |
| PI209332 | R | R | R | R | S | S | S |
| Essex | S | S | S | S | S | S | S |
| Williams 82 | S | S | S | S | S | S | S |
| PI603428C | S | S | S | S | R | S | R |

Figure 2:
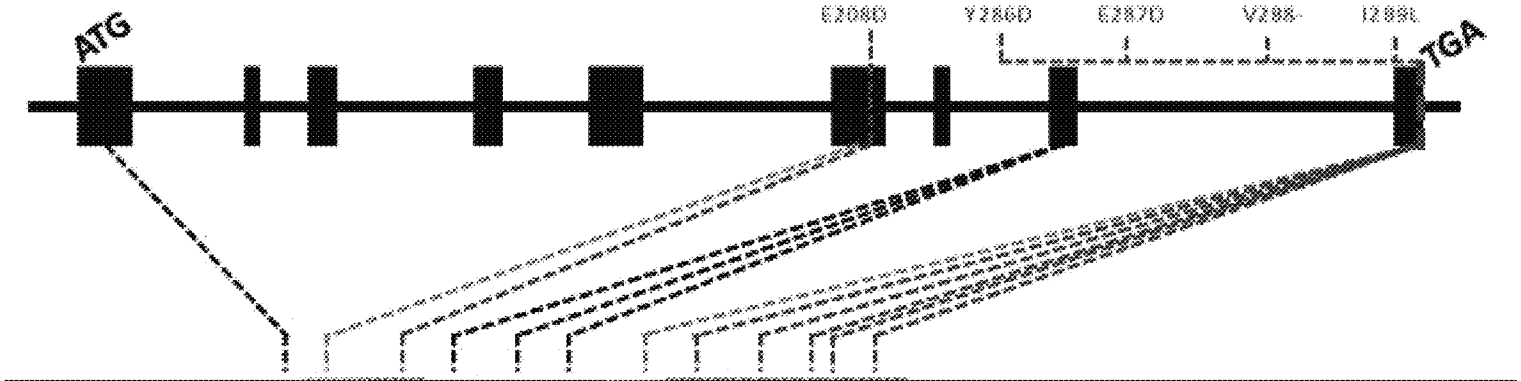
FIG. 2 is a schematic representation of the amino acid differences in the predicted SNAP protein sequences in 11 soybean lines with the number indicating amino acid position. Amino acid differences detected in the exons between Forrest and Essex are boxed along with the special amino acids of the PI88788-type PIs in SNAP. Amino acids marked in the boxes are the different amino acids between Peking type SNAP, PI88788 type SNAP, and susceptible type SNAP.

In addition, a detailed haplotype analysis was conducted for the SNAP gene. The SNAP coding region from 11 soybean lines was sequenced, representing the SCN-resistance variability in soybean germplasm. The amino acid differences in the predicted protein sequences of SNAP from the 11 soybean lines are shown with the number indicating the amino acid position in the predicted protein (see e.g., FIG. 2B). Haplotyping results from these 11 soybean lines indicate three types of SNAP haplotypes. The data further indicates there are at least two resistant types: Peking Type I including Peking, Forrest, PI437654, PI89772 and PI90763, and PI88788 Type II including PI88788, PI548316 and PI209332; and one susceptible Type III including Essex, Williams 82 and PI603428C.

Example 3

Virus-Induced Gene-Silencing (VIGS)

The following example describes VIGS in soybean. Bean pod mottle virus (BPMV) VIGS vectors, pBPMV IA-R1M, and pBPMV-IA-D35 were used in this example (Zhang et. al., 2010). pBPMV-IA-D35 is a derivative of pBPMV-IA-R2 containing BamHI and KpnI restriction sites between the cistrons encoding the movement protein and the large coat protein 15 subunit. Briefly, a 328 bp fragment of the SNAP cDNA sequence was amplified from soybean (cv. Forrest) root cDNA by RT-PCR. PCR products were digested with BamHI and KpnI and ligated into pBPMV-IA-D35 digested with the same enzymes to generate pBPMV-IA-SNAP. Gold particles coated with plasmid DNA corresponding to pBPMV-IA-R1M and pBPMV-IA-SNAP were co-bombarded into soybean leaf tissue (Zhang et al., 2010). At 3-4 weeks post-inoculation, BPMV-infected leaves were collected, lyophilized, and stored at −20° C. for future experiments. Infected soybean leaf tissues were ground with a mortar and pestle in 0.05 M potassium phosphate buffer (pH 7.0) and used as virus inoculum for VIGS assays.

Figure 3:
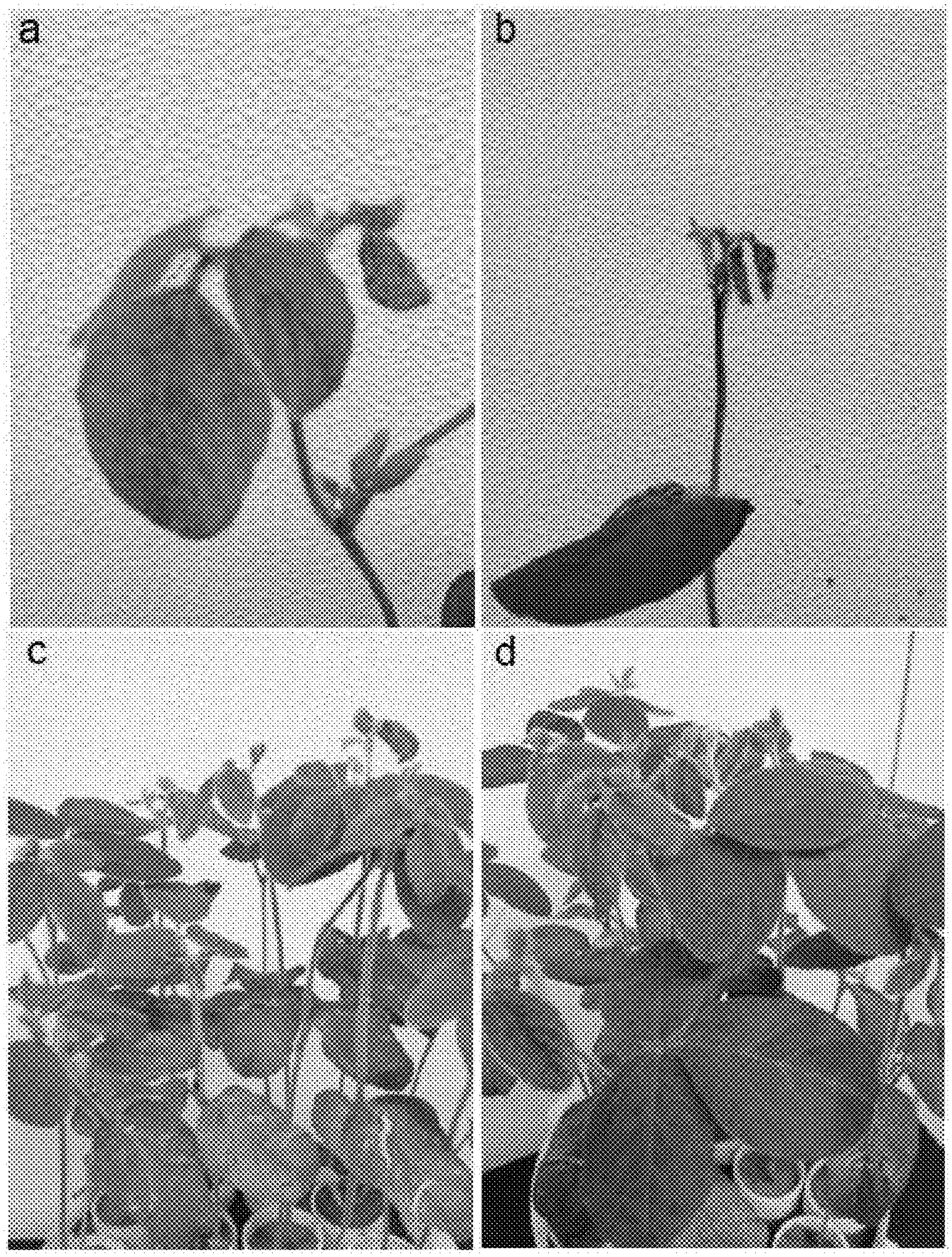
FIG. 3 shows images of a soybean plant.

The SCN-resistant RIL ExF67 was inoculated with pBPMV-IA-SNAP (Glyma18g02590). Control plants were infected with BPMV only. Each treatment consisted of at least 12 plants. Unifoliate leaves of 9-day-old plants were rub-inoculated with virus using carborundum (Zhang et al., 2010). Plants were grown in a growth chamber set to the following conditions: 20-21° C., 16 h light/8 h dark, and 100 mE m-2s-1 light intensity. A strong hypersensitive cell death-like response was observed in the leaves of infected pBPMV-IA-SNAP plants (see e.g., FIG. 3) and also resulted in poor root development that compromised the ability to conduct nematode infection assays on these plants.

Plants silenced for Glyma18g02590.1 in soybean leaves caused a strong hypersensitive cell death response (necrotic lesions) and compromised root growth. Consequently, the plants were not phenotyped against SCN (see e.g., FIG. 3).

SCN-resistance can be manifested at the site of nematode feeding as a strong hypersensitive response (HR) that leads to death of the feeding cell and nematode. Thus, these data indicate that interference in SNAP gene function in the resistant cultivar can mediate the SCN-resistance response.

Example 4

Near Isogenic Lines (NILs)

The following example describes additional evidence from Near Isogenic Lines (NILs). NILs that differ in SCN-resistance because of variations at the Rhg1 locus, but not the Rhg4 locus, were analyzed by genome resequencing and GoldenGate SNP analysis. SNPs in and around the three additional genes were found to be polymorphic (see e.g., TABLE 3) and therefore were identified as conferring SCN-resistance.

TABLE 3

NIL polymorphisms around the three additional genes underlying SCN-resistance.

| Index | Name | Position | EXF34-23Sus | EXF34-32 Res |
|---|---|---|---|---|
| 43751 | Gm18_1552671_A_G | 1552671 | BB | AA |
| 43760 | Gm18_1562162_G_A | 1562162 | AA | BB |
| 43771 | Gm18_1567581_G_A | 1567581 | BB | NC |
| 43784 | Gm18_1582570_T_C | 1582570 | BB | BB |
| 43815 | Gm18_1612017_G_A | 1612017 | BB | AA |
| 43823 | Gm18_1620585_T_C | 1620585 | BB | BB |
| 43829 | Gm18_1625693_A_G | 1625693 | BB | BB |
| 43836 | Gm18_1630870_C_A | 1630870 | BB | BB |
| 43840 | Gm18_1634453_G_A | 1634453 | AA | AA |
| 43845 | Gm18_1640404_C_A | 1640404 | BB | AA |
| 43849 | Gm18_1652357_C_T | 1652357 | BB | AA |
| 43859 | Gm18_1663298_A_G | 1663298 | BB | BB |
| 43863 | Gm18_1671483_A_G | 1671483 | AA | BB |
| 43865 | Gm18_1674972_C_T | 1674972 | AA | AA |
| 43869 | Gm18_1677273_T_G | 1677273 | NC | BB |

Example 5

Sequencing Recombinant Inbred Lines

The following example describes additional evidence from sequencing recombinant Inbred lines (RILs). RILs that differ in SCN-resistance because of variations at the Rhg1 locus, but not the Rhg4 locus, were analyzed by genome resequencing. SNPs in and around the three additional genes were found to be polymorphic (see e.g., TABLE 4) and therefore conferring SCN-resistance.

TABLE 4

SNPs among RILs from Illumina Sequencing.

| | | | | | | | |
|---|---|---|---|---|---|---|---|
| >SNP_Gm18_15187890 Essex: A Forrest: G | | | | | | | |
| 1 | SNP | A | 17 | 17 | 0.000008 | PARENT_A | Essex |
| 2 | COV | G | 31 | 31 | 0.000000 | PARENT_B | Forrest |
| 3 | SNP | A | 19 | 19 | 0.000002 | PARENT_A | RIL-1 |
| 4 | COV | G | 12 | 12 | 0.000244 | PARENT_B | RIL-10 |
| 5 | COV | G | 19 | 19 | 0.000002 | PARENT_B | RIL-11 |
| 6 | SNP | A | 33 | 33 | 0.000000 | PARENT_A | RIL-12 |
| 7 | SNP | A | 15 | 15 | 0.000031 | PARENT_A | RIL-13 |
| 9 | COV | G | 30 | 37 | 0.000075 | PARENT_B | RIL-15 |
| 10 | SNP | A | 13 | 13 | 0.000122 | PARENT_A | RIL-17 |
| 11 | SNP | A | 25 | 25 | 0.000000 | PARENT_A | RIL-18 |
| 12 | SNP | A | 19 | 19 | 0.000002 | PARENT_A | RIL-19 |
| 13 | COV | G | 8 | 9 | 0.017578 | PARENT_B | RIL-2 |
| 14 | COV | G | 11 | 11 | 0.000488 | PARENT_B | RIL-20 |
| 16 | COV | G | 24 | 24 | 0.000000 | PARENT_B | RIL-22 |
| 17 | COV | G | 21 | 21 | 0.000000 | PARENT_B | RIL-23 |
| 18 | COV | G | 18 | 18 | 0.000004 | PARENT_B | RIL-24 |
| 19 | COV | G | 10 | 10 | 0.000977 | PARENT_B | RIL-25 |
| 20 | SNP | A | 8 | 8 | 0.003906 | PARENT_A | RIL-26 |
| 21 | COV | G | 33 | 33 | 0.000000 | PARENT_B | RIL-27 |
| 22 | COV | G | 19 | 19 | 0.000002 | PARENT_B | RIL-28 |
| 24 | COV | G | 15 | 15 | 0.000031 | PARENT_B | RIL-37 |
| 25 | SNP | A | 6 | 6 | 0.015625 | PARENT_A | RIL-38 |
| 26 | SNP | A | 8 | 8 | 0.003906 | PARENT_A | RIL-4 |
| 27 | SNP | A | 28 | 28 | 0.000000 | PARENT_A | RIL-40 |
| 28 | COV | G | 18 | 18 | 0.000004 | PARENT_B | RIL-41 |
| 29 | COV | G | 23 | 23 | 0.000000 | PARENT_B | RIL-42 |
| 30 | COV | G | 22 | 25 | 0.000069 | PARENT_B | RIL-44 |
| 31 | COV | G | 19 | 26 | 0.009802 | PARENT_B | RIL-46 |
| 32 | SNP | A | 28 | 28 | 0.000000 | PARENT_A | RIL-47 |
| 34 | COV | G | 9 | 9 | 0.001953 | PARENT_B | RIL-49 |
| 35 | SNP | A | 15 | 15 | 0.000031 | PARENT_A | RIL-51 |
| 37 | SNP | A | 53 | 53 | 0.000000 | PARENT_A | RIL-53 |
| 38 | COV | G | 39 | 39 | 0.000000 | PARENT_B | RIL-54 |
| 39 | COV | G | 22 | 25 | 0.000069 | PARENT_B | RIL-55 |
| 40 | COV | G | 26 | 26 | 0.000000 | PARENT_B | RIL-56 |
| 41 | COV | G | 25 | 25 | 0.000000 | PARENT_B | RIL-57 |
| 42 | COV | G | 34 | 34 | 0.000000 | PARENT_B | RIL-58 |
| 43 | SNP | A | 6 | 6 | 0.015625 | PARENT_A | RIL-6 |
| 44 | SNP | A | 27 | 27 | 0.000000 | PARENT_A | RIL-67 |
| 45 | SNP | A | 73 | 73 | 0.000000 | PARENT_A | RIL-7 |
| 46 | SNP | A | 17 | 17 | 0.000008 | PARENT_A | RIL-72 |
| 47 | COV | G | 20 | 25 | 0.001583 | PARENT_B | RIL-74 |
| 48 | SNP | A | 31 | 31 | 0.000000 | PARENT_A | RIL-75 |
| 50 | COV | G | 23 | 23 | 0.000000 | PARENT_B | RIL-79 |
| 51 | COV | G | 40 | 40 | 0.000000 | PARENT_B | RIL-8 |
| 52 | SNP | A | 43 | 43 | 0.000000 | PARENT_A | RIL-80 |
| 53 | COV | G | 53 | 53 | 0.000000 | PARENT_B | RIL-84 |
| 54 | SNP | A | 26 | 26 | 0.000000 | PARENT_A | RIL-85 |
| 55 | COV | G | 40 | 40 | 0.000000 | PARENT_B | RIL-89 |
| 56 | SNP | A | 47 | 47 | 0.000000 | PARENT_A | RIL-9 |
| 57 | COV | G | 26 | 26 | 0.000000 | PARENT_B | RIL-91 |
| 58 | COV | G | 34 | 34 | 0.000000 | PARENT_B | RIL-92 |
| 59 | COV | G | 28 | 28 | 0.000000 | PARENT_B | RIL-94 |
| 60 | COV | G | 27 | 27 | 0.000000 | PARENT_B | RIL-95 |
| 61 | SNP | A | 37 | 37 | 0.000000 | PARENT_A | RIL-96 |
| >SNP_Gm18_1608702 Essex: A Forrest: T | | | | | | | |
| 1 | SNP | A | 58 | 58 | 0.000000 | PARENT_A | Essex |
| 2 | COV | T | 114 | 114 | 0.000000 | PARENT_B | Forrest |
| 3 | COV | T | 58 | 58 | 0.000000 | PARENT_B | RIL-1 |
| 4 | COV | T | 42 | 65 | 0.006155 | PARENT_B | RIL-10 |
| 5 | COV | T | 38 | 44 | 0.000000 | PARENT_B | RIL-11 |
| 6 | COV | T | 70 | 70 | 0.000000 | PARENT_B | RIL-12 |
| 7 | COV | T | 44 | 46 | 0.000000 | PARENT_B | RIL-13 |
| 8 | SNP | A | 47 | 47 | 0.000000 | PARENT_A | RIL-14 |
| 9 | COV | T | 41 | 72 | 0.047140 | PARENT_B | RIL-15 |
| 10 | COV | T | 51 | 58 | 0.000000 | PARENT_B | RIL-17 |
| 11 | SNP | A | 46 | 46 | 0.000000 | PARENT_A | RIL-18 |
| 12 | SNP | A | 52 | 52 | 0.000000 | PARENT_A | RIL-19 |
| 13 | COV | T | 27 | 27 | 0.000000 | PARENT_B | RIL-2 |
| 14 | COV | T | 30 | 30 | 0.000000 | PARENT_B | RIL-20 |
| 15 | COV | T | 65 | 65 | 0.000000 | PARENT_B | RIL-21 |
| 16 | SNP | A | 77 | 77 | 0.000000 | PARENT_A | RIL-22 |
| 17 | COV | T | 30 | 30 | 0.000000 | PARENT_B | RIL-23 |
| 18 | COV | T | 53 | 53 | 0.000000 | PARENT_B | RIL-24 |
| 19 | COV | T | 30 | 30 | 0.000000 | PARENT_B | RIL-25 |
| 20 | COV | T | 28 | 36 | 0.000440 | PARENT_B | RIL-26 |
| 21 | SNP | A | 111 | 111 | 0.000000 | PARENT_A | RIL-27 |
| 22 | SNP | A | 23 | 23 | 0.000000 | PARENT_A | RIL-28 |
| 23 | COV | T | 29 | 29 | 0.000000 | PARENT_B | RIL-36 |
| 24 | COV | T | 25 | 25 | 0.000000 | PARENT_B | RIL-37 |
| 25 | COV | T | 37 | 37 | 0.000000 | PARENT_B | RIL-38 |
| 26 | COV | T | 32 | 41 | 0.000159 | PARENT_B | RIL-4 |
| 27 | COV | T | 72 | 72 | 0.000000 | PARENT_B | RIL-40 |
| 28 | SNP | A | 49 | 49 | 0.000000 | PARENT_A | RIL-41 |
| 29 | SNP | A | 51 | 51 | 0.000000 | PARENT_A | RIL-42 |
| 30 | COV | T | 57 | 57 | 0.000000 | PARENT_B | RIL-44 |
| 32 | COV | T | 47 | 47 | 0.000000 | PARENT_B | RIL-47 |
| 33 | SNP | A | 18 | 18 | 0.000004 | PARENT_A | RIL-48 |
| 34 | SNP | A | 40 | 40 | 0.000000 | PARENT_A | RIL-49 |
| 35 | SNP | A | 24 | 24 | 0.000000 | PARENT_A | RIL-51 |
| 36 | SNP | A | 87 | 87 | 0.000000 | PARENT_A | RIL-52 |
| 37 | SNP | A | 99 | 99 | 0.000000 | PARENT_A | RIL-53 |
| 38 | SNP | A | 88 | 91 | 0.000000 | PARENT_A | RIL-54 |
| 39 | COV | T | 28 | 43 | 0.017227 | PARENT_B | RIL-55 |
| 40 | COV | T | 59 | 59 | 0.000000 | PARENT_B | RIL-56 |
| 41 | COV | T | 79 | 80 | 0.000000 | PARENT_B | RIL-57 |
| 43 | SNP | A | 27 | 27 | 0.000000 | PARENT_A | RIL-6 |
| 44 | COV | T | 91 | 91 | 0.000000 | PARENT_B | RIL-67 |
| 45 | COV | T | 148 | 148 | 0.000000 | PARENT_B | RIL-7 |
| 46 | SNP | A | 50 | 50 | 0.000000 | PARENT_A | RIL-72 |
| 47 | COV | T | 65 | 65 | 0.000000 | PARENT_B | RIL-74 |
| 48 | COV | T | 74 | 83 | 0.000000 | PARENT_B | RIL-75 |
| 49 | SNP | A | 124 | 124 | 0.000000 | PARENT_A | RIL-76 |
| 50 | SNP | A | 78 | 78 | 0.000000 | PARENT_A | RIL-79 |
| 51 | SNP | A | 83 | 83 | 0.000000 | PARENT_A | RIL-8 |
| 52 | SNP | A | 103 | 103 | 0.000000 | PARENT_A | RIL-80 |
| 53 | COV | T | 102 | 102 | 0.000000 | PARENT_B | RIL-84 |
| 54 | SNP | A | 70 | 70 | 0.000000 | PARENT_A | RIL-85 |
| 55 | COV | T | 121 | 121 | 0.000000 | PARENT_B | RIL-89 |
| 56 | SNP | A | 123 | 123 | 0.000000 | PARENT_A | RIL-9 |
| 57 | SNP | A | 73 | 73 | 0.000000 | PARENT_A | RIL-91 |
| 58 | SNP | A | 81 | 81 | 0.000000 | PARENT_A | RIL-92 |
| 59 | SNP | A | 79 | 79 | 0.000000 | PARENT_A | RIL-94 |
| 60 | COV | T | 48 | 49 | 0.000000 | PARENT_B | RIL-95 |
| 61 | SNP | A | 124 | 124 | 0.000000 | PARENT_A | RIL-96 |
| >SNP_Gm18_1608832 Essex: G Forrest: A | | | | | | | |
| 1 | SNP | G | 5 | 5 | 0.031250 | PARENT_A | Essex |
| 2 | COV | A | 9 | 9 | 0.001953 | PARENT_B | Forrest |
| 3 | COV | A | 14 | 14 | 0.000061 | PARENT_B | RIL-1 |
| 4 | COV | A | 17 | 19 | 0.000326 | PARENT_B | RIL-10 |
| 5 | COV | A | 9 | 10 | 0.009766 | PARENT_B | RIL-11 |
| 6 | COV | A | 31 | 31 | 0.000000 | PARENT_B | RIL-12 |
| 7 | COV | A | 11 | 12 | 0.002930 | PARENT_B | RIL-13 |
| 8 | SNP | G | 11 | 11 | 0.000488 | PARENT_A | RIL-14 |
| 10 | COV | A | 21 | 22 | 0.000005 | PARENT_B | RIL-17 |
| 11 | SNP | G | 18 | 18 | 0.000004 | PARENT_A | RIL-18 |
| 12 | SNP | G | 5 | 5 | 0.031250 | PARENT_A | RIL-19 |
| 14 | COV | A | 11 | 11 | 0.000488 | PARENT_B | RIL-20 |
| 15 | COV | A | 19 | 19 | 0.000002 | PARENT_B | RIL-21 |
| 16 | SNP | G | 20 | 20 | 0.000001 | PARENT_A | RIL-22 |
| 17 | COV | A | 10 | 10 | 0.000977 | PARENT_B | RIL-23 |
| 18 | COV | A | 20 | 20 | 0.000001 | PARENT_B | RIL-24 |
| 19 | COV | A | 11 | 11 | 0.000488 | PARENT_B | RIL-25 |
| 21 | SNP | G | 31 | 31 | 0.000000 | PARENT_A | RIL-27 |
| 22 | SNP | G | 17 | 17 | 0.000008 | PARENT_A | RIL-28 |
| 24 | COV | A | 9 | 9 | 0.001953 | PARENT_B | RIL-37 |
| 28 | SNP | G | 20 | 20 | 0.000001 | PARENT_A | RIL-41 |

TABLE 4-continued

| SNPs among RILs from Illumina Sequencing. | | | | | | | |
|---|---|---|---|---|---|---|---|
| 29 | SNP | G | 16 | 16 | 0.000015 | PARENT_A | RIL-42 |
| 30 | COV | A | 11 | 11 | 0.000488 | PARENT_B | RIL-44 |
| 32 | COV | A | 15 | 15 | 0.000031 | PARENT_B | RIL-47 |
| 33 | SNP | G | 5 | 5 | 0.031250 | PARENT_A | RIL-48 |
| 36 | SNP | G | 13 | 13 | 0.000122 | PARENT_A | RIL-52 |
| 37 | SNP | G | 38 | 39 | 0.000000 | PARENT_A | RIL-53 |
| 38 | SNP | G | 38 | 40 | 0.000000 | PARENT_A | RIL-54 |
| 40 | COV | A | 18 | 18 | 0.000004 | PARENT_B | RIL-56 |
| 41 | COV | A | 26 | 26 | 0.000000 | PARENT_B | RIL-57 |
| 43 | SNP | G | 14 | 14 | 0.000061 | PARENT_A | RIL-6 |
| 44 | COV | A | 28 | 28 | 0.000000 | PARENT_B | RIL-67 |
| 45 | COV | A | 44 | 44 | 0.000000 | PARENT_B | RIL-7 |
| 46 | SNP | G | 24 | 24 | 0.000000 | PARENT_A | RIL-72 |
| 47 | COV | A | 11 | 11 | 0.000488 | PARENT_B | RIL-74 |
| 48 | COV | A | 18 | 18 | 0.000004 | PARENT_B | RIL-75 |
| 49 | SNP | G | 39 | 39 | 0.000000 | PARENT_A | RIL-76 |
| 50 | SNP | G | 19 | 19 | 0.000002 | PARENT_A | RIL-79 |
| 51 | SNP | G | 28 | 28 | 0.000000 | PARENT_A | RIL-8 |
| 52 | SNP | G | 34 | 34 | 0.000000 | PARENT_A | RIL-80 |
| 53 | COV | A | 30 | 30 | 0.000000 | PARENT_B | RIL-84 |
| 54 | SNP | G | 25 | 25 | 0.000000 | PARENT_A | RIL-85 |
| 55 | COV | A | 42 | 42 | 0.000000 | PARENT_B | RIL-89 |
| 56 | SNP | G | 29 | 29 | 0.000000 | PARENT_A | RIL-9 |
| 57 | SNP | G | 26 | 26 | 0.000000 | PARENT_A | RIL-91 |
| 58 | SNP | G | 28 | 28 | 0.000000 | PARENT_A | RIL-92 |
| 59 | SNP | G | 30 | 30 | 0.000000 | PARENT_A | RIL-94 |
| 61 | SNP | G | 28 | 28 | 0.000000 | PARENT_A | RIL-96 |

Example 6

Targeted Genome Enrichment and Snap Identification

The following example describes additional evidence for the identification of Rhg1 gene, Glyma18g02590 (SNAP), conferring resistance to SCN, by next-generation sequencing of a targeted 300 kb region of Gm18 in soybean.

TABLE 5

SNPs, insertions, and deletions at the targeted 300 kb region of Gm18 (Gm18: 1480001-1780000) in Essex, Forrest, Peking, and PI88788.

| | Essex | Forrest | Peking | PI88788 | Total |
|---|---|---|---|---|---|
| SNPs | 632 | 618 | 649 | 736 | 1081 |
| Insertions | 109 | 120 | 123 | 120 | 183 |
| Deletions | 146 | 97 | 100 | 165 | 208 |
| Total | 887 | 835 | 872 | 1021 | 1472 |

| Position | Sequence | SEQ ID NO: |
|---|---|---|
| 1552732 | TGGGGG-G--KGGGGGGGGGTGGTTGGTGTGG | SEQ ID NO: 9 |
| 1552753 | AGAGAAGGA-AGGGGAGGAGAAGAARAAA-GA | SEQ ID NO: 10 |
| 1552799 | CCCCCCAACCCCCC-CCCCCCCCCCCCCCCCC | SEQ ID NO: 11 |
| 1553174 | GAGAGGGGGGGAAAAGAAGGGGGGGGGGGGGG | SEQ ID NO: 12 |
| 1553377 | CTCTCCCTCCCTTTTCTTCTCCTCCYCCCCTC | SEQ ID NO: 13 |
| 1553485 | TCTCTTTTTTTCCCCTCCTTTTTTTTTTTTTT | SEQ ID NO: 14 |
| 1553949 | ACACAAAAAAACCC-ACCAAAAAAAAAAAAAA | SEQ ID NO: 15 |
| 1554124 | GGGGGG-GGGGGGGGGGGGTG-TG--GGGGT- | SEQ ID NO: 16 |
| 1554570 | AAAAAACCAAAAAAA-AAAAAAAA-AAAAAAA | SEQ ID NO: 17 |
| 1554604 | AAAAAAGGAAAAAAA-AARAAAAA-AAA-AAA | SEQ ID NO: 18 |
| 1554733 | T-TWTT-TTTTWWT--T--TTTTA-TTTTTTT | SEQ ID NO: 19 |
| 1554848 | TTTTTTCCTTTTTTT-TTTTTTTTTTTTTTTT | SEQ ID NO: 20 |
| 1554938 | TATAT-AATTTAAAATAA-AT-ATTATTTT-T | SEQ ID NO: 21 |
| 1554942 | AAAAAAAAAA-AAAAAAA-AAAAAAAWAAA-W | SEQ ID NO: 22 |
| 1555085 | ACAC-ACCAAACCCC--CACAACAAM---ACA | SEQ ID NO: 23 |
| 1555204 | AT-TAAT-AAA-TTTATTATAATAA-AAAATA | SEQ ID NO: 24 |
| 1555236 | AAAAAAAAAAA-AAAAA-ATAATAAAAAA-TA | SEQ ID NO: 25 |
| 1555481 | A-A-AA---AA-AA-AAAA-AA-AAWAA--TA | SEQ ID NO: 26 |
| 1555562 | AAA-AAAMAAA-AA----A-A-M-A--AA--- | SEQ ID NO: 27 |
| 1555572 | A--TAA-AAAA----AT--AA-A-A--A---- | SEQ ID NO: 28 |
| 1555739 | ACACAAA-A-A-CCC-CCAAAAAA-AAAA-A- | SEQ ID NO: 29 |
| 1555772 | G-G-GGG-G-G-TTTG--GGGGGGGGGGG-GG | SEQ ID NO: 30 |

-continued

| Position | Sequence | SEQ ID NO: |
|---|---|---|
| 1556277 | GAGAGGGGGGGAAAAGAAGAGG-GGRGGGGAG | SEQ ID NO: 31 |
| 1556372 | GAGAGGGGGGGAAA-GAAG-GGGGGGGGGGG | SEQ ID NO: 32 |
| 1556588 | GCGCGGGGG-GCCCCGCCGGGGGGGGGGGGG | SEQ ID NO: 33 |
| 1556678 | AA-AGG-GAGRAAAAGAAGAAAAAARGAGAAG | SEQ ID NO: 34 |
| 1556781 | TCTCTTCCTTTCCC-TCCTTTTTTTTTTTTT | SEQ ID NO: 35 |
| 1557165 | CTTTTTTTCTYTTTTTT-TTCCTTCTTCTCTT | SEQ ID NO: 36 |
| 1557549 | AAAAAWA-A-AAAAAAAAAAAATAAWTA--A- | SEQ ID NO: 37 |
| 1557751 | AGA-AAAAAAA--G-A-GAAAAAAAAAAAAAA | SEQ ID NO: 38 |
| 1557752 | CGC-CCCCCCC--G-C-GCCCCCCCCCCCCCC | SEQ ID NO: 39 |
| 1557771 | TATATTTTTTT--A-TA-TTTTTTTTTTTTT | SEQ ID NO: 40 |
| 1557934 | GGRGGAGGGGGGGGGGGGAGGGGGGRAGAGGA | SEQ ID NO: 41 |
| 1557991 | TTTTTTTTTTTTTTTTT-TTTTTCTTTTTTCT | SEQ ID NO: 42 |
| 1558100 | AAAAAAAAAAAAAAAAAAATAATTAWAAAA-A | SEQ ID NO: 43 |
| 1558103 | CCTCTTCCCCCCCCCTCCTTCCTTCTTCTC-- | SEQ ID NO: 44 |
| 1558128 | GG-GGGG-GTGGGGT-GG--GGGGGG-GGG-- | SEQ ID NO: 45 |
| 1558129 | TT-TTTT-TGTTTTG-TT--TTTTTT-TTT-- | SEQ ID NO: 46 |
| 1558137 | T----TT-TTT-ATT-----TT-TT--TWT-- | SEQ ID NO: 47 |
| 1558318 | AA-ATTA-AAWAAAAT-ATTAATTA--A-AT- | SEQ ID NO: 48 |
| 1558319 | AA-AATA-AAAAAAAA-A-TAATTA--A-AT- | SEQ ID NO: 49 |
| 1558322 | AAAAT-A-AAWAAAAT-A-AAATAA--A-AA- | SEQ ID NO: 50 |
| 1558323 | TTATA-T-TTWTTTTA-T-TTTA-T--T-TT- | SEQ ID NO: 51 |
| 1558334 | TTGTGGT-TTKTTTT--TGGTTGGT--T-TGG | SEQ ID NO: 52 |
| 1558551 | TCTCTTCCTCTCCCCTCCTTTTTTTYTTTTTT | SEQ ID NO: 53 |
| 1558913 | AAAAAGAAAAAAAAAAAAAGAAAAAAR-AGAAG | SEQ ID NO: 54 |
| 1558979 | GGAGAGGGGGGGGGGG--GGGGGGGGGGGGGG | SEQ ID NO: 55 |
| 1559151 | ATTTTATTAT-TTTTTTTATAATT-WAAAATA | SEQ ID NO: 56 |
| 1559399 | ATATAA-AAAATTTTATTAAAAAAAAAAAAAA | SEQ ID NO: 57 |
| 1559585 | CACA-CCCCCCAAAACAACCCCCCCC-CCCCC | SEQ ID NO: 58 |
| 1559603 | CCCC-T-CCCCCCCCCCCTCCCCC-TTCTCCT | SEQ ID NO: 59 |
| 1559659 | GAGAGA-AGAGAAAAGAAAAGGAAGAAGAGAA | SEQ ID NO: 60 |
| 1559787 | AAAAACAAAAAAAAAAAACAAAA-AMC-CAAC | SEQ ID NO: 61 |
| 1559970 | TTKTTG-TTTT-TTTTTTGTTTTTTKGTGTTG | SEQ ID NO: 62 |
| 1560043 | TTATAT-TTATTTTTATTTTTTTT-TTTTTTT | SEQ ID NO: 63 |
| 1560088 | CCCCCCTCCTCCCCCCCCCCCCCCCCCCCCCC | SEQ ID NO: 64 |
| 1560108 | TGTGTTTTTTTGGGGTGGTTTTT-TTTTTTTT | SEQ ID NO: 65 |
| 1560166 | GGAGAGAGR-GGGGGAGGG-GGGGGGGGGGG- | SEQ ID NO: 66 |
| 1560182 | TTGTGTGTT-TTTTT-TTTTTTTTTTTTTTT | SEQ ID NO: 67 |
| 1560390 | AAMACACAA-AAAAAC-AAAAAAAAAAAA-AA | SEQ ID NO: 68 |
| 1560442 | TTTTTTATTATTTTTTTT-TTTTTTTTTTTTT | SEQ ID NO: 69 |

-continued

| Position | Sequence | SEQ ID NO: |
|---|---|---|
| 1560517 | GARAGAAAGAGAAAAGAAAGGGAA-AAGAGAA | SEQ ID NO: 70 |
| 1560584 | CAMACA-ACCCAAAACAAACCCAA-AACACAA | SEQ ID NO: 71 |
| 1560705 | ACCMCCCCAC-CCCCCCCCAA-CCACCACACC | SEQ ID NO: 72 |
| 1560784 | AAAAAAG--G-AAAAAAAAAAAAAAAA-AAAA | SEQ ID NO: 73 |
| 1560860 | CTCTCTYTCCCTTTTCTTTCCCTTCTTCTCTT | SEQ ID NO: 74 |
| 1561009 | GGGGGGAGGA-GGGGG-GGGGGGGGGGGGGGG | SEQ ID NO: 75 |
| 1561036 | ACCCCCCCACACCCCCCCCAAACCACCACACC | SEQ ID NO: 76 |
| 1561047 | AAGAGAAAAAAAAAAGAAAAAAAA-AAAAAAA | SEQ ID NO: 77 |
| 1561190 | TTTTTTATTATTTT-TTTTTTTTTTTTTTTTT | SEQ ID NO: 78 |
| 1561230 | A-GAGAAAAAAAAAAGAA-AAAAA-AAA-AAA | SEQ ID NO: 79 |
| 1561392 | AA-AAAAAAA-AAAAAAAAAAAGG-GAAAAGA | SEQ ID NO: 80 |
| 1561412 | CC-CACCCCCCCCC-ACCCCCCCCC-C-CCCC | SEQ ID NO: 81 |
| 1561429 | CC-CTCTCCTCCCCCTCCCCCCCCC--CCCCC | SEQ ID NO: 82 |
| 1561461 | AARAGAAAAAAAAAAGAAAAAA-AAAAAA-AA | SEQ ID NO: 83 |
| 1561493 | AAAAAAAAAAAAAAA-AAAAAAGGAGAAA-GA | SEQ ID NO: 84 |
| 1561533 | CC-C-C--C--CCC---CCCCCAA--CCC-AC | SEQ ID NO: 85 |
| 1561651 | CT-T-CTC-TCTTTT-TTCCCCCCC-CCCCCC | SEQ ID NO: 86 |
| 1561706 | CC-CTCC-CCCCCCCTCC-CCCCCC-CCC-CC | SEQ ID NO: 87 |
| 1561766 | T----T-TT-T-AA-AA-TTTT--TTTTTT-T | SEQ ID NO: 88 |
| 1561783 | AAAA-A-AA-A-AA-A-AAAAAGGARAAAA-A | SEQ ID NO: 89 |
| 1561792 | TTCT-T-TTTT-TTTC-TT-TTTTTTTTTT-T | SEQ ID NO: 90 |
| 1561828 | ACGCAA-AACA-CCCGCCAAAACCAAAAAACA | SEQ ID NO: 91 |
| 1561849 | GGAGAGGGGGGGGGGAGGGGGGGGGGGGGG-G | SEQ ID NO: 92 |
| 1561866 | CC-CACCCCCCCCCCACCCCCCCCC-CCCC-C | SEQ ID NO: 93 |
| 1561983 | GGG-GG-GGGGARGR-R-GGGGGGGGGGGGGG | SEQ ID NO: 94 |
| 1561989 | ATTATA-AAAAWWWATW-AAAAAAAAAAAAAA | SEQ ID NO: 95 |
| 1562128 | GGGGSG-GG-GGGGG-GGGGGGSGGGGGGGGG | SEQ ID NO: 96 |
| 1562155 | AATATATAA-WAAAATAAAAAATTAWAAAATA | SEQ ID NO: 97 |
| 1562239 | CACACC-CC-CAAAACA-CCCCCCCCCCCCCC | SEQ ID NO: 98 |
| 1562453 | CCCCCTCTC-YCCCCCCCTCCCCCCTTCTCCT | SEQ ID NO: 99 |
| 1562660 | GGGGG--CGGCGGG-G--CGGGGGGSCGCGGC | SEQ ID NO: 100 |
| 1562719 | ATTTT-TTA-TTTTTTT-TAAAAAAWTATAAT | SEQ ID NO: 101 |
| 1562751 | GTGTGGGGG-GTTTTGT-GGGGGGGGGGGGGG | SEQ ID NO: 102 |
| 1562768 | GGSGCGGGG-GGGGGCG-GGGGGGGGGGGGGG | SEQ ID NO: 103 |
| 1562844 | AG-GGG-GAGRGGG-GGGGAAAAAARGAGAA- | SEQ ID NO: 104 |
| 1562877 | A-ATAWAWAAAW--AAA-AAAAAAAAWAAAAA | SEQ ID NO: 105 |
| 1562884 | A-A-AAGAAGAAAAAAA-AAAAAAAAAAAAAA | SEQ ID NO: 106 |
| 1563239 | TTTTTKT-TTTTTTTTTTTTTTTTTK-TKTT- | SEQ ID NO: 107 |

-continued

| Position | Sequence | SEQ ID NO: |
|---|---|---|
| 1563245 | GGGGGTGTGGGGGGGGGGTGGGGGGK-GTGG- | SEQ ID NO: 108 |
| 1563541 | AGGGGG-GA-AGGGGGGGGAAAAAARGAGAAG | SEQ ID NO: 109 |
| 1563768 | AAAAACACAAAAAA-AAACAAAAAAMCACAAC | SEQ ID NO: 110 |
| 1563924 | GTTTTTTTGTKTTTTTTTTGGGGGGKTGTGGT | SEQ ID NO: 111 |
| 1564092 | AAAAAATAATAAAAAAA-AAAAAAAAAAAAAA | SEQ ID NO: 112 |
| 1564318 | GTGTGGGGGGGTTTTGTTGGGGGGGGGGGGGG | SEQ ID NO: 113 |
| 1564390 | CTCTCCCCCCCTTTTCTTCCCCCCCCCCCCCC | SEQ ID NO: 114 |
| 1564756 | AACAAAAAAAAAAAAACAAAAAAAAAAAAAAA | SEQ ID NO: 115 |
| 1564816 | CCMCACCCCCMCCCCACMCCCCCCCCCCCCCC | SEQ ID NO: 116 |
| 1565451 | CCTCTTC-CCYCCCCTCCTCCCCCCYTCTCCT | SEQ ID NO: 117 |
| 1565457 | TTGTGGT-TTKTTTTGTTGTTTTTTKGTGTTG | SEQ ID NO: 118 |
| 1565592 | GGTGTTGTGGTGGGGTGGTGGGGGGKTGTGGT | SEQ ID NO: 119 |
| 1565646 | TTTTTTGTTGTTTTTTTTTTTTTTTTTTTKTT | SEQ ID NO: 120 |
| 1565826 | TTAT-A-AT-WTTTTAT-ATTTTTTWATATTA | SEQ ID NO: 121 |
| 1565857 | CT-T----C-CTT---T--CCCCCCC-C-CC- | SEQ ID NO: 122 |
| 1565858 | TC-C----C-C-C---C--CTCCCCC-C-CC- | SEQ ID NO: 123 |
| 1565931 | A------AA-AG---G---AAAAAA--A-AA- | SEQ ID NO: 124 |
| 1565944 | T--C----T-TCC--T---TTTTTT--T-TT- | SEQ ID NO: 125 |
| 1566440 | C--CG---C-CCCC-CCC-CCCCCC-SCSCCS | SEQ ID NO: 126 |
| 1566449 | G-GTG---G-GTT---TT-GGGGGGGGGKGGG | SEQ ID NO: 127 |
| 1566453 | CCTCTC--CCYCCC-TCCCCCCCCCCCCCCCC | SEQ ID NO: 128 |
| 1566550 | GGCGCCGCGGSGGGGCGGCGGGGGGSCGCGGC | SEQ ID NO: 129 |
| 1566626 | GGKGTGGTGGKGGGGTG-GGGGGGGGGGGGGG | SEQ ID NO: 130 |
| 1566638 | TTKTGTTTTTKTTTTGT-TTTTTTTTTTTTTT | SEQ ID NO: 131 |
| 1566726 | GGTGTTGTGGKGGGGTGGTGGGGGGKTGTGGT | SEQ ID NO: 132 |
| 1566728 | TTCTCCTCTTYTTTTCTTCTTTTTTYCTCT-C | SEQ ID NO: 133 |
| 1566793 | TTCT-CTCTTTTTTTCTTCTTTTTTYCTCTTC | SEQ ID NO: 134 |
| 1566821 | T-CT--TCTTTTTTTCT-CTTTT-T--TCTTC | SEQ ID NO: 135 |
| 1566823 | A-CC--CCACACCCCCC-CAAAA-A--ACAAC | SEQ ID NO: 136 |
| 1566867 | T-CT-CT-TTTTTTTCT--TTTTT---T-TT- | SEQ ID NO: 137 |
| 1566882 | C-CC-CT-CTCCCCCCCC-CCCCC---CCCC- | SEQ ID NO: 138 |
| 1566890 | G-AG-AG-GGGGGGGAGG-GGGGGGG-GAGG- | SEQ ID NO: 139 |
| 1566891 | C-CT-CC-CCCTTTTCTT-CCCCCCC-CCCC- | SEQ ID NO: 140 |
| 1566906 | TTTT-YT-TTTTTTTTTT-TTTTTTTC-YTTC | SEQ ID NO: 141 |
| 1566911 | GG-G-GA-GAGGGGG-GG--GGGGGGG-GGGG | SEQ ID NO: 142 |
| 1566963 | TC-C----T-TCC---C--TTTTTTT-T-TT- | SEQ ID NO: 143 |
| 1566964 | TC-C----T-TCC---C--TTTTTTT-T-TT- | SEQ ID NO: 144 |
| 1566975 | T--T----TCTCCCC-C--TTTTTTT-T-TT- | SEQ ID NO: 145 |
| 1567049 | GGAGGAGGG-GGGGGGGGAGGGGG-AAGAGGA | SEQ ID NO: 146 |

-continued

| Position | Sequence | SEQ ID NO: |
|---|---|---|
| 1567111 | TATATTTTT-TAAAATAA-TTTTTTTTT-TT | SEQ ID NO: 147 |
| 1567133 | GGAG-AGAGGRGGGGAGGAGGGGGGRAGA-GA | SEQ ID NO: 148 |
| 1567183 | CCTCTTCTCCYCCCCTC-TCCCCCCTTCTCCT | SEQ ID NO: 149 |
| 1567261 | TTCTCTTCT--TTTTCTTTTTT-TTTTTTTTT | SEQ ID NO: 150 |
| 1567327 | GGAGAAGAGGRG-GGAGGAGGGGGGRAGAGGA | SEQ ID NO: 151 |
| 1567332 | ACCC-CCCACMC-CCCCCCAAAAAAMCACAAC | SEQ ID NO: 152 |
| 1567385 | ACACAAAAAAACCCCACCAAAAAAAAAAAAAA | SEQ ID NO: 153 |
| 1567427 | G-GGGG-GG-GGTKKGGGGGGGGGG-G-GGKG | SEQ ID NO: 154 |
| 1567428 | T-TTTT-KT-TTGKKTT-TTTTTTT-T-TTKT | SEQ ID NO: 155 |
| 1567438 | TTCTC--TT-TTTTTCT--TTTTTT--TCTT- | SEQ ID NO: 156 |
| 1567439 | TTCTC---T-TYTTYCT--TTTTYT--TCTY- | SEQ ID NO: 157 |
| 1567449 | TTGTGGTTTTTTTTTGT--TTTTTT-GTGTTG | SEQ ID NO: 158 |
| 1567459 | CCACAACCCCCCCCCAC--CCCCCC-ACACCA | SEQ ID NO: 159 |
| 1567536 | GAGAGG-GGGGAAAAGAAGGGGGGGGGGGGGG | SEQ ID NO: 160 |
| 1567581 | GGGGGA-GG-GGGGGGGGAGGGGG-GAGAGGA | SEQ ID NO: 161 |
| 1567585 | CCTCTT-CC-YCCCCTCC-CCCCC-CTCTCCT | SEQ ID NO: 162 |
| 1567588 | TTTTTCTTT-TTTTTTTT-TTTTT-TCTCTT- | SEQ ID NO: 163 |
| 1567602 | AGGGGGGGA-RGGGGGGGGAAAAAARGAGAAG | SEQ ID NO: 164 |
| 1567636 | AAGAGAAAAAAAAAAGAAAAAAAAAAAAAAAA | SEQ ID NO: 165 |
| 1567642 | TTTTTATTTTTTTTTTTTATTTTTTWATATTA | SEQ ID NO: 166 |
| 1567648 | AAGAGGAAAAAAAAAGAAGAAAAAAARGAGAAG | SEQ ID NO: 167 |
| 1567659 | GGGGGAGGGGGGGGGGGGAGGGGGGRAGAGGA | SEQ ID NO: 168 |
| 1567661 | CCCCCCTCCTCCCCCCCCCCCCCCCCCCC-CC | SEQ ID NO: 169 |
| 1567665 | CC-CCCTCCTCCCCCCCCCCCCCCCCCC-CC | SEQ ID NO: 170 |
| 1567673 | GG-GAGGGGGRGGGGAGGGGGGGGGGGGGGG | SEQ ID NO: 171 |
| 1567679 | TTCTCCTTTTYTTTTCTTCTTTTTTTCTCTTC | SEQ ID NO: 172 |
| 1567685 | CCCCCCTCCTCCCCCCCCCCCCCCCCCCCCC | SEQ ID NO: 173 |
| 1567691 | TTTTTGTTTTTTTTTTTTGTTTTTTTGTGTTG | SEQ ID NO: 174 |
| 1567714 | AAAAAGAAAAAAAAAAAAA-ARAAAAAGAGAAG | SEQ ID NO: 175 |
| 1567716 | CCCCCTCCCCCCCCCCC-CCCCCCCTCTCCT | SEQ ID NO: 176 |
| 1567728 | TTYT-CTTTTTTTTTCTT-TTTTTTTCTCTT- | SEQ ID NO: 177 |
| 1567768 | CCTCTC-CCC-CCCCTCCCCCCCCCCCCCCC | SEQ ID NO: 178 |
| 1567770 | CCCCCT-CCC-CCCCCCCTCCCCCCYTCTCCT | SEQ ID NO: 179 |
| 1567788 | CCCCCT-CCCCCCCCCC-TCCCCCCYTCTCCT | SEQ ID NO: 180 |
| 1567986 | ATTTTT-TATWTTTTTTTTAAAAAAWTATAAT | SEQ ID NO: 181 |
| 1568005 | AGGGG-AAAARGGGGGGGGAAAAAAR-AGA-G | SEQ ID NO: 182 |
| 1568012 | GGGGG-GGGGGGGGGGG-GGGGGGG-GAGGA | SEQ ID NO: 183 |
| 1568019 | AAAAA-AAAAWAAAAAAA-AAAAAAA-ATAA- | SEQ ID NO: 184 |

-continued

| Position | Sequence | SEQ ID NO: |
| --- | --- | --- |
| 1568021 | CTCTC-CCCCCTTTTCTT-CCCCCCC-C-CC- | SEQ ID NO: 185 |
| 1568085 | ATTTT-AAAAWTTTTTTT-AAAAWAA-A-AA- | SEQ ID NO: 186 |
| 1568120 | AAGAG-AAAAAAAAAGAA-AAAAAAA-A-AA- | SEQ ID NO: 187 |
| 1568124 | CCTCT-CCCCSCCCCTCC-CCCCCCC-C-CC- | SEQ ID NO: 188 |
| 1568168 | AAAAA-AAAAAAAAAAAAAAAAAAM-ACAAC | SEQ ID NO: 189 |
| 1568196 | GGRGAGGGGGGGGG-AGGGGGGGGGGGGGGG | SEQ ID NO: 190 |
| 1568214 | AARAAGAAAARAAAAAAAGAAAAAAARGAGAAG | SEQ ID NO: 191 |
| 1568478 | GGGGGCGGGGSGGGGGGGCGGGGGGSCGCGGC | SEQ ID NO: 192 |
| 1568490 | AAAAAACAACAAAAAAAAAAAAAAAAAAAAAA | SEQ ID NO: 193 |
| 1568548 | TTWTTATTTTTTTTTTT-ATTTTTTWATATTA | SEQ ID NO: 194 |
| 1568634 | TTTTTATTTTTTTTTTTTATTTTTTTA-ATTA | SEQ ID NO: 195 |
| 1568727 | TTTTTGTTTTTTTTTTTTGTTTTTTTGTGTTG | SEQ ID NO: 196 |
| 1568784 | CCCCCG-CCCCCCCCCC-GCCCCCCCG--CC- | SEQ ID NO: 197 |
| 1568820 | GGGGGA-GGGGGGGGGG-AGGGGGGGGAGAGG- | SEQ ID NO: 198 |
| 1568826 | AAAAAG-AAAAAAAAAA-GAAAAAAAGAGAA- | SEQ ID NO: 199 |
| 1568868 | CCCCCACCCC-CCCCCC-ACCCCCCCA-A-C- | SEQ ID NO: 200 |
| 1568870 | TTTTTGTTTT-TTTTTT-GTTTTTTTG-G-T- | SEQ ID NO: 201 |
| 1568916 | G--G-G--G-GG---GG--GGGAA-G-GGGA- | SEQ ID NO: 202 |
| 1568919 | G--K-T--G-GG---GG--GGGGG-G-G-GG- | SEQ ID NO: 203 |
| 1568929 | A-GAG---AGAAA-AGA--AAAAA-A-A-AA- | SEQ ID NO: 204 |
| 1568939 | G-GGG---GGGGG-GGG--GGGGG-G-G-GGA | SEQ ID NO: 205 |
| 1568952 | C-CTCC--CCCTT-TCT-CCCCCC-CCC-CCC | SEQ ID NO: 206 |
| 1568963 | G-GGGA--GARGGGG-G-AGGGGG-GAG-GGA | SEQ ID NO: 207 |
| 1569035 | GG-G-TTGGTKGGGG-GG-GGGGGG--G-GG- | SEQ ID NO: 208 |
| 1569058 | CTCTCCCCC-CTTTTCT--CCYCCC-CCCCCC | SEQ ID NO: 209 |
| 1569074 | TTTTTCTTTTTTTTTTTTCTTTTT--CTCTTC | SEQ ID NO: 210 |
| 1569093 | AAAAACAAAAAAAAAAAAACAAAAA-ACACAAC | SEQ ID NO: 211 |
| 1569128 | CCCCCTCCCCCCCCCCCC-CCCCC-CTCTCC- | SEQ ID NO: 212 |
| 1569136 | TTTTTCTTTTTTTTTTTT-TTTTTTTCTCTT- | SEQ ID NO: 213 |
| 1569138 | TTCTCTTTTTTTTTTCTT-TTTTTTTTTTTT- | SEQ ID NO: 214 |
| 1569140 | AAAWATAAAAAAAAAAAA-AAAAAAATATAA- | SEQ ID NO: 215 |
| 1569146 | CCCCCCTCCTCCCCCCCC-CCCCCCCCCCCC- | SEQ ID NO: 216 |
| 1569167 | AGGGG-AGAARGGGGG-G-AAAAAAA-AGAA- | SEQ ID NO: 217 |
| 1569185 | GGAGA-GGGGRGGGGA-G-GGGGGGG---GG- | SEQ ID NO: 218 |
| 1569190 | CTCT--TCC-CTTTTC-T-CCCCCCC---CC- | SEQ ID NO: 219 |
| 1569227 | CAA-----C-CA--A----CC-CCCC---CC- | SEQ ID NO: 220 |
| 1569374 | TCCCCCC-T--CCC-CCCCTT-TTT--T-TT- | SEQ ID NO: 221 |
| 1569395 | GGGGGAG-GGGGGG-GGGAGGGGGG--GAGG- | SEQ ID NO: 222 |
| 1569396 | GGAGAGG-GGGGGG-AGGGGGGGGG--GGGG- | SEQ ID NO: 223 |

-continued

| Position | Sequence | SEQ ID NO: |
|---|---|---|
| 1569405 | GGGGGTG-GGGGGG-GGGTGGGGGGT-GTGGT | SEQ ID NO: 224 |
| 1569441 | TTTTTTTTTTTTTTTTTTTTTTTTT-GTGTT- | SEQ ID NO: 225 |
| 1569442 | GGGGGKGGGGGGGGGGGGGGGGGG-TGTGG- | SEQ ID NO: 226 |
| 1569557 | TTWTATTTT--TTTTTT-TTTTTTTWTT-TTA | SEQ ID NO: 227 |
| 1569564 | AAWAA-AAA-AAAAAWA-TAAAAAAAWA-AAA | SEQ ID NO: 228 |
| 1569704 | TTWTATTTTTTTTTAT-TTTTTTTTTTTTT | SEQ ID NO: 229 |
| 1569788 | C-CCCGCCCCCCCCCCCCGCCCCCC-GCGCCG | SEQ ID NO: 230 |
| 1569791 | G-GGGTGGGGGGKKGGGG-GGGGGG--GTGGT | SEQ ID NO: 231 |
| 1569794 | T-TTTWTTTTTTTTTTTTATTTTTT-ATTTTT | SEQ ID NO: 232 |
| 1569797 | A-AAATAAAAAWWWAAWAGAAAAAA-AATAAT | SEQ ID NO: 233 |
| 1570104 | AAAA--AA--AAAA-AA--AAAAAA--A-AAT | SEQ ID NO: 234 |
| 1570126 | GGGG-CGGG-GGGG-GG-CGGGGGGSCGCGGC | SEQ ID NO: 235 |
| 1570416 | GGTGTGGGGGGGGGGTGGGGGGGGGGGGGGG | SEQ ID NO: 236 |
| 1570660 | TTTTTTCTTCTTTTTTTT-TTTTTTTTTTTTT | SEQ ID NO: 237 |
| 1570881 | TTTWTT-T-TTWWWATWW--TTTTTTTTTTT | SEQ ID NO: 238 |
| 1571274 | TTYTTC-TTTTTTT-TTTCTTT-TTYCTCTTC | SEQ ID NO: 239 |
| 1571487 | TCCCCCCCTCYCCCCCC-CTTTTTTYCTCTTC | SEQ ID NO: 240 |
| 1571774 | AGGGGGGGA-GGGGGGGGGAAAAAAARGAGAAG | SEQ ID NO: 241 |
| 1572279 | GAAAAAAAGARAAAAA-AAGGGGGGRAGAGGA | SEQ ID NO: 242 |
| 1572432 | TT-TTC-TTTTTTT-TT--TTTTTTYCTCT-C | SEQ ID NO: 243 |
| 1572888 | T--TGTTTT-TTTTTGT-TTTTT-TTTTTTT- | SEQ ID NO: 244 |
| 1572987 | ACCCCCCC-CMCCCCCCCCAAAAAAMCAC-AC | SEQ ID NO: 245 |
| 1573060 | CGGGGGGGCGGGGGGGGGGCCCCCCSGCGCCG | SEQ ID NO: 246 |
| 1573221 | ACCCCCCCACMCCCCCC-CAAAAAAACACAAC | SEQ ID NO: 247 |
| 1573239 | AAMACA-AAAAAAAACA-AAAAAAAAAAAAA | SEQ ID NO: 248 |
| 1573328 | GGCGGC-GGGGGGGGGGGCGGGGGGCCGCGGC | SEQ ID NO: 249 |
| 1573482 | CCTCTC-CCCCCCCCTCCCCCCCCCCCCCCC | SEQ ID NO: 250 |
| 1574247 | AATAATAAAAAAAAAAAATAAAAAAWTATAAT | SEQ ID NO: 251 |
| 1574545 | GGGGGTGGGGGGGGGGGGTGGGGGGKTGTGGT | SEQ ID NO: 252 |
| 1575684 | TCTCTT-TTTTCCCCTCCTTTTTTTTYTTTTT | SEQ ID NO: 253 |
| 1575961 | CGCGCCCCCCCGGGGCG--CCC-CCCCCCCCC | SEQ ID NO: 254 |
| 1576052 | G--G-A--GGGAAG-A---GGGGGGGGG-GG- | SEQ ID NO: 255 |
| 1576055 | TG-K-G--TTTGGT-G---TTTTTTT-T-TT- | SEQ ID NO: 256 |
| 1576059 | CCCS-C--C-CCCG-C---CCCCCCCCCCCC- | SEQ ID NO: 257 |
| 1576291 | CCCC-TC-CC-CCCCC-C--CCCCCCTCTCC- | SEQ ID NO: 258 |
| 1576327 | A----A--A----T-----WWAAAA----AA- | SEQ ID NO: 259 |
| 1576345 | A-------A-A-TAT----AAAAAA----AA- | SEQ ID NO: 260 |
| 1576372 | AACACA--A-A-AAAC-A-AAAAAAAAAAAA | SEQ ID NO: 261 |

-continued

| Position | Sequence | SEQ ID NO: |
|---|---|---|
| 1576552 | A-T-TT-AAAW-TTTTTTTAAAAAATT---AT | SEQ ID NO: 262 |
| 1576569 | G-G-GG--GGG-GRGG-AGGGGGGGG----G- | SEQ ID NO: 263 |
| 1576597 | GGGGGG--GGGGGGGGGGAGGGGGG-A-A-R- | SEQ ID NO: 264 |
| 1576682 | GTTTTTTTGTGTTTTTTTTGG-GGGGT-TGGT | SEQ ID NO: 265 |
| 1576719 | GGRGGAG-GGGGGGGGGGRGGGGGGGAGAGGA | SEQ ID NO: 266 |
| 1576755 | G-A--G--G-G-AAAA---GGGGGGGGGGGGG | SEQ ID NO: 267 |
| 1576816 | ACACAAA-AAACCCCACCAAA-AAAAAAAAAA | SEQ ID NO: 268 |
| 1576824 | CTCTCCCCCCCTTTTCTTC-C-CCCCCCCCCC | SEQ ID NO: 269 |
| 1576881 | CC-CCTCCCCCCCCCCCCT-CCCCCTTYTCCT | SEQ ID NO: 270 |
| 1577186 | AAA-AATAATAAAAAAA-AAAAAAAAAAAAA- | SEQ ID NO: 271 |
| 1577187 | AAA-AATAAT-AAAAAA-AAAAAAAAAAAAA- | SEQ ID NO: 272 |
| 1577188 | AAA-AATAATTAAAAAA-AAAAAAAAAAAAA- | SEQ ID NO: 273 |
| 1577205 | ACC-CCCCACACCCCC--CAAAAAAMCACAAC | SEQ ID NO: 274 |
| 1577558 | T----A--T-TT-T-TTT-TTTTTTTAT-TTT | SEQ ID NO: 275 |
| 1577559 | T----A--T-TT-T-TTT-TTTTTTTAT-TTA | SEQ ID NO: 276 |
| 1577560 | A----A--A-WT-T-TTT-AAAAAAAAA-AAA | SEQ ID NO: 277 |
| 1577562 | A----T--A-AA-A--AA-AAAAAAA-A-AAT | SEQ ID NO: 278 |
| 1577563 | A----T--A-AA-A--AA-AAAAAAA-A-AAT | SEQ ID NO: 279 |
| 1577633 | TT-T-TG-TGTTTTTT-T-TTTTTTTTTTTTT | SEQ ID NO: 280 |
| 1577638 | AG-G-AA-AAAGGGG--G-AAAAAAAAAAAAA | SEQ ID NO: 281 |
| 1577661 | TT-T--C-T-TTTTT-TT-TTTTTTYC-CTTC | SEQ ID NO: 282 |
| 1577669 | TT-T--G-T-TTTTT-TT-TTTTTTTGT-TTG | SEQ ID NO: 283 |
| 1577673 | CT-T--C-CCCTTTT-TT-CCCCCCCCC-CCC | SEQ ID NO: 284 |
| 1577684 | TC----C-TCYCCCC-CC-TTTTTTT-T-TT- | SEQ ID NO: 285 |
| 1577691 | TC-C----TCTCCCC--C-TTTCTTT-T-TT- | SEQ ID NO: 286 |
| 1577708 | GG-GC---GCGGG-G--G-GGGGGGGCG-GG- | SEQ ID NO: 287 |
| 1577712 | TC-CCTT-TTTCC-C--C-TTTTTTTTT-TT- | SEQ ID NO: 288 |
| 1577745 | CCCCCAC-CCCCCCCC-CACCCCCCCA-ACCA | SEQ ID NO: 289 |
| 1577746 | GGRGGAG-GGGGGGGGGGAGGGGGGGA-AGGA | SEQ ID NO: 290 |
| 1577755 | GCGCGGG-GGGCCCCGCCGGGGGGGGG-GGGG | SEQ ID NO: 291 |
| 1577762 | GAGAGGG-GGGAAAAGAAGGGGGGGGG-GGGG | SEQ ID NO: 292 |
| 1577765 | AAWATAA-AAAAAAATAAAAAAAAAAA-AAAA | SEQ ID NO: 293 |
| 1577792 | GGTGTG--GGAGGGGTGGGGGGGGGGGGGGGG | SEQ ID NO: 294 |
| 1577795 | CGCGCC--CCCGGGGCGGCCCCCCCCCCCCCC | SEQ ID NO: 295 |
| 1577857 | TWTTTTTTTTTTATTTWTTTTTTTT-TTTTTT | SEQ ID NO: 296 |
| 1577867 | CCCTCCCCCCCC-TTCTTCCCCCCCCCCCCCC | SEQ ID NO: 297 |
| 1577890 | TTTTTTTGTTKTTTTTTTTTTTTTTTTTTTTT | SEQ ID NO: 298 |
| 1578154 | TCCCCC-CTCYCCCCCCCCTTTTTTYCTCTTC | SEQ ID NO: 299 |
| 1578364 | TATATT-TT-TAAAA-AA-TTTTTTT-T-TTT | SEQ ID NO: 300 |

-continued

| Position | Sequence | SEQ ID NO: |
|---|---|---|
| 1578462 | AAAAAG-AAAAAAAAAAAGAAAAAARGAGAAG | SEQ ID NO: 301 |
| 1578538 | TTYTTC-TTTTTTTTTTTCTTTTTTYCTCTTC | SEQ ID NO: 302 |
| 1578727 | GGGGGGTGGTGGGGGGGGGGGGGGGGGGGKG | SEQ ID NO: 303 |
| 1578925 | AAAAAAACAAMAAAAAAAAAAAAAAAAAAAA | SEQ ID NO: 304 |
| 1579270 | AAAAAAGAAGAAAAAAAAAAAAAA-AAAAAAA | SEQ ID NO: 305 |
| 1579346 | TGKG-TGGTGKGGG-GGGT-TTTTTTTT-TTT | SEQ ID NO: 306 |
| 1579707 | TTTTTTGTTGTTTTTTTTTTTTTTTTTTTTT | SEQ ID NO: 307 |
| 1579708 | CCCCCCTCCTCCCCCCCCCCCCCCCCCCCCC | SEQ ID NO: 308 |
| 1580305 | CTTTTTTTCTYTTT-TTTTCCCCCCYYCTCCT | SEQ ID NO: 309 |
| 1581345 | GGRGAGGGGGGGGGGAGG-GGGGGGGGGGGG | SEQ ID NO: 310 |
| 1581602 | TCCCCCCCTCYCCCCCCCCTTTTTTCCTCTTC | SEQ ID NO: 311 |
| 1581762 | TTYTTCTCTTTTTTTTTTTCTTTTTTTTCTCTTC | SEQ ID NO: 312 |
| 1581931 | TTTTTGTTKTTTTTTTTTTGTTTTTTKGTGTTG | SEQ ID NO: 313 |
| 1582195 | CTTTTTTTCTYTTTTTTTTTCCCTTCYTCTCTT | SEQ ID NO: 314 |
| 1582351 | AGGGGG-GAAAGGGGGGGGAAAAAAR-AGAAG | SEQ ID NO: 315 |
| 1582357 | GAAAAA-AGGGAAAAAAAAAGGGGGGRAGAGGA | SEQ ID NO: 316 |
| 1582363 | CTT-TTTTCCCTTTTTTTTTCCCCCCYTCTCCT | SEQ ID NO: 317 |
| 1582479 | A-GA-A-AAAAAA-AG--AAAAAAAAAAAAAA | SEQ ID NO: 318 |
| 1582483 | A-AA-R--AAA---AA--AAAAAAAAARAGAAA | SEQ ID NO: 319 |
| 1582484 | T-TT-W--TTT---TTA-TTTTTTTTWTATTT | SEQ ID NO: 320 |
| 1582487 | T-GT-K--TTT-T-G-T-GTTTTTTTTTTTTG | SEQ ID NO: 321 |
| 1582566 | AAAAAAAAATTAAAAAAAAAAAAAAAAAAAAA | SEQ ID NO: 322 |
| 1582570 | TCCCCCCCTTTCCCCCCCCTTTTTTYCTCTTC | SEQ ID NO: 323 |
| 1582623 | G--G-K--G-G-G---KT-GGGGGGK-G-G-- | SEQ ID NO: 324 |
| 1582625 | G--G-K--G-G-G---KTGGGGGGGG-G-G-- | SEQ ID NO: 325 |
| 1582636 | TT-T-A--T-T-TT-TTTATTT---W-T-T-- | SEQ ID NO: 326 |
| 1582637 | TT-T-G--TTT-TT-TTTGTTT---K-T-T-- | SEQ ID NO: 327 |
| 1582694 | CC-C-CCCCCCCCC-CCCCCCC-ACCCC-CAC | SEQ ID NO: 328 |
| 1582722 | GAGG-G--GG-------AAGGG-RGGAG-GG- | SEQ ID NO: 329 |
| 1582723 | ATAA-A--AA-----A--TAAA-WAATA-AA- | SEQ ID NO: 330 |
| 1582737 | G-GG-G-GGG-----G--GGGG-AGG-G-GA- | SEQ ID NO: 331 |
| 1582739 | A-GA-G-GAA-A---A--GAAA-AAA-A-AA- | SEQ ID NO: 332 |
| 1582767 | C-TT-T-TCCCT---T--TCCC-CCC-C-CCT | SEQ ID NO: 333 |
| 1582785 | A-G-----AAA--------AAA-AAA-A-AAG | SEQ ID NO: 334 |
| 1582786 | T-G-----TTT--------TTT-TTT-T-TTG | SEQ ID NO: 335 |
| 1582824 | GGGGGGG-GGGGGG----GGGG-AGGGG-GAG | SEQ ID NO: 336 |
| 1582825 | CCCCCCC-CCCCCC-C--CCCC-TCCCC-CTC | SEQ ID NO: 337 |
| 1582843 | AGGGGGGGAAAGGG-GGGGAAAAAARGAGAAG | SEQ ID NO: 338 |

-continued

| Position | Sequence | SEQ ID NO: |
|---|---|---|
| 1582860 | GAAAAAAAGGGAAA-AAAAGGGGGGGAGAGGA | SEQ ID NO: 339 |
| 1582871 | CCCCCCCCCCCCCCCCCCCCCCTTC-CCCCTC | SEQ ID NO: 340 |
| 1582941 | AAAAAAAAAAAAAAAAAAAAAACCAAAAAACA | SEQ ID NO: 341 |
| 1582946 | TAAAAATATAWAAAAAAAATTTAATWATATAA | SEQ ID NO: 342 |
| 1583115 | AAAAAAAAAAAAAAAAAAAAAARGAAAAAAGA | SEQ ID NO: 343 |
| 1583431 | GCCCCCCCGCSCCCCCCCCGGGCCGSCGCGCC | SEQ ID NO: 344 |
| 1583461 | GAGAGG-GGGGAARAGAAGGGGGGGGGGGGG | SEQ ID NO: 345 |
| 1583655 | TTTTTTG-TTTTTTTTTT-TTT--TK-T-T-- | SEQ ID NO: 346 |
| 1583764 | CCMCCAAACCCCCCCCM-ACCCAACMACACAA | SEQ ID NO: 347 |
| 1583859 | GGGGGTTTGGGGGGGGG-TGGGTTGKTGTG-- | SEQ ID NO: 348 |
| 1583939 | ATWTAT-TAAA-TT-AT--AAATTA-TATATT | SEQ ID NO: 349 |
| 1584144 | TAWATAAATAWAAAATA-ATTTAATWATW-AA | SEQ ID NO: 350 |
| 1584266 | TKTTTT-KT-T-TT-T--TTTT-TTTTT-TTT | SEQ ID NO: 351 |
| 1584267 | GRGGGG-RG-G-GG-G--GGGG-RGGGR-G-G | SEQ ID NO: 352 |
| 1584541 | AAGAGG-GAGAAAAAGAAGAAAGGARGAGAGG | SEQ ID NO: 353 |
| 1584669 | AGGG-GGGAGGGGGGGR-GAAAGGARGAGAGG | SEQ ID NO: 354 |
| 1585055 | TTTTTA-ATTTTTTTTTTATTTTTTWWTATTA | SEQ ID NO: 355 |
| 1585295 | TTTTTT-AT-TTT---TT-TTTTTTT-T-TA- | SEQ ID NO: 356 |
| 1585304 | T-TW---TTTT-WT--T-TTTT--TT-T--T- | SEQ ID NO: 357 |
| 1585332 | T-GG---GTGT-GG-GG-GTTT--TK-TG-G- | SEQ ID NO: 358 |
| 1585543 | GAAAAAAAGAAAAAA-AAAGGGAAGRAGAGAA | SEQ ID NO: 359 |
| 1585768 | TA--AA-A-AT-AA-AT-AT--AA---TAT-- | SEQ ID NO: 360 |
| 1586016 | TA--TT-TT-T-WT-TT-TTTTTTTT-TTTT- | SEQ ID NO: 361 |
| 1586018 | AT--AA-AA-A-WA-AA-AAAAAAAA-A-AA- | SEQ ID NO: 362 |
| 1586074 | AA-AT--WA-AAAA-AA-AAAAAAAA-A-A-- | SEQ ID NO: 363 |
| 1586080 | AM-MAA-AA-MCAC-CM--AAA--AA-A-A-- | SEQ ID NO: 364 |
| 1586082 | CM-MCC-CC-C-CA-AM--CCC--CCCC-C-- | SEQ ID NO: 365 |
| 1586217 | ATTTTT-TATWTTTTTT--AAATTAWTATATT | SEQ ID NO: 366 |
| 1586324 | TAT-TAATTT---AAT-A-TTTTTTW-TATTA | SEQ ID NO: 367 |
| 1586325 | AAA-AAAAAA---AAA-A-AAAAAAW-AWAAT | SEQ ID NO: 368 |
| 1586334 | ACC-MCCCACC--CCC-C-AAACCAACACACC | SEQ ID NO: 369 |
| 1586942 | GTTT-TT-GTTTTTTTTT-GGGTTGGTGTGT- | SEQ ID NO: 370 |
| 1586943 | TAAA-AA-TAAAA-AAAA-TTTAATTATATA- | SEQ ID NO: 371 |
| 1586945 | TGGG-GG-TGGGGGGGGG-TTTGGTTGT-TG- | SEQ ID NO: 372 |
| 1587141 | GTTTTT-TGTKTTTTTTTTGGGTTGKTGTGTT | SEQ ID NO: 373 |
| 1587173 | CTTTTT-TCTCTTTTTTTTCCCTTCYTCTCTT | SEQ ID NO: 374 |
| 1587518 | CTTTTTTTCTYTTTTTTTTCYCTTCYTCTCTT | SEQ ID NO: 375 |
| 1587643 | GTKTTTTTGTGTTTTTTTTGGGTTGKTGTGTT | SEQ ID NO: 376 |
| 1588896 | AAWATAAA--AAAAATAAAAAAAAAAAAAAAA | SEQ ID NO: 377 |

-continued

| Position | Sequence | SEQ ID NO: |
|---|---|---|
| 1589020 | ATATATTAAAATTTTATTTAAAAAAWTATAAT | SEQ ID NO: 378 |
| 1589177 | T-T-T--WTT-TTW--W-TTTTA-TT-TWTTA | SEQ ID NO: 379 |
| 1589187 | G--GAG-GGR-R-G--G-GGGGGGGG-GGG-G | SEQ ID NO: 380 |
| 1589259 | TTATATTTTTTTTTTAT-TTTTTTTTTTT-TT | SEQ ID NO: 381 |
| 1589715 | GTTTTTTTGTKTTTTTTTTGGGTTGKTGTGTT | SEQ ID NO: 382 |
| 1589780 | AT-TTTTTATTTTT-TT-TAAATTAWTATATT | SEQ ID NO: 383 |
| 1589870 | TTTTTTTTTTTTTTTTTTTTTTCCTTTTTTCT | SEQ ID NO: 384 |
| 1589938 | CCGSGCCCCCCCCCCGC-CCCCCCCCCCCCCC | SEQ ID NO: 385 |
| 1591968 | GTGKGGGGGGGGGGGGGGGGGGGGGGGGGGGG | SEQ ID NO: 386 |
| 1592485 | GGAGAGG-GGGGGGGAGG-GGGGGGGGGG-G | SEQ ID NO: 387 |
| 1592711 | TYYTTTTTTTTTTTTTTTTYTYTTTTT--TTTT | SEQ ID NO: 388 |
| 1592832 | TYCTTTYTYTTTTT-YYTTTYTYCTTYTTYTY | SEQ ID NO: 389 |
| 1592838 | CYYCCCYCYCCCCC-YCCCCYCYTCCCCCCCY | SEQ ID NO: 390 |
| 1593700 | AAAAAAAAAAAAAA-AAAAAAACCAAAAAACA | SEQ ID NO: 391 |
| 1593863 | AAWATAAAA-AAAA-TAAAAAATTAAAAAATA | SEQ ID NO: 392 |
| 1594079 | TTWTATTTTTTTTTTATTTTTTT-TTTTTT-T | SEQ ID NO: 393 |
| 1594162 | GGKGTGGGGGGGGGGTGGGGGGGGGGGGGGGG | SEQ ID NO: 394 |
| 1594233 | TTYTCTTTTTTYTTTCTTTTTTTTTTTTTTTT | SEQ ID NO: 395 |
| 1594426 | A-GGGGG-AGRGGGGGGGGAAAGG-RGAGAGG | SEQ ID NO: 396 |
| 1594480 | T-TYTCTTTTTCCCCTC-CTTTTTTYCTCTTC | SEQ ID NO: 397 |
| 1594800 | A-TATAAAAAAAAAATAAA-AAAAAAAAAAAA | SEQ ID NO: 398 |
| 1594961 | GGGKGTGG-GGTTTTGTTTGGGGGGKTGTGGT | SEQ ID NO: 399 |
| 1594983 | AAWATAAAAAAAAAATAAAAAAAAAAAAAAAA | SEQ ID NO: 400 |
| 1595159 | TTTTTTTTKTKTTTTTTTTTTTTTTKTTTTTTT | SEQ ID NO: 401 |
| 1595360 | AAARAGA-AAAGGGGAGGGAAAAAAGGAGAAG | SEQ ID NO: 402 |
| 1595545 | GGGGG-GGGGG-AR-G-A-GGGGGG--G-GG- | SEQ ID NO: 403 |
| 1595560 | TTCTCTTCTT-TTT-CTT-TTTTTT-TT-TT- | SEQ ID NO: 404 |
| 1595571 | CCTCTCCTCC-CYC-TCC-CCCCCC-CCCCC- | SEQ ID NO: 405 |
| 1595887 | CT-Y-C--CTCCCC-C-C-CCCCCC-CCCCCC | SEQ ID NO: 406 |
| 1595916 | TTCTCT-CTTYTTTT--T-TTTTTTTTTTTTT | SEQ ID NO: 407 |
| 1595942 | AAGAGAAGAAAAAAAGAAAAAAAAAA-AAAA- | SEQ ID NO: 408 |
| 1596204 | TT-TCTT-TYTTTTTCTTTTTT-TTTTTTT-T | SEQ ID NO: 409 |
| 1596317 | TTCTCTT-TTY-TTTCTTTTTTTTTTTT-TTT | SEQ ID NO: 410 |
| 1596434 | AATATA--AWTAAAATAAAAAAAAA-AAAA-A | SEQ ID NO: 411 |
| 1596445 | AATATA--AWWAAAATAAAAAAAAA-A-AA-A | SEQ ID NO: 412 |
| 1597089 | CAAAAAAAM-AAAA-AAAACCCCAC-ACACA- | SEQ ID NO: 413 |
| 1597188 | TAAAAAATTATAAAAAAAATTTTATTATATAA | SEQ ID NO: 414 |
| 1597206 | ATWT-TTAA--TTTTTTTTAAAATAWTATATT | SEQ ID NO: 415 |

-continued

| Position | Sequence | SEQ ID NO: |
|---|---|---|
| 1597307 | CTTTTT-CC-CTTT-TTTTCCCCTCTTCTCTT | SEQ ID NO: 416 |
| 1597320 | TCCCCC-TT-TCCC-CCCCTTTTCTCCTCTCC | SEQ ID NO: 417 |
| 1597401 | CCCCCTCCCCCTTTTCTTTCCCCCCY-CTCCT | SEQ ID NO: 418 |
| 1597531 | G-GC-C-GGCG---C-C--GG-G-GG-G-G-C | SEQ ID NO: 419 |
| 1597534 | G-GA-G-GG-G----GA--GG-G-GG-GGG-A | SEQ ID NO: 420 |
| 1597566 | A-TTTT-AATATTT-TTTTAA-ATAWTATATT | SEQ ID NO: 421 |
| 1597599 | TAWAAAATTATAAAAAAAATTTTATWATATAA | SEQ ID NO: 422 |
| 1597812 | CCYCTCCCCCCCCCCTCCCCCCCCCCCCCCC- | SEQ ID NO: 423 |
| 1597849 | TCCCCC-TTCTCCCCCC-CTTTTCTYCTCTC- | SEQ ID NO: 424 |
| 1597865 | ATTTTT-AATATTT--T-TAAAA-AATA-AT- | SEQ ID NO: 425 |
| 1597868 | A-TAAA-A-AA-AA--W-AAAAA-AA-ATAA- | SEQ ID NO: 426 |
| 1597869 | G-AGRG-G-GG-GG--R-GGGGGAGG-GAGR- | SEQ ID NO: 427 |
| 1598084 | AAAWA-AAAAA----A---AA-AAAA-ATAAT | SEQ ID NO: 428 |
| 1598085 | CCCMC-CCCCC----C---CC-CCCC-CACCA | SEQ ID NO: 429 |
| 1598141 | GCGGGGGGG-G-GG-GGGGGGGGCGGGGGG-G | SEQ ID NO: 430 |
| 1598160 | G-AA-A-GG-G--A-AAAAGGGG-GGAGAG-A | SEQ ID NO: 431 |
| 1598175 | GGTT---TG-K-GT--TT-GGG--G--GTG-- | SEQ ID NO: 432 |
| 1598279 | ACMCCCAAACACCCCCCCCAAAACAMCACACC | SEQ ID NO: 433 |
| 1598409 | A-A--AAAA-A-AATAA--AAAAAAA---AT- | SEQ ID NO: 434 |
| 1598416 | TGTG-KTTKGT--TGTT--TTTTTTTG--TGG | SEQ ID NO: 435 |
| 1598417 | AAAA-AAAAAA--TAT---AAAA-AAA-AAAA | SEQ ID NO: 436 |
| 1598418 | TTTT-TTTTTT--ATW-T-TTTTTTTT-TTTT | SEQ ID NO: 437 |
| 1598562 | TGGGGGTTT-TGGGGGGG-TT-TGTTGTGTGG | SEQ ID NO: 438 |
| 1599197 | T-W-TT---WTT-T-----T--TT----TT-T | SEQ ID NO: 439 |
| 1599227 | CGCGCCC--CCCCCCCC-CCCCCC-C-CCC-C | SEQ ID NO: 440 |
| 1599306 | TCCCCC-T-CTCCCCCCCCTTTTCTYCTCTCC | SEQ ID NO: 441 |
| 1599529 | A---T-AAA-A--------AAAA-AA-A-A-T | SEQ ID NO: 442 |
| 1599531 | GA--A-GGG-G-A------GGGGAGG-G-G-A | SEQ ID NO: 443 |
| 1599532 | ACC-C-AAA-ACC------AAAACAA-A-A-C | SEQ ID NO: 444 |
| 1599608 | CTYTTTCCCTCTTTTTTTTCCCCTCYTCTCTT | SEQ ID NO: 445 |
| 1599686 | TGKGGG-TTGTGGGGG-GGTTTTGTK-TGTGG | SEQ ID NO: 446 |
| 1599688 | TCYCCC-TTCTCCCCCCCCTTTTCTY-TCTCC | SEQ ID NO: 447 |
| 1599708 | GGGGAG-GGGGGG--AGGGGGGGGGG-GGGGG | SEQ ID NO: 448 |
| 1599712 | GG-GGG-GGGGGG--GGGGGGGGAGG-GGGAG | SEQ ID NO: 449 |
| 1599720 | CG-GGG-CCGCGGG-GGGGCCCCGCS-CGCGG | SEQ ID NO: 450 |
| 1599826 | T-A-AGTTT-T--GGA--GTTTTGTT-T-TGG | SEQ ID NO: 451 |
| 1599827 | C-C-CTCCC-C--TTC--TCCCCCCC-C-CCT | SEQ ID NO: 452 |
| 1599828 | G-R-AAGGG-G--A-A--AGGGGAGG-G-GA- | SEQ ID NO: 453 |
| 1599836 | T-K-GGTTT-T----G--GTTTTGTK-T-TG- | SEQ ID NO: 454 |

-continued

| Position | Sequence | SEQ ID NO: |
|---|---|---|
| 1599868 | T---T--CT-Y-C------TTTTCTY-TCT-- | SEQ ID NO: 455 |
| 1599869 | G------GG-G-A------GGGGAGR-GAG-- | SEQ ID NO: 456 |
| 1599900 | G------GG-G--------GGGG-GG-GCGC- | SEQ ID NO: 457 |
| 1599907 | AG-G---GA-RG-G-GG-GAAAA-AA-AGAG- | SEQ ID NO: 458 |
| 1599975 | A-AG-GAAA-AGG-GGG-GAAAAGAAGAG-GG | SEQ ID NO: 459 |
| 1599986 | C-C---CCC-C-T-TCT-TCCCC-CCTCTCCT | SEQ ID NO: 460 |
| 1599993 | G-G---GGG-G----AA--GGGG-GG-G-G-- | SEQ ID NO: 461 |
| 1600015 | G-----GGG-G--A-A---GGGG-G--GAGA- | SEQ ID NO: 462 |
| 1600017 | G-----GGG-G--A-A---GGGG-G--GAGA- | SEQ ID NO: 463 |
| 1600060 | CGG-G-ACC---GG-----CCCC-CSGCGC-- | SEQ ID NO: 464 |
| 1600072 | G-C---GGG-G-CC-----GGGG-GGCG-G-- | SEQ ID NO: 465 |
| 1600084 | T----CTTT-T-CC--C--TTTT-TT-T-T-- | SEQ ID NO: 466 |
| 1600128 | C-C-TCCCC-CC-CCTCC-CCCC-CC-CCCC- | SEQ ID NO: 467 |
| 1600162 | C-C---CCC-C-G-G----CCCC-CC-C-C-- | SEQ ID NO: 468 |
| 1600179 | A--TT-TAA-ATTTTTTT-AAAA-AW-A-A-T | SEQ ID NO: 469 |
| 1600193 | T--CCCCTT-TCCCCCCC-TTTT-TY-T-T-C | SEQ ID NO: 470 |
| 1600209 | G-GGGGGGG-GGGGGGGGGGGG-GGCG-G-C | SEQ ID NO: 471 |
| 1600945 | TCYCCCCTTCTCCCCC--CTTTTCTCCT-TCC | SEQ ID NO: 472 |
| 1600951 | CTYTTTTCCTCTTTTT--TCCCCTC-TCTCTT | SEQ ID NO: 473 |
| 1600980 | CTYTTT-CCTCTTTT-TTTCCCCTC-TCTCTT | SEQ ID NO: 474 |
| 1600987 | TTWTATTTTTTTTTATTTTTTTTT-TTTTTT | SEQ ID NO: 475 |
| 1601238 | AATATAAAAAAWAAATAAAAA-AAAAAAA-AA | SEQ ID NO: 476 |
| 1601551 | ATTTTTTTA-WTTTTTTTTAAAATAWTATTTT | SEQ ID NO: 477 |
| 1602219 | GGGKGTGGGGGTTTTGTTTGGGGGGKTGTGGT | SEQ ID NO: 478 |
| 1602244 | CCSCGCGGCCCCCCCGCCCCCCCCCCCCCCCC | SEQ ID NO: 479 |
| 1602297 | ATATAAAAATAAAAAAAAAAAAATAAAAAATA | SEQ ID NO: 480 |
| 1602308 | ACAMAAAAACAAAAAAAAAAAAACAAAAAACA | SEQ ID NO: 481 |
| 1602593 | GGGGGGGGG-GTGG-K---GGG--G--G-G-G | SEQ ID NO: 482 |
| 1602594 | ATAWTTAAA-AA-A-T---AAA--A--A-A-T | SEQ ID NO: 483 |
| 1603109 | TTTT-ATTTTT-A-T-T--TTTT-TWAT-TA- | SEQ ID NO: 484 |
| 1603138 | AA-A-TAAAAA-----A--AAAA-AAA--AA- | SEQ ID NO: 485 |
| 1603142 | AG-R-GAA-AAGGG-----AAAAGAAAA-AA- | SEQ ID NO: 486 |
| 1603143 | AA-A-AAA--AAAA-----AAAAAAW-A-AT- | SEQ ID NO: 487 |
| 1603220 | CCCYCTC-CCCTTTT-TTTCCCCTCYTCTC-T | SEQ ID NO: 488 |
| 1603235 | CCCYCTC-CCCTTTTCTTTCCCCTCYTCTC-T | SEQ ID NO: 489 |
| 1603332 | TTYTCTTTTTTTTTCTTTTTTTTT-TTTTTT | SEQ ID NO: 490 |
| 1603367 | CTTTTTCCCTCTTTTTTT-CCCCTC-TCTCTT | SEQ ID NO: 491 |
| 1603440 | TTTT----TTTTKT-T-G-TTTT-TTTT-TK- | SEQ ID NO: 492 |

-continued

| Position | Sequence | SEQ ID NO: |
|---|---|---|
| 1603441 | GGGG----GGGGGG-G-A-GGGG-GGGG-GR- | SEQ ID NO: 493 |
| 1603653 | AAAAAGAAAAAGGGGAG-GAAAAGARGAGAGG | SEQ ID NO: 494 |
| 1603713 | AGG-GGGGA-GGGGGGGGGAAA-GARGAGAGG | SEQ ID NO: 495 |
| 1603719 | ATA-AAAAA-TAAAAA-AAAAAAAAAAAAAAA | SEQ ID NO: 496 |
| 1603723 | CCC-CGCCC-CGGGGC-GGCCCCGCSGCGCGG | SEQ ID NO: 497 |
| 1603741 | TTTTT-TTT-T--CCT---TTTTCTYCT-TCC | SEQ ID NO: 498 |
| 1603750 | TTTTT-TTT-T----T---TTTT-TYCT-TCC | SEQ ID NO: 499 |
| 1603771 | GGGGG-GGG-G--C-G---GGGG-GG-GC--C | SEQ ID NO: 500 |
| 1603774 | CCTCTCCCC-C--C-T---CCCC-CC-CC--C | SEQ ID NO: 501 |
| 1603778 | TCCCCCCCT-Y--C-C---TTTT-TT-TC--C | SEQ ID NO: 502 |
| 1603794 | GGGGGAGGGGGAAA-GA--GGGGAGGAGA-AA | SEQ ID NO: 503 |
| 1603797 | TCCCCTCCTCYTTT-CT--TTTTTTTTTT-TT | SEQ ID NO: 504 |
| 1603800 | AAAAAGAAAAAGGG-AG--AAAAGAAGAG-GG | SEQ ID NO: 505 |
| 1603857 | CGARGA-GCGCAAAAGA-ACCCCACCAC-CAA | SEQ ID NO: 506 |
| 1603877 | CTCTCCCCCTY--YYC--YCCCCCCCCC-CCC | SEQ ID NO: 507 |
| 1603887 | AAAAAAAWAAA--AA---A-AAAAAATAAAWW | SEQ ID NO: 508 |
| 1603952 | GGGRGAGGGGGAAAAGA-AGG-GAGRA-AGAA | SEQ ID NO: 509 |
| 1604000 | CCCYCT-CCCCTTTTCTTTCCCCTCYTCT-TT | SEQ ID NO: 510 |
| 1604145 | TATATT-TTAT-TTTT--TTTTTTTTTTTTTT | SEQ ID NO: 511 |
| 1604181 | TTYTCT-TTTT-TTTCTTTTTTTTTTTTTTTT | SEQ ID NO: 512 |
| 1604183 | GGGGGA-GGGG-AAAGAAAGGGGAGRAGAGAA | SEQ ID NO: 513 |
| 1604206 | CCCCCT-CCCCTTTTCTTTCCCCTCYTCTCTT | SEQ ID NO: 514 |
| 1604236 | CCCYCTCCCCCTTTTCTTTCCCCTCYTCT-TT | SEQ ID NO: 515 |
| 1604259 | GGGGGAGGGGGAAAAGAAAGGGGAGRAGAGAA | SEQ ID NO: 516 |
| 1604304 | GGAGAGGG--RGGG-AGGGGGGGGGGGGGGGG | SEQ ID NO: 517 |
| 1604307 | GGGGGAGGG-GAAA-GAAAGGGGAGRAGAGAA | SEQ ID NO: 518 |
| 1604385 | TTTTT--TTTTTTA-TT-ATTTTTTTTTATT- | SEQ ID NO: 519 |
| 1604387 | CCCCC--CCCCCCA-CC-ACCCCCCCCCACC- | SEQ ID NO: 520 |
| 1604388 | AAAAA--AAAATTT-AT-TAAAA-AATATAT- | SEQ ID NO: 521 |
| 1604389 | TTTTT--TTTTCTT-T--TTTTT-TTCTTTC- | SEQ ID NO: 522 |
| 1604437 | CCTCTCCCCCCCCC-TC-CCCCCCCCCCCCCC | SEQ ID NO: 523 |
| 1604478 | CCCCCTCCCCCTTTTCT-TCCCCTCYTCTCTT | SEQ ID NO: 524 |
| 1604482 | TTTTTATTTTTAAAATA-WTTTTATWATATAA | SEQ ID NO: 525 |
| 1604540 | TCTT-T-YT-T--T-T---TTTT-T--TTT-- | SEQ ID NO: 526 |
| 1604541 | TTGGT--KT-T----T---TTTT-T--TGT-- | SEQ ID NO: 527 |
| 1604542 | GGCCG--SG-G----G---GGGG-G--GCG-- | SEQ ID NO: 528 |
| 1604543 | CCA-C--MC-C----C---CCCC-C--C-C-- | SEQ ID NO: 529 |
| 1604568 | TTATA-TTT-TT-T-A---TTTTTTTTT-T-- | SEQ ID NO: 530 |
| 1604611 | CGGGGGGGCGCGGG-GG-GCCCCGCSGC-CGG | SEQ ID NO: 531 |

-continued

| Position | Sequence | SEQ ID NO: |
|---|---|---|
| 1604637 | T--TTKTTGT-TGT----TTTTTTTKT-TT- | SEQ ID NO: 532 |
| 1604638 | A--AAAAAAA-ATW----AAAAA-AAWA-AA- | SEQ ID NO: 533 |
| 1604653 | CCCYCTCCC-CTTT-CT-YCCCC-CYTC-C-- | SEQ ID NO: 534 |
| 1604820 | T-T-T-T-TTTT---TA--TTTTATT-T-TAA | SEQ ID NO: 535 |
| 1604867 | AAAMACAAAAACCCCAMCCAAAACAMCACACC | SEQ ID NO: 536 |
| 1605056 | T-TY-CTTTTTCCCCT-CCTTTTCTCCTCTC- | SEQ ID NO: 537 |
| 1605193 | TGTKTTTTT-TTTT-TTTTTTTTT-T-TTTTT | SEQ ID NO: 538 |
| 1605226 | CCCCCACCCCCAAM-CAAACCCCA-CACACAA | SEQ ID NO: 539 |
| 1605297 | GGGGGA-GG-GGGGGGGG-GGGGGGRA--GG- | SEQ ID NO: 540 |
| 1605327 | TTTT-T-TT--GTK--GT-TTTTTTTT-GTTG | SEQ ID NO: 541 |
| 1605336 | TTT-TA-TT--T-T--TT-TTTT-TAT-TTTT | SEQ ID NO: 542 |
| 1605337 | TTT-TC--T--T-T--TT-TTTT-TCT-TT-T | SEQ ID NO: 543 |
| 1605389 | CCCCC--CC-CAAA-CAAACCCCACMACA-AA | SEQ ID NO: 544 |
| 1605417 | GGGG---GG-GAAA-GAAAGGGG-GR-GA-A- | SEQ ID NO: 545 |
| 1605443 | A-AA-A-TAAA----T---AAAA-AA-AAA-A | SEQ ID NO: 546 |
| 1605445 | GA-AAA-AGAG----A---GGGGAGR-GAG-A | SEQ ID NO: 547 |
| 1605467 | GGGGGA-GGGGAAA-GAAAGGGGAGRAGAGAA | SEQ ID NO: 548 |
| 1605520 | GGRGAGGGGGGGGGGAGGGGGGGGGGGGGGGG | SEQ ID NO: 549 |
| 1605526 | AGGGGGAAAGGGGGGGG-GAAAAGARGAGAGG | SEQ ID NO: 550 |
| 1605527 | CCCCCTCCCCCTTTTCT-TCCCCTCYTCTCTT | SEQ ID NO: 551 |
| 1605559 | CGGGGT-GCGSTT---T-TCCCCTCYTCTCTT | SEQ ID NO: 552 |
| 1605573 | GGGGGAGGGGGAAA----AGGGGGGRAGA--A | SEQ ID NO: 553 |
| 1605598 | GGGGGG-GGGGG-G----GGGGG-GG-GGG-A | SEQ ID NO: 554 |
| 1605606 | AAAAAG-AAAAG------GAAAA-AA-A-AGG | SEQ ID NO: 555 |
| 1605613 | GAAAGG-GGAAG------GGGGG-GG-G-GGG | SEQ ID NO: 556 |
| 1605623 | GGAGGG-GGGAG------GGGGG-GG-GGGGG | SEQ ID NO: 557 |
| 1605629 | GCGC-G-GGCGGG--G--GGGGG-GG-GGGGG | SEQ ID NO: 558 |
| 1605631 | CCCC-T-CCCCTT--C--TCCCC-CC-CTCCT | SEQ ID NO: 559 |
| 1605665 | AAAAA-AAAAA-G--A---AAAA-AA-A-AGG | SEQ ID NO: 560 |
| 1605667 | C-CCC-CCCCC-T--C---CCCC-CC-C-CTT | SEQ ID NO: 561 |
| 1605687 | GGGGGAGGGGG--G-G---GGGGGGG-GAGG- | SEQ ID NO: 562 |
| 1605702 | AAAAAAAAAAAATAAAT-AAA-AAAA-AAAAA | SEQ ID NO: 563 |
| 1605716 | GGGGGAGGGGGAAAAGA-AGGGGAGR-GAGAA | SEQ ID NO: 564 |
| 1605853 | CCCYCT-CCCCTTTTCTT-CCCCTCYTYTCTT | SEQ ID NO: 565 |
| 1605879 | CTCTCC-CCTYCCCCCCCCCCCCCCCC-CCC | SEQ ID NO: 566 |
| 1605938 | TCTCTCT-TCC-CCCTC-CTTTTC-Y-T-T-C | SEQ ID NO: 567 |
| 1605946 | AAAAAGAAAAA-GGGA--GAAAAG-A-A-A-G | SEQ ID NO: 568 |
| 1605957 | C-CCC-CCCCC--T-C--TCCCCTCC-C-C-- | SEQ ID NO: 569 |

-continued

| Position | Sequence | SEQ ID NO: |
|---|---|---|
| 1605958 | C-CCC-CCCCC--T-C--TCCCCTCC-C-C-- | SEQ ID NO: 570 |
| 1605965 | A-AAACAAAAA----A--CAAAACAACA-A-- | SEQ ID NO: 571 |
| 1605983 | A-AAAGAAAAA-G--A---AAAARAAGRG-G- | SEQ ID NO: 572 |
| 1605993 | G-GGGAGGGGG-A--GA--GGGGRGGARA-AA | SEQ ID NO: 573 |
| 1606046 | TTT-------T----T----TTT-TT-WAT-- | SEQ ID NO: 574 |
| 1606053 | GAA-----A-A---------GGG-GG-G-G-- | SEQ ID NO: 575 |
| 1606065 | AAA-A---A-R--G------AAA-AA-A-A-- | SEQ ID NO: 576 |
| 1606094 | CTY-CT-TC-Y-TTTCT-TCCCC-CCTCT-TT | SEQ ID NO: 577 |
| 1606158 | GCCCCCCCG-SCCCSCCCCGGGGCGSCGCGCC | SEQ ID NO: 578 |
| 1606358 | AGARAAAAA-AAAAAAAAAAAAAAAAAAAAA- | SEQ ID NO: 579 |
| 1606360 | CCYYCTCCC-CTTTTCTTTCCCCTCYTCTCT- | SEQ ID NO: 580 |
| 1606554 | GGGGG-GG-GG-AA-G-A-GGGGAGG-GAG-A | SEQ ID NO: 581 |
| 1606615 | TTTYTCTTTTTCCCCTC-CTTTTCTCCTC-CC | SEQ ID NO: 582 |
| 1606726 | CTTTT-TTCTY-T-C---ACCCCACC-C-C-- | SEQ ID NO: 583 |
| 1606727 | AAAAA-AAAAA-A-----GAAAAGAAGA-AG- | SEQ ID NO: 584 |
| 1606728 | GGGGG-GGGGG-G-----TGGGGTGGTG-GT- | SEQ ID NO: 585 |
| 1606768 | CA-AC--CCAM----C---CCCC-CC-C-C-- | SEQ ID NO: 586 |
| 1606777 | GGGGG--GGGG-TT-G--TGGGG-GKTGTG-T | SEQ ID NO: 587 |
| 1607231 | TAWWTTTTTAATTTTTTTTTTTTTTTTTTTTT | SEQ ID NO: 588 |
| 1607235 | GCSSGGGGGCCGGGGGGGGGGGGGGGGGGGGG | SEQ ID NO: 589 |
| 1607243 | GTGKGGGGGTTGGGGGGGGGGGGGGGGGGGGG | SEQ ID NO: 590 |
| 1607470 | ATAWAAATATAAAAAAAAAAAAAAAAAAAAAA | SEQ ID NO: 591 |
| 1607624 | AARRAGGAAARGGGGAGGGAAAAGARGAGAGG | SEQ ID NO: 592 |
| 1607724 | CCCCCCCCCCCCCCCCCCCCCCCACCCCCCAC | SEQ ID NO: 593 |
| 1607885 | CCYYCTTCCCYTTTTCTTTCCCCTCTTCTCTT | SEQ ID NO: 594 |
| 1608109 | TTGTGTTTTTTTTTTGTTTTTTTTTTTTT-TT | SEQ ID NO: 595 |
| 1608326 | AAAAAAAGAARAAAAAAAAAAAAAGAAAAAAGA | SEQ ID NO: 596 |
| 1608370 | GGGKGTGGGGGTTTTGTTTGGGGGGKTGTGGT | SEQ ID NO: 597 |
| 1608498 | AAAAAACCAAMAAAAAAAAAAAAACAAAAAACA | SEQ ID NO: 598 |
| 1608523 | AAAAAAAMAAMAAAAAA-AAAAA-AAAAAA-A | SEQ ID NO: 599 |
| 1608720 | TTTTTTTTTATTTTTTTTTTTTTTATTTTTTAT | SEQ ID NO: 600 |
| 1608832 | AGAGAGAAAAAGGGGA--GAAAAAARGAGAAG | SEQ ID NO: 601 |
| 1609704 | TGGG-GGGTGKGGGGGGGGTTTTTTGGTGTTG | SEQ ID NO: 602 |
| 1609752 | GGGGGCGGGGGCGGGGGGCGGGGGGSCGCGGC | SEQ ID NO: 603 |
| 1610363 | T----K------T---G--TT--G----TG-- | SEQ ID NO: 604 |
| 1610368 | CC-C-M---C--A---C--A---C-----C-C | SEQ ID NO: 605 |
| 1610369 | AA-A-A---A--C---A--C---A-----A-A | SEQ ID NO: 606 |
| 1610748 | GGGGGG-GGGGGAAAGAAGGGGGGGGGGG-G | SEQ ID NO: 607 |
| 1610778 | GAGAGGGGGGG-GGGGGGGGG-GGGGGGGG-G | SEQ ID NO: 608 |

-continued

| Position | Sequence | SEQ ID NO: |
|---|---|---|
| 1610902 | TCCCTTTTTTYTCC-CC-T-TTTCTTTT--TT | SEQ ID NO: 609 |
| 1611052 | A--G--A-A---G-AA-G-AAAAGA----A-A | SEQ ID NO: 610 |
| 1611054 | G--A--A-A---A-AA-A-GGGGAG----G-A | SEQ ID NO: 611 |
| 1611234 | GGKGKGGGGTGKGKKKGG--GGGG-GGGGGGT | SEQ ID NO: 612 |
| 1611303 | AAA--GG-AAAGAAAAAAGAAAAAAAG-GAAG | SEQ ID NO: 613 |
| 1611422 | GAAAGAA-GARAAAAAAAAAGGGGAGRAGAGG- | SEQ ID NO: 614 |
| 1611490 | TT-TTTTTTTTAAAA-ATTTTTATT--TTT- | SEQ ID NO: 615 |
| 1611491 | TT-TTTTTTTTAAAA-ATTT-TATT--TTT- | SEQ ID NO: 616 |
| 1611492 | TT-TTTTTTWTAAAA-ATTT-TATT--TTT- | SEQ ID NO: 617 |
| 1611666 | AGGGAGGGAGR-GGGGGGGAAAAGA-GAGAA- | SEQ ID NO: 618 |
| 1611710 | GTTTGTTTGGKTTTTTTT-GGGGTG-T-T-GT | SEQ ID NO: 619 |
| 1611901 | TTKTTTTTTTTTTTTTTTTTTT-KTTGTT-TT | SEQ ID NO: 620 |
| 1611921 | CTTTCTTTCCCTTTTTTTTCCCCT-TTCTCCT | SEQ ID NO: 621 |
| 1612042 | A-GGAGG-AGRGGGGGG-GAAAAGARGA--AG | SEQ ID NO: 622 |
| 1612060 | T-GGTGGG-GK-GGGGG-GTTTTGTK-T--TG | SEQ ID NO: 623 |
| 1612073 | A-ATATATAAA-AAAAA--AAAAAAW-A--A- | SEQ ID NO: 624 |
| 1612200 | ATAWATATAAATAAAAAAT-AAAAAWTAT-A- | SEQ ID NO: 625 |
| 1612354 | AAAAAGAAAAAGAAAAAAGAAAAAAARGAGAAG | SEQ ID NO: 626 |
| 1612360 | AAAAACAAAAACAAAAAACAAAAAAACAC-AC | SEQ ID NO: 627 |
| 1612711 | TT-WTW-WTTTTTTTTW-TTTTTTTTTT-TTT | SEQ ID NO: 628 |
| 1612712 | TT-YTC-YTTTTTTTTY-TTTTTTTTTT-TTT | SEQ ID NO: 629 |
| 1612720 | GC-SGG-GGCG-GS-SG-GGGGGGGSGG-GG- | SEQ ID NO: 630 |
| 1612721 | CACMCC-CCAC-CM-MC-CCCCCCCMCC-CC- | SEQ ID NO: 631 |
| 1612760 | TAAATA-ATAWAAA-AA-ATTTTATWATATTA | SEQ ID NO: 632 |
| 1613279 | CCCCC--MC-CCCC-CMCMCCCCCCCCCC-C- | SEQ ID NO: 633 |
| 1613280 | AAAAA--WA-AAAA-AWAWAAAAAAAAAA-AT | SEQ ID NO: 634 |
| 1613290 | AAAWAAAAAAAATWW-AAAAAAAAAAATA--AA | SEQ ID NO: 635 |
| 1613292 | TTTTTTTTTTT-WT-TTTTTTTTTT-T--TT | SEQ ID NO: 636 |
| 1613314 | GGGRGGGGGGGGAA-GAAGGGGGGGGGGGGGG | SEQ ID NO: 637 |
| 1613355 | GTGKGGGGGGGGGGGG-GGGGGGGGGGGGGGG | SEQ ID NO: 638 |
| 1613593 | CTCTCC-CC-CCCCCCCCCCCCCCCCCCCCCC | SEQ ID NO: 639 |
| 1613850 | TTTTTATWTTTATTTTTTATTTTTTWTTATTT | SEQ ID NO: 640 |
| 1614075 | CCCMCCCCCCCCAAACAACCCCCACCCCCCCC | SEQ ID NO: 641 |
| 1614423 | TGGGTTGG-GKTGGGGGGTTTTTGTTGTTTTG | SEQ ID NO: 642 |
| 1614447 | GGGGGTGGGGGTGGGGGGTGGGGGGKGG-GGG | SEQ ID NO: 643 |
| 1614490 | AAAAAWAAAAA-AAAA-ATAAA-AAAAA-AAA | SEQ ID NO: 644 |
| 1614715 | T-WTTTT-WTTTTW-TTTTTTTTATTTTTTTT | SEQ ID NO: 645 |
| 1614758 | GCCCGGGCGCSGCCCCCCGGGGGGGGCGGGGC | SEQ ID NO: 646 |

-continued

| Position | Sequence | SEQ ID NO: |
|---|---|---|
| 1614819 | AGGG-AAGA-RAGGGGG-AAAAAGAAGAAAAG | SEQ ID NO: 647 |
| 1615080 | AGGGAAGAAGRAGGGGGGAAAAAAAAGAAAAG | SEQ ID NO: 648 |
| 1615669 | AAA-A---R-R--RG-A--AAAAAAA-A-A-A | SEQ ID NO: 649 |
| 1615670 | GAG-R---G-R--RA-G--GGGGAGG-G-G-G | SEQ ID NO: 650 |
| 1615672 | AGA-A---A-A--AA-A--AAAAGAA-A-A-A | SEQ ID NO: 651 |
| 1615675 | AGA-A---A-A-GAA-A--AAAAGAA-A-A-A | SEQ ID NO: 652 |
| 1615684 | TGTGTGG-T-T-GTTTT--TTTTGTT-T-T-T | SEQ ID NO: 653 |
| 1615728 | AGAGAGGAAAAGGAAAAAGAAAAGAAAA-AAA | SEQ ID NO: 654 |
| 1615729 | TCTCTCCTTTTCCTTTTTCTTTTCTTTT-TTT | SEQ ID NO: 655 |
| 1615738 | G-GA-AAGGGG-AGGGGGAGGGGAGRGG-GGG | SEQ ID NO: 656 |
| 1615882 | AGARAGG-AGAGGAAAAAGAAAAGA-AAGAAA | SEQ ID NO: 657 |
| 1615940 | C-TTCTT-CTYTTTTTTTTCCCC-CCTCTCCT | SEQ ID NO: 658 |
| 1615996 | T-T-TC--T-T-CTTTTT-TTTT-T-T--TTT | SEQ ID NO: 659 |
| 1615997 | T-T-TA--T-T-ATTTTT-TTTT-T-T--TTT | SEQ ID NO: 660 |
| 1616062 | T-TTTGTTTTTGGTTT-TGTTTTTT-TTGTT- | SEQ ID NO: 661 |
| 1616174 | TCTC-CCCTCTCCTTTTTCTTTTCTYTTCTTT | SEQ ID NO: 662 |
| 1616203 | C-CA-AA-CACAACCCCCACCCCACACCACCC | SEQ ID NO: 663 |
| 1616335 | T-TCT-Y-T-TTTTTTT--TTTT-TTTTCTT- | SEQ ID NO: 664 |
| 1616336 | A-AAA-M-A-AMCAAAA--AAAA-AAAAAAA- | SEQ ID NO: 665 |
| 1616538 | TCTCTCCCTCTCCTTTTTCTTTTCTYTTCTTT | SEQ ID NO: 666 |
| 1616691 | GA-AGAAAGARAAAAAA-AGGGGAGAAGA-GA | SEQ ID NO: 667 |
| 1617198 | AGGGAGGGAGRGGGGGGGGAAA---RGAGAAG | SEQ ID NO: 668 |
| 1617696 | AGRRAG-GAGAGGAAGAAGAAAA-AGGAGAAG | SEQ ID NO: 669 |
| 1617770 | CTTTCTTTCTYTTTTTTTTCCCCTCYTCTCCT | SEQ ID NO: 670 |
| 1618051 | ATTTATTTATWTTTTTTTTAAAATAWTAT-AT | SEQ ID NO: 671 |
| 1618090 | AAAWA-AWAWATWAA-AAAAAAATAA-AAAA- | SEQ ID NO: 672 |
| 1618231 | CGSGCC-CCCCCCCCGCCCCCCCG-CG-CCCG | SEQ ID NO: 673 |
| 1618254 | A-WTAAAAAAAAAAATAAAAAAATAATAAAAT | SEQ ID NO: 674 |
| 1618273 | TCTCTTTTTTTTTTTTTTTTTT-TTTTTTTTT | SEQ ID NO: 675 |
| 1618347 | T-TTTT--T-T-TC-TTC-TTTTT-TTTTTTT | SEQ ID NO: 676 |
| 1618372 | C-TCCC--C-C-TC--CC-CCCC----C-Y-C | SEQ ID NO: 677 |
| 1618374 | T-GTT---T-T-GK--TT-TTTT----T-K-T | SEQ ID NO: 678 |
| 1618376 | A-ARAA--A-AAAA-AA--AAAA----A-A-G | SEQ ID NO: 679 |
| 1618456 | CTT-CTT-CTTTTT-TTTTCCCCTCCTCTCC- | SEQ ID NO: 680 |
| 1618461 | CTC-CCC-CCCCCC-TCCCCCCC-CC-CCCC- | SEQ ID NO: 681 |
| 1618502 | C-YYCC-TCCCCCCCTCYCCCCCTCCTCCCCT | SEQ ID NO: 682 |
| 1618804 | GGGRGGGGG-GGGAAGGAGGGGGGGGGGGGGG | SEQ ID NO: 683 |
| 1618913 | CCMCCCCCCCCCCC-ACCCCCCCACCACCCCA | SEQ ID NO: 684 |
| 1618914 | AAWAAAAAAAAAAA-TAAAAAAATAATAAAAT | SEQ ID NO: 685 |

-continued

| Position | Sequence | SEQ ID NO: |
|---|---|---|
| 1619145 | AAGAAAGGAGRAAAAGG--AAAAGAAGAAAAG | SEQ ID NO: 686 |
| 1619316 | A--C----A----C-C---AAA-C-A-A-AA- | SEQ ID NO: 687 |
| 1619317 | C--G----C--G-C-G---CCC-GGC-CGCC- | SEQ ID NO: 688 |
| 1619428 | T-WTTTTTTTTTTTAT--TTTTATTATTTT- | SEQ ID NO: 689 |
| 1619605 | AAWAAAATATWAAAAATAAAAAAAAAAAAAA | SEQ ID NO: 690 |
| 1619793 | AGGGGGGGAGRGGGGGGGGAAAAGGRGAGAAG | SEQ ID NO: 691 |
| 1619889 | CCCT-C-CC-YC-CCTC-CCCCCCC--CCCCC | SEQ ID NO: 692 |
| 1619893 | TTTA-T-TT-WT-T-AT-TTTTT-T--T-TTA | SEQ ID NO: 693 |
| 1619897 | T-ATTA--T-T-TA-TT--TTTT-A--T-TTT | SEQ ID NO: 694 |
| 1619898 | A-TAAW--A-A-AT-AA--AAAA----A-AAA | SEQ ID NO: 695 |
| 1619989 | GG-GAAGGGGG-AG-GGGAGGGGGAA-GAGG- | SEQ ID NO: 696 |
| 1619991 | AC-CCCCCACA-CC-CCCCAAAACCC-ACAA- | SEQ ID NO: 697 |
| 1620043 | CCYCCCCT---CCC-CTCCCC-CCCC-CCCCC | SEQ ID NO: 698 |
| 1620056 | CCCCTTCCC--TTC-CCCTCCCCCTC--TCCC | SEQ ID NO: 699 |
| 1620095 | TTT-TTA-T---WT---A-TTTT----TWTTT | SEQ ID NO: 700 |
| 1620101 | AAAT-AT-A--AAWT--T-AAAA----AAAAA | SEQ ID NO: 701 |
| 1620103 | ATTA-AA-A--AAWA--A-AAAA-A--AAAA- | SEQ ID NO: 702 |
| 1620104 | TAAT-WT-T--TWWT--T-TTTT-A--TWTT- | SEQ ID NO: 703 |
| 1620185 | CAMAAAACMCCAAAA-CAACCCCAAAACACC- | SEQ ID NO: 704 |
| 1620249 | GCCCCCCCGC--CCCCCCCGGGGCCS-GCGGC | SEQ ID NO: 705 |
| 1620527 | TTTYTTTTTTTTTCCTTCTTTTTTTT-TTT-T | SEQ ID NO: 706 |
| 1620544 | CCMCCCCACCMCCCCCACCCCCCCCC-CCC-C | SEQ ID NO: 707 |
| 1620585 | TCCCCC-CTCYCCCCCCCCTTTTCCYCTCT-C | SEQ ID NO: 708 |
| 1620728 | TTT--T-T--T-TG--KT-TTTTTTT-T-T-- | SEQ ID NO: 709 |
| 1620739 | T-T--G-----GGT-TTT-TTTT-GK-T--TT | SEQ ID NO: 710 |
| 1620813 | TGTGTTGTTTTTTTTTTT-TTTTTTTTTTTTT | SEQ ID NO: 711 |
| 1620946 | ATTT-A--A-AAAW---AAAAAAAAA-A-AA- | SEQ ID NO: 712 |
| 1620954 | TAWW-A----TAAW-TATATTTTTAW-T-TTT | SEQ ID NO: 713 |
| 1620955 | TAAA-A----TAAW-AATATTTTTAW-T-TTA | SEQ ID NO: 714 |
| 1621237 | A--TTTT----TT--T----A---TTTA---T | SEQ ID NO: 715 |
| 1621391 | GGGKGGGGGG-GGTTGG-GGGGGGGGGGGGGG | SEQ ID NO: 716 |
| 1621467 | CCACAACCCCCAACCACCA-CCCAAMACACCA | SEQ ID NO: 717 |
| 1621759 | CCCCCCC-C-CCCA-CCACCCCCCCCCCC-CC | SEQ ID NO: 718 |
| 1621770 | AAAAAAAAAAAAAT-AATAAAAAAAAAAAAAA | SEQ ID NO: 719 |
| 1621799 | AAAAAAAAAAAAAT-AATAAAAAAAAAAAAAA | SEQ ID NO: 720 |
| 1621800 | CCCCCCCCCCCCCA-CCA-CCCCCCCCCCCCC | SEQ ID NO: 721 |
| 1621931 | TTTTCCT-T-TCCTTTTTCTTTTTCYTTCTTT | SEQ ID NO: 722 |
| 1622029 | A--A-W-AAAA--AAW-AAAAAA-AA-A-AAA | SEQ ID NO: 723 |

-continued

| Position | Sequence | SEQ ID NO: |
| --- | --- | --- |
| 1622034 | A-TA-T--ATATTA-T-ATAAAA--ATA-AAT | SEQ ID NO: 724 |
| 1622108 | A-TTTT--A-WTTTTTTTTAAAATTTTATAAT | SEQ ID NO: 725 |
| 1622131 | G-ARAA--G-RAAGG-AGAGGGGAARAGAGGA | SEQ ID NO: 726 |
| 1622144 | C-TYTT--CTYTTCC--CTCCCCTTYTC-CCT | SEQ ID NO: 727 |
| 1622152 | TAAWAA---AWAATTA-TATTTTAAWAT-TTA | SEQ ID NO: 728 |
| 1622535 | CCTYTT-TCCCTTTTTT-TC-CCCTYTCTCCT | SEQ ID NO: 729 |
| 1622598 | T-TWTTTTTTTTTAATTATTTTTTTTTTTTTT | SEQ ID NO: 730 |
| 1622610 | A-GRGGAGAAAGGGGGGGGAAAAAGAGAGAAG | SEQ ID NO: 731 |
| 1622623 | TTTTTTTTTTTTTGGTT-TTTTTTTTTTTTTT | SEQ ID NO: 732 |
| 1622630 | TTAWAATATTTAAAAAA-ATTTTTATATATTA | SEQ ID NO: 733 |
| 1622659 | ATAWAATAATAAAAAAA-AAAAATAAAAAAAA | SEQ ID NO: 734 |
| 1622728 | CCACAACAC-CAAA-AA-ACCCCCAMACACCA | SEQ ID NO: 735 |
| 1622766 | TATATTATTTTTTTTTT-TTTTTTTTTTTTTT | SEQ ID NO: 736 |
| 1622876 | GGRGGGGGGGGGGGGAG-GGGGGGGGAGGGGA | SEQ ID NO: 737 |
| 1622961 | TTCTTTTTTTTTTTTCT-TTTTTTTTCTTTTC | SEQ ID NO: 738 |
| 1623024 | TCCCCCCCTCYCCTTCC-CTTTTCCYCTCTTC | SEQ ID NO: 739 |
| 1623076 | GGGGGGGGGG-GGK-GGTGGGGGGGGGGGGGG | SEQ ID NO: 740 |
| 1623155 | TT-TTTTTTTTTTTATTTTTTTTTT-TTTTW | SEQ ID NO: 741 |
| 1623157 | TA-ATTATTATTTT-TTTTTTTATT-TTTTT | SEQ ID NO: 742 |
| 1623183 | CTCTCCTCCTCCCCC-CCCCCCCTCCCCCCCC | SEQ ID NO: 743 |
| 1623346 | AGARAA-AA-AAAAAAAAAAAAARAAAAAAAA | SEQ ID NO: 744 |
| 1623426 | CTCYCCTCCTCCCCCCCCCCCCCTCCCCCCCC | SEQ ID NO: 745 |
| 1623482 | AGARAAGAAGAAAAAAAAAAAAAGAA-AAAAA | SEQ ID NO: 746 |
| 1623619 | GGGG-T-GGGGTTGGGGGTGGGGG-GGGTGGG | SEQ ID NO: 747 |
| 1623625 | AGARGG--AGAGGAAAAAGAAAAG--AAGAAA | SEQ ID NO: 748 |
| 1623626 | CTCTAA--CTCAACCCCCACCCCT-MCC-CCC | SEQ ID NO: 749 |
| 1623789 | TTCTTTTCT-YTTTTCCTTTTTTTTTCTTTTC | SEQ ID NO: 750 |
| 1623925 | TTTYCCTTTTTCCT-TTTCTTTTTCYTTCTTT | SEQ ID NO: 751 |
| 1624123 | GAGAGG--GAGGGGGGGGGGGG-GGGGGGGGG | SEQ ID NO: 752 |
| 1624435 | TCTYTTCT-TTTTTT-TTTTTTTTTTTTTTTT | SEQ ID NO: 753 |
| 1624569 | GTGK-GTTGTGGGGGGGTGGGGGGGGGGGGGG | SEQ ID NO: 754 |
| 1624739 | GGGGGGGG--GGGAAGA-GGGGGGGGG-GGGG | SEQ ID NO: 755 |
| 1624817 | AAAATT-AAAA-TA-AA-T-AAAAT-A-TAAA | SEQ ID NO: 756 |
| 1625263 | TCCC-CCCTCYC-CCCCCCTTTTCCYCTCTT- | SEQ ID NO: 757 |
| 1625295 | A-TA-T-AA-AT---TA--AAAAATA-A-AA- | SEQ ID NO: 758 |
| 1625296 | A-TA-T-AA-AT---TA--AAAAATA-A-AA- | SEQ ID NO: 759 |
| 1625300 | A------AA-W-----T--AAAAT-A-A-AA- | SEQ ID NO: 760 |
| 1625304 | A------AA-W--------AAAAT-A-A-AA- | SEQ ID NO: 761 |
| 1625331 | T----C-TT-T--CC-C--TTT-CCT-T-TT- | SEQ ID NO: 762 |

-continued

| Position | Sequence | SEQ ID NO: |
|---|---|---|
| 1625346 | CT---T-TC-C--TT-T--CCCCTTC-C-CC- | SEQ ID NO: 763 |
| 1625392 | T-GG-GG-T-T--------TTTT-G-G-G-TG | SEQ ID NO: 764 |
| 1625409 | TCCCCCC-T-T---CC--CTTTT-CTCTCTTC | SEQ ID NO: 765 |
| 1625424 | GAGAGGAAG-G---AG-AGGGGG-GGGGGGGG | SEQ ID NO: 766 |
| 1625443 | CCYCCCCCC-CC-CCTCC-CCCCCCCTCCCCT | SEQ ID NO: 767 |
| 1625454 | GAAAAA-AG-RA-AAAAA-GGGGAARAGAGGA | SEQ ID NO: 768 |
| 1625472 | GGGGAA-GG-GAAG-AGG-GGGGGARAGAGG- | SEQ ID NO: 769 |
| 1625548 | G-------G---AA-----GGGG----G-GG- | SEQ ID NO: 770 |
| 1625586 | GAA----GG-G-GG-----GGGG--G-G-GG- | SEQ ID NO: 771 |
| 1625587 | TGG----TT-T-TT-----TTTT--T-T-TT- | SEQ ID NO: 772 |
| 1625588 | ATT----AA-A-AA-----AAAA--A-A-AA- | SEQ ID NO: 773 |
| 1625599 | CCY---C-C-C-C--TC-CCCCC--C---CC- | SEQ ID NO: 774 |
| 1625658 | C-YT-CT-CTCCCTTCTTCCCCCTCCC-CCCC | SEQ ID NO: 775 |
| 1625660 | C-AA-AA-CACAAAAAAAACCCCAAMA-ACCA | SEQ ID NO: 776 |
| 1625677 | T-CC-CCCTCTCCCCCCC-TTTTCCYC-CTTC | SEQ ID NO: 777 |
| 1625693 | AG-G-GGGAGAGGGGGGG-AAAAGGRG-GAAG | SEQ ID NO: 778 |
| 1625694 | CT-T-CTCCTCCCCCCCC-CCCCCCCC-CCCC | SEQ ID NO: 779 |
| 1625725 | CCAC-ACCCCCAAC-ACC-CCCCC-MACACCA | SEQ ID NO: 780 |
| 1625788 | CT-T--TTCTY-TTT-TT-CCCCT---C-CC- | SEQ ID NO: 781 |
| 1625833 | AA-W-TA-A-A--A-TAW-AAAAA-WTA-AAT | SEQ ID NO: 782 |
| 1625895 | AGAG-AG-AGAAAGGAGG-AAAAG-AA-AAAA | SEQ ID NO: 783 |
| 1625923 | AGAG-AGGAGAAAAAAAAAAAAAAAAAAAAAA | SEQ ID NO: 784 |
| 1625924 | TCTC-TCCTCTTTTTTTTTTTTTTTTTTTTTT | SEQ ID NO: 785 |
| 1626140 | CCACAACACCCAACCACCACCCCCAMACACCA | SEQ ID NO: 786 |
| 1626248 | T----C-CT-TTT--TT--TT-TT-T-TTTT- | SEQ ID NO: 787 |
| 1626250 | C----T-TC-C-C---C--CC-CC-C-CCCC- | SEQ ID NO: 788 |
| 1626252 | A----A-AA-A-T---A--AA-AA-A-ATAA- | SEQ ID NO: 789 |
| 1626253 | T----T-TT-T-A--TT--TT-TT-T-TATT- | SEQ ID NO: 790 |
| 1626254 | G----G-GG-A----GA--GG-GA-G-G-GG- | SEQ ID NO: 791 |
| 1626263 | T----TGTT-TTT--TTG-TT-TTTT-TTTT- | SEQ ID NO: 792 |
| 1626278 | GAG--GAGG-GGGAAGGAGGG-GGGG-GGG-G | SEQ ID NO: 793 |
| 1626298 | CCTCTTCCCCCTTCCTCCTCCCCCTC-CT-CT | SEQ ID NO: 794 |
| 1626400 | ACACAACAA-AAACCAA-AAAAAAAAAAA-A | SEQ ID NO: 795 |
| 1626505 | CCYCCCCC-CCCCCCTCCCCCCCC-CTCCC-T | SEQ ID NO: 796 |
| 1626585 | AAAAAAATAAA-AAAATAAAAAAAAAAAAAAA | SEQ ID NO: 797 |
| 1626676 | TCYYCCCCTCTCCTTCCTCTTTTTCTCTCTTC | SEQ ID NO: 798 |
| 1626838 | GGGGGG-AGGRGGGGGG-GGGGGGGGGGGGG | SEQ ID NO: 799 |
| 1626935 | ATTWTTTTATATTAATTATAAAAATWTATAAT | SEQ ID NO: 800 |

-continued

| Position | Sequence | SEQ ID NO: |
|---|---|---|
| 1626986 | TATWA-ATTAT-ATTTAA-TTTTTATTTATTT | SEQ ID NO: 801 |
| 1627040 | AAAAAWAA-AATWAAAAAWAAAAAWWAAAAAA | SEQ ID NO: 802 |
| 1627079 | GTGTGGT-GTGGGGGGGGGGGGG-GG--GGGG | SEQ ID NO: 803 |
| 1627098 | TTTTTY--TTTTTTTTTTTTTT--TYT-Y-TT | SEQ ID NO: 804 |
| 1627135 | GGGG---GG-GCCGGGGG-GGGGG--G--G-G | SEQ ID NO: 805 |
| 1627136 | TTTT---TT-T-CTTTTT-TTTTT--T--T-T | SEQ ID NO: 806 |
| 1627245 | A----A--A--AAAAT----AAA----AA--T | SEQ ID NO: 807 |
| 1627248 | T----T--T---TTTA----TTT----TT--A | SEQ ID NO: 808 |
| 1627489 | T-TA-TA-TATTTTTTATTTTTTATTTTTTTT | SEQ ID NO: 809 |
| 1627535 | TA-AAA--TAWAA-T--TATTTT-A--TA-T- | SEQ ID NO: 810 |
| 1627607 | ACCMCC-CACCCCAAC-ACAAAACCMCACAA- | SEQ ID NO: 811 |
| 1627619 | TTGTTT-TTTTTTTTG-TTTTTTTTTGTTTT- | SEQ ID NO: 812 |
| 1627637 | AGARAA-AAGAAAA-A-AAAAAAGAAAAAAAA | SEQ ID NO: 813 |
| 1627649 | CCTCCCCCCCCCCCCT-CCCCCCCCCTCCCCT | SEQ ID NO: 814 |
| 1627669 | GGCGGGG-GGGGGGGC---GGGGGG-CGGGGC | SEQ ID NO: 815 |
| 1627686 | AAAAATA-A-AAAAAA--A-AA-ATAAAW--A | SEQ ID NO: 816 |
| 1627687 | TTTTTAT-T-TTTTTT--T-TT-TATTTW--T | SEQ ID NO: 817 |
| 1627688 | AAAAATA-A-AAAAAA--A-AA-ATAAAW--A | SEQ ID NO: 818 |
| 1627771 | TGGKGG-GTGKGGTTGGTGTTTTG-GGTGTTG | SEQ ID NO: 819 |
| 1627780 | CCCCAA-CCCCAACCCC-ACCCCC--CCACCC | SEQ ID NO: 820 |
| 1627783 | GAARAA-AGARAAGGAA--GGGGA--AGAGGA | SEQ ID NO: 821 |
| 1627802 | GAGAGG-GGGGGGGGGG-GGGGGGGGGGGGGG | SEQ ID NO: 822 |
| 1627934 | T-TT---TTTTT-T-TTTCTTTT-TT-TTTT- | SEQ ID NO: 823 |
| 1628083 | AATATT-TAATTTA-T-ATAAAATTWTAT-AT | SEQ ID NO: 824 |
| 1628315 | TT-TTTCT-CTTTTTTCTTTTTTCTTTTTTTT | SEQ ID NO: 825 |
| 1628562 | GGGGCC-GG-GCCGGGGGCGGGGGCSGGCGGG | SEQ ID NO: 826 |
| 1628644 | A--AAACC--MAAAACCA-AAAACAACAAAAC | SEQ ID NO: 827 |
| 1628651 | T--TTTAA--WTTTTAAT-TTTTATTATTTTA | SEQ ID NO: 828 |
| 1628760 | TTCTTT-CT-YTTTT-CTTTTTTCT-CTTTTC | SEQ ID NO: 829 |
| 1628782 | AA-AAW--A-A-WAA-AAAAAAAA-TAAAAA- | SEQ ID NO: 830 |
| 1628793 | TT-TTT--T-T-TTTA-TTTTT---TAT-W-- | SEQ ID NO: 831 |
| 1628955 | TTGT-T--T--TTTTGGTTTTT-KTTTT-T-- | SEQ ID NO: 832 |
| 1628956 | TTTT-T--T--TTTTTTTTTTT-KTTKT-TT- | SEQ ID NO: 833 |
| 1628957 | GGGG-G--G--TKGGGGGGGGG-GGGKG-GG- | SEQ ID NO: 834 |
| 1629663 | C-TC-C---CCCCCC-C-CCCCT-CC-CCCT- | SEQ ID NO: 835 |
| 1629665 | T-AT-T---TTTTTT-T-TTTT---T-T-TAT | SEQ ID NO: 836 |
| 1629698 | C--C-C--CCCCCCCA-CCCCCAA-CACCC-A | SEQ ID NO: 837 |
| 1629751 | CCTCCC-TCTCCCCCTTCCCCCTTCCTCC-TT | SEQ ID NO: 838 |
| 1629813 | A-GAAAAGAARAAA-GAAAAAAGGAA-AAAGG | SEQ ID NO: 839 |

-continued

| Position | Sequence | SEQ ID NO: |
|---|---|---|
| 1629885 | TTGTTT--TTTTTTTGTTTTTT--TTGTTT-G | SEQ ID NO: 840 |
| 1629924 | TTWTTT--TTTTTTTTATTTTT-TT-TTTTTT | SEQ ID NO: 841 |
| 1629966 | GGAGGG--GGR-GG-AGG-GGG-AGG-GG-AA | SEQ ID NO: 842 |
| 1629972 | CC-CCC--CCCCCC-TCCCCCC-TCC-CC-TT | SEQ ID NO: 843 |
| 1629986 | GG-GGGA-GGGGGG-AGGGGGG--GG-GGGAA | SEQ ID NO: 844 |
| 1630016 | A-GAAAA-AAAAAAAGAAAAAA--AA-AAA-- | SEQ ID NO: 845 |
| 1630038 | A-AAAAGAAGAAAAAAGAAAAA-AAAAAAAAA | SEQ ID NO: 846 |
| 1630042 | T--TTTTCTTYTTTTCTTTTTT-CTTCTTTCC | SEQ ID NO: 847 |
| 1630059 | TT-TTTTCTTYTTTTCTTTTTT-CTTCTTTCC | SEQ ID NO: 848 |
| 1630073 | GG-GGG-AGGAGGGGAGG-GGG-AGGAGGGAA | SEQ ID NO: 849 |
| 1630087 | AAAATT-AA-ATTAAA-A-AAA-ATTAATAAA | SEQ ID NO: 850 |
| 1630090 | GGAGGG-AG-RGGGGA-G-GGG-AGGAGGGAA | SEQ ID NO: 851 |
| 1630106 | TTCTTTT-T-TTTTTCTT-TTT-CTTCTT-CC | SEQ ID NO: 852 |
| 1630132 | TT-TTTT-TTYTTTT-TT-TTT-CTT-TTTC- | SEQ ID NO: 853 |
| 1630139 | GG-GGGG-GGRGGGG-GG-GGG-AGG-GGGA- | SEQ ID NO: 854 |
| 1630142 | CC-CCCC-CCYCCCC-CC-CCC-TCC-CCCT- | SEQ ID NO: 855 |
| 1630154 | GGAGGGG-GGR-GGG-GG-GGG-AGGAGGGA- | SEQ ID NO: 856 |
| 1630196 | A-CAAAA-AAAAAAACAAAAAAC-AA-AAAC- | SEQ ID NO: 857 |
| 1630198 | T-ATTTT-TTTTTTTATTTTTTA-TT-TTTA- | SEQ ID NO: 858 |
| 1630217 | CCTCCCC-CCCCCCCTCCCCCCT-CC-CCCT- | SEQ ID NO: 859 |
| 1630219 | AA-AAAA-AAAAAAAG-AAAAAG-AA-AAAG- | SEQ ID NO: 860 |
| 1630225 | CC-CCCC-CCCCCCCT-CCCCCT-CC-CCCT- | SEQ ID NO: 861 |
| 1630284 | TTATTTTAT-ATTTTATT-TTT-A-TAT-TAA | SEQ ID NO: 862 |
| 1630303 | AAAAAW-AA-A-WAAAAA-AAA-A-AAA-AAA | SEQ ID NO: 863 |
| 1630311 | AA-AAM-AA-A-AAAA-A-AAA-A-MAA-AAA | SEQ ID NO: 864 |
| 1630325 | TT-TTT-ATTTTTTTTTTTTTT-TTTAT-T-T | SEQ ID NO: 865 |
| 1630357 | C-TCCCC-CCYCCCCTCCCCCCTTCCTCCCTT | SEQ ID NO: 866 |
| 1630376 | CCGCCCC-CCSCCCCGCCCCCCGGCCGCCCGG | SEQ ID NO: 867 |
| 1630447 | TT---G--T-TGGT---TGTTT---T-T-T-- | SEQ ID NO: 868 |
| 1630475 | CC-CAAAACAM-AAA-AA-CCC---M-CACA- | SEQ ID NO: 869 |
| 1630513 | AA-AAA--AARAAAA-AAAAAA-GAA-AAAG- | SEQ ID NO: 870 |
| 1630515 | CC-CCC--CCYCCCC-CCCCCC-TCC-CCCT- | SEQ ID NO: 871 |
| 1630608 | TT-TTTTATTTTTTTAT-TTTT--TT-TTTA- | SEQ ID NO: 872 |
| 1630765 | TTWTTT--TTATTTTTTTTTTTAWTTATTT-- | SEQ ID NO: 873 |
| 1630766 | TTATTT-ATTATTTTAATTTTTAATT-TTT-- | SEQ ID NO: 874 |
| 1630870 | CCACCCCAC-ACCC-AACCCCCAACCACCC-A | SEQ ID NO: 875 |
| 1631079 | GGGGGGGGGGGGGGGGG-GGG-AAGGGGGGAG | SEQ ID NO: 876 |
| 1631156 | GGCGGGCCGCSGGGGCCGGGGGCCGGCGGGCC | SEQ ID NO: 877 |

-continued

| Position | Sequence | SEQ ID NO: |
|---|---|---|
| 1631191 | AAWAAAATA-AAAAA-AAAWAA-TAAWAAA-- | SEQ ID NO: 878 |
| 1631193 | CCMCCCCAC-CCCCC-CCCCCC--CCMCCC-- | SEQ ID NO: 879 |
| 1631316 | TTATTTTATTW-TTTAATTTTTAA-TATTTAA | SEQ ID NO: 880 |
| 1631449 | CCCCCCTCCTCCCCCCCCCCCCCCCCCCCCCC | SEQ ID NO: 881 |
| 1631761 | GGTGGGTTGTGGGGGTTGGGGGTTGGTGGGTT | SEQ ID NO: 882 |
| 1631765 | AATAAAATAAAAAAATTAAAAATTAATAAATT | SEQ ID NO: 883 |
| 1632488 | TTCTTTTCTTYTTTTCTTTTTTCCTTCTTTCC | SEQ ID NO: 884 |
| 1633118 | TTCTTTTCTTYTTTTCCTTTTTCCTTCTTTCC | SEQ ID NO: 885 |
| 1633465 | AAGAAAAGAARAAAAG-AAAAAGGAARAAAGG | SEQ ID NO: 886 |
| 1633629 | TTTTTTA-TATTTTTTTTTTTTTTTTTTTTTT | SEQ ID NO: 887 |
| 1633840 | GGGGGGAGGAGGGGGGGGGGGGGGGGGGGGGG | SEQ ID NO: 888 |
| 1633948 | GGAGGGAAG-RGGGGAAGGGGGAAGGAGGG-A | SEQ ID NO: 889 |
| 1633983 | TTCTTTCCT-YTTTTCT-TT-TCCTTCTTTCC | SEQ ID NO: 890 |
| 1634118 | GGAGGGAAGARGGGGAAGGGGGAAGGAGG-AA | SEQ ID NO: 891 |
| 1634206 | TT-TTTTGTTTTTTT--TTTTT--TT-TTTGG | SEQ ID NO: 892 |
| 1634213 | GG-GGG--GGGGGGK--GGGGG--GG-GG-TT | SEQ ID NO: 893 |
| 1634260 | CCTCCCTTCTYCCCCTTCCCC-TTCCTCCCTT | SEQ ID NO: 894 |
| 1634452 | TTTTCCCTT-TCCCCTTCCTTTTTCYTTCTTT | SEQ ID NO: 895 |
| 1634453 | GGGGAAAGG-GAAAAGAAAGGGGGARGGAGGG | SEQ ID NO: 896 |
| 1634537 | TTW----AT-W----TA--TTTAA-TTT--AT | SEQ ID NO: 897 |
| 1634543 | TTTY-C-TT-T-CC-TTC-TTTTT-YTT--TT | SEQ ID NO: 898 |
| 1634611 | AAAW-T-AA-A-TT-A-T-AAAAATWAA-AAA | SEQ ID NO: 899 |
| 1634612 | TTTW-A-TT-T-AA-T-A-TTTTTAWTT-TTT | SEQ ID NO: 900 |
| 1634643 | CCCC-TTCC-C----C-T-CCCCC-CCC-CCC | SEQ ID NO: 901 |
| 1634649 | CCCC-TCCC-C-TT-C-TTCCCCC-CCC-CCC | SEQ ID NO: 902 |
| 1634854 | AAARGGAAA-AGGGGAAGGAAAAAGRAAGAAA | SEQ ID NO: 903 |
| 1634907 | AAAATTT-ATATTTT-TT-AAAAATWAATAAA | SEQ ID NO: 904 |
| 1634974 | A-AAGGG-AGAGGGGAGGGAAAAAGRA-GAAA | SEQ ID NO: 905 |
| 1635001 | CCCCCCTCCTCCCCCCTCCCCCCCCCC-CCCC | SEQ ID NO: 906 |
| 1635093 | A-AAAAG-AGAAAAAAAAAAAAAA--AAAAAA | SEQ ID NO: 907 |
| 1635121 | C-CCTT--C-CTTTTCTTTCCC-C-YCCTCCC | SEQ ID NO: 908 |
| 1635161 | T-TTCCT-TTTC-CCTTCCTTTTTCYTTCTTT | SEQ ID NO: 909 |
| 1635172 | T-TTA-T-TTT-TA-TTAATTTTTTTTTATTT | SEQ ID NO: 910 |
| 1635188 | A-AA-TA-AAATTT-AA--AAAAATWAA-AAA | SEQ ID NO: 911 |
| 1635269 | G-GKTTG-GGGTTTTG-TTGG-GGTTGGTGGG | SEQ ID NO: 912 |
| 1635378 | C-CC-T-C--CTTT-C-T-C--CCTTCCTCC- | SEQ ID NO: 913 |
| 1635479 | A-AA---AA-AC---A----A-AA--AA-AA- | SEQ ID NO: 914 |
| 1635553 | CCCSGGGCCGCGGGGCGGGCC-CCGSCCGCCC | SEQ ID NO: 915 |
| 1635588 | A-AAAATA-TAAAAAATAAAA-AAAAAAAAAA | SEQ ID NO: 916 |

-continued

| Position | Sequence | SEQ ID NO: |
|---|---|---|
| 1635621 | A-AACCMAAAACCCCAACCAAAAACCAAC-AA | SEQ ID NO: 917 |
| 1635628 | T-TTGGTTTTGGGGTTGGTTTTTGGTTG-TT | SEQ ID NO: 918 |
| 1635716 | AAAA--AAAAAT-T-AA--AAAAA-WAA-AAA | SEQ ID NO: 919 |
| 1635908 | CCCC-C-CC-CYYC-Y-CTCCC-YCCCCCC-- | SEQ ID NO: 920 |
| 1635913 | TTTT-W--T-TAWT-T--ATTT-TTTTTWT-- | SEQ ID NO: 921 |
| 1635916 | TTTT-W--T-TTWW-T--TTTT-TATTTWT-- | SEQ ID NO: 922 |
| 1635919 | AWAA-W----AAAT-A--AAAAAW-ATAAA-- | SEQ ID NO: 923 |
| 1636172 | TTCYCCTCTCYCCCCCCCCTTTCCCYCTCTCC | SEQ ID NO: 924 |
| 1636305 | CCCCCCTCCCCCCC-CCCCCCCCCCCCCCCCC | SEQ ID NO: 925 |
| 1636413 | TTTYTTTTTTTTTCCTTCTTTTTTTTTTTTTT | SEQ ID NO: 926 |
| 1638089 | CCCCCTCCCCC-CT-CCCCCCCCC-CCCYCCC | SEQ ID NO: 927 |
| 1638581 | AAAA-AAAA-AAWA--A-WAAAAW-AWAAAA- | SEQ ID NO: 928 |
| 1638591 | CCTC-CY-C-CYCYC-T-CCCCYC-CYC-C-C | SEQ ID NO: 929 |
| 1638593 | TTCT-TY-T-TTTTT---TTTTYT-TYT-T-T | SEQ ID NO: 930 |
| 1638641 | CCYC-TCCCCYTTTTC-TTCC-CCTYCCTCCC | SEQ ID NO: 931 |
| 1639354 | AAAAAATAAAAATAAATAAAAAAAAAAA-AAA | SEQ ID NO: 932 |
| 1639358 | TTWTTTAATTTTTTTATTTTTTAATTAT-TAA | SEQ ID NO: 933 |
| 1639379 | CCTYTTTTCTYTTTTTTTTCCCTT-YTC-CTT | SEQ ID NO: 934 |
| 1639405 | T-ATAA-ATA-AAAAAAA-TTTAA-WAT-T-A | SEQ ID NO: 935 |
| 1639422 | T--T----T-----AW---TTTA--W---T-- | SEQ ID NO: 936 |
| 1639423 | T--T----T------T---TTTA--W---T-- | SEQ ID NO: 937 |
| 1639425 | T--T-A--T------A-A-TTTT--T---T-- | SEQ ID NO: 938 |
| 1639589 | CCGCGGGGCGGGCGGGCGGCCCGG-SGCGCGG | SEQ ID NO: 939 |
| 1639649 | T--T-A--T--AA--AA--TTTA--T-TAT-- | SEQ ID NO: 940 |
| 1639650 | T--T-C--T--CT--CT--TTTC--T-TCT-- | SEQ ID NO: 941 |
| 1639656 | G--GA-A-G--AG-AAG-AGGG---G-GAGAA | SEQ ID NO: 942 |
| 1639658 | T--TCCC-T--CT-CCT-CTTT---T-TCTCC | SEQ ID NO: 943 |
| 1639685 | AAWAAAATAAAAAAATAAAAAATTAATAAATT | SEQ ID NO: 944 |
| 1639720 | CCCCCCCCCCCCGCCCGCC-CCCCCCCCCCCC | SEQ ID NO: 945 |
| 1640319 | TTTTAATATAWAAA-T--ATTTTTATTTATTT | SEQ ID NO: 946 |
| 1640338 | AAAACCCCACACCC-AC-CAAAAAC-AACAAA | SEQ ID NO: 947 |
| 1640347 | CCCCTTCTCTYTTT-CT-TCCCCCTTCCTCCC | SEQ ID NO: 948 |
| 1640404 | CCCCAACACAMAAAACAAACCCCCAMCCACCC | SEQ ID NO: 949 |
| 1640483 | CCMMAAAACAMAAAACAAACCCCCAMCCACCC | SEQ ID NO: 950 |
| 1641130 | TTTKGG-GTGK-TGGTGGGTTTTTGKTTGTTT | SEQ ID NO: 951 |
| 1641172 | TTTWAA-ATAWTTAATTAATTTTTAWTTATTT | SEQ ID NO: 952 |
| 1641442 | AAAAGGGGA-AAAG-AA-GAAAAAGRAAGAAA | SEQ ID NO: 953 |
| 1641449 | CCCC-CC-C-CCCCACC-CCCCCCMCCCACCC | SEQ ID NO: 954 |

-continued

| Position | Sequence | SEQ ID NO: |
|---|---|---|
| 1641451 | TTTT-AATT-TTTTTTT-TTTTTTTWTTTTTT | SEQ ID NO: 955 |
| 1641714 | CCYYTTCTCTTCCYTCCTTCCCCCTCCCTCCC | SEQ ID NO: 956 |
| 1642236 | TTTTCCCCTCY-TCCTT-CTTTTTCYTTCTTT | SEQ ID NO: 957 |
| 1642267 | CCYYTTTTCTYCCTTCC-TCCCCCTCCCTCCC | SEQ ID NO: 958 |
| 1642307 | CCYYTTTTCTYCCTTCC-TCCCCCTYCCTCCC | SEQ ID NO: 959 |
| 1642711 | TTTTGKTKTGK-TGGTTGGTTT-TGKTTGTTT | SEQ ID NO: 960 |
| 1643324 | CCYCTTT-CTTCCTTCC-TCCCCCTYCCTCCC | SEQ ID NO: 961 |
| 1643682 | TYTTTTTTYTTTTYTTYTTTTTTT-TTTTTTT | SEQ ID NO: 962 |
| 1643963 | GGGRAAGGGGGGGAAGGAAGGGGGAAGGAGGG | SEQ ID NO: 963 |
| 1644011 | CCTYTTTTCTTTTTTTTTTCCCTTTYTCTCTT | SEQ ID NO: 964 |
| 1644076 | GGGSCCCCGCSGGCCGGCCGGGGGCSGGC-GG | SEQ ID NO: 965 |
| 1644328 | TTTYCCTCTCYTTC-TTCC-TT-TCYTTCTTT | SEQ ID NO: 966 |
| 1644511 | TTTT--T-T-T-CT-TCT-TTTTT-TTTTT-T | SEQ ID NO: 967 |
| 1644513 | GGGG-TG-G-KGGT-GGT-GGGGG-GGGTG-G | SEQ ID NO: 968 |
| 1644525 | TTTTTTCTT-TTTT-TTTTTTTTT-T-TTTTT | SEQ ID NO: 969 |
| 1644537 | AAWAAAATA-WAAAAAAAAAAAAAAAAAAAAA | SEQ ID NO: 970 |
| 1644750 | GGGGGGGGGGGTTGGTTGGGGGGGGGTGGGGT | SEQ ID NO: 971 |
| 1645218 | AATAAATAA-ATTAATT-AAAAATAA-AAAAT | SEQ ID NO: 972 |
| 1645228 | GGGKTTGGG-GGGTTGG-TGGG-GTTGGTGGG | SEQ ID NO: 973 |
| 1645334 | CYCCTTCCCCCCCTTCCT-CCCCCTYC-TCCC | SEQ ID NO: 974 |
| 1645582 | GGCGGGCGGGGCCGGCC-GGGGGGGGCGGSCC | SEQ ID NO: 975 |
| 1645815 | AAGAAAAAA--GGAAGGAAAAAAAAAGAAAAG | SEQ ID NO: 976 |
| 1646008 | AACMCCCCM-ACCCC-CC-AAAAACMCACAAC | SEQ ID NO: 977 |
| 1646226 | AAAAAA-MA-AAA--CA--AAAAA-AAAA-AA | SEQ ID NO: 978 |
| 1646229 | CCCCCC-CC-CYY--CC-CCCCCC-C-CC-C- | SEQ ID NO: 979 |
| 1646564 | TTTYTTTTTTTTC-TTCTTTTTTTTTTTTTTT | SEQ ID NO: 980 |
| 1646600 | AAWW-ATAA-ATATAW-ATAAAAAAATAAAA- | SEQ ID NO: 981 |
| 1646602 | GGRR-GAGG-GAG-GR-GAGGGGGGGAGGGG- | SEQ ID NO: 982 |
| 1646890 | AAWAAAATAAWAAAAAA-AAAAAAAAAAAAA- | SEQ ID NO: 983 |
| 1647863 | GGGSGSGGG-GGGS-GSGGGGGGSG-SGSGGC | SEQ ID NO: 984 |
| 1648561 | AAMACCAAAAACCCCCC-CAAAACCCCACAAC | SEQ ID NO: 985 |
| 1649069 | GGGGGGTGGGGKGGGGGGG-GGGT-GGGG-GG | SEQ ID NO: 986 |
| 1649189 | AATWTTTTATWTTT-TTTTAAAATTATATAAT | SEQ ID NO: 987 |
| 1649194 | TTAWAAAATAWAAA-AAAAWTTTAATATATTA | SEQ ID NO: 988 |
| 1649212 | AAAAAACAAAAAAA-AAAAAAAACAAAAAAAA | SEQ ID NO: 989 |
| 1649292 | A-GAAAAAAAAGGA--G-AAAAAAAAGAAAAG | SEQ ID NO: 990 |
| 1649335 | T--TTWT-TTTWTT--TTTTTT-A-T--TT-T | SEQ ID NO: 991 |
| 1649343 | A-AAAA-AAAAWW--AWAAAAAAAAAA-AA-A | SEQ ID NO: 992 |
| 1649385 | AAA-AAGA-AAAAA-AAAAAAAAGAAAAAAAA | SEQ ID NO: 993 |

-continued

| Position | Sequence | SEQ ID NO: |
|---|---|---|
| 1649892 | TTATTTATTTWAATTAATTTTTTTTTATTTTA | SEQ ID NO: 994 |
| 1649975 | AAGAAAAAAAARGGAAGG-AAAAARAAGAAAAG | SEQ ID NO: 995 |
| 1650007 | AAGAAAAAAAAG-AAGGAAAAAAAAAAGAAAAG | SEQ ID NO: 996 |
| 1650035 | TTCTTTTTTTYCCTTCCTTTTTTTTTCTTTT- | SEQ ID NO: 997 |
| 1650053 | TTYTTTTTTTTCCTT-CTTTTTTTTTCTTTT- | SEQ ID NO: 998 |
| 1650057 | AARAAAAAAAARGGAAGGAAAAAAAAAGAAAA- | SEQ ID NO: 999 |
| 1650062 | AARAAAAAAAARGGAAGGAAAAAAAAAGAAAA- | SEQ ID NO: 1000 |
| 1650140 | GGTGGGTGGGKTTGGTTGGGGGGGGGTGGG-T | SEQ ID NO: 1001 |
| 1650162 | T-TTTTTTTTTTTTTTTTTTTTWTTTTTTTAT | SEQ ID NO: 1002 |
| 1650201 | G-GGGGAGGGGGGG-GG-GGGGGGGGGGGGG | SEQ ID NO: 1003 |
| 1650312 | GGARAAAGGGRAAAAAAAAG-GGGAR-GAGGA | SEQ ID NO: 1004 |
| 1650501 | TTTTTTATTTATTTTTTTTTTTTTTTTTTTTT | SEQ ID NO: 1005 |
| 1650892 | TTTT-AT-T-T-T--T--ATTTTTT--TWT-- | SEQ ID NO: 1006 |
| 1651006 | TTYTTTTTTC--TTTC-T-TTTTT--CTTT-C | SEQ ID NO: 1007 |
| 1651019 | TTWTA-T-TAT--AAATA-TTTTT--AT-T-A | SEQ ID NO: 1008 |
| 1651075 | AAAAGGA-AAAAAGGAAGGAAAAAGRAAGAAA | SEQ ID NO: 1009 |
| 1651085 | CCCCCCC-CCCAACCCACCCCCCCCCCCCCCC | SEQ ID NO: 1010 |
| 1651266 | TTTTTTTCTTTTTTTTT-TTTT-YTTTTTTCT | SEQ ID NO: 1011 |
| 1651404 | AAWAAAATATWAAA-TAAAAAA-A-ATAAATT | SEQ ID NO: 1012 |
| 1651496 | AAAA-AAAAAAGGAAAGAAA-AAAA-AAAAAA | SEQ ID NO: 1013 |
| 1651574 | A--AAAAAAAAWTAA-TAAAAA-AAA-AAAA- | SEQ ID NO: 1014 |
| 1651575 | T--TTTTTTATW-TT-TTTTTT-TTT-TWTT- | SEQ ID NO: 1015 |
| 1651579 | AA-AAAA-AAARGAAAAAAAAAA-AAA-AAA-A | SEQ ID NO: 1016 |
| 1651787 | A-AAAAA-AA-GGAAA-A-AAAAAAAAAAAAA | SEQ ID NO: 1017 |
| 1651950 | A-AMCCM-AAM-ACCAA-CAAACACCAACACA | SEQ ID NO: 1018 |
| 1651977 | AAAWTTT-AAW-TTTATT-AAATATWAATA-A | SEQ ID NO: 1019 |
| 1651991 | AAWWTTT-ATT-ATTTAT-AAA-ATWTATA-T | SEQ ID NO: 1020 |
| 1651993 | TTTTTTT-TTT-ATTTAT-TTT-TTTTTTT-T | SEQ ID NO: 1021 |
| 1651996 | TTTWAA--TTW-TAATTA-TTT-TAWTTAT-T | SEQ ID NO: 1022 |
| 1652011 | CCCMAAA-CCCAAAACAAACCCACAMCCACAC | SEQ ID NO: 1023 |
| 1652098 | AAAAAAAAAAACCAAACAAAAAAAAAAAAAAA | SEQ ID NO: 1024 |
| 1652139 | AACAAAAAACAAAAACAAAAAAAAAACAAAAC | SEQ ID NO: 1025 |
| 1652235 | GGCGCCCCGCGCCCCCC-CGGGCGCSCGCGCC | SEQ ID NO: 1026 |
| 1652253 | AAAACCCCAAACCCCAC-CAAACACMAACA-A | SEQ ID NO: 1027 |
| 1652352 | TTTTTTTTTTTTTTTCTTTTTTTTTTCTTTTC | SEQ ID NO: 1028 |
| 1652357 | CCCYTTCCCCCTTTTCTCTCCCCCTYCCTCCC | SEQ ID NO: 1029 |
| 1652401 | TTTTTYCCTTYTTTTTTCTTTTCTTTTTTTCT | SEQ ID NO: 1030 |
| 1652453 | AAGRGGGGAGRGGGGGG--AAAGAGRGAGAGG | SEQ ID NO: 1031 |

-continued

| Position | Sequence | SEQ ID NO: |
|---|---|---|
| 1652715 | GCGGG-GGSG--SG-GG-CG-SGGG---SGG- | SEQ ID NO: 1032 |
| 1652723 | TTT-T-CCT-TTTT-TT-TTTTC-TT--T-C- | SEQ ID NO: 1033 |
| 1652747 | GGGGGGGAGGGGGG-G--GGGGAGGGGGG-AG | SEQ ID NO: 1034 |
| 1653494 | AAAAAAAAAAAGGAAAGAAAAAAA-AAAAAAA | SEQ ID NO: 1035 |
| 1653520 | CCMCCCCCCCACCCCACACCCCCC-CACCCCA | SEQ ID NO: 1036 |
| 1653597 | GGGGGGGAGGGGGGGGGGGGGGAG--GGGGAG | SEQ ID NO: 1037 |
| 1653769 | CCCCCCCCCCSCCCCCCGCCCCCCCCCCCCCC | SEQ ID NO: 1038 |
| 1653795 | AAAAAAAGAAAAAAAAAAAAAAAGAAAAAAAGA | SEQ ID NO: 1039 |
| 1653979 | GGGGGGGTGGGTTGGG--GGGGTGGGGGGGTG | SEQ ID NO: 1040 |
| 1654008 | AAAAAAAAAAATTAAA--AAAA-AAAAAAAAA | SEQ ID NO: 1041 |
| 1654084 | TTTTTTTTTTTGGTTTGTTTTTTTTTTTTTTT | SEQ ID NO: 1042 |
| 1654113 | CCCCCCCCCCC-GCCCGCCCCCCCCCCCCCCC | SEQ ID NO: 1043 |
| 1654119 | GGAGAAAAGAR-AAAAAAA-GGAGARAGAGAA | SEQ ID NO: 1044 |
| 1654174 | GGGGGGGTGGGGGGGGG-GGGG-GGGGGGGTG | SEQ ID NO: 1045 |
| 1654178 | TTTTTTTCTTTTTTTTT-TTTT-TTTTTTTCT | SEQ ID NO: 1046 |
| 1654234 | AAAAAAAAAAAGAAAAR-AAAAAAAA-AAA-G | SEQ ID NO: 1047 |
| 1654235 | AAAAAACAAAA-AAAAM-AAAA-AAA-AAA-- | SEQ ID NO: 1048 |
| 1654287 | AAAAAAT-AAA--AA-T-AAAA-AAA-AAA-T | SEQ ID NO: 1049 |
| 1654362 | TTTTTTTCTTTTTTTTT-TTTCT-TTTTTCT | SEQ ID NO: 1050 |
| 1654368 | GGAGGGGAGGGAAGGAAGGGGGAG-GAGGGAA | SEQ ID NO: 1051 |
| 1654467 | TTKTTTTTTTTGGTTGG-TTTTTT-TGTTTTG | SEQ ID NO: 1052 |
| 1654484 | AAGAAAGGAAAGGAAGGAAAAAGA-AGAAAGG | SEQ ID NO: 1053 |
| 1654519 | TTATTTTTTTTAATTAATTTTTTTTTTATTTA | SEQ ID NO: 1054 |
| 1654529 | CC-C-CCCCCC--CC--CCCCCCCCCGCCCCG | SEQ ID NO: 1055 |
| 1654530 | TT-T-TTATTT--TT--TTTTTATTTTTTTAT | SEQ ID NO: 1056 |
| 1654634 | GGGGGGGGGG-AAGGGAGGGGGGGGGGGGGG | SEQ ID NO: 1057 |
| 1654649 | GGGGGGGGGGGAAGGGAGGGGGGGGGGGGGG | SEQ ID NO: 1058 |
| 1654795 | TTTTTTAATTAAAT-TAATTTTATTTTTTTAT | SEQ ID NO: 1059 |
| 1654849 | CCYCCCTTCCYTTCCTTTCCCCTCCCTCCCTT | SEQ ID NO: 1060 |
| 1654906 | CCCCCCAACCMCCC-CCACCCCMCCCCCCCAC | SEQ ID NO: 1061 |
| 1655007 | CCCCCC-ACCCCCC-CC-CCCCACCCCCCCAC | SEQ ID NO: 1062 |
| 1655042 | GGGGGGGGGGGCCG-GCGGGGGGGGGGGGGG | SEQ ID NO: 1063 |
| 1655195 | CCCCCCTTCCYCCCCCC-CCCCCCCCCCCCC- | SEQ ID NO: 1064 |
| 1655349 | TTTTTT--TTT-ATT-T-TTTT-TTTATTTTT | SEQ ID NO: 1065 |
| 1655353 | GG-GGGAAGGR-AGG-AAGGGG-GGGAGGGG- | SEQ ID NO: 1066 |
| 1655408 | GGGGGGAAGGGGGGGGGGGGGGGGGGGGGGG- | SEQ ID NO: 1067 |
| 1655881 | TTGTTTTTT-TTTTTGTT-TTTTTTTGTTTTG | SEQ ID NO: 1068 |
| 1656044 | GGGGGGAGGGGAAGGGAGGGGGGGGGGGGGGG | SEQ ID NO: 1069 |
| 1656188 | AARAAAG-AAAAAA-AA--RAAAAAARAAAAA | SEQ ID NO: 1070 |

-continued

| Position | Sequence | SEQ ID NO: |
|---|---|---|
| 1656189 | GGSGGGC-GGGGGG-GG--GGGGGGGSGGGGG | SEQ ID NO: 1071 |
| 1656263 | GGG-GGCCGGGGGGGGGGGGGGGGGGGGGGG | SEQ ID NO: 1072 |
| 1656348 | TTATAAAATAAAAA-AAAATTTATATATATAA | SEQ ID NO: 1073 |
| 1656394 | CCYCCC-TCCCTTCCTTTCCCCCCCCTCCCCT | SEQ ID NO: 1074 |
| 1656622 | TTYTTTTTTTTTTTTCTTTTTTTTTTCTTTTC | SEQ ID NO: 1075 |
| 1656645 | TTTTTTTTTTTCCTTTCTTTTTTTTTTTTTT- | SEQ ID NO: 1076 |
| 1656898 | C-CCCCTTCCCCCCC-C-CCCCCCCCC-CCCC | SEQ ID NO: 1077 |
| 1656979 | GGGGGGAGGGGGGGGGGGGGGGGGGGGGGGG | SEQ ID NO: 1078 |
| 1657025 | AAWAAATT-AWTWAATT-AAAAAAAATAAAA- | SEQ ID NO: 1079 |
| 1657162 | CCCCCCTTCCCCCCCCCCCCCC-CCCCCCCCC | SEQ ID NO: 1080 |
| 1657319 | GGGGGGGGGGGCCG-G---GGGGGGGGGGSG- | SEQ ID NO: 1081 |
| 1657593 | AAAAAAATAAATAAAA-AAAAAAAAA-AAAAA | SEQ ID NO: 1082 |
| 1657661 | AAAAAAATAAATTAAAT-AAAAAAAAAAAAAA | SEQ ID NO: 1083 |
| 1657803 | TTTTTT--TTAAAT-TA-TTTTTTTT-TTTTT | SEQ ID NO: 1084 |
| 1657814 | AAAATT--AAT-TT-A--TAAAAAWWAATAAA | SEQ ID NO: 1085 |
| 1657857 | TTTTTTTC-TTCCTTT--TTTTTTTTTTTTTT | SEQ ID NO: 1086 |
| 1657867 | AAAAAAAGAAAGGAAA-AAAAAAAAAAAAAAA | SEQ ID NO: 1087 |
| 1658176 | CCCCCCCCCC-T-CCCTTCCCCCCCCCCCCC- | SEQ ID NO: 1088 |
| 1658177 | GGGGGGGGGG-TKGGGTTGGGGGGGGGGGGG- | SEQ ID NO: 1089 |
| 1658205 | CCCCCCC-CCCAAC-CACCCC-CCCCCCCCC- | SEQ ID NO: 1090 |
| 1658219 | CCCCCCC-CCTTTCCCTT-CCCCCCCCCCCC- | SEQ ID NO: 1091 |
| 1658281 | TTTT-TTTT-YCCTTTCCT-TTTTTTTT-TTT | SEQ ID NO: 1092 |
| 1658580 | AAAAAAAA-AAAAAATTAAAAAAAA--AAAAT | SEQ ID NO: 1093 |
| 1658589 | AAAAAAACAACAAAAC-CAAAAAAA--AAAA- | SEQ ID NO: 1094 |
| 1658590 | CCCCAACCCCCCCCCC-CAACCCCC---ACC- | SEQ ID NO: 1095 |
| 1658617 | AAAA-AGAAAAGGAAAGAAAAAAAA-AAAAAA | SEQ ID NO: 1096 |
| 1658632 | CCCCCCC-CCCTTCCCTCCCCCCCC-CCCCCC | SEQ ID NO: 1097 |
| 1658707 | GGAGGGA-GGG-AGGAA-GGG-GGGGAGGGG- | SEQ ID NO: 1098 |
| 1658756 | GG-GGGGGGGGTTGGGT-GGGGGGGGGGGG- | SEQ ID NO: 1099 |
| 1659101 | AAAAAAAAAAAGGAAAGAAAAAAAAAAAAAAA | SEQ ID NO: 1100 |
| 1659190 | AAAAAAAAAAAGGAAAGAAAAAAAAAAAAAAA | SEQ ID NO: 1101 |
| 1659382 | TTTTTWTTTTT-TT--TT-TTTTT-W-TTTT- | SEQ ID NO: 1102 |
| 1659384 | AWWAAAATAAW-AA---T-AAAAA-ATAAAA- | SEQ ID NO: 1103 |
| 1660414 | CCMCCCCACCMAACCAAACCCCCCCCACCCCA | SEQ ID NO: 1104 |
| 1660604 | AAWA---AA-A-AT-WT--AAAAA--AA-AA- | SEQ ID NO: 1105 |
| 1660606 | TTTT---TT-T-AA-TA--TTTTT--TT-TT- | SEQ ID NO: 1106 |
| 1660618 | GGGGT--GG-GTG--G---GGGGG-GGG-GGG | SEQ ID NO: 1107 |
| 1660621 | AAAAG--AA-AGAG-A-A-AAAAA-AAA-AAA | SEQ ID NO: 1108 |

-continued

| Position | Sequence | SEQ ID NO: |
|---|---|---|
| 1660668 | AAAAGGAAA-AAAG-AAAGAAAAA-RAAGAAA | SEQ ID NO: 1109 |
| 1660682 | TTATAAATT-TTAA-ATAATT-TT-WATATTA | SEQ ID NO: 1110 |
| 1660704 | TT-TTTTTTTTCTTCT-TTTTTT-TC-TTT- | SEQ ID NO: 1111 |
| 1660795 | CCCCCCWCC-CCCY-CC--CCCCCTC-C--CC | SEQ ID NO: 1112 |
| 1660796 | TTTTTTTTT-TTTY-TT--TTTTTCT-T--TT | SEQ ID NO: 1113 |
| 1660935 | T-YTTTTTTTTT--TCTC-TTTTTTTCTT-TC | SEQ ID NO: 1114 |
| 1660958 | CCMCCCCCCCCCAC-AC--CCCCCCCACCCCA | SEQ ID NO: 1115 |
| 1660963 | TTCTTTTTTTTTCT-CT--TTTTTTTCTTTTC | SEQ ID NO: 1116 |
| 1661003 | CC-CCCC-CCCTTCCTT-CCCCCCCCTCCCC- | SEQ ID NO: 1117 |
| 1661011 | TT-TTTT-TTTTCTTCT-TTTTTTTTCT-TT- | SEQ ID NO: 1118 |
| 1661015 | GG-RAAG-GAGGGAAGG-AGGGGGAGG--GG- | SEQ ID NO: 1119 |
| 1661025 | CC-SGGCCCGCC-GGCC-GCCCCCGCC--CC- | SEQ ID NO: 1120 |
| 1661066 | A-AA-AAAAAAAAAWAAA-AAAAA-AAA-AAA | SEQ ID NO: 1121 |
| 1661084 | T-CT-TTTT-TCC-TCCC-TTTTTTTCT-TTC | SEQ ID NO: 1122 |
| 1661088 | A-GA-GGAA-AGG-GGGG-AAA-AGAGA--AG | SEQ ID NO: 1123 |
| 1661104 | T-CT-CCTT-TCC-CCCC-TTT-TCTCT--TC | SEQ ID NO: 1124 |
| 1661128 | A-GA-GG-A-AGGGGG-G-AAAAAGAGA-AAG | SEQ ID NO: 1125 |
| 1661129 | C-CC-TC-C-C-CTTC-C-CCCCCTCCC-CCC | SEQ ID NO: 1126 |
| 1661131 | G--G-GG-G-GG-GGC-C-GGGGGGGCG-GGC | SEQ ID NO: 1127 |
| 1661150 | C--C-CC-C-CCT----T-CCCCCCC-C-CCT | SEQ ID NO: 1128 |
| 1661160 | T--T---TT-TCC----C-TTTTT-TCT-TTC | SEQ ID NO: 1129 |
| 1661214 | T-GTTTTTTTKGGTT-GG-TTTTT-TGTTTTG | SEQ ID NO: 1130 |
| 1661239 | TTCYCCCTTCC-CCCC-CCTTTTT-TCTCTTC | SEQ ID NO: 1131 |
| 1661259 | CCSSGGGCCGCCCGGCCCGCCCCCGCCCGCCC | SEQ ID NO: 1132 |
| 1661275 | CCYCCC-CCCYCTCCTCTCCCCCCCCTCCCCT | SEQ ID NO: 1133 |
| 1661328 | T-CYCCCTTC-CCCCCCCC-TTTTCTCTCTTC | SEQ ID NO: 1134 |
| 1661356 | A-RAGGGAAGAAAGGAAAG-AAAAG-A-GAAA | SEQ ID NO: 1135 |
| 1661456 | TT---AA-TAT---A----TTT-T-T-TATT- | SEQ ID NO: 1136 |
| 1661461 | AA---AA--AA---AG-G-AAAAA-AGAA--- | SEQ ID NO: 1137 |
| 1661539 | T--TTTTTT-CTCTT-TCTTT-TTTTCTTTTC | SEQ ID NO: 1138 |
| 1661560 | T-ATTTT-T--T-TTAT--TT-TTTT-TTTT- | SEQ ID NO: 1139 |
| 1661768 | CCYCCCCCCCYCTCCTCTCCCCCCCCTCCC-T | SEQ ID NO: 1140 |
| 1661783 | GGRGGGGGGGRAAGGAA-GGGGGGGGAGGGGA | SEQ ID NO: 1141 |
| 1661971 | AAWAAAA-AAWATAATAT-AAAAAAATAAA-T | SEQ ID NO: 1142 |
| 1662071 | CCMCCC--CCCCACCAC-C-CCCCCC--CCC- | SEQ ID NO: 1143 |
| 1662122 | TT-T-T-TTTTTT---T--TTTTT-TATATTT | SEQ ID NO: 1144 |
| 1662124 | AATATT-AATAAA---A--AAAAA-WAAAAAA | SEQ ID NO: 1145 |
| 1662258 | CCYCCCCCCCYCTCCTCTCCCCCCCCTCCCCT | SEQ ID NO: 1146 |
| 1662283 | CCACCCCCCCMCACCACACCCCCCCCACCCCA | SEQ ID NO: 1147 |

-continued

| Position | Sequence | SEQ ID NO: |
|---|---|---|
| 1662373 | CCCCCCCGCCCGCCCCG-CCCCCCCCCCCCC | SEQ ID NO: 1148 |
| 1662399 | TT-TTTGKTTTGKTTT--TTTTTTTTKTTTTT | SEQ ID NO: 1149 |
| 1662401 | TT-TTTTTTTKTTTTGT-TTTTTTTTKTTTTT | SEQ ID NO: 1150 |
| 1662555 | GGGGAAGGGAGGGAAGGGAGGGGGAGGGA-GG | SEQ ID NO: 1151 |
| 1662568 | AARAAAAAAA-AGAAGAGAAAAAAAAGAAAAG | SEQ ID NO: 1152 |
| 1662576 | AACAAAAAAA-ACAACACAAAAAAAAC-AAAC | SEQ ID NO: 1153 |
| 1662653 | GGKGGG-GGGKGTGGTG--GGGGGGGTGGGGT | SEQ ID NO: 1154 |
| 1662656 | CCSCCC-CCCSCGCCGC--CCCCCCCGCCCCG | SEQ ID NO: 1155 |
| 1662666 | GG-GGG-GGGSGCGGCG--GGGGGGGCGGGGC | SEQ ID NO: 1156 |
| 1662672 | TT-KGG-TTGTTTGGTT--TTTTTGKTTGTTT | SEQ ID NO: 1157 |
| 1662692 | CC-CCC-CC-YCTCCTCT-CCCCCCCTCCCCT | SEQ ID NO: 1158 |
| 1662694 | TTCTGG-TT-YCCGGCCC-TTTTTGTCTGTTC | SEQ ID NO: 1159 |
| 1662706 | CCCCTT-CC--TCTT-TC-CCCCCTYCC-CCC | SEQ ID NO: 1160 |
| 1662725 | GGCG-G-GG---CGG-GC-GGG-G-G-G-GGC | SEQ ID NO: 1161 |
| 1662758 | GG-G---GG-RGA----A-GGGGG-G-G-GG- | SEQ ID NO: 1162 |
| 1662766 | TTCTCC-CT-YCCC---CCTTTTTCY-T-TT- | SEQ ID NO: 1163 |
| 1662804 | CCTCTT-CC-C--T--C--CCCCCTY-CTCC- | SEQ ID NO: 1164 |
| 1662841 | CC-CTT-CC----T----TCCCCCTY-CTCC- | SEQ ID NO: 1165 |
| 1662854 | TT-T-GTT--T--G----GTTTTTTT-TKTT- | SEQ ID NO: 1166 |
| 1662858 | GG-R--GGG-G--------GGGGGAR-GAGG- | SEQ ID NO: 1167 |
| 1662879 | GG-R-AGAG-GG-A--G--GGGGGAR-GAGG- | SEQ ID NO: 1168 |
| 1662882 | GG-G-GGGG-GT-G--T--GGGKGGG-GGGG- | SEQ ID NO: 1169 |
| 1662894 | AAGR-GGAA-AG-G--G-GAAAAAGG-AGAA- | SEQ ID NO: 1170 |
| 1662916 | GGKGGGGGGGKGTGGTG-GGGGGGGGTGGGGT | SEQ ID NO: 1171 |
| 1662935 | TTCTCCCCTCYCCCCCCCCTTTTTCYCTCTTC | SEQ ID NO: 1172 |
| 1662980 | GGAGGGGGGGR-AGGA-RGGGGGGGGRGGGGA | SEQ ID NO: 1173 |
| 1662997 | CCCCCMCCCCCCCCCC-MCCCCCCCCMCCCCC | SEQ ID NO: 1174 |
| 1663007 | TT-TTTCTTTTCTTTT-TTTTTTTTTTTTTTT | SEQ ID NO: 1175 |
| 1663014 | GG-GGRTGGGGGGGGG-RGGGGGGGGRGGGGG | SEQ ID NO: 1176 |
| 1663032 | GG-GGRAGGGGGAGG--AGGGGGGGGAGGGG- | SEQ ID NO: 1177 |
| 1663033 | CC-CCYCCCCCCCCC--TCCCCCCCCTCCCC- | SEQ ID NO: 1178 |
| 1663051 | GGARAAAGGAG--A-A-AAGGGGGAR-GAGG- | SEQ ID NO: 1179 |
| 1663064 | AAGAAAGAAAAGGA-G-GAAAAAAAR-AAAA- | SEQ ID NO: 1180 |
| 1663110 | GGGGGGGAGGG--GG--AGGGGGGGG-GGGG- | SEQ ID NO: 1181 |
| 1663143 | AAGAGGGGAGA-GGG-G-GAAAAAGR-AGAAG | SEQ ID NO: 1182 |
| 1663181 | CCTYTTTCCTCATTTTA-TCCCCCTYTCTCCT | SEQ ID NO: 1183 |
| 1663182 | GGGGGGGGGGGAGGGGA-GGGGGGGGGGGGG | SEQ ID NO: 1184 |
| 1663188 | AAGAAAAAAAAAGAAGA-AAAAAAAAGAAAAG | SEQ ID NO: 1185 |

-continued

| Position | Sequence | SEQ ID NO: |
|---|---|---|
| 1663219 | CC-CCCCCC-CA-C--A--CCCCCCC-C-CC- | SEQ ID NO: 1186 |
| 1663226 | CC-CTTTCC-CT-T-----CCCCCTC-C-CC- | SEQ ID NO: 1187 |
| 1663237 | CC-CC--CC-CA-MC-A-CCCCCCCC-CCCC- | SEQ ID NO: 1188 |
| 1663250 | GGAGGGAGG-GA-GG-A-GGGGGGGGAGGGG- | SEQ ID NO: 1189 |
| 1663251 | CCTCCCCCC-CC-CC-C-CCCCCCCCTCCCC- | SEQ ID NO: 1190 |
| 1663288 | CCSCCCCCCCCCGCCGCGCCCCCCCCCGCCCCG | SEQ ID NO: 1191 |
| 1663298 | AAGRGGGAAG-GGG-GGGGAAAAAGAGAGAAG | SEQ ID NO: 1192 |
| 1663445 | GGGGGG-GGGGAGGGGAGGGGGGGGGGGGGG | SEQ ID NO: 1193 |
| 1663463 | CCCCCC-CCCCTCCCCTCCCCCCCCCCCCCC | SEQ ID NO: 1194 |
| 1663479 | AAGRGG-AA-AGGGGGGGGAAAAAGR-AGAAG | SEQ ID NO: 1195 |
| 1663486 | GGARAA-GG-GG-A-GG--GGGGGAR-GAGGG | SEQ ID NO: 1196 |
| 1663501 | CC-Y---CC-CC-T--C--CCCCCTY-C-CC- | SEQ ID NO: 1197 |
| 1663505 | CC-CA--CC-CM-C--C--CCCCCCC-C-CC- | SEQ ID NO: 1198 |
| 1663520 | CCCCC-CCCCCT-CC-TC-CC-CC-CCCCCCC | SEQ ID NO: 1199 |
| 1663534 | GGRRAAGGGAGGGAA-GG-GG-GG-GGGAGGR | SEQ ID NO: 1200 |
| 1663535 | TTTTTTCTTTTCTTT-CT-TT-TT-TTTTTTT | SEQ ID NO: 1201 |
| 1663553 | TTYTTT-TTTTCCT---C-TT-TTTT-T-TTC | SEQ ID NO: 1202 |
| 1663562 | CCMCCC-CCCCCAC-A--CCCCCCCCACCCC- | SEQ ID NO: 1203 |
| 1663564 | AARAAA-AAAAGGA-G--AAAAAAAAGAAAA- | SEQ ID NO: 1204 |
| 1663568 | AARRGG-AAGAGAG-A-AGAAAAAGRAAGAA- | SEQ ID NO: 1205 |
| 1663573 | AAARGG-AAAAAAG-A-AGAAAAAGRAAGAA- | SEQ ID NO: 1206 |
| 1663620 | TTCT-C-TT-TC-----C-TTTTT-TCT-TT- | SEQ ID NO: 1207 |
| 1663628 | TT-T-G-TT-TT---GGTGTTTTTGTTT-TT- | SEQ ID NO: 1208 |
| 1663698 | CCYCCCC-CCYCTCCTCTCCCCCCCCTCCCCT | SEQ ID NO: 1209 |
| 1663719 | CCYCCCC--CYCTCCTCTCCCCCCCCTCCCCT | SEQ ID NO: 1210 |
| 1663724 | GGRGAAG--AGGGAA-GGAGGGGGA-GGAGGG | SEQ ID NO: 1211 |
| 1663731 | CCACAA-CCAMAAAA-AAACCCCCAC-CACCA | SEQ ID NO: 1212 |
| 1663747 | TTKTTT-TTTKT-TT-TG-TTTTTTTG-TTTG | SEQ ID NO: 1213 |
| 1663777 | GGRGGGGGGGRA-GGAAA-GGGGGGGAG-GGA | SEQ ID NO: 1214 |
| 1663798 | GG-G--GGG-KG---TG-GGGGGG-GTG-G-T | SEQ ID NO: 1215 |
| 1663907 | CCGSGG-CC-CGGGG-G--CCCCCGSGCGCC- | SEQ ID NO: 1216 |
| 1663935 | AA-AGA-A--AAAGAAAA-AAAAA-A-A-AAA | SEQ ID NO: 1217 |
| 1663957 | AA-ATT-AATAAA-TAAATAAAA-TW-A--AA | SEQ ID NO: 1218 |
| 1664033 | AAGAAAA-AARGGAAGGGAAAAAA-AGAA-AG | SEQ ID NO: 1219 |
| 1664115 | GGARAAAGGARAAAAAA-AGGGGGARAGAGGA | SEQ ID NO: 1220 |
| 1664472 | AAAA-T-AA-A-ATTA-AWAAA-A-AAAAAAA | SEQ ID NO: 1221 |
| 1664473 | TTTT-A-WT-W-TA-T-TTTTT-T-TTTTTTT | SEQ ID NO: 1222 |
| 1664494 | AAW----AA-A-A--TTAAAAAAA--AAAAA- | SEQ ID NO: 1223 |
| 1664496 | TTW---TTT-T-T--AATTTTTTT-TTTTTT- | SEQ ID NO: 1224 |

-continued

| Position | Sequence | SEQ ID NO: |
|---|---|---|
| 1664567 | AATATTTTATTATTTTATTAAAAATWTATAAT | SEQ ID NO: 1225 |
| 1665072 | AAAAAAAAA-ACAAA-CAAAAAAA-AAAAAAA | SEQ ID NO: 1226 |
| 1665111 | GGGGGGGGGGGTGGG-TGG-GGGGGGGGGGGG | SEQ ID NO: 1227 |
| 1665167 | CCCCCCC-C-CACCCCACCCCCCCCCCCCCC- | SEQ ID NO: 1228 |
| 1665182 | T-AWAAAATAWAAAAAAAATTT-TAWATATT- | SEQ ID NO: 1229 |
| 1665185 | AAAAAAAAAAATAAAATAWAAA-AAAAAAAA- | SEQ ID NO: 1230 |
| 1665206 | AATATTATATWTTTTTTTTAAAAATATATAA- | SEQ ID NO: 1231 |
| 1665230 | AAAAAAAAAAAGAAAAGAAAAAAAAAAAAAAA | SEQ ID NO: 1232 |
| 1665914 | TTTTTT-TTTTATTTTATTTTTTTTTTTTTTT | SEQ ID NO: 1233 |
| 1665941 | AAWAAA-AAAWATAATATAAAAAAAAATAAAAT | SEQ ID NO: 1234 |
| 1666046 | TTATTT-TTTT-TTTWT-TTTTTTTT-TTTTA | SEQ ID NO: 1235 |
| 1666527 | TTTTTTATTTTATTTTATTTTTTTTTTTTTTT | SEQ ID NO: 1236 |
| 1666561 | TTCTTTCTTTYCCTTCCCTTTTTTTTCTTTTC | SEQ ID NO: 1237 |
| 1666912 | AAAAAAAAAAAGAA-AG-AAAAAAAAAAAAAA | SEQ ID NO: 1238 |
| 1667354 | TTTT-TCTTTTCTTTTC-TTTTTTTTTT--TT | SEQ ID NO: 1239 |
| 1667743 | TTTTTTATTTTAWTT-A-TTTTTTTTTTTTT- | SEQ ID NO: 1240 |
| 1667747 | GGSGGGGGGGGGSGG-G-GGGGGGGGCGGGGG | SEQ ID NO: 1241 |
| 1667810 | CCCCCCCCCCCTCCCCTCCCCCCCCCCCCCC- | SEQ ID NO: 1242 |
| 1668348 | AAAWTTATAAAAATTAA-TAAAAATWAATAAA | SEQ ID NO: 1243 |
| 1668441 | AAGAAAGAAARGGAAGGGAAAA-AAAGAAAAG | SEQ ID NO: 1244 |
| 1668887 | GGRGGGAGG-RAAGGAA-GGGGGGGGAGGGGA | SEQ ID NO: 1245 |
| 1668893 | CCYCCCCCC-YCTCCTC-CCCCCCCCTCCCCT | SEQ ID NO: 1246 |
| 1668996 | TTGTTTTTTTKTTTTGT-TTTTTTTTGTT-TG | SEQ ID NO: 1247 |
| 1669034 | AA-A---AA-W-WA-A--AAAAAAAAWAAAA- | SEQ ID NO: 1248 |
| 1669145 | AAAATTA-A-AAATTAA-TAAAAATAAA--AA | SEQ ID NO: 1249 |
| 1669151 | TTATTTA-T-TTATTAT-TTTTTTT-AT--TA | SEQ ID NO: 1250 |
| 1669190 | GGRGGGAGGGRAAGGAAAGGGGGGGGAGGGGA | SEQ ID NO: 1251 |
| 1669348 | CCTYTT-TCTYTTTTTTTTCCCCCTYTCTCCT | SEQ ID NO: 1252 |
| 1669541 | TTYTTT-TTT-TCTTCTC-TTTTTTTCTTTTC | SEQ ID NO: 1253 |
| 1669557 | GGGGGG-GGG-GAGG-G-GGGGGG-GAGGGGA | SEQ ID NO: 1254 |
| 1669564 | AAAAAA-AAA-A-AATA-AAAAAA-ATAAAAT | SEQ ID NO: 1255 |
| 1669584 | CCMCCC-CCCCCACCACACCCCCCACACCCCA | SEQ ID NO: 1256 |
| 1670005 | GGARAA-AGAGAAAAAAAAGGGGGAAAGAGGA | SEQ ID NO: 1257 |
| 1670010 | TTTTTT-TTTTCTTTTCTTTTTTTTTTTTTTT | SEQ ID NO: 1258 |
| 1670034 | TTCTTT-TTTTTCTTCTCTTTTTTTTCTTTTC | SEQ ID NO: 1259 |
| 1670046 | TTGTTTGTTTTTGTT-T-TTTTTTTT-TTTTG | SEQ ID NO: 1260 |
| 1670786 | TTCTCC--TC-TCCCCTCCTTTTTCC-TCTTC | SEQ ID NO: 1261 |
| 1671225 | TTCYCCTCTCCTTCCCTTCTTTTTCYCTC-TC | SEQ ID NO: 1262 |

-continued

| Position | Sequence | SEQ ID NO: |
|---|---|---|
| 1671483 | AAGAGGAGAGRAAGGGAAGAAAAAGRGAGGAG | SEQ ID NO: 1263 |
| 1671607 | TT-T--TAT-T-TA--TT-TTTTT-T-T-TT- | SEQ ID NO: 1264 |
| 1671644 | GGGG--GRG-G-GG-GRGGGGGGGRG-GR-G- | SEQ ID NO: 1265 |
| 1671646 | TTKT--TKT-T-TT-TKTTTTTTTKTGTK-TK | SEQ ID NO: 1266 |
| 1671655 | TTTT-T-TTTT-T-TCT-CTTTTTTTTTTTTT | SEQ ID NO: 1267 |
| 1672660 | CCCCCCCCCCCCACCCCACCCCCCCCCCCCCC | SEQ ID NO: 1268 |
| 1673096 | TTGKGGGGTGKGGGGGGGGTTTTTGKGTGGTG | SEQ ID NO: 1269 |
| 1673273 | AAWWTT-TWTAATTTAAT-AAAAATWAATAAA | SEQ ID NO: 1270 |
| 1673437 | AAAAAAAAAAAAGAAAAGAAAAAAAAAAAAAA | SEQ ID NO: 1271 |
| 1673454 | CCCYTTCTCCCCTTTCCTTCCCCCTYCCTCCC | SEQ ID NO: 1272 |
| 1673470 | AA-AGGAGAAAAAGGAAAGAAAAAGR-AGA-- | SEQ ID NO: 1273 |
| 1673499 | CCCYTTCTCCCCTTTCCTTCCCCCTY-CTCCC | SEQ ID NO: 1274 |
| 1673512 | GGRGGGGGGAGGGGGGG--GGGGGRGGGGGGG | SEQ ID NO: 1275 |
| 1673576 | GGAGGGGGGGAGGGGAG-GGGGGGGGAGGGGA | SEQ ID NO: 1276 |
| 1674853 | CCCCCC-CCCSCCCCCC-CCCCCCCCCCCGCC | SEQ ID NO: 1277 |
| 1674957 | TTTTTTATT-TTTTTTTTTTTTTTTTTTTATT | SEQ ID NO: 1278 |
| 1674960 | CCCCCCTCC-CCCCCCYCCCCCCCCCCCCTCC | SEQ ID NO: 1279 |
| 1674972 | CCCYTTTTC-CCTTTCCTTCCCCCTYCCTTCC | SEQ ID NO: 1280 |
| 1675064 | GG-RAA-AGGGGAAAGGAAGGGGGARGGAAGG | SEQ ID NO: 1281 |
| 1675070 | GG-RAA-AGGGGAAAGGAAGGGGGARGGAAGG | SEQ ID NO: 1282 |
| 1675285 | CCCCCC-CCCCTCCCCTCCCCCCCCCCCCCCC | SEQ ID NO: 1283 |
| 1675368 | AA-A-T--AAAT---A----AAAAAAAA--AA | SEQ ID NO: 1284 |
| 1675396 | AAAA-G-GAAA-G--A----AAAAAAAA--AA | SEQ ID NO: 1285 |
| 1675397 | GGGG-A-AGGG-A--G----GGGGGGGGAAGG | SEQ ID NO: 1286 |
| 1675405 | TTTT-T-TTTTTTTTTT---TTTTTTTTTTTT | SEQ ID NO: 1287 |
| 1675552 | AAGAAAAAAGAAAAAGAAA-AAAAA-GAAAAG | SEQ ID NO: 1288 |
| 1675709 | GGAGGGGGGAGGGGGAGGGGGGGGGGGAGGGGA | SEQ ID NO: 1289 |
| 1675849 | AAAMCCACAAAACCCAA-CAAAAACM-ACAAA | SEQ ID NO: 1290 |
| 1675982 | CCTCCCCCCTCCCCCCCCCCCCCCCCCCCCCC | SEQ ID NO: 1291 |
| 1676018 | AACMCCCCACM-CCCA-CCAAAAACMAACCAA | SEQ ID NO: 1292 |
| 1676087 | AAAAAAMAA-A-AAA-AAAAAAAAAACAACAA | SEQ ID NO: 1293 |
| 1676145 | AATTTTTTA-WTTT--TTT-AA-T-A-ATTAT | SEQ ID NO: 1294 |
| 1676226 | AATA-TTAA-A-ATTT--AAAAAA---ATTA- | SEQ ID NO: 1295 |
| 1676227 | TTGT-GGTT-T-TGGG--TTTTTT---TGGT- | SEQ ID NO: 1296 |
| 1676291 | CCTCCCC-C-CCCCCTCCCCCCCC-CTCCCC- | SEQ ID NO: 1297 |
| 1676587 | TTGT-TG-TGKGGK-GG--TTTTT-KGTK-TG | SEQ ID NO: 1298 |
| 1676704 | GGAGA---G-GA-------GGGGG---G--G- | SEQ ID NO: 1299 |
| 1676705 | AACAC---A-AC-------AAAAA---A--A- | SEQ ID NO: 1300 |
| 1676732 | TT-TAAA-T--AA------TTTTT---TA-T- | SEQ ID NO: 1301 |

-continued

| Position | Sequence | SEQ ID NO: |
|---|---|---|
| 1676809 | T--T-TA----T-T-TAT-TTTTTTTWT--T- | SEQ ID NO: 1302 |
| 1676925 | TTAWAA--TA--AAA--AATTTT--AATAAT- | SEQ ID NO: 1303 |
| 1676981 | TTCTC----C--CC-----T-------T--T- | SEQ ID NO: 1304 |
| 1677110 | C--Y----C---T--T---CC---------CT | SEQ ID NO: 1305 |
| 1677142 | G--K----G-G--T-T---GG--G------GT | SEQ ID NO: 1306 |
| 1677210 | A-GAGG--A-G-G----G--AAA--A---GA- | SEQ ID NO: 1307 |
| 1677244 | TTCYCCCCT-Y-C-CCCC-TTTT--TCTCCT- | SEQ ID NO: 1308 |
| 1677273 | TTGKGGGGTGKGGGGGGGGTTTTTGKGTGGT- | SEQ ID NO: 1309 |
| 1552671 | AGAG-AGGAA-GGG-AG-AGAAGA--AAAAGA (SNAP Stop) | SEQ ID NO: 1310 |

Figure 4:
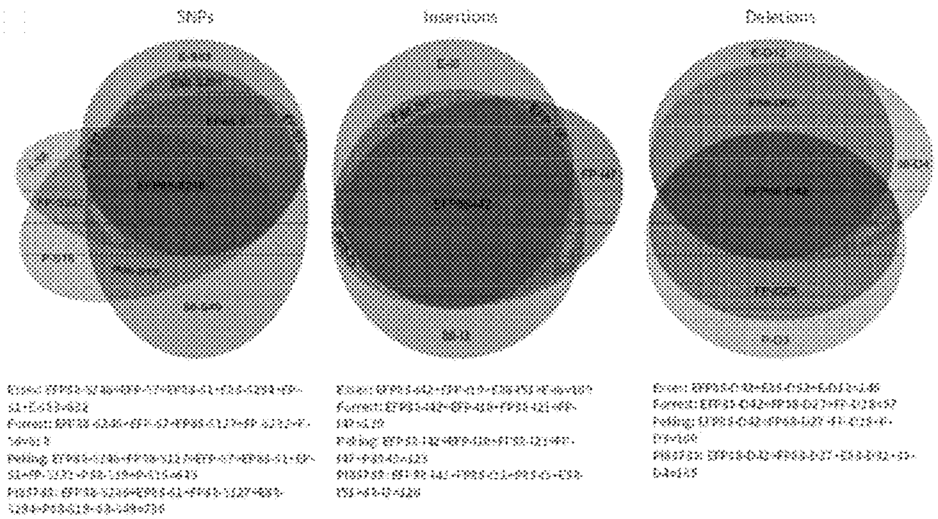
FIG. 4 is Venn diagram illustrating the overlapping SNPs, insertions, and deletions conferring resistance of Rhg1 to SCN. The number following S, I, and D represents the number of SNPs (S), insertions (I), or deletions (D). EFP88, EFP, EF88, EP88, FP88, EP, E88, FP, F88, and P88 represent the overlapping SNPs, insertions, or deletions of Essex (E), Forrest (F), Peking (P), and PI88788 (88); Essex, Forrest, and PI88788; Essex, Forrest, and PI88788; Essex, Peking, and P188788; Forrest, Peking, and P188788; Essex and Peking; Essex and P188788; Forrest and Peking; Forrest and PI88788; and Peking and PI88788, respectively.

127 SNPs (FP88-S127, light-grey), 21 insertions (FP88-121, light-grey), and 27 deletions (FP88-D27, light-grey), possessed by Forrest, Peking, and PI88788, but not by Essex, confer resistance of Rhg1 to SCN (see e.g., FIG. 4). 6 SNPs (C163208A, C163225G, G164965C, G164968T, G164968C and C164974A) and 4 insertions (A164972AGGT and A164972AGGC) locate within the exons of SNAP, and cause amino acid (AA) changes to the predicted SNAP protein (see e.g., TABLE 7).

TABLE 7

| Gene | SNPs/Insertions | Total AA changes | AA (nucleotide) changes in Forrest/Peking | AA (nucleotide) changes in PI88788 |
|---|---|---|---|---|
| Glyma18g02353 | 1 | 1 | 1 | — |
| Glyma18g02420 | 1 | 1 | 1 | — |
| Glyma18g02450 | 3 | 3 | 3 | — |
| Glyma18g02520 | 1 | 1 | — | 1 |
| Glyma18g02590 (SNAP) | 10 | 9 | 3 + 2*<br>D208E (C163225G)<br>D286Y (G164968T)<br>D287E* and −288V (A164972AGGT)<br>L289I* (C164974A) | 4 + 2*<br>Q203K (C163208A)<br>E285Q (G164965C)<br>D286H (G164968C)<br>D287E* and −288A (A164972AGGC)<br>L289I* (C164974A) |
| Glyma18g02650 | 1 | 1 | 1 | — |
| Glyma18g02660 | 1 | 1 | 1 | — |
| Glyma18g02681 | 1 | 1 | 1 | — |
| Glyma18g02690 | 3 | 3 | 3 | — |
| Glyma18g02700 | 1 | 1 | 1 | — |
| Glyma18g02720 | 2 | 2 | — | 2 |
| Glyma18g02741 | 1 | 1 | — | 1 |

Where * indicates that the amino acid changes take place in both Forrest/Peking and PI88788.

Example 7

Tilling Screening and Phenotyping

The following example describes additional evidence for the identification of a missense Forrest SNAP Type III mutation of A111D in SEQ ID NO: 7.

Forrest SNAP Type III missense mutant A111D was screened by TILLING from the newly developed, chemically mutagenized SCN-resistant soybean Forrest population. SNAP in the A111D mutant was sequenced to characterize the identified allele and its subsequent amino acid changes within the predicted protein sequence. SIFT predictions were performed on the identified mutation. SIFT predicts whether an amino acid substitution affects protein function based on sequence homology and the physical properties of amino acids (reviewed in Henikoff and Comai, Annu Rev Plant Biol., 54:375-401, 2003). SIFT predictions with MC<3.25 are considered confident. Changes within a SIFT score<0.05 are predicted to be damaging to the protein.

As shown in TABLE 8, the A111D SIFT score (0.03) is <0.05. This mutation is predicted to damage the SNAP protein. The A111D mutation identified had MC value (3.00)<3.25, thus the SIFT prediction of the A111D mutant can be considered confident.

TABLE 8

SIFT and MC prediction of TILLING-identified soybean mutant.

| Mutant line no. | Effect: Nucleotide | Effect: Amino acid | SIFT (MC) |
|---|---|---|---|
| F1292 | C322A | A111D | 0.03 (3.00) |

Figure 5:
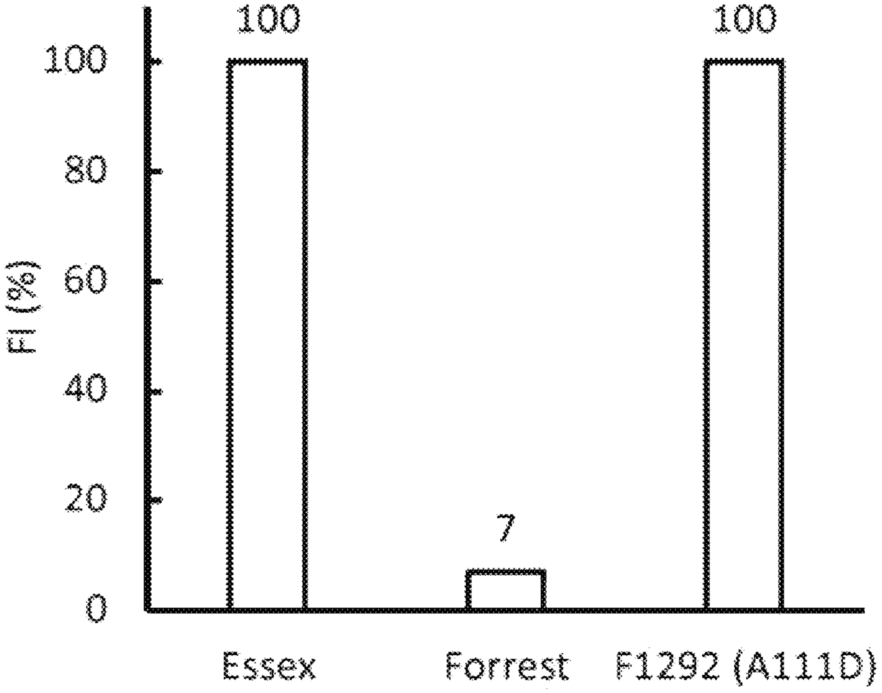
FIG. 5 is a histogram illustrating SCN susceptibility of Forrest SNAP Type III mutant A111D, as compared to SCN-resistant wild-type Forrest.

SCN susceptibility of Forrest SNAP Type III mutant A111D, as compared to SCN-resistant wild-type Forrest, indicates functionality of SNAP A111D mutation in soybean resistance to SCN (see e.g., FIG. 5).

SEQUENCES

>Gm18:1625005..1645004

SEQ ID NO: 1

AAGGAGAAGCAACAAATCAAAGGATGTTTACTTCTGATTTTGGAATGCATCCAAACACTC

CTCACGGGGAATTTTTTAGGCTCTCTACTCCCGCGCGATCTCTCTTGTATCACCAGCAAT

GAAACTTTGTCATATTTTTCCTTCTCTCTCCACACGAGCCATCTCCTATCCTTCTTTTTC

ATATTAGACATTAATTCAAACCCTCTTTCATTTAACTTTCCCTCATGAAAGTGAAATTTA

AATGATAATATTGGATTCTGATTGTGCAAATTAAATACAAGTAAAGGCTTAAATAAATAA

ATAAATAAATATATATATATATATATTCCAATAAATTAATACGTAATTTTATGATTTTGG

TCTTAATAATTTTTTTTAATATAATTTTTCTGTGCCTTTTCTAATAAGGATGATGTCAAG

TTAAAATCATGATGATGTCATTAAGTATCGCATCATCAAATGATGAAGTCATCCATTATC

ATATTAATAAAAAAAATGATATCATTAAATAGGTCGCCTACATCATCAAATGATATCATT

AAGGATTAAAAATAAAAGTTATATATATGCAAGAATAAAAAGTAAAAAAAATGACATTTG

TAAGAACAAAAAAAATATTTAAACATTAAATTAAATGTTTACTTCTATATACTCCCTTAT

CACACTTATCACTCTCAAGTTTGTTTATACAAATTCTATTTATCAAATATTATCACCAAA

CTTTCTCATACTAAAAACTTTTAGTCATGAATGTTGAATTGAGATACCATCTTTCATTTG

AATCAGGGACCAAAATAGTAAAAAAATATTCATTTACTAAAATTCAAAATAATATAATTA

TATAATTTTTTTGGTGAAAACATAATTATATAAATAAATAAAAGAAAGTAATGAAAAATA

TAAACACATATTAAATTAATCTAACAAATAAAAGGTATTTCAATTAGTTGACAATAAAAA

ATATACATTATTAACAAGATTATGACTTAAATTGTCTATCCACAATTGCCAATCAAAATA

CATCACTAAATATAATTATTATAATTATTGATTAAAAAAAAGCTATCAATCCATATTTTG

TAGAATAATACCTTAAAACAAGCATAAACATAAATTCTTAGAACTTAACAAAATACAATT

ATTATTATATTTAAATATATATTAATATAAAGTTCAATTTTGATCCTTATAGTTATATAA

ATTTTATCTTTTAGTTTCTATACTTAAAAATCATCTCTTTTAATCCTATGCATAATATTT

TTAATCTCTTTTAGTTCTTATTATGAGTTTAAACGGTATGGATTAAAAGAAATAAAAATG

ATACAAATTAAAAAAGATTAAAAATAATATGTGTAAAGATTAAAATACACAAATTTAAGT

ATAAGAATTAGGATAAAAATTATATAATTATAAAAATTAAATGAGTAATTAAGCATTAAT

ATAATACTATTATATGAAAAGTTTTGTTTCTAAGAAGAGTCTCGTCCACTTTGCTTTTTA

CAATCACATGTTAAAAAAATTATATCATATTAAGGGATGGCCAATTATCTATGCCTATAT

AGTTTATATGTTTTGAAAAAATTTGGGGCGTCGTGACTCCCCCGCCCTCAAATAGCTCCG

TCAATGACCATTCACATCTTATAGTTCAAGTATCATTGTTACAAGTACACATATTTATTA

CAATATATATACCTAAAGTAAGGTTGTTTTTGCTAACTTAAACATCAAAGTGATTTTGTG

GATAACCCACTGCCACTCAAGGAGTTCGGTGTCGCAGAGTTCAGGCATCTAAAATCTAGA

CCATCGCTTGTCGCACTTTGAACCAAACATGAAGGATGGAGCTTTGAGAAGGAGGGGTGG

AGAAGAAAATGGGGTGCAAATATATATAGCGATGAGGAGTATTTTAATATTTAATTGAAT

GCTTAAATATATTTTTATCTCCTAAATATGTCATTTATTACTTTTAATTCCAGTAAAAAA

ATATATTTTAATCCTTGTAAATTTGTTACTATTACATTTTGTGTTTAATAACATCATCAT

TTGATGATGTAACATTTTAATTATACAATCATTTGATGACATAATTTTATCTTTATATTA

TATTTGATTACATTATCATTTAGTAATGTGGTGCTTGATGATATTATTATGATGCCAATA

TAATATCATCACTATCGGTTCTGATGGTTTTTTTTTTAACAGCGAGAGAAACTAATTAAA

-continued

| SEQUENCES |
| --- |

>Gm18:1625005..1645004

SEQ ID NO: 2

AGACACATAAAAAAGATAGAAAGTAATATATATATATATATATATATATATATATATATA

TATATATGTGTGTGTGTGTGTGAGTGTGTGTGTGTATACGGGTTTACAGGGTATGTAC

AACATGGTTATATATCATATAGTATCTAACTAACTATATATGAAAATAATTTCATAAATT

GTCATGAGTGGTTAGTATAATTTATTGTAAAAATTATTGAGATATGTATGTTTTTTAACT

GCATTGAGATATAGTTTTTTTGACTCATAATATATATTTTATCTGCACTCATAATATATA

GTATCAAGATTTTTTTTTTTGTCAGCGTCATATGTGATGTTAAATGTGATACTTTATATT

GATGAAAAATGCTAATAAGTTTATTTAGCATATTTTTTAAGGAATTAAAAATAATTTTTT

TATTCGAATGCATAAAATTGTGTTGTTTATAATTTTTTTTTATAATTTCCTAAATATTTA

CTTTTTTTAGTTTTTTAACCCATGAGCACTGGTTAACAAAACCATATATCAATTAGGGGT

TATAAATTTTTTAGGCATGATAATTAATGATAATAAAGTTTTAAACTTATGATTTATAAT

GCAGTGCAAAAGTCAATTTTCCAAGACATGTTAGGCAAAACTTGGATTTGAATTCTCTGC

CATCGGAGAAATCAGGCATTCACGTAGTCAGATGATTAAAAGCGTCGACTAGTGAAGATC

TAACAATTCATAAGTCATTTAATAACTTCAACTTTAAAAATATCTAAAAAAATACTAACCA

TATGATGAAATCAAACGGTCCATAATTATGACTGTGTGAATGCAGAGAATCCAAATCCGT

AAAACTTCTGAAAAATGCATATCGAGCGTAAAATTTTATCGAGAATGAGCACGTACTCAG

AAGCATCTAGTATGAATTGAATTATACATATAGATTCAGATGTCTACATGCACACACATA

TATAATGAGACGGATCTTAGATCATATCATACGTATTTGGTATTTAGAGCTGTTACTTCC

TTGTGTTGCTTCCAGTATTGTCACCATTCCACAAGGACAAATCAGGTACCCACCTCTATT

CACATCTGTGTCCATTAATCATCACAACAAAACAATATCCTCCATACATATATCCTGCTC

CTACCTTGTCTATTGCCTTATATGCTCTGAACTCTCCTAGAGTACTCTTTTAGATCCCAT

AATGTTCACCATTCATCAAGGTTTTCCTAATTACTTTAATTAAGTGTTGGAAATGTTGTA

TTTTGAGTTGTTGGCCATATTTTGATGAGTTCTCAAAAGACCAGTTTACTTAGAAATTAT

TAATTTTTTTTAAGTTAGTATGTTCGCTATATGGCCAAGACTAGGGGAAAAAAACATAAC

ATGCATGTAACCCTAGGTCATAATAAAGAATTAAAACCAAGTTATTTTATTAAATAGTAT

AAGGGCTATCAATAAATAATTTTTACAAAAATTAAAATTAAAATATTGATATTTTTACAA

AAGTTCAACTTCTATGTTACTAATTAATAATATTCTGCAAATAGAAAATCATGTTAAATT

TTTTTTTTTAAGATAATTATTATAAAAGTTGATAAAATTATGCATGCATGATTATTTTAA

TGACTATTTGAAAGTGTAAGAATTATTTACATTATCTATATATATAATCGTTATTTTCTG

AGTTGAATGAACGTGTCCGAGTCATTATCCATATATTTGTATTTTTTTTTTGAGTATTT

TTTTGTTGTTGAATAGTCCATATATTTGATGGTATCAGGAAAATGTGGAAAAGATACAAA

ATCATACAGGTAAGCAATTTGTCTTGAGTCGTCATGAGTCTGTTAAAAGTCTATCGATCA

GCAACCTTATGTAATATATACACTTTGGGTGCGATCATTTCAATCAAAATCACATTCCCT

AGCTTTGGCTCAGAAATCAATAATTGAGCAAGTAATTTTGTGGATACATAAAATAAAAAG

AGTTGGCCTGTATGGTGAGGTTCACAGGTAATTACACATTATTCCAGTTTATTTTAGATC

GAAACCAGATATTAATGATCACAAAAAAAGATGGATCGAAGAAAATAAAATATTGCTGGC

CCTCCCTTATGCTATTTCCTATTTCTTCTTATGCTTTGAACCTATTAATAGCACATTTTA

GCCTGAGCAAGGAGTCCGAATGTCCTTTTTCATGGACTTGGCAGTTGCAATAAAGTTGGA

GAAGCTGATAAGATTCTGTTTCAGATTTGATTATTCTTACTCACATGTTCCACGATTGAC

-continued

| SEQUENCES |
|---|
| GAGAATATATATATATATATATATATATATATATATATATATATATATATATATATATTGGT |
| TTTTAAGTGTGTCTCTATCCTCCCGTTTAATTTGAATTTGATGACTTTTTGGTAGGGTTA |
| AAGACTAAAGCTAAAACTCCTCTAAATAGTAACTTGTTCTTAAAAAAAATGATTTTTTTT |
| TATCAGAGTTAACCACACATACTTAATTTAAAAGATTTGAACTCCTTTAACTTGAATCAA |
| AAGATGCTAGCTTTTTATTAATGAATATGATGATATGTACGAGGTAATGTTTTAGTATGA |
| TTATTGGAAATTTGGCATCTTGCTAGCATGTAGGTGATACTCTTATTTCTCATGTTAAAT |
| AGTTAAATTCATTTTAAAAGTATAGAATACCAATAAATTGATTCTTAAAAAATAAAAATT |
| TAAATTTAATTATTGAATATGTAAAAAAATATGATAAATTAGTCTTGCAAATAATTTAAT |
| GGCAAGTTAGTTCTTGAAAATATAATTTATTATCAAATTAATCATTAAAAATTATAATTT |
| AATGACAAAATAGTTTCACAAATTTAATGACAAGAATAATTTATTGCATTTTTTACCTAT |
| TTAGAAATTAAATTTATGTTTTTCATTTTTTAAGGACCAATTTATCATCGTATCATACTT |
| TCGATAACAAATTTGACTATTTATATTTCTTATTAACATGCTCAATGATGATCTATTTTT |
| CTGTCTATATAGATAGATCTATGTTCTATAATTTACAATTGAATTATATACAAATATCAT |
| TATATAACAACATATATTAAAAAAAAACTTGTATTTTTTTTATTTTAGAGAGTTTTTGTA |
| TCTTTTTATCTTCCTGTTGGATGAATAATTTCCATGTACATATATACTAGTGCTTTGTAT |
| CATGGAACTTTTACATTTTTTTTTTCCTGGAAACAAGCCATGTTCATAGGCTTAAAAATA |
| ATTAAAGTGACTTTTATCTTTTTCAACAAAGTCTTCTTCATACGCATAACCAACAAATAC |
| ATATTTAAGAAATTCAATCATCTATCAACTGTGTTAAATCTTGTTGATATCTCTATTACA |
| ACACTTTTTATTAATCCGTGTATTAAACTTGAGATGTGGACTTAATTTTAACAATTAATT |
| AGAAAGCTATGCTAACTAAATGAGAGTAATTACAAGTAATAGAACCAAAATACAATAAAA |
| ACGTTCCAGAAATTAATGTTCAACTAGTATATTTTTTATGAAAAATAAACAGAAAAGTTT |
| TTAAAAAAATAAAGGGTTATAAATCACCTTGGTTGACACCCAATGAGATAATGGGCTAAA |
| ATTACTCATTCATTTCAAGCCCAGTAAGTCTGGGCCTAGCATTAGCTTCAAGTAGTTCGG |
| ATTCACCCGACCCAGATAAGACATTCGGGTTCGGATCCTGTAGTGTCATCACTCGTTAGA |
| TTTCGATGAAGAATAGTTAGAGAGTGCTGTGAGCTTCAGCAAAATGCGCGCCCTAGCAGC |
| TCAGTTCTCTAATGTAATGTTCTCTTTAATCCTTGTCTCTGCCTCTGTTCAATTTTAACC |
| CTTTATAATTTAAAGAAGAAAATAAAGTAATCATTTTCAAATTCAATTCATATTTGAAAT |
| CGATGTTGATCTTAAGTAAGTACCCATTTGCGGATTCATTTTATTCTTAACTTTTTTCAT |
| TTTTTTAACCCTTTTTGCAGTATTTATGCAGAAGAAAAGTTGGGGTCAATCTGCGATCTC |
| GTAATTTTTCATCATATAACAGTAAAGGTATCACCTTGTTTTTTTCTATCGGTACTTTTG |
| AAAGAAAGAAATAATTATAAGAAATTATGACTAATTTTGTCAGGCTATGGAATCATTCTG |
| TTGAGAACGAGAAAAATGAAATAGGTACTTGTATTGAACGTTCTAGTAGTAAATGATAGG |
| TACATATGTTGATTTTGGGGATTTCTGGGATTAGATCATCAAGCCAAAATCTTGCACTGT |
| AAAATACTAAAATACAAAGAAAATGGTTTTCTTTTTTCGTTCAATTTTTGGTTTCATTGT |
| TTGAGCTGCAATTATGTTGCGTGACTTCACTTGTAACTCTTTTGATTTCCAGATGAGCTA |
| ACCATCGAGGAAGAAGCTGAGAGAAAAGTTGGATGGCTATTGAAGACGATATTTTTTGTC |
| ACTGCAGGGGTAGCAGGATACCATTTCTTTCCTTATATGGGTATATCAGCAAAATCCCTG |
| CAACAATTTTTAACTTGCAAAGCCTTCATTTGCTCTGGGTAGTTCAAGCTTCACAATGCT |

-continued

| SEQUENCES |
|---|
| GTTAAAATTCATATTTTCAGGAGAGAATTTGATGCAACAGTCTGTTTCGCTTTTGCGTGT |
| CAAGGATCCCTTGTTCAAAAGGATGGGAGCTTCTAGATTGGCTCGTTTTGCAGTAGATGG |
| TAAGTTTTACTATCTGTATCTTTGTGTCACTAATTGCTTGCTGTTGTTGTTTTATGACCC |
| ATATTTCTTTGGCACATGACATATATATTGAATTGTTTATTAATTGTTAGTCATTTGCAT |
| ATTAGGGCAGTTGTTTTCTAGAACAGATTCCTATTCTTGCAACAAGCATATTTTCATTAT |
| CCTTGTGCTTTACACTAGTGACATTTAGTCATTTAGTATTAATCTCAGCTTATTCTTGAA |
| ATGACAATTTTGGTTGAAGGGGAGAGTTGATGGGAGATTTTGAACTTGGATAAAAGAGTC |
| ATAGATTGAAATTTTTCTCTTGAACTGATAATCAAATAGTTATTGAGATTTTTAATTGAG |
| CTGCATTTGTTAAGAAGTCACGGCTAAAAGAGTTACCTAGTTGTCAGTTATACTATTTTC |
| ATGACTAAGCAGCAAGCACAGATATTGCAGTGATACACAACCGAGAGCATATTCTCCAAA |
| AGGCAAATTGCCTTGATGCAATTTGCTAGTTTGTACACTGATAGAATTGCTTATTTATCA |
| ATAGTGTTCCAATGTATAGGTATCTCATGGCACTGATTAAGGATAAAACATGGTGATTTA |
| TTCCTTTCTAAAATCTTTTGTCCCTGCACAAGTTGTTTATATTAAACATTGTTTACCTTA |
| CTTTTGCTCACAAGATGAAAGAAGGAAGAAGATAGTTGAGATGGGTGGAGCTCAAGAACT |
| CTTAAATATGTTAAGCACTGCTAAAGACGACCGTACACGGAAAGAAGCATTGCATGCTCT |
| TGATGCACTGTCACAATCAGGTGAAATCATAATTTTAATATTTTTTTAAATAGTTATTAT |
| CATGCTGGTGGAGAGGTAGATTATTGTGATCAATTAGTACCTTTGTGGTTCTAAATAGTA |
| AACCAGAAATGCCCAACCACTTATGGAATTTGTTAATTTATTTGTATAATATTGAGCTGG |
| AAATCAATTTTATGAGCAAAGTGTGATAAGAAGCATATGAAACTTTTATATGTTTCCAGT |
| TTCTGTTATCCTTATTCAATAGATATGGGCTTGTAAAGATGAAAATGAACATAAATTGTT |
| TTGTGCATTAATTTTGGGACATATTATACGTGCACAAGCTTATGTGTAACAATATCTATA |
| CCTGCTACTTTCCCTGTCAACATATTGATTTTTAAGAATCCAGTTCAAGTAATATTTATG |
| AGGTTGAAAGATATGCAACAGTACAACCAAATTAGTAGTGCTAGCTAGTACTAGCCTTTT |
| CTGTTCTCTTTCGATTGAGATAAGCTACTTCAATGTTATAGATGAAGCTCTTGCATCCTT |
| GCATCATGCTGGGGCCATTTCAGTAATTAGGTCTGCACCAAATTCACTTGAGGATGCAGA |
| AGTTGAGGGATTCAAGTTGAGCTTGATGAAAAGATTTCAAGATCTCAGATATGATGTGCC |
| ATCATGACTTGAGGTGCATGCCTCCTTTTGCTTTATGTTTTTGGTTGGTTGGAGCATGAA |
| ATAACATGATATGAGAAATTAAGCTGGCAACCAAAGCTTTTGTGGGGAAGAGTACTTGAA |
| ATTACTGTGTATCATTTGACCAAATCTAATGGAAGATTATAGTTCTATTGTCATTTTAGT |
| TTTTTTCACTTGTCAAATGCGATTTGTCGCTCATTGTTCTGTCAATCATAATAAAATGGA |
| AAAGATTTATGTGCATGTCAATTTTTATTTTTTGAAATATGTGTTTAGAAGATAAAAGAT |
| TACAACAAACTAGTATTGAAGTTGTAAGTGTTTAGATACTGTAATTGTATATTTGGTTAA |
| CACTACTAGATTAAATTTAAGCCTCAACTTTCAAATGTGATTGATCATATAATGTCATAA |
| AATGTGTGTAATTATAGGTTGATGCTTTAATTGTTATTTACATATGCCTCAACTCTCAAC |
| CGTATGTCATCATCAGGCTTCTTGTTTAGGTTCAGCTGGCGCCTTGCTCGTTCTATTTTG |
| TTCGTATTCCTTTGTTCATTCGATGTTTTTTTAGGAAAATATGTTCGTTGAAAGAAAAAA |
| TCAGTCAACAGAAGATACATGCCCTTACTTTTCTCTACTCCACGTCTCCACCTACCCTAA |
| CCCTTGGAGTTACTTTTCAATTGAGCACGTTAACAAGCCTAACTAAACGTGGTTCTGTGG |
| AGATAATATACTAAAAAAATATTATTTTTTATTTAATTTAATAAGACTTGTGCGCGTAAC |

-continued

| SEQUENCES |
| --- |

TCTTTTCAAAGTGCTAGCTTTCTTTTTTGGTGAATTTTCAAAGTGCTAGGTGAATATGCG
TATTTGGAGATAGAAAGCTTTTTTTTTTGGGACACAAAAGCTTGTTTAACATGTGATAAA
CTTAAAACTAATAATCATTTTTTTTAATTATCCCTATTCAATGTTTTAGTTTTAAAAATA
CCCCATTTGGGAAAATAGCCCATCTGTGGATGTAAAAATTACTAGAGTACAAGTTAATTA
GGGTTAGTTGTTTTTTTTTTCTTTCTTCTTTTCCTACGAGATCAAGAGGAACGGAGCAAA
ATCATGTTTTTTCTTCCACCAAAATAATGTAAAATTTTAAAACAAAATACTAAAATAATA
GGTTATAATATATTTCTTTTCCTTCATTTTATACTTAGTCTTTTATTTTTTTTAAAAATA
TCATTCTAGTTATTTAACTCTCACATTTGAGTTAATGTTATACTTTTGAAACTTCAGTCA
TTTTTTATTTATTTTGGATACGATTTTGAGCCTTTTTTCTTTTACTAATTAAAGATATAA
AATTTGTCTCATTAAATTAAACTATGAATCCAATTAATGTTCAAACAAAACATAAATCCT
TAACATGATGAAAATTGAATGAAAAATGAATTTCATAAGCAATTGGAAAACTGAAAAAAA
AAATCTAATAACAATATTTGAAAATCTATTAACAATGAGCAGTAGGCTTCTTTGGAACTT
GAAATGAAGAATAAAAGAGTCATTGGAAATAAATCTCAATTAATTGAAAGATATTTTTTA
GAAAATGTCATTAAATAGAATAAAAATAATCAAAATTTGCTTATATTTGAATCTAATAAA
AAAATTGTTAATTACTCTTTTTGTCTCGAATATAAACAAAAAATACTTTGAGTATTAGTC
TCAAATAAAAGTAAAATTTAACTATTGTTACTTTATTTAATGAGATATTCCTAAATTATA
TTTTATTTAATTAAAGTTTTATTACTTATTATCTCTCTTTTTTATTTTTGATATGAACTT
TCAAGAAAGTGTAGTTTAGAAGAAGAATTTTTTTAATAAGAAAGGTGTAATTAAATAAT
CTAATTATCTAACTACTAACTTTTTGAATAAACCGTAAGTTAATTTCTTTTATATAGAAA
GAAGGGATTAAATTAATTTTAAAAGAGTTCCTCTTCATTTTAATCATTAATTTTTTTGAA
ATTCAATAATCAATACCTACTCATTACAATAATAAAATACAAAAACTTCTTCACGAAATA

>Gm18:1625005..1645004

SEQ ID NO: 3

AATTGATTCCTTGTGTTATATATATATATATATATATATATATATATATATATATATATA
TATATATATATATATATATATATATATATTCAGTATATAATTTAGTGTAGCTGGACACAT
ATTAGTGCCCCGTGGCCGTGTGTTGTGCTTTTTTGTTGGGCGAAACAACGGCCAAAGCGA
CGAATCACTTCCTTACGTGACACACCTCTGTCTAATAGACGATAGGCCAAAGTCACAAAT
ACTTTTTGATTGAGTATTTTTTAATGCCACATATCATATCTGTCAGCGTCACATGTTCAA
ATAAATCCCTAGTAAAAACGCCAGAAAACAAATGCATGAGCAATTTTTGGACTTTGGACT
AGTTACAATTTTTCAACGTCACATCTTTAAATGATTTCGTCTCTATTTAGTAGTTGTTTT
TAATGCGGCCATGCCCACTTTCTCGTTACAAAGCATGCATTTTATTATTTGAACGAAAAT
ATTTAATATTGTGTATTACTCGTTTTACACAATTGCTTTTATTCTTTTTTTTTTATTTTT
TAAATACAGTCATCTTTAAAAACAAAATCTTCGATCATTCCATTTCATTGTTCACAAAAC
ATTATCCTATCACATGCACCCTATGTAATATAATACACGGTTGTGGATAAAATAATTCTG
CACCTGCCCAACTTTTGTATTGATATCATTTTTTTATTTCCTCTATATTTTCCATATTTA
TATATTAATTCTATCACTTTCCTGCACCCCAATAAGTCATGCTCCAAATATTATTGTTTT
GGATAAGTATATTGCACAATCTATTCTTGGCTTCTTCATGACCATGACACGGCAATGGAG
ACGAACGATAATGAAAGGCGCGTAAATCATTTGAAAGGTTGAATTATGTACCAAATGCTA
TTATATTAGCATTTCATACGCCATTCTAACAATAATGAGAACGAGTTGCCCCACAATTGA

-continued

| SEQUENCES |
| --- |
| TCAATATTTGTATCCTTGCACGGCACAAACTTGTAAGATATGGCCCCAACTTCGTCACCC |
| CATCAAGTTGATTTCATTTCTTTAATATTTGGTATTTTACATAGAAATGCTGCCACAAGA |
| CATGAATTCTACAATAAACAACAAGGGATCCAAAATACAAAAGTAACACAATCGCCACAG |
| CAACCAAATGCCTCTAGAATCTCCCCAGCCATACCCTCTCTCCCCAAATAAAATTTTCTA |
| TACATATAAAAAAAACAATAGAAGGGGAGAAATGAGAGAACCAGCTTGTATTTATGACTT |
| GCTACTAAAAGCATTATATATGTTGGTGGAAATGGCAAGCACACTTGTAACCACAGCTAG |
| TATAATCATTATCAGTGCAATAATTTTGTCTCTTCTCGTTGATATACCTTTAACATCCCT |
| GTCATCAGAAACAATGAAAATTAAGAGACTAATTTATTTATTTATTCAATTCAATTTTCA |
| ACTTGAGCTCTACTTTATCAGAAGTCAATAAGTCTATGCTAGATTACCTTAAAACAATAG |
| AGCCGGGGAAAATGAAGGCAAGGCACACTGCGGATGAGGATCCCAGGAACTGAAAGAAGT |
| ACCAAATATCTGGGATTGCTATAGCTGCAAGGTAGGAGAATACAAGCAGCACCAGAGTGA |
| GGATCATAAATCTTTTGTTGTCTGTGGCTAGCATAGGCTTCTTAGGGAAGAGAACTTCAT |
| CTATGTTGGTTCTCAAAGAGAAGTTCAAGAGAGGAAACACCAGCATGATGTGGAGGGCAT |
| AGCTTACACGGACCAAACTATTGAGCAAGGAACCAACTGCTGAACCAGCATTCTGGTCAA |
| AATTGATGAGAATGTCTGACTGGGTTGAATCCCCAAATAACATGTACCCAAATAAGCCTA |
| TTGCAAGGTAGATCACAGCACAAAGCAATAATGCTAATCGAACTGCTGTTGTCATTTGGG |
| ATGCCTTGGCAAGCTCAAACCCAATGGGGTGCACTGAAAGTAAAATCAACCATCAGCACA |
| GAAATTTTCTAGGCATACCCTTAAAAAAAATGAGCAAATCCATTAGGCCAATTACCATTA |
| AAGTGAAATGTGAAGGCTGTGACAACAACAGGAACTGCAGTGAACAGATCAAAGAATGAG |
| GTTTGGTAGTCTAGCCGAGGAAACAATCTAGGAGTTTGTGTTTTTCCTTGCACCAGAGCT |
| GTGATAGCCAACCCACAACATATGCCAACAAATGCCACTGCAAGAAGAGTTGACACTGCA |
| GAGCTGTACTTCAAGGACTCTACCAATTCCAAAACACCAAGAGGAAGAACCCATGTTAGT |
| TACTGAAACTCTTCAATTCCAAATACACAAGAAAGCATGTTATATAACAAAATATTCAAT |
| TGTAACACTCACCTACACGTTTGTACAATACCAATGGAAGCATAACAAAGACCAAGGTGA |
| AAAGCAAAGCAAATTCCCGGGAATTCCACCAGTGAATTCCAAACCACTGTTGCAAAATGC |
| CCAAATGCACTTCCCCTCCATTTTGCTTTCCAGATAGCACATCTCCTGTTGTTCAACAAA |
| AGGTAATTATTAAAATACATCTATTTTTTTCTTTCATCTTCTTTCTACTACATTTTCTTC |
| TTATATTTCTCTTTATTTCCTGTCATTTCACTTTTTTTTTTCCTGTCTTTCTTCTACCCA |
| TTACATAGACCAAAAATTGAGGTGTGCATTGCGGAAACAGATTCCCCACATTCACTTTTT |
| TTTTCATGAATCAGAACTATTAGATTGAATATCGAAGGTTATATTTGGAATACATATTTT |
| AAGAGTATGTTTGGATACAAAGTTAGAAGTGCATTTGACAACTTTTGGGAGCTCCTCTAA |
| TGGAAAAAGATTAATATTTTTAGTAGAAAACTCTCAAAAACACTTCTAGTTTGTATCGAA |
| ACAGGCCTAAGTTAGATTCATTGAGATAAGTTATGAGTAATACAATCTGTATTTAACAGT |
| GAATTCCCAGCGGTAGGAAATCCCGATCCTTACATTTCCATTATCTTGTTAAATTAATTA |
| CCATACACAAACATTAAAGAAAACGACTTACTACATATATTTTTTCAAAAAATGAACCTT |
| TCTATTTATAGTAAAAAAAATAAAAAACAAATTTCACTTATTATTAGCAACAATTTCACC |
| AATCAAAATGAATCTGACTGAAAACCCGGCAAAACTCAGAACAAGCATACCAAACCAAAA |
| ACATGAAAAAATCTACATTTTTTTTTCCTTTTTTACGAATTCAGTAGAAAGGAAATTAAA |
| AAAAAAGGGAAAAGTTCCGTTACGTTACCGATGATGATAAGGTAGAGAATTAAACCCCCA |

-continued

| SEQUENCES |
| --- |

ACGTTGGTGATGATGACGCAAACTTGCGCGGCTAATGCTCCACCCGATCCGAACGCCTCC
CTCATGACGCCAGCGTACGTCGTCGTTTCGCCGGAGTGCGTGAACCGCATCAGGAAGTCC
ACGGACAGTTCCGCCAGCACGGCCACCACGAGAATCATCGCGAAAGCGGGAACTACGCCG
AGAACCTTCATGATCGCCGGAATCGACATGATTCCGGCGCCGACTATGCTGGTGGCCACG
TTGAACACCGCGCCGGGGACGGAAGCCGGCGGCGGCGTTCCTTTGGAATCCCCCAGGAGG
GGGACGCTGACTCCGGCGGCCGGAGACATGCCGGAGGCAAAATTGTGAGGATCGGAGAAA
GTGCGGTGGCGGTGTGCGGTGCCTGGCAGCCTACTATCTTTGAATTGAATGGTTTTTGTT
TTGTTGTCTCTCACGAAAATTTCACTTCCTCTCTCTTTATAAATGATACAAGTGGATTTG
GGAAGTTAAGAAAACAAAAAATGAAGTTATAATAAGTAAGATTTTATTTTATAAGTTTTG
TAGGATGAAAAGAAATATAGTTGAATGAGGAAATTTCATTGAAAATAGTTAGCTAGATTT
TATAATAGAGATTAAACAATAATAAAATCTGCAGATACTTCAACATGAGTATGATAATAA
TAATAATAAAAAATTGTTGTTTTCTATTTTTACTCCAACATGGACTGAAATTCATATGAA
TTTTTTTGAATAGTCTATTTTTTTTTATTTAATTTAATATTCATATCAAAGTTATTTCAT
ACTGAAAAAAATATTAAATACTAGCATTCTATTATTACCATTTGGAGGAATGATTGAAAG
AGTGTTAAAGTGCACCTTTTCAGTCAACAGTTAAAAATAAGGCGTTTAATTCAATTCAAT
ATTACAAAGTTAAGTTGGCTGTATAATAATAACAGTGGTAGTAAGTAGTAGAGTGAAAGA
AAAATTTTTTTGGTCAAAATATTTAAATCAAGACTAGAAGATATGCAAATCAGAGATTAC
ATTGGATGATACGGTCGACCAATAAAAAATAAAAGAAAAAACATAAATTGGGATGTTCAA
ATACTAATAATAATAACTCTAAACAAACATTAACACGTGAGTTTTCTTTCCCACGTTGTA
ATCATTTTGAATTTTTAAAATGTTATGACACAAATAATAAGTTAATAATAATTATAATTT
AACATTTGAATTGATAAAAGTGTTTAGTTTTATTGTAGATTAAACTAATCTTTCTTCGAG
TAAAAATAACATTAAATTCCTACACAACAGGTTTATCAGTTTATAGAGTAATAACACTCT
TATTCTTAATCGTTTTCTTTTCTGGAAGAAAAAATAAATCTTAGTCTTGTTATTTTTTTG
AGAATGTAAAATATACCTTAAAAAATTCCCTTAAAGTTTGTATAATTTTTTGGTATGTAA
ATATATTTATAAATAAAAAAATGTTTGCGAAAAGTAATATTTACATAACAAACACTATTT
ACAGAACATTGATGAAATTATTTTTAGATATATAATTATTAATACGAATATATGAATATG
TTATTAAAGTAATCAATAGTTATGTTAAAACTGATCTGTTGACTAGACAGTTTGTCAATT
TATTTTTTATTCACTTAATTGCTATTTTTTTCTAGGTTTGTTCTTTCGTTAAAAAACCTT
GCATTGGAGGAAGGCCAATGCTAGTTATAAAAATATAAACCATGATTTGAATATAAAATT
ATTTTTAGTCGAAAAACAATGAATTATGTTGCAAGTATCACTATTGAAAAAATGCCAACG
GAGCCCAAGAAGGTGAGGCCCAAACTGAAAGCGTGAAGCGGCCCAAGACTGAGTGAGGAA
ATAAATAATTATCCAGAAAATCGGAAATGGACAATCCTTCTTGTTACGCAATTCTGAATT
TGCGGGTTTTGGATTTGGACTTGGTCGTCAACACAGTCTAATTAATATCTTTTTGCTCCT
TCGCTTATGAATCTTCTTCTTCTTCTTCTTGTTCCTGCAACGCACTGAATTCGATCAATC
AATCCATCTTCAATTGCTTTGTTTCGATCGGAGGAAAATGGCCGATCAGTTATCGAAGGG
AGAGGAATTCGAGAAAAAGGCTGAGAAGAAGCTCAGCGGTTGGGGCTTGTTTGGCTCCAA
GTATGAAGATGCCGCCGATCTCTTCGATAAAGCCGCCAATTGCTTCAAGCTCGCCAAATC
ATGTTTTTCCTCTTTCTCTCTACTTTTTTTAAATTCCATTTCGTGTCTCCTCAAAATGCT

-continued

| SEQUENCES |
| --- |
| GATTTAGTGTCATAAATCATAATTATTATTCTCTTCTATTGTTGTTATTTTATTGTTATT |
| ACTTCAATCGACGAGTGTGTTGAGTTTTGAGGTGTCCGATTTCCCGATTAATTGAAGTAT |
| AGTTTTAATCTGATTTTACTGGAAAATATTTTTTGCCTGATTTTTTTTTTTTGGAACAAT |
| TACTAGCATATAAATTAGAATTGTGGATGAAGTACGACAATCAACTCTGTGTTGTTTGTG |
| ACTGCGCTCACTTTCAATTTGACGACTAATCTCTTTATTTTGTTGAAAGTGACGAACTTT |
| GAAATTGATGTTGGAATAGTTCTGTTTATTGTTCTTGATTTGATCTATGTGGCATTTTAG |
| GGGACAAGGCTGGAGCGACATACCTGAAGTTGGCAAGTTGTCATTTGAAGGTAACATTCA |
| TCAGACTTGGGGTTTTGGAGTGGGCTGAATCTCTTTTGCATCCTTTAGTTCTCTATTAAG |
| CCTGCATGACATTGTTGTGTTCTGTTTCCATTTAGTTGGAAAGCAAGCATGAAGCTGCAC |
| AGGCCCATGTCGATGCTGCACATTGCTACAAAAAGACTAATATAAACGGTATGCATGTGT |
| CTCAGTTGTTACCACTACATGCACTACAATACTTTCTCATTTATGATTTGTGCTTTAAAT |
| GCTGCTCTTGCTTCCATGCAGCAAGGCCAATTCCTTTTAGCCTCAATGTTTCTCTGTATA |
| ACTTTAATGTAAATCATATAAAACAATTGCTACCTTTTTGCATGAACAAATTATATAAAG |
| CAAATCTCTTTGTTTAATCTTTACATATGTGTAAATCAAATACTGGGCTTCATATCGATA |
| AGGTCTAAGTAGGGGTTCAGTCTTTTATTTGGATTAGTTTAAGTCAGAAATTGAAGTTAA |
| TTTGTGCTTGCATAAGTTGCTTCCATCTGATTGCTTTCTTTTTATGGCTGTCTGTATGTC |
| ATAGCCTTATTTTGATTTGTTATTTGCTGACTATTATTAGATTGGAACTCATGATCATAT |
| CCCTAAGCAGGAGCAAATTATTTTGCTGTCTTGCTTGTCTTAGTATGTCCCACTTGCATT |
| AGGAAGAACTAAGACAATTAAAGTTACCTTTTCTTTCTTTGAATACAGAGTCTGTATCTT |
| GCTTAGACCGAGCTGTAAATCTTTTCTGTGACATTGGAAGACTCTCTATGGCTGCTAGAT |
| ATTTAAAGGTATATTATGTTTATGATATTGATATCTCTTCTCCTGGGTATGATTTTTAAT |
| TTATTCTCTTGTCCATATCCCAGATTTTAGATATTGATCCTGCAATAAAATGCGTTGAAG |
| TATACTAAGTTATCTGAATCCCCATTAACATGTTTTAACTGGGTTCACTATTTTATACAC |
| AGGAAATTGCTGAATTGTACGAGGGTGAACAGAATATTGAGCAGGCTCTTGTTTACTATG |
| AAAAATCAGCTGATTTTTTTCAAAATGAAGAAGTGACAACTTCTGCGAACCAATGCAAAC |
| AAAAAGTTGCCCAGTTTGCTGCTCAGCTAGAACAGTAAGATATTGTCCTTTCTGCATATA |
| TTATCTCTTTTATTATGCTGATGAATTGATCAATATTTCTTCAACTTGGGTTTATTCTTT |
| AATTGGTTAGTAATTTCTTCTGAGAACTTTCTTTCTGGCCTTTATTTTGTTCAGTACCCT |
| TTCTCTAACCCACTCTCCTCAGGTTAACATTAGCTTAGGTCAGTGTAGGTTGTTTGACAC |
| TGAGTTTTTATTGGTATGGATGTATGGTCTATTATGATCTCAATGGAAATCTAGCATATT |
| TTTTTTCCACAATCCATAATATGATGACTTGTGTACATGGTGTGAATAAAAGTCAGTCCA |
| TTGCTGCATTTGGTATTGGTTACGTGTTACTGTACTTTCTGCATATATTATCTCTTTTAT |
| CATGTCGATGATTTGATTAATATTTCTTCAATTTGGATTTATTCTTTAATTGGTTAGTAA |
| TTTCTTCTGTGAACTTCTAGTTAGAGCATGAACTGCTAAAGAAATCCAAAACTTTATTTT |
| TTACATGGAAGGAACTTTATCAGAGTTTTATTTATTTATTTATTTTTATGTTAAATTGAA |
| CTTTAACTGTTTCTATGTTATGATAACTCTTCTTCAGATATCAGAAGTCGATTGACATTT |
| ATGAAGAGATAGCTCGCCAATCCCTCAACAATAATTTGCTGAAGTATGGAGTTAAAGGAC |
| ACCTTCTTAATGCTGGCATCTGCCAACTCTGTAAAGAGGACGTTGTTGCTATAACCAATG |
| CATTAGAACGATATCAGGTCTAAGTTTTTTCAATAGTTCACTTCTGGAGACTGGACAGCT |

-continued

| SEQUENCES |
| --- |

TATTTGTTGCTAAATTATTCAGATATGTTTTTATTTTGCAGGAACTGGATCCAACATTTT

CAGGAACACGTGAATATAGATTGTTGGCGGTAGGTCACTGGTTTTGAAATTTCGTTATGA

ATTTTTTATGACCAAGTAAATTGGATTAGAATATTTGAACTTCTTTGTAGCTGTCTCCTG

GGTCATAATGTTTTATTATATTTTTGTATTTATCATAGCATTGTGATAGCCCTGTTACTA

CTTTGTTTGCTGATTTACTCATACATTTGCCAGATGAAACTGACATTTTTTTTTAATCCT

GGTGGATAGGACATTGCTGCTGCAATTGATGAAGAAGATGTTGCAAAGTTTACTGATGTT

GTCAAGGAATTTGATAGTATGACCCCTCTGGTAAGCTCCAAAAGTTGTTAAATAGGATAA

CTTCTAGTGGTGTTTAACAAAAAAAAAAATTCCACTTGTATTTTTTATCCACATTTTATA

ACAGAATAATCATAACCTTTCACAACTTAATTCTCAATTTTCACAGTAATTAAATGTGTA

ATTTTAAAAAAATATTTTCCTTAACTTAAACCTGATTGAAATTTCCCCCTGAAATTTAAG

TTCTATTTGATTACCTAGAGTGTAATTTCCGTGTTTTGTCACTTAATCACTGTGTAAAGT

TAATTTTTTTGCTTACAAAGGTGTCTTGTTTGGAATGCTAAAATAACAAGTACACGTGTC

ACCAAATTTAGTAGGATTAACATTTGTTGTTTTTTGCCATAATAAACGGTTGAACTTAAC

ATTTGTTGTACGTGTCATCAAATTCTACAAATTGTGAGCTGCTTAGTGGGTTGGACAAAC

ATTTTAGCAGGTGGTTTCGATTGCCTGTTGAATACGTGAAATTAAACCAAGGCAAAATTA

TAATTTGTTTCTTTTGTCTGTGTTTCACTCATACACATTGAATCTTGATGATACACAGCC

TTGTTAATTGTTATCCTTCCAATTTTTTTTAGTGTTTTTGAGCATCTATTCTTGTTGGTC

ATGTGTTTTCTTCACTCATGTACCTGGTTCTTTTCCTACAACGATAAATATGTATCCTTT

GTTTTTTTTTTCCAACTAAATATGTAATTTCAAATTTCTAATCAATCATTGCTTCCAAAA

TACTCTCTCTGTTTCAAAATAAGTATTATCCTATATTGTTTTACAAGACCAAGAAAAGCT

AATATATAGATGAAAGAAATTAGTAATTTTACAAAACTAACCTTAGTATTAATATTATAC

TGAAAAACTAAATTGACACTTATTAGGGGTGTTAGTGTAAAAAAGCAATTAATATTACAT

TGAAAAGCTAACATGATACTTATTTTGGGACAACTTTTTTCTTTCAAATGCAACACTTGT

TTTGGAACGGAGGGAATACTAGATATTGTGCTCCCTTGTATGCCCTGGACATAACGTATT

TAACTGGTCTGGATGAGTTTATGAATGTCATTAATTTAGGGGGAGTCATTTAGAATAGCT

TACCTATAAGTACTTTCTAACTTTTCTCAATTAGTTTCACAGTGCAATTTATTAAAAATG

TCTGTATCTAATCAACATTGTCTGTGTGCTTGTGCAGGATTCTTGGAAGACCACACTTCT

CTTAAGGGTGAAGGAAAAGCTGAAAGCCAAAGAACTTGAGGAGGATGATCTTACTTGAAT

TGTACCTTTAATATTCCTGG

Glyma18g02570.1:peptide

SEQ ID NO: 4

MRALAAQFSN YLCRRKVGVN LRSRNFSSYN SKDELTIEEE AERKVGWLLK TIFFVTAGVA

GYHFFPYMGE NLMQQSVSLL RVKDPLFKRM GASRLARFAV DDERRKKIVE MGGAQELLNM

LSTAKDDRTR KEALHALDAL SQSDEALASL HHAGAISVIR SAPNSLEDAE VEGFKLSLMK

RFQDLRYDVP S*

Glyma18g02580.1:peptide

SEQ ID NO: 5

MSPAAGVSVP LLGDSKGTPP PASVPGAVFN VATSIVGAGI MSIPAIMKVL GVVPAFAMIL

VVAVLAELSV DFLMRFTHSG ETTTYAGVMR EAFGSGGALA AQVCVIITNV GGLILYLIII

GDVLSGKQNG GEVHLGILQQ WFGIHWWNSR EFALLFTLVF VMLPLVLYKR VESLKYSSAV

-continued

| SEQUENCES |
|---|
| STLLAVAFVG ICCGLAITAL VQGKTQTPRL FPRLDYQTSF FDLFTAVPVV VTAFTFHFNV |
| HPIGFELAKA SQMTTAVRLA LLLCAVIYLA IGLFGYMLFG DSTQSDILIN FDQNAGSAVG |
| SLLNSLVRVS YALHIMLVFP LLNFSLRTNI DEVLFPKKPM LATDNKRFMI LTLVLLVFSY |
| LAAIAIPDIW YFFQFLGSSS AVCLAFIFPG SIVLRDVKGI STRRDKIIAL IMIILAVVTS |
| VLAISTNIYN AFSSKS* |
| Glyma18g02590.1:peptide<br>SEQ ID NO: 6 |
| MADQLSKGEE FEKKAEKKLS GWGLFGSKYE DAADLFDKAA NCFKLAKSWD KAGATYLKLA |
| SCHLKLESKH EAAQAHVDAA HCYKKTNINE SVSCLDRAVN LFCDIGRLSM AARYLKEIAE |
| LYEGEQNIEQ ALVYYEKSAD FFQNEEVTTS ANQCKQKVAQ FAAQLEQYQK SIDIYEEIAR |
| QSLNNNLLKY GVKGHLLNAG ICQLCKEDVV AITNALERYQ ELDPTFSGTR EYRLLADIAA |
| AIDEEDVAKF TDVVKEFDSM TPLDSWKTTL LLRVKEKLKA KELEEDDLT* |
| Forrest SNAP Type III polypeptide mutant A111D:<br>SEQ ID NO: 7 |
| MADQLSKGEE FEKKAEKKLS GWGLFGSKYE DAADLFDKAA NCFKLAKSWD KAGATYLKLA |
| SCHLKLESKH EAAQAHVDAA HCYKKTNINE SVSCLDRAVN LFCDIGRLSM DARYLKEIAE |
| LYEGEQNIEQ ALVYYEKSAD FFQNEEVTTS ANQCKQKVAQ FAAQLEQYQK SIDIYEEIAR |
| QSLNNNLLKY GVKGHLLNAG ICQLCKEEVV AITNALERYQ ELDPTFSGTR EYRLLADIAA |
| AIDEEDVAKF TDVVKEFDSM TPLDSWKTTL LLRVKEKLKA KELEEYEVIT |

What is claimed is:

1. A transgenic soybean plant resistant to soybean cyst nematode (SCN), or a seed, plant part, or progeny thereof, the soybean plant transformed with an artificial DNA construct comprising, as operably associated components in the 5' to 3' direction of transcription:

(a) a promoter that functions in a soybean plant;

(b) a transcribable nucleic acid molecule comprising (i) a nucleotide sequence at least 99% identical to SEQ ID NO:3, wherein said nucleotide sequence comprises a C163225G mutation, and wherein said nucleotide sequence encodes a polypeptide having soluble NSF-attachment protein (SNAP) activity;

(ii) a nucleotide sequence encoding a polypeptide at least 99% identical to SEQ ID NO:6, wherein said polypeptide comprises a D208E mutation, and wherein said polypeptide has SNAP activity, or;

(iii) a nucleotide sequence which is the full length complement of (i) or (ii); and (c) a transcriptional termination sequence;

wherein the promoter is heterologous to the transcribable nucleic acid molecule, and the transgenic soybean plant exhibits increased SCN resistance compared to a control transgenic soybean plant expressing SEQ ID NO:3.

2. The transgenic soybean plant of claim 1, wherein:

the nucleotide sequence further comprises one of more mutations selected from the group consisting of A164972AGGT, C164974A, C163208A, G164965C, G164968C, and A164972AGGC; or the encoded polypeptide further comprises one of more mutations selected from the group consisting of D286Y, D287E, −288V, L289I, Q203K, E285Q, D286H, and −288A.

3. The transgenic soybean plant of claim 1, wherein the transcribable nucleic acid molecule is expressed in epidermis, vascular tissue, meristem, cambium, cortex, pith, leaf, sheath, root, flower, developing ovule or seed.

4. The transgenic soybean plant of claim 1, wherein the promoter comprises an inducible promoter or a tissue-specific promoter.

5. The transgenic soybean plant of claim 4, wherein the promoter comprises a nematode-inducible promoter.

6. The transgenic soybean plant of claim 1, wherein the promoter is selected from the group consisting of factor EF1α gene promoter; rice tungro bacilliform virus (RTBV) gene promoter; cestrum yellow leaf curling virus (CmYLCV) promoter; tCUP cryptic promoter system; T6P-3 promoter; S-adenosyl-L-methionine synthetase promoter; Raspberry E4 gene promoter; cauliflower mosaic virus 35S promoter; figwort mosaic virus promoter; conditional heat-shock promoter; promoter sub-fragments of sugar beet V-type H+-ATPase subunit c isoform; and beta-tubulin promoter.

7. The transgenic soybean plant of claim 1, wherein increased SCN resistance corresponds to a decrease in SCN susceptibility of at least about 20%compared to a control transgenic soybean plant expressing SEQ ID NO:3.

8. The transgenic soybean plant of claim 1, wherein the nucleotide sequence further comprises a G164968T mutation.

9. The transgenic soybean plant of claim 1, wherein the nucleotide sequence further comprises a A164972AGGT mutation.

10. The transgenic soybean plant of claim 1, wherein the polypeptide further comprises a D286Y mutation.

11. The transgenic soybean plant of claim 1, wherein the polypeptide further comprises a D287E and a −288V mutation.

12. The transgenic progeny, seed, or plant part from the transgenic soybean plant of claim 1, wherein the transgenic progeny, seed, or part comprises the transcribable nucleic acid molecule.

13. An artificial DNA construct comprising, as operably associated components in the 5' to 3' direction of transcription:

(a) a promoter that functions in a soybean plant;

(b) a transcribable nucleic acid molecule comprising (i) a nucleotide sequence at least 99% identical to SEQ ID NO:3, wherein said nucleotide sequence comprises a C163225G mutation, and wherein said nucleotide sequence encodes a polypeptide having SNAP activity, (ii) a nucleotide sequence encoding a polypeptide least 99% identical to SEQ ID NO:6, wherein said polypeptide comprises a D208E mutation, and wherein said polypeptide has SNAP activity, or;

(iii) a nucleotide sequence which is the full length complement of (i) or (ii); and (c) a transcriptional termination sequence.

14. A method of increasing soybean cyst nematode (SCN) resistance of a soybean plant comprising:

transforming a soybean plant with an artificial DNA construct according to claim 13;

wherein the transformed soybean plant exhibits increased SCN resistance compared to a control transgenic soybean plant expressing SEQ ID NO:3.

15. The transgenic soybean plant of claim 1, wherein the nucleotide sequence further comprises a C164974A mutation.

16. The transgenic soybean plant of claim 1, wherein the polypeptide further comprises a L289I mutation.

17. The transgenic soybean plant of claim 1, wherein the nucleotide sequence further comprises a G164968T, a A164972AGGT, and a C164974A mutation.

18. The transgenic soybean plant of claim 1, wherein the polypeptide further comprises a D286Y, a D287E, a −288V and a L289I mutation.

19. The artificial DNA construct of claim 13, wherein the nucleotide sequence further comprises one of more mutations selected from the group consisting of A164972AGGT, C164974A, C163208A, G164965C, G164968C, and A164972AGGC; or the encoded polypeptide further comprises one of more mutations selected from the group consisting of D286Y, D287E, −288V, L289I, Q203K, E285Q, D286H and −288A.

* * * * *

SEQUENCE LISTING

<160> NUMBER OF SEQ ID NOS: 1310

<210> SEQ ID NO 1
<211> LENGTH: 2220
<212> TYPE: DNA
<213> ORGANISM: Glycine max

<400> SEQUENCE: 1

```
aaggagaagc aacaaatcaa aggatgttta cttctgattt tggaatgcat ccaaacactc      60
ctcacgggga attttttagg ctctctactc ccgcgcgatc tctcttgtat caccagcaat     120
gaaactttgt catatttttc cttctctctc cacacgagcc atctcctatc cttctttttc     180
atattagaca ttaattcaaa ccctctttca tttaactttc cctcatgaaa gtgaaattta     240
aatgataata ttggattctg attgtgcaaa ttaaatacaa gtaaaggctt aaataaataa     300
ataaataaat atatatatat atatattcca ataaattaat acgtaatttt atgattttgg     360
tcttaataat ttttttaat ataatttttc tgtgcctttt ctaataagga tgatgtcaag      420
ttaaaatcat gatgatgtca ttaagtatcg catcatcaaa tgatgaagtc atccattatc     480
atattaataa aaaaaatgat atcattaaat aggtcgccta catcatcaaa tgatatcatt     540
aaggattaaa aataaaagtt atatatatgc aagaataaaa agtaaaaaaa atgacatttg     600
taagaacaaa aaaaatattt aaacattaaa ttaaatgttt acttctatat actcccttat     660
cacacttatc actctcaagt ttgtttatac aaattctatt tatcaaatat tatcaccaaa     720
ctttctcata ctaaaaactt ttagtcatga atgttgaatt gagataccat ctttcatttg     780
aatcagggac caaaatagta aaaaaatatt catttactaa aattcaaaat aatataatta     840
```

```
tataattttt ttggtgaaaa cataattata taaataaata aaagaaagta atgaaaaata    900

taaacacata ttaaattaat ctaacaaata aaaggtattt caattagttg acaataaaaa    960

atatacatta ttaacaagat tatgacttaa attgtctatc cacaattgcc aatcaaaata   1020

catcactaaa tataattatt ataattattg attaaaaaaa agctatcaat ccatattttg   1080

tagaataata ccttaaaaca agcataaaca taaattctta gaacttaaca aaatacaatt   1140

attattatat ttaaatatat attaatataa agttcaattt tgatccttat agttatataa   1200

attttatctt ttagtttcta tacttaaaaa tcatctcttt taatcctatg cataatattt   1260

ttaatctctt ttagttctta ttatgagttt aaacggtatg gattaaaaga aataaaaatg   1320

atacaaatta aaaaagatta aaaataatat gtgtaaagat taaaatacac aaatttaagt   1380

ataagaatta ggataaaaat tatataatta taaaaattaa atgagtaatt aagcattaat   1440

ataatactat tatatgaaaa gttttgtttc taagaagagt ctcgtccact ttgcttttta   1500

caatcacatg ttaaaaaaat tatatcatat taagggatgg ccaattatct atgcctatat   1560

agtttatatg ttttgaaaaa atttggggcg tcgtgactcc cccgccctca aatagctccg   1620

tcaatgacca ttcacatctt atagttcaag tatcattgtt acaagtacac atatttatta   1680

caatatatat acctaaagta aggttgtttt tgctaactta aacatcaaag tgattttgtg   1740

gataacccac tgccactcaa ggagttcggt gtcgcagagt tcaggcatct aaaatctaga   1800

ccatcgcttg tcgcactttg aaccaaacat gaaggatgga gctttgagaa ggaggggtgg   1860

agaagaaaat ggggtgcaaa tatatatagc gatgaggagt attttaatat ttaattgaat   1920

gcttaaatat atttttatct cctaaatatg tcatttatta cttttaattc cagtaaaaaa   1980

atatatttta atccttgtaa atttgttact attacatttt gtgtttaata acatcatcat   2040

ttgatgatgt aacattttaa ttatacaatc atttgatgac ataattttat ctttatatta   2100

tatttgatta cattatcatt tagtaatgtg gtgcttgatg atattattat gatgccaata   2160

taatatcatc actatcggtt ctgatggttt tttttttaac agcgagagaa actaattaaa   2220
```

<210> SEQ ID NO 2
<211> LENGTH: 8160
<212> TYPE: DNA
<213> ORGANISM: Glycine max

<400> SEQUENCE: 2

```
agacacataa aaaagataga aagtaatata tatatatata tatatatata tatatatata     60

tatatatgtg tgtgtgtgtg tgtgagtgtg tgtgtgtata cgggtttaca gggtatgtac    120

aacatggtta tatatcatat agtatctaac taactatata tgaaaataat ttcataaatt    180

gtcatgagtg gttagtataa tttattgtaa aaattattga gatatgtatg ttttttaact    240

gcattgagat atagtttttt tgactcataa tatatatttt atctgcactc ataatatata    300

gtatcaagat tttttttttt gtcagcgtca tatgtgatgt taaatgtgat actttatatt    360

gatgaaaaat gctaataagt ttatttagca tattttttaa ggaattaaaa ataatttttt    420

tattcgaatg cataaaattg tgttgtttat aatttttttt tataatttcc taaatattta    480

cttttttag tttttaacc catgagcact ggttaacaaa accatatatc aattaggggt    540

tataaatttt ttaggcatga taattaatga taataaagtt ttaaacttat gatttataat    600

gcagtgcaaa agtcaatttt ccaagacatg ttaggcaaaa cttggatttg aattctctgc    660

catcggagaa atcaggcatt cacgtagtca gatgattaaa agcgtcgact agtgaagatc    720

taacaattca taagtcattt aataacttca actttaaaaa tatctaaaaa atactaacca    780
```

```
tatgatgaaa tcaaacggtc cataattatg actgtgtgaa tgcagagaat ccaaatccgt    840
aaaacttctg aaaaatgcat atcgagcgta aaattttatc gagaatgagc acgtactcag    900
aagcatctag tatgaattga attatacata tagattcaga tgtctacatg cacacacata    960
tataatgaga cggatcttag atcatatcat acgtatttgg tatttagagc tgttacttcc   1020
ttgtgttgct tccagtattg tcaccattcc acaaggacaa atcaggtacc cacctctatt   1080
cacatctgtg tccattaatc atcacaacaa aacaatatcc tccatacata tatcctgctc   1140
ctaccttgtc tattgcctta tatgctctga actctcctag agtactcttt tagatcccat   1200
aatgttcacc attcatcaag gtttcctaa ttactttaat taagtgttgg aaatgttgta   1260
ttttgagttg ttggccatat tttgatgagt tctcaaaaga ccagtttact tagaaattat   1320
taattttttt taagttagta tgttcgctat atggccaaga ctaggggaaa aaaacataac   1380
atgcatgtaa ccctaggtca taataaagaa ttaaaaccaa gttattttat taaatagtat   1440
aagggctatc aataaataat ttttacaaaa attaaaatta aaatattgat atttttacaa   1500
aagttcaact tctatgttac taattaataa tattctgcaa atagaaaatc atgttaaatt   1560
ttttttttta agataattat tataaaagtt gataaaatta tgcatgcatg attattttaa   1620
tgactatttg aaagtgtaag aattatttac attatctata tatataatcg ttattttctg   1680
agttgaatga acgtgtccga gtcattatcc atatatttgt attttttttt ttgagtattt   1740
ttttgttgtt gaatagtcca tatatttgat ggtatcagga aaatgtggaa aagatacaaa   1800
atcatacagg taagcaattt gtcttgagtc gtcatgagtc tgttaaaagt ctatcgatca   1860
gcaaccttat gtaatatata cactttgggt gcgatcattt caatcaaaat cacattccct   1920
agctttggct cagaaatcaa taattgagca agtaattttg tggatacata aaataaaaag   1980
agttggcctg tatggtgagg ttcacaggta attacacatt attccagttt attttagatc   2040
gaaaccagat attaatgatc acaaaaaaag atggatcgaa gaaaataaaa tattgctggc   2100
cctcccttat gctatttcct atttcttctt atgctttgaa cctattaata gcacatttta   2160
gcctgagcaa ggagtccgaa tgtccttttt catggacttg gcagttgcaa taaagttgga   2220
gaagctgata agattctgtt tcagatttga ttattcttac tcacatgttc cacgattgac   2280
gagaatatat atatatatat atatatatat atatatatat atatatatat atatattggt   2340
ttttaagtgt gtctctatcc tcccgtttaa tttgaatttg atgacttttt ggtagggtta   2400
aagactaaag ctaaaactcc tctaaatagt aacttgttct taaaaaaaat gatttttttt   2460
tatcagagtt aaccacacat acttaattta aaagatttga actcctttaa cttgaatcaa   2520
aagatgctag ctttttatta atgaatatga tgatatgtac gaggtaatgt tttagtatga   2580
ttattggaaa tttggcatct tgctagcatg taggtgatac tcttatttct catgttaaat   2640
agttaaattc attttaaaag tatagaatac caataaattg attcttaaaa aataaaaatt   2700
taaatttaat tattgaatat gtaaaaaaat atgataaatt agtcttgcaa ataatttaat   2760
ggcaagttag ttcttgaaaa tataatttat tatcaaatta atcattaaaa attataattt   2820
aatgacaaaa tagtttcaca aatttaatga caagaataat ttattgcatt ttttacctat   2880
ttagaaatta aatttatgtt tttcattttt taaggaccaa tttatcatcg tatcatactt   2940
tcgataacaa atttgactat ttatatttct tattaacatg ctcaatgatg atctattttt   3000
ctgtctatat agatagatct atgttctata atttacaatt gaattatata caaatatcat   3060
tatataacaa catatattaa aaaaaaactt gtattttttt tattttagag agtttttgta   3120
```

-continued

```
tctttttatc ttcctgttgg atgaataatt tccatgtaca tatatactag tgctttgtat   3180
catggaactt ttacattttt tttttcctgg aaacaagcca tgttcatagg cttaaaaata   3240
attaaagtga cttttatctt tttcaacaaa gtcttcttca tacgcataac caacaaatac   3300
atatttaaga aattcaatca tctatcaact gtgttaaatc ttgttgatat ctctattaca   3360
acacttttta ttaatccgtg tattaaactt gagatgtgga cttaatttta acaattaatt   3420
agaaagctat gctaactaaa tgagagtaat tacaagtaat agaaccaaaa tacaataaaa   3480
acgttccaga aattaatgtt caactagtat attttttatg aaaaataaac agaaaagttt   3540
ttaaaaaaat aaagggttat aaatcacctt ggttgacacc caatgagata atgggctaaa   3600
attactcatt catttcaagc ccagtaagtc tgggcctagc attagcttca agtagttcgg   3660
attcacccga cccagataag acattcgggt tcggatcctg tagtgtcatc actcgttaga   3720
tttcgatgaa gaatagttag agagtgctgt gagcttcagc aaaatgcgcg ccctagcagc   3780
tcagttctct aatgtaatgt tctctttaat ccttgtctct gcctctgttc aattttaacc   3840
ctttataatt taaagaagaa aataaagtaa tcattttcaa attcaattca tatttgaaat   3900
cgatgttgat cttaagtaag tacccatttg cggattcatt ttattcttaa ctttttttcat   3960
ttttttaacc ctttttgcag tatttatgca gaagaaaagt tggggtcaat ctgcgatctc   4020
gtaatttttc atcatataac agtaaaggta tcaccttgtt tttttctatc ggtacttttg   4080
aaagaaagaa ataattataa gaaattatga ctaattttgt caggctatgg aatcattctg   4140
ttgagaacga gaaaaatgaa ataggtactt gtattgaacg ttctagtagt aaatgatagg   4200
tacatatgtt gattttgggg atttctggga ttagatcatc aagccaaaat cttgcactgt   4260
aaaatactaa aatacaaaga aaatggtttt ctttttttcgt tcaatttttg gtttcattgt   4320
ttgagctgca attatgttgc gtgacttcac ttgtaactct tttgatttcc agatgagcta   4380
accatcgagg aagaagctga gagaaaagtt ggatggctat tgaagacgat atttttttgtc   4440
actgcagggg tagcaggata ccatttcttt ccttatatgg gtatatcagc aaaatccctg   4500
caacaatttt taacttgcaa agccttcatt tgctctgggt agttcaagct tcacaatgct   4560
gttaaaattc atattttcag gagagaattt gatgcaacag tctgtttcgc ttttgcgtgt   4620
caaggatccc ttgttcaaaa ggatgggagc ttctagattg gctcgttttg cagtagatgg   4680
taagttttac tatctgtatc tttgtgtcac taattgcttg ctgttgttgt tttatgaccc   4740
atatttcttt ggcacatgac atatatattg aattgtttat taattgttag tcatttgcat   4800
attagggcag ttgttttcta gaacagattc ctattcttgc aacaagcata ttttcattat   4860
ccttgtgctt tacactagtg acatttagtc atttagtatt aatctcagct tattcttgaa   4920
atgacaattt tggttgaagg ggagagttga tgggagattt tgaacttgga taaaagagtc   4980
atagattgaa atttttctct tgaactgata atcaaatagt tattgagatt tttaattgag   5040
ctgcatttgt taagaagtca cggctaaaag agttacctag ttgtcagtta tactattttc   5100
atgactaagc agcaagcaca gatattgcag tgatacacaa ccgagagcat attctccaaa   5160
aggcaaattg ccttgatgca atttgctagt ttgtacactg atagaattgc ttatttatca   5220
atagtgttcc aatgtatagg tatctcatgg cactgattaa ggataaaaca tggtgattta   5280
ttcctttcta aaatcttttg tccctgcaca agttgtttat attaaacatt gtttacctta   5340
cttttgctca caagatgaaa gaaggaagaa gatagttgag atgggtggag ctcaagaact   5400
cttaaatatg ttaagcactg ctaaagacga ccgtacacgg aaagaagcat tgcatgctct   5460
tgatgcactg tcacaatcag gtgaaatcat aattttaata ttttttaaa tagttattat    5520
```

-continued catgctggtg gagaggtaga ttattgtgat caattagtac ctttgtggtt ctaaatagta 5580
aaccagaaat gcccaaccac ttatggaatt tgttaattta tttgtataat attgagctgg 5640
aaatcaattt tatgagcaaa gtgtgataag aagcatatga aacttttata tgtttccagt 5700
ttctgttatc cttattcaat agatatgggc ttgtaaagat gaaaatgaac ataaattgtt 5760
ttgtgcatta attttgggac atattatacg tgcacaagct tatgtgtaac aatatctata 5820
cctgctactt tccctgtcaa catattgatt tttaagaatc cagttcaagt aatatttatg 5880
aggttgaaag atatgcaaca gtacaaccaa attagtagtg ctagctagta ctagcctttt 5940
ctgttctctt tcgattgaga taagctactt caatgttata gatgaagctc ttgcatcctt 6000
gcatcatgct ggggccattt cagtaattag gtctgcacca aattcacttg aggatgcaga 6060
agttgaggga ttcaagttga gcttgatgaa aagatttcaa gatctcagat atgatgtgcc 6120
atcatgactt gaggtgcatg cctccttttg ctttatgttt ttggttggtt ggagcatgaa 6180
ataacatgat atgagaaatt aagctggcaa ccaaagcttt tgtggggaag agtacttgaa 6240
attactgtgt atcatttgac caaatctaat ggaagattat agttctattg tcattttagt 6300
ttttttcact tgtcaaatgc gatttgtcgc tcattgttct gtcaatcata ataaaatgga 6360
aaagatttat gtgcatgtca atttttattt tttgaaatat gtgtttagaa gataaaagat 6420
tacaacaaac tagtattgaa gttgtaagtg tttagatact gtaattgtat atttggttaa 6480
cactactaga ttaaatttaa gcctcaactt tcaaatgtga ttgatcatat aatgtcataa 6540
aatgtgtgta attataggtt gatgctttaa ttgttattta catatgcctc aactctcaac 6600
cgtatgtcat catcaggctt cttgtttagg ttcagctggc gccttgctcg ttctattttg 6660
ttcgtattcc tttgttcatt cgatgttttt ttaggaaaat atgttcgttg aaagaaaaaa 6720
tcagtcaaca gaagatacat gcccttactt ttctctactc cacgtctcca cctaccctaa 6780
cccttggagt tacttttcaa ttgagcacgt taacaagcct aactaaacgt ggttctgtgg 6840
agataatata ctaaaaaaat attatttttt atttaattta ataagacttg tgcgcgtaac 6900
tcttttcaaa gtgctagctt tctttttttgg tgaattttca aagtgctagg tgaatatgcg 6960
tatttggaga tagaaagctt tttttttgg gacacaaaag cttgtttaac atgtgataaa 7020
cttaaaacta ataatcattt tttttaatta tccctattca atgttttagt tttaaaaata 7080
ccccatttgg gaaaatagcc catctgtgga tgtaaaaatt actagagtac aagttaatta 7140
gggttagttg tttttttttt ctttcttctt ttcctacgag atcaagagga acggagcaaa 7200
atcatgtttt ttcttccacc aaaataatgt aaaattttaa aacaaaatac taaaataata 7260
ggttataata tatttctttt ccttcatttt atacttagtc ttttattttt tttaaaaata 7320
tcattctagt tatttaactc tcacatttga gttaatgtta tacttttgaa acttcagtca 7380
ttttttattt attttggata cgattttgag ccttttttct tttactaatt aaagatataa 7440
aatttgtctc attaaattaa actatgaatc caattaatgt tcaaacaaaa cataaatcct 7500
taacatgatg aaaattgaat gaaaaatgaa tttcataagc aattggaaaa ctgaaaaaaa 7560
aaatctaata acaatatttg aaaatctatt aacaatgagc agtaggcttc tttggaactt 7620
gaaatgaaga ataaaagagt cattggaaat aaatctcaat taattgaaag atattttta 7680
gaaaatgtca ttaaatagaa taaaaataat caaaatttgc ttatatttga atctaataaa 7740
aaaattgtta attactcttt ttgtctcgaa tataaacaaa aaatactttg agtattagtc 7800
tcaaataaaa gtaaaattta actattgtta ctttatttaa tgagatattc ctaaattata 7860
ttttatttaa ttaaagtttt attacttatt atctctcttt tttatttttg atatgaactt 7920
tcaagaaagt gtagtttaga agaagaattt tttttaataa gaaaggtgta attaaataat 7980
ctaattatct aactactaac tttttgaata aaccgtaagt taatttcttt tatatagaaa 8040
gaagggatta aattaatttt aaaagagttc ctcttcattt taatcattaa tttttttgaa 8100
attcaataat caatacctac tcattacaat aataaaatac aaaaacttct tcacgaaata 8160

<210> SEQ ID NO 3
<211> LENGTH: 9620
<212> TYPE: DNA
<213> ORGANISM: Glycine max

<400> SEQUENCE: 3
aattgattcc ttgtgttata tatatatata tatatatata tatatatata tatatatata 60
tatatatata tatatatata tatatatatt cagtatataa tttagtgtag ctggacacat 120
attagtgccc cgtggccgtg tgttgtgctt ttttgttggg cgaaacaacg gccaaagcga 180
cgaatcactt ccttacgtga cacacctctg tctaatagac gataggccaa agtcacaaat 240
actttttgat tgagtatttt ttaatgccac atatcatatc tgtcagcgtc acatgttcaa 300
ataaatccct agtaaaaacg ccagaaaaca aatgcatgag caatttttgg actttggact 360
agttacaatt tttcaacgtc acatctttaa atgatttcgt ctctatttag tagttgtttt 420
taatgcggcc atgcccactt tctcgttaca aagcatgcat tttattattt gaacgaaaat 480
atttaatatt gtgtattact cgttttacac aattgctttt attctttttt ttttattttt 540
taaatacagt catctttaaa aacaaaatct tcgatcattc catttcattg ttcacaaaac 600
attatcctat cacatgcacc ctatgtaata taatacacgg ttgtggataa aataattctg 660
cacctgccca acttttgtat tgatatcatt tttttatttc ctctatattt tccatattta 720
tatattaatt ctatcacttt cctgcacccc aataagtcat gctccaaata ttattgtttt 780
ggataagtat attgcacaat ctattcttgg cttcttcatg accatgacac ggcaatggag 840
acgaacgata atgaaaggcg cgtaaatcat ttgaaaggtt gaattatgta ccaaatgcta 900
ttatattagc atttcatacg ccattctaac aataatgaga acgagttgcc ccacaattga 960
tcaatatttg tatccttgca cggcacaaac ttgtaagata tggccccaac ttcgtcaccc 1020
catcaagttg atttcatttc tttaatattt ggtattttac atagaaatgc tgccacaaga 1080
catgaattct acaataaaca acaagggatc caaaatacaa aagtaacaca atcgccacag 1140
caaccaaatg cctctagaat ctccccagcc ataccctctc tccccaaata aaattttcta 1200
tacatataaa aaaaacaata gaaggggaga aatgagagaa ccagcttgta tttatgactt 1260
gctactaaaa gcattatata tgttggtgga aatggcaagc acacttgtaa ccacagctag 1320
tataatcatt atcagtgcaa taattttgtc tcttctcgtt gatatacctt taacatccct 1380
gtcatcagaa acaatgaaaa ttaagagact aatttattta tttattcaat tcaattttca 1440
acttgagctc tactttatca gaagtcaata agtctatgct agattacctt aaaacaatag 1500
agccggggaa aatgaaggca aggcacactg cggatgagga tcccaggaac tgaaagaagt 1560
accaaatatc tgggattgct atagctgcaa ggtaggagaa tacaagcagc accagagtga 1620
ggatcataaa tcttttgttg tctgtggcta gcataggctt cttagggaag agaacttcat 1680
ctatgttggt tctcaaagag aagttcaaga gaggaaacac cagcatgatg tggagggcat 1740
agcttacacg gaccaaacta ttgagcaagg aaccaactgc tgaaccagca ttctggtcaa 1800
aattgatgag aatgtctgac tgggttgaat ccccaaataa catgtaccca aataagccta 1860

-continued

```
ttgcaaggta gatcacagca caaagcaata atgctaatcg aactgctgtt gtcatttggg   1920
atgccttggc aagctcaaac ccaatggggt gcactgaaag taaaatcaac catcagcaca   1980
gaaattttct aggcataccc ttaaaaaaaa tgagcaaatc cattaggcca attaccatta   2040
aagtgaaatg tgaaggctgt gacaacaaca ggaactgcag tgaacagatc aaagaatgag   2100
gtttggtagt ctagccgagg aaacaatcta ggagtttgtg tttttccttg caccagagct   2160
gtgatagcca acccacaaca tatgccaaca aatgccactg caagaagagt tgacactgca   2220
gagctgtact tcaaggactc taccaattcc aaaacaccaa gaggaagaac ccatgttagt   2280
tactgaaact cttcaattcc aaatacacaa gaaagcatgt tatataacaa aatattcaat   2340
tgtaacactc acctacacgt ttgtacaata ccaatggaag cataacaaag accaaggtga   2400
aaagcaaagc aaattcccgg gaattccacc agtgaattcc aaaccactgt tgcaaaatgc   2460
ccaaatgcac ttcccctcca ttttgctttc cagatagcac atctcctgtt gttcaacaaa   2520
aggtaattat taaaatacat ctattttttt ctttcatctt ctttctacta cattttcttc   2580
ttatatttct ctttatttcc tgtcatttca cttttttttt tcctgtcttt cttctaccca   2640
ttacatagac caaaaattga ggtgtgcatt gcggaaacag attccccaca ttcacttttt   2700
ttttcatgaa tcagaactat tagattgaat atcgaaggtt atatttggaa tacatatttt   2760
aagagtatgt ttggatacaa agttagaagt gcatttgaca acttttggga gctcctctaa   2820
tggaaaaaga ttaatatttt tagtagaaaa ctctcaaaaa cacttctagt ttgtatcgaa   2880
acaggcctaa gttagattca ttgagataag ttatgagtaa tacaatctgt atttaacagt   2940
gaattcccag cggtaggaaa tcccgatcct tacatttcca ttatcttgtt aaattaatta   3000
ccatacacaa acattaaaga aaacgactta ctacatatat tttttcaaaa aatgaacctt   3060
tctatttata gtaaaaaaaa taaaaaaacaa atttcactta ttattagcaa caatttcacc   3120
aatcaaaatg aatctgactg aaaacccggc aaaactcaga acaagcatac caaaccaaaa   3180
acatgaaaaa atctacattt ttttttcctt ttttacgaat tcagtagaaa ggaaattaaa   3240
aaaaaaggga aaagttccgt tacgttaccg atgatgataa ggtagagaat taaacccccca   3300
acgttggtga tgatgacgca aacttgcgcg gctaatgctc cacccgatcc gaacgcctcc   3360
ctcatgacgc cagcgtacgt cgtcgtttcg ccggagtgcg tgaaccgcat caggaagtcc   3420
acggacagtt ccgccagcac ggccaccacg agaatcatcg cgaaagcggg aactacgccg   3480
agaaccttca tgatcgccgg aatcgacatg attccggcgc cgactatgct ggtggccacg   3540
ttgaacaccg cgccggggac ggaagccggc ggcggcgttc ctttggaatc ccccaggagg   3600
gggacgctga ctccggcggc cggagacatg ccggaggcaa aattgtgagg atcggagaaa   3660
gtgcggtggc ggtgtgcggt gcctggcagc ctactatctt tgaattgaat ggtttttgtt   3720
ttgttgtctc tcacgaaaat ttcacttcct ctctctttat aaatgataca agtggatttg   3780
ggaagttaag aaaacaaaaa atgaagttat aataagtaag attttatttt ataagttttg   3840
taggatgaaa agaaatatag ttgaatgagg aaatttcatt gaaaatagtt agctagattt   3900
tataatagag attaaacaat aataaaatct gcagatactt caacatgagt atgataataa   3960
taataataaa aaattgttgt tttctatttt tactccaaca tggactgaaa ttcatatgaa   4020
tttttttgaa tagtctattt ttttttattt aatttaatat tcatatcaaa gttatttcat   4080
actgaaaaaa atattaaata ctagcattct attattacca tttggaggaa tgattgaaag   4140
agtgttaaag tgcacctttt cagtcaacag ttaaaaataa ggcgtttaat tcaattcaat   4200
```

-continued

```
attacaaagt taagttggct gtataataat aacagtggta gtaagtagta gagtgaaaga   4260
aaaatttttt tggtcaaaat atttaaatca agactagaag atatgcaaat cagagattac   4320
attggatgat acggtcgacc aataaaaaat aaaagaaaaa acataaattg ggatgttcaa   4380
atactaataa taataactct aaacaaacat taacacgtga gttttctttc ccacgttgta   4440
atcattttga atttttaaaa tgttatgaca caaataataa gttaataata attataattt   4500
aacatttgaa ttgataaaag tgtttagttt tattgtagat taaactaatc tttcttcgag   4560
taaaaataac attaaattcc tacacaacag gtttatcagt ttatagagta ataacactct   4620
tattcttaat cgttttcttt tctggaagaa aaaataaatc ttagtcttgt tatttttttg   4680
agaatgtaaa atatacctta aaaaattccc ttaaagtttg tataattttt tggtatgtaa   4740
atatatttat aaataaaaaa atgtttgcga aaagtaatat ttacataaca aacactattt   4800
acagaacatt gatgaaatta tttttagata tataattatt aatacgaata tatgaatatg   4860
ttattaaagt aatcaatagt tatgttaaaa ctgatctgtt gactagacag tttgtcaatt   4920
tatttttat tcacttaatt gctatttttt tctaggtttg ttctttcgtt aaaaaacctt   4980
gcattggagg aaggccaatg ctagttataa aaatataaac catgatttga atataaaatt   5040
atttttagtc gaaaaacaat gaattatgtt gcaagtatca ctattgaaaa aatgccaacg   5100
gagcccaaga aggtgaggcc caaactgaaa gcgtgaagcg gcccaagact gagtgaggaa   5160
ataaataatt atccagaaaa tcggaaatgg acaatccttc ttgttacgca attctgaatt   5220
tgcgggtttt ggatttggac ttggtcgtca acacagtcta attaatatct ttttgctcct   5280
tcgcttatga atcttcttct tcttcttctt gttcctgcaa cgcactgaat tcgatcaatc   5340
aatccatctt caattgcttt gtttcgatcg gaggaaaatg gccgatcagt tatcgaaggg   5400
agaggaattc gagaaaaagg ctgagaagaa gctcagcggt tggggcttgt ttggctccaa   5460
gtatgaagat gccgccgatc tcttcgataa agccgccaat tgcttcaagc tcgccaaatc   5520
atgtttttcc tctttctctc tactttttt aaattccatt tcgtgtctcc tcaaaatgct   5580
gatttagtgt cataaatcat aattattatt ctcttctatt gttgttattt tattgttatt   5640
acttcaatcg acgagtgtgt tgagttttga ggtgtccgat ttcccgatta attgaagtat   5700
agttttaatc tgattttact ggaaaatatt ttttgcctga tttttttttt ttggaacaat   5760
tactagcata taaattagaa ttgtggatga agtacgacaa tcaactctgt gttgtttgtg   5820
actgcgctca ctttcaattt gacgactaat ctctttattt tgttgaaagt gacgaacttt   5880
gaaattgatg ttggaatagt tctgtttatt gttcttgatt tgatctatgt ggcattttag   5940
gggacaaggc tggagcgaca tacctgaagt tggcaagttg tcatttgaag gtaacattca   6000
tcagacttgg ggttttggag tggctgaat ctcttttgca tcctttagtt ctctattaag   6060
cctgcatgac attgttgtgt tctgtttcca tttagttgga aagcaagcat gaagctgcac   6120
aggcccatgt cgatgctgca cattgctaca aaaagactaa tataaacggt atgcatgtgt   6180
ctcagttgtt accactacat gcactacaat actttctcat ttatgatttg tgctttaaat   6240
gctgctcttg cttccatgca gcaaggccaa ttccttttag cctcaatgtt tctctgtata   6300
actttaatgt aaatcatata aaacaattgc taccttttg catgaacaaa ttatataaag   6360
caaatctctt tgtttaatct ttacatatgt gtaaatcaaa tactgggctt catatcgata   6420
aggtctaagt aggggttcag tcttttattt ggattagttt aagtcagaaa ttgaagttaa   6480
tttgtgcttg cataagttgc ttccatctga ttgctttctt tttatggctg tctgtatgtc   6540
atagccttat tttgatttgt tatttgctga ctattattag attggaactc atgatcatat   6600
```

```
ccctaagcag gagcaaatta ttttgctgtc ttgcttgtct tagtatgtcc cacttgcatt   6660
aggaagaact aagacaatta aagttacctt ttctttcttt gaatacagag tctgtatctt   6720
gcttagaccg agctgtaaat cttttctgtg acattggaag actctctatg gctgctagat   6780
atttaaaggt atattatgtt tatgatattg atatctcttc tcctgggtat gatttttaat   6840
ttattctctt gtccatatcc cagattttag atattgatcc tgcaataaaa tgcgttgaag   6900
tatactaagt tatctgaatc cccattaaca tgttttaact gggttcacta ttttatacac   6960
aggaaattgc tgaattgtac gagggtgaac agaatattga gcaggctctt gtttactatg   7020
aaaaatcagc tgattttttt caaaatgaag aagtgacaac ttctgcgaac caatgcaaac   7080
aaaaagttgc ccagtttgct gctcagctag aacagtaaga tattgtcctt tctgcatata   7140
ttatctcttt tattatgctg atgaattgat caatatttct tcaacttggg tttattcttt   7200
aattggttag taatttcttc tgagaacttt ctttctggcc tttattttgt tcagtaccct   7260
ttctctaacc cactctcctc aggttaacat tagcttaggt cagtgtaggt tgtttgacac   7320
tgagttttta ttggtatgga tgtatggtct attatgatct caatggaaat ctagcatatt   7380
ttttttccac aatccataat atgatgactt gtgtacatgg tgtgaataaa agtcagtcca   7440
ttgctgcatt tggtattggt tacgtgttac tgtactttct gcatatatta tctcttttat   7500
catgtcgatg atttgattaa tatttcttca atttggattt attctttaat tggttagtaa   7560
tttcttctgt gaacttctag ttagagcatg aactgctaaa gaaatccaaa actttatttt   7620
ttacatggaa ggaactttat cagagtttta tttatttatt tatttttatg ttaaattgaa   7680
ctttaactgt ttctatgtta tgataactct tcttcagata tcagaagtcg attgacattt   7740
atgaagagat agctcgccaa tccctcaaca ataatttgct gaagtatgga gttaaaggac   7800
accttcttaa tgctggcatc tgccaactct gtaaagagga cgttgttgct ataaccaatg   7860
cattagaacg atatcaggtc taagtttttt caatagttca cttctggaga ctggacagct   7920
tatttgttgc taaattattc agatatgttt ttattttgca ggaactggat ccaacatttt   7980
caggaacacg tgaatataga ttgttggcgg taggtcactg gttttgaaat ttcgttatga   8040
atttttatg accaagtaaa ttggattaga atatttgaac ttctttgtag ctgtctcctg   8100
ggtcataatg ttttattata tttttgtatt tatcatagca ttgtgatagc cctgttacta   8160
ctttgtttgc tgatttactc atacatttgc cagatgaaac tgacattttt ttttaatcct   8220
ggtggatagg acattgctgc tgcaattgat gaagaagatg ttgcaaagtt tactgatgtt   8280
gtcaaggaat ttgatagtat gacccctctg gtaagctcca aaagttgtta aataggataa   8340
cttctagtgg tgtttaacaa aaaaaaaaat tccacttgta tttttatcc acattttata   8400
acagaataat cataaccttt cacaacttaa ttctcaattt tcacagtaat taaatgtgta   8460
attttaaaaa aatattttcc ttaacttaaa cctgattgaa atttccccct gaaatttaag   8520
ttctatttga ttacctagag tgtaatttcc gtgttttgtc acttaatcac tgtgtaaagt   8580
taatttttt gcttacaaag gtgtcttgtt tggaatgcta aaataacaag tacacgtgtc   8640
accaaattta gtaggattaa catttgttgt tttttgccat aataaacggt tgaacttaac   8700
atttgttgta cgtgtcatca aattctacaa attgtgagct gcttagtggg ttggacaaac   8760
attttagcag gtggtttcga ttgcctgttg aatacgtgaa attaaaccaa ggcaaaatta   8820
taatttgttt cttttgtctg tgtttcactc atacacattg aatcttgatg atacacagcc   8880
ttgttaattg ttatccttcc aattttttt agtgtttttg agcatctatt cttgttggtc   8940
```

-continued

```
atgtgttttc ttcactcatg tacctggttc ttttcctaca acgataaata tgtatccttt   9000

gttttttttt tccaactaaa tatgtaattt caaatttcta atcaatcatt gcttccaaaa   9060

tactctctct gtttcaaaat aagtattatc ctatattgtt ttacaagacc aagaaaagct   9120

aatatataga tgaaagaaat tagtaatttt acaaaactaa ccttagtatt aatattatac   9180

tgaaaaacta aattgacact tattaggggt gttagtgtaa aaaagcaatt aatattacat   9240

tgaaaagcta acatgatact tattttggga caactttttt ctttcaaatg caacacttgt   9300

tttggaacgg agggaatact agatattgtg ctcccttgta tgccctggac ataacgtatt   9360

taactggtct ggatgagttt atgaatgtca ttaatttagg gggagtcatt tagaatagct   9420

tacctataag tactttctaa cttttctcaa ttagtttcac agtgcaattt attaaaaatg   9480

tctgtatcta atcaacattg tctgtgtgct tgtgcaggat tcttggaaga ccacacttct   9540

cttaagggtg aaggaaaagc tgaaagccaa agaacttgag gaggatgatc ttacttgaat   9600

tgtaccttta atattcctgg                                               9620
```

<210> SEQ ID NO 4
<211> LENGTH: 191
<212> TYPE: PRT
<213> ORGANISM: Glycine max

<400> SEQUENCE: 4

```
Met Arg Ala Leu Ala Ala Gln Phe Ser Asn Tyr Leu Cys Arg Arg Lys
1               5                   10                  15

Val Gly Val Asn Leu Arg Ser Arg Asn Phe Ser Ser Tyr Asn Ser Lys
            20                  25                  30

Asp Glu Leu Thr Ile Glu Glu Glu Ala Glu Arg Lys Val Gly Trp Leu
        35                  40                  45

Leu Lys Thr Ile Phe Phe Val Thr Ala Gly Val Ala Gly Tyr His Phe
    50                  55                  60

Phe Pro Tyr Met Gly Glu Asn Leu Met Gln Gln Ser Val Ser Leu Leu
65                  70                  75                  80

Arg Val Lys Asp Pro Leu Phe Lys Arg Met Gly Ala Ser Arg Leu Ala
                85                  90                  95

Arg Phe Ala Val Asp Asp Glu Arg Arg Lys Lys Ile Val Glu Met Gly
            100                 105                 110

Gly Ala Gln Glu Leu Leu Asn Met Leu Ser Thr Ala Lys Asp Asp Arg
        115                 120                 125

Thr Arg Lys Glu Ala Leu His Ala Leu Asp Ala Leu Ser Gln Ser Asp
    130                 135                 140

Glu Ala Leu Ala Ser Leu His His Ala Gly Ala Ile Ser Val Ile Arg
145                 150                 155                 160

Ser Ala Pro Asn Ser Leu Glu Asp Ala Glu Val Glu Gly Phe Lys Leu
                165                 170                 175

Ser Leu Met Lys Arg Phe Gln Asp Leu Arg Tyr Asp Val Pro Ser
            180                 185                 190
```

<210> SEQ ID NO 5
<211> LENGTH: 436
<212> TYPE: PRT
<213> ORGANISM: Glycine max

<400> SEQUENCE: 5

```
Met Ser Pro Ala Ala Gly Val Ser Val Pro Leu Leu Gly Asp Ser Lys
1               5                   10                  15
```

-continued

```
Gly Thr Pro Pro Pro Ala Ser Val Pro Gly Ala Val Phe Asn Val Ala
            20                  25                  30

Thr Ser Ile Val Gly Ala Gly Ile Met Ser Ile Pro Ala Ile Met Lys
        35                  40                  45

Val Leu Gly Val Val Pro Ala Phe Ala Met Ile Leu Val Val Ala Val
    50                  55                  60

Leu Ala Glu Leu Ser Val Asp Phe Leu Met Arg Phe Thr His Ser Gly
65                  70                  75                  80

Glu Thr Thr Thr Tyr Ala Gly Val Met Arg Glu Ala Phe Gly Ser Gly
                85                  90                  95

Gly Ala Leu Ala Ala Gln Val Cys Val Ile Ile Thr Asn Val Gly Gly
            100                 105                 110

Leu Ile Leu Tyr Leu Ile Ile Ile Gly Asp Val Leu Ser Gly Lys Gln
        115                 120                 125

Asn Gly Gly Glu Val His Leu Gly Ile Leu Gln Gln Trp Phe Gly Ile
    130                 135                 140

His Trp Trp Asn Ser Arg Glu Phe Ala Leu Leu Phe Thr Leu Val Phe
145                 150                 155                 160

Val Met Leu Pro Leu Val Leu Tyr Lys Arg Val Glu Ser Leu Lys Tyr
                165                 170                 175

Ser Ser Ala Val Ser Thr Leu Leu Ala Val Ala Phe Val Gly Ile Cys
            180                 185                 190

Cys Gly Leu Ala Ile Thr Ala Leu Val Gln Gly Lys Thr Gln Thr Pro
        195                 200                 205

Arg Leu Phe Pro Arg Leu Asp Tyr Gln Thr Ser Phe Phe Asp Leu Phe
    210                 215                 220

Thr Ala Val Pro Val Val Val Thr Ala Phe Thr Phe His Phe Asn Val
225                 230                 235                 240

His Pro Ile Gly Phe Glu Leu Ala Lys Ala Ser Gln Met Thr Thr Ala
                245                 250                 255

Val Arg Leu Ala Leu Leu Leu Cys Ala Val Ile Tyr Leu Ala Ile Gly
            260                 265                 270

Leu Phe Gly Tyr Met Leu Phe Gly Asp Ser Thr Gln Ser Asp Ile Leu
        275                 280                 285

Ile Asn Phe Asp Gln Asn Ala Gly Ser Ala Val Gly Ser Leu Leu Asn
    290                 295                 300

Ser Leu Val Arg Val Ser Tyr Ala Leu His Ile Met Leu Val Phe Pro
305                 310                 315                 320

Leu Leu Asn Phe Ser Leu Arg Thr Asn Ile Asp Glu Val Leu Phe Pro
                325                 330                 335

Lys Lys Pro Met Leu Ala Thr Asp Asn Lys Arg Phe Met Ile Leu Thr
            340                 345                 350

Leu Val Leu Leu Val Phe Ser Tyr Leu Ala Ala Ile Ala Ile Pro Asp
        355                 360                 365

Ile Trp Tyr Phe Phe Gln Phe Leu Gly Ser Ser Ser Ala Val Cys Leu
    370                 375                 380

Ala Phe Ile Phe Pro Gly Ser Ile Val Leu Arg Asp Val Lys Gly Ile
385                 390                 395                 400

Ser Thr Arg Arg Asp Lys Ile Ile Ala Leu Ile Met Ile Ile Leu Ala
                405                 410                 415

Val Val Thr Ser Val Leu Ala Ile Ser Thr Asn Ile Tyr Asn Ala Phe
            420                 425                 430

Ser Ser Lys Ser
```

435

<210> SEQ ID NO 6
<211> LENGTH: 289
<212> TYPE: PRT
<213> ORGANISM: Glycine max

<400> SEQUENCE: 6

Met Ala Asp Gln Leu Ser Lys Gly Glu Glu Phe Glu Lys Lys Ala Glu
1 5 10 15

Lys Lys Leu Ser Gly Trp Gly Leu Phe Gly Ser Lys Tyr Glu Asp Ala
20 25 30

Ala Asp Leu Phe Asp Lys Ala Ala Asn Cys Phe Lys Leu Ala Lys Ser
35 40 45

Trp Asp Lys Ala Gly Ala Thr Tyr Leu Lys Leu Ala Ser Cys His Leu
50 55 60

Lys Leu Glu Ser Lys His Glu Ala Ala Gln Ala His Val Asp Ala Ala
65 70 75 80

His Cys Tyr Lys Lys Thr Asn Ile Asn Glu Ser Val Ser Cys Leu Asp
85 90 95

Arg Ala Val Asn Leu Phe Cys Asp Ile Gly Arg Leu Ser Met Ala Ala
100 105 110

Arg Tyr Leu Lys Glu Ile Ala Glu Leu Tyr Glu Gly Glu Gln Asn Ile
115 120 125

Glu Gln Ala Leu Val Tyr Tyr Glu Lys Ser Ala Asp Phe Phe Gln Asn
130 135 140

Glu Glu Val Thr Thr Ser Ala Asn Gln Cys Lys Gln Lys Val Ala Gln
145 150 155 160

Phe Ala Ala Gln Leu Glu Gln Tyr Gln Lys Ser Ile Asp Ile Tyr Glu
165 170 175

Glu Ile Ala Arg Gln Ser Leu Asn Asn Asn Leu Leu Lys Tyr Gly Val
180 185 190

Lys Gly His Leu Leu Asn Ala Gly Ile Cys Gln Leu Cys Lys Glu Asp
195 200 205

Val Val Ala Ile Thr Asn Ala Leu Glu Arg Tyr Gln Glu Leu Asp Pro
210 215 220

Thr Phe Ser Gly Thr Arg Glu Tyr Arg Leu Leu Ala Asp Ile Ala Ala
225 230 235 240

Ala Ile Asp Glu Glu Asp Val Ala Lys Phe Thr Asp Val Val Lys Glu
245 250 255

Phe Asp Ser Met Thr Pro Leu Asp Ser Trp Lys Thr Thr Leu Leu Leu
260 265 270

Arg Val Lys Glu Lys Leu Lys Ala Lys Glu Leu Glu Glu Asp Asp Leu
275 280 285

Thr

<210> SEQ ID NO 7
<211> LENGTH: 290
<212> TYPE: PRT
<213> ORGANISM: Glycine max

<400> SEQUENCE: 7

Met Ala Asp Gln Leu Ser Lys Gly Glu Glu Phe Glu Lys Lys Ala Glu
1 5 10 15

Lys Lys Leu Ser Gly Trp Gly Leu Phe Gly Ser Lys Tyr Glu Asp Ala
20 25 30

```
Ala Asp Leu Phe Asp Lys Ala Ala Asn Cys Phe Lys Leu Ala Lys Ser
        35                  40                  45

Trp Asp Lys Ala Gly Ala Thr Tyr Leu Lys Leu Ala Ser Cys His Leu
    50                  55                  60

Lys Leu Glu Ser Lys His Glu Ala Ala Gln Ala His Val Asp Ala Ala
65                  70                  75                  80

His Cys Tyr Lys Lys Thr Asn Ile Asn Glu Ser Val Ser Cys Leu Asp
                85                  90                  95

Arg Ala Val Asn Leu Phe Cys Asp Ile Gly Arg Leu Ser Met Asp Ala
            100                 105                 110

Arg Tyr Leu Lys Glu Ile Ala Glu Leu Tyr Glu Gly Glu Gln Asn Ile
        115                 120                 125

Glu Gln Ala Leu Val Tyr Tyr Glu Lys Ser Ala Asp Phe Phe Gln Asn
    130                 135                 140

Glu Glu Val Thr Thr Ser Ala Asn Gln Cys Lys Gln Lys Val Ala Gln
145                 150                 155                 160

Phe Ala Ala Gln Leu Glu Gln Tyr Gln Lys Ser Ile Asp Ile Tyr Glu
                165                 170                 175

Glu Ile Ala Arg Gln Ser Leu Asn Asn Asn Leu Leu Lys Tyr Gly Val
            180                 185                 190

Lys Gly His Leu Leu Asn Ala Gly Ile Cys Gln Leu Cys Lys Glu Glu
        195                 200                 205

Val Val Ala Ile Thr Asn Ala Leu Glu Arg Tyr Gln Glu Leu Asp Pro
    210                 215                 220

Thr Phe Ser Gly Thr Arg Glu Tyr Arg Leu Leu Ala Asp Ile Ala Ala
225                 230                 235                 240

Ala Ile Asp Glu Glu Asp Val Ala Lys Phe Thr Asp Val Val Lys Glu
                245                 250                 255

Phe Asp Ser Met Thr Pro Leu Asp Ser Trp Lys Thr Thr Leu Leu Leu
            260                 265                 270

Arg Val Lys Glu Lys Leu Lys Ala Lys Glu Leu Glu Glu Tyr Glu Val
        275                 280                 285

Ile Thr
    290


<210> SEQ ID NO 8
<211> LENGTH: 290
<212> TYPE: PRT
<213> ORGANISM: Glycine max

<400> SEQUENCE: 8

Met Ala Asp Gln Leu Ser Lys Gly Glu Glu Phe Glu Lys Lys Ala Glu
1               5                   10                  15

Lys Lys Leu Ser Gly Trp Gly Leu Phe Gly Ser Lys Tyr Glu Asp Ala
            20                  25                  30

Ala Asp Leu Phe Asp Lys Ala Ala Asn Cys Phe Lys Leu Ala Lys Ser
        35                  40                  45

Trp Asp Lys Ala Gly Ala Thr Tyr Leu Lys Leu Ala Ser Cys His Leu
    50                  55                  60

Lys Leu Glu Ser Lys His Glu Ala Ala Gln Ala His Val Asp Ala Ala
65                  70                  75                  80

His Cys Tyr Lys Lys Thr Asn Ile Asn Glu Ser Val Ser Cys Leu Asp
                85                  90                  95

Arg Ala Val Asn Leu Phe Cys Asp Ile Gly Arg Leu Ser Met Ala Ala
```

```
            100                 105                 110

Arg Tyr Leu Lys Glu Ile Ala Glu Leu Tyr Glu Gly Glu Gln Asn Ile
        115                 120                 125

Glu Gln Ala Leu Val Tyr Tyr Glu Lys Ser Ala Asp Phe Phe Gln Asn
    130                 135                 140

Glu Glu Val Thr Thr Ser Ala Asn Gln Cys Lys Gln Lys Val Ala Gln
145                 150                 155                 160

Phe Ala Ala Gln Leu Glu Gln Tyr Gln Lys Ser Ile Asp Ile Tyr Glu
                165                 170                 175

Glu Ile Ala Arg Gln Ser Leu Asn Asn Asn Leu Leu Lys Tyr Gly Val
            180                 185                 190

Lys Gly His Leu Leu Asn Ala Gly Ile Cys Gln Leu Cys Lys Glu Glu
        195                 200                 205

Val Val Ala Ile Thr Asn Ala Leu Glu Arg Tyr Gln Glu Leu Asp Pro
    210                 215                 220

Thr Phe Ser Gly Thr Arg Glu Tyr Arg Leu Leu Ala Asp Ile Ala Ala
225                 230                 235                 240

Ala Ile Asp Glu Glu Asp Val Ala Lys Phe Thr Asp Val Val Lys Glu
                245                 250                 255

Phe Asp Ser Met Thr Pro Leu Asp Ser Trp Lys Thr Thr Leu Leu Leu
            260                 265                 270

Arg Val Lys Glu Lys Leu Lys Ala Lys Glu Leu Glu Glu Tyr Glu Val
        275                 280                 285

Ile Thr
    290


<210> SEQ ID NO 9
<211> LENGTH: 29
<212> TYPE: DNA
<213> ORGANISM: Glycine Max

<400> SEQUENCE: 9

tgggggkgg gggggggtgg ttggtgtgg                                        29


<210> SEQ ID NO 10
<211> LENGTH: 30
<212> TYPE: DNA
<213> ORGANISM: Glycine Max

<400> SEQUENCE: 10

agagaaggaa ggggaggaga agaaraaaga                                      30


<210> SEQ ID NO 11
<211> LENGTH: 31
<212> TYPE: DNA
<213> ORGANISM: Glycine Max

<400> SEQUENCE: 11

ccccccaacc cccccccccc cccccccccc c                                    31


<210> SEQ ID NO 12
<211> LENGTH: 32
<212> TYPE: DNA
<213> ORGANISM: Glycine Max

<400> SEQUENCE: 12

gagaggggggg gaaaagaagg gggggggggg gg                                  32
```

-continued

<210> SEQ ID NO 13
<211> LENGTH: 32
<212> TYPE: DNA
<213> ORGANISM: Glycine Max

<400> SEQUENCE: 13
ctctccctcc cttttcttct cctccycccc tc 32

<210> SEQ ID NO 14
<211> LENGTH: 32
<212> TYPE: DNA
<213> ORGANISM: Glycine Max

<400> SEQUENCE: 14 tctcttttt tcccctcctt tttttttttt tt 32

<210> SEQ ID NO 15
<211> LENGTH: 31
<212> TYPE: DNA
<213> ORGANISM: Glycine Max

<400> SEQUENCE: 15
acacaaaaaa acccaccaaa aaaaaaaaaa a 31

<210> SEQ ID NO 16
<211> LENGTH: 27
<212> TYPE: DNA
<213> ORGANISM: Glycine Max

<400> SEQUENCE: 16
gggggggggg gggggggtg tgggggt 27

<210> SEQ ID NO 17
<211> LENGTH: 30
<212> TYPE: DNA
<213> ORGANISM: Glycine Max

<400> SEQUENCE: 17
aaaaaaccaa aaaaaaaaaa aaaaaaaaaa 30

<210> SEQ ID NO 18
<211> LENGTH: 29
<212> TYPE: DNA
<213> ORGANISM: Glycine Max

<400> SEQUENCE: 18
aaaaaaggaa aaaaaaaraa aaaaaaaaa 29

<210> SEQ ID NO 19
<211> LENGTH: 25
<212> TYPE: DNA
<213> ORGANISM: Glycine Max

<400> SEQUENCE: 19
ttwttttttw wttttttatt ttttt 25

<210> SEQ ID NO 20
<211> LENGTH: 31
<212> TYPE: DNA
<213> ORGANISM: Glycine Max

<400> SEQUENCE: 20
ttttttcctt tttttttttt tttttttttt t 31

<210> SEQ ID NO 21
<211> LENGTH: 28
<212> TYPE: DNA
<213> ORGANISM: Glycine Max

<400> SEQUENCE: 21
tatataattt aaaataaata ttattttt 28

<210> SEQ ID NO 22
<211> LENGTH: 29
<212> TYPE: DNA
<213> ORGANISM: Glycine Max

<400> SEQUENCE: 22
aaaaaaaaaa aaaaaaaaaa aaaawaaaw 29

<210> SEQ ID NO 23
<211> LENGTH: 26
<212> TYPE: DNA
<213> ORGANISM: Glycine Max

<400> SEQUENCE: 23
acacaccaaa cccccacaac aamaca 26

<210> SEQ ID NO 24
<211> LENGTH: 28
<212> TYPE: DNA
<213> ORGANISM: Glycine Max

<400> SEQUENCE: 24
attaataaat ttattataat aaaaaata 28

<210> SEQ ID NO 25
<211> LENGTH: 29
<212> TYPE: DNA
<213> ORGANISM: Glycine Max

<400> SEQUENCE: 25
aaaaaaaaaa aaaaaaataa taaaaaata 29

<210> SEQ ID NO 26
<211> LENGTH: 21
<212> TYPE: DNA
<213> ORGANISM: Glycine Max

<400> SEQUENCE: 26
aaaaaaaaaa aaaaaawaat a 21

<210> SEQ ID NO 27
<211> LENGTH: 18
<212> TYPE: DNA
<213> ORGANISM: Glycine Max

<400> SEQUENCE: 27
aaaaaamaaa aaaamaaa 18

<210> SEQ ID NO 28
<211> LENGTH: 15
<212> TYPE: DNA
<213> ORGANISM: Glycine Max

<400> SEQUENCE: 28
ataaaaaaat aaaaa 15

<210> SEQ ID NO 29
<211> LENGTH: 25
<212> TYPE: DNA
<213> ORGANISM: Glycine Max

<400> SEQUENCE: 29
acacaaaaac ccccaaaaaa aaaaa 25

<210> SEQ ID NO 30
<211> LENGTH: 24
<212> TYPE: DNA
<213> ORGANISM: Glycine Max

<400> SEQUENCE: 30
gggggggttt gggggggggg gggg 24

<210> SEQ ID NO 31
<211> LENGTH: 31
<212> TYPE: DNA
<213> ORGANISM: Glycine Max

<400> SEQUENCE: 31 gagaggggggg gaaaagaaga ggggrgggga g 31

<210> SEQ ID NO 32
<211> LENGTH: 30
<212> TYPE: DNA
<213> ORGANISM: Glycine Max

<400> SEQUENCE: 32 gagaggggggg gaaagaaggg gggggggggg 30

<210> SEQ ID NO 33
<211> LENGTH: 31
<212> TYPE: DNA
<213> ORGANISM: Glycine Max

<400> SEQUENCE: 33
gcgcgggggg ccccgccggg gggggggggg g 31

<210> SEQ ID NO 34
<211> LENGTH: 30
<212> TYPE: DNA
<213> ORGANISM: Glycine Max

<400> SEQUENCE: 34
aaagggagra aaagaagaaa aaargagaag 30

<210> SEQ ID NO 35
<211> LENGTH: 31
<212> TYPE: DNA
<213> ORGANISM: Glycine Max

<400> SEQUENCE: 35
tctcttcctt tccctccttt tttttttttt t 31

<210> SEQ ID NO 36
<211> LENGTH: 31
<212> TYPE: DNA
<213> ORGANISM: Glycine Max

<400> SEQUENCE: 36
ctttttttct yttttttttc cttcttctct t 31

<210> SEQ ID NO 37
<211> LENGTH: 27
<212> TYPE: DNA
<213> ORGANISM: Glycine Max

<400> SEQUENCE: 37
aaaaawaaaa aaaaaaaaaa taawtaa 27

<210> SEQ ID NO 38
<211> LENGTH: 27
<212> TYPE: DNA
<213> ORGANISM: Glycine Max

<400> SEQUENCE: 38
agaaaaaaaa gagaaaaaaa aaaaaaa 27

<210> SEQ ID NO 39
<211> LENGTH: 27
<212> TYPE: DNA
<213> ORGANISM: Glycine Max

<400> SEQUENCE: 39
cgcccccccc gcgccccccc ccccccc 27

<210> SEQ ID NO 40
<211> LENGTH: 28
<212> TYPE: DNA
<213> ORGANISM: Glycine Max

<400> SEQUENCE: 40
tatatttttt tatatttttt tttttttt 28

<210> SEQ ID NO 41
<211> LENGTH: 32
<212> TYPE: DNA
<213> ORGANISM: Glycine Max

<400> SEQUENCE: 41
ggrggagggg ggggggggag gggggragag ga 32

<210> SEQ ID NO 42
<211> LENGTH: 31
<212> TYPE: DNA
<213> ORGANISM: Glycine Max

<400> SEQUENCE: 42
tttttttttt tttttttttt ttcttttttc t 31

<210> SEQ ID NO 43
<211> LENGTH: 31
<212> TYPE: DNA
<213> ORGANISM: Glycine Max

<400> SEQUENCE: 43
aaaaaaaaaa aaaaaaaaat aattawaaaa a 31

<210> SEQ ID NO 44
<211> LENGTH: 30
<212> TYPE: DNA
<213> ORGANISM: Glycine Max

<400> SEQUENCE: 44

```
cctcttcccc ccccctcctt ccttcttctc                                   30


<210> SEQ ID NO 45
<211> LENGTH: 24
<212> TYPE: DNA
<213> ORGANISM: Glycine Max

<400> SEQUENCE: 45

ggggggtgg ggtggggggg gggg                                          24


<210> SEQ ID NO 46
<211> LENGTH: 24
<212> TYPE: DNA
<213> ORGANISM: Glycine Max

<400> SEQUENCE: 46

tttttttgtt ttgttttttt tttt                                         24


<210> SEQ ID NO 47
<211> LENGTH: 16
<212> TYPE: DNA
<213> ORGANISM: Glycine Max

<400> SEQUENCE: 47

tttttattt ttttwt                                                   16


<210> SEQ ID NO 48
<211> LENGTH: 25
<212> TYPE: DNA
<213> ORGANISM: Glycine Max

<400> SEQUENCE: 48

aaattaaawa aaatattaat taaat                                        25


<210> SEQ ID NO 49
<211> LENGTH: 24
<212> TYPE: DNA
<213> ORGANISM: Glycine Max

<400> SEQUENCE: 49

aaaataaaaa aaaaataatt aaat                                         24


<210> SEQ ID NO 50
<211> LENGTH: 24
<212> TYPE: DNA
<213> ORGANISM: Glycine Max

<400> SEQUENCE: 50

aaaataaawa aaataaaata aaaa                                         24


<210> SEQ ID NO 51
<211> LENGTH: 23
<212> TYPE: DNA
<213> ORGANISM: Glycine Max

<400> SEQUENCE: 51

ttatatttwt tttattttat ttt                                          23


<210> SEQ ID NO 52
<211> LENGTH: 26
<212> TYPE: DNA
<213> ORGANISM: Glycine Max
```

<400> SEQUENCE: 52
ttgtggtttk tttttggttg gtttgg 26

<210> SEQ ID NO 53
<211> LENGTH: 32
<212> TYPE: DNA
<213> ORGANISM: Glycine Max

<400> SEQUENCE: 53
tctcttcctc tcccctcctt tttttytttt tt 32

<210> SEQ ID NO 54
<211> LENGTH: 31
<212> TYPE: DNA
<213> ORGANISM: Glycine Max

<400> SEQUENCE: 54
aaaaagaaaa aaaaaaaaga aaaaaragaa g 31

<210> SEQ ID NO 55
<211> LENGTH: 30
<212> TYPE: DNA
<213> ORGANISM: Glycine Max

<400> SEQUENCE: 55
ggagaggggg gggggggggg gggggggggg 30

<210> SEQ ID NO 56
<211> LENGTH: 30
<212> TYPE: DNA
<213> ORGANISM: Glycine Max

<400> SEQUENCE: 56
attttattat tttttttata attwaaaata 30

<210> SEQ ID NO 57
<211> LENGTH: 31
<212> TYPE: DNA
<213> ORGANISM: Glycine Max

<400> SEQUENCE: 57
atataaaaaa ttttattaaa aaaaaaaaaa a 31

<210> SEQ ID NO 58
<211> LENGTH: 30
<212> TYPE: DNA
<213> ORGANISM: Glycine Max

<400> SEQUENCE: 58
cacacccccc aaaacaaccc cccccccccc 30

<210> SEQ ID NO 59
<211> LENGTH: 29
<212> TYPE: DNA
<213> ORGANISM: Glycine Max

<400> SEQUENCE: 59
cccctccccc cccccctccc ccttctcct 29

<210> SEQ ID NO 60
<211> LENGTH: 31
<212> TYPE: DNA
<213> ORGANISM: Glycine Max

<400> SEQUENCE: 60
gagagaagag aaaagaaaag gaagaagaga a 31

<210> SEQ ID NO 61
<211> LENGTH: 30
<212> TYPE: DNA
<213> ORGANISM: Glycine Max

<400> SEQUENCE: 61
aaaaacaaaa aaaaaaaaca aaaamccaac 30

<210> SEQ ID NO 62
<211> LENGTH: 30
<212> TYPE: DNA
<213> ORGANISM: Glycine Max

<400> SEQUENCE: 62
ttkttgtttt ttttttgttt tttkgtgttg 30

<210> SEQ ID NO 63
<211> LENGTH: 30
<212> TYPE: DNA
<213> ORGANISM: Glycine Max

<400> SEQUENCE: 63
ttatatttat ttttattttt tttttttttt 30

<210> SEQ ID NO 64
<211> LENGTH: 32
<212> TYPE: DNA
<213> ORGANISM: Glycine Max

<400> SEQUENCE: 64
cccccctcct cccccccccc cccccccccc cc 32

<210> SEQ ID NO 65
<211> LENGTH: 31
<212> TYPE: DNA
<213> ORGANISM: Glycine Max

<400> SEQUENCE: 65
tgtgtttttt tggggtggtt tttttttttt t 31

<210> SEQ ID NO 66
<211> LENGTH: 29
<212> TYPE: DNA
<213> ORGANISM: Glycine Max

<400> SEQUENCE: 66
ggagagagrg ggggaggggg ggggggggg 29

<210> SEQ ID NO 67
<211> LENGTH: 30
<212> TYPE: DNA
<213> ORGANISM: Glycine Max

<400> SEQUENCE: 67
ttgtgtgttt tttttttttt tttttttttt 30

<210> SEQ ID NO 68
<211> LENGTH: 29
<212> TYPE: DNA

<213> ORGANISM: Glycine Max

<400> SEQUENCE: 68
aamacacaaa aaaacaaaaa aaaaaaaaa 29

<210> SEQ ID NO 69
<211> LENGTH: 31
<212> TYPE: DNA
<213> ORGANISM: Glycine Max

<400> SEQUENCE: 69 tttttatta ttttttttt ttttttttt t 31

<210> SEQ ID NO 70
<211> LENGTH: 31
<212> TYPE: DNA
<213> ORGANISM: Glycine Max

<400> SEQUENCE: 70
garagaaaga gaaaagaaag ggaaaagaga a 31

<210> SEQ ID NO 71
<211> LENGTH: 30
<212> TYPE: DNA
<213> ORGANISM: Glycine Max

<400> SEQUENCE: 71
camacaaccc aaaacaaacc caaaacacaa 30

<210> SEQ ID NO 72
<211> LENGTH: 30
<212> TYPE: DNA
<213> ORGANISM: Glycine Max

<400> SEQUENCE: 72
accmccccac cccccccaa ccaccacacc 30

<210> SEQ ID NO 73
<211> LENGTH: 28
<212> TYPE: DNA
<213> ORGANISM: Glycine Max

<400> SEQUENCE: 73
aaaaaaggaa aaaaaaaaaa aaaaaaaa 28

<210> SEQ ID NO 74
<211> LENGTH: 32
<212> TYPE: DNA
<213> ORGANISM: Glycine Max

<400> SEQUENCE: 74
ctctctytcc cttttctttc ccttcttctc tt 32

<210> SEQ ID NO 75
<211> LENGTH: 30
<212> TYPE: DNA
<213> ORGANISM: Glycine Max

<400> SEQUENCE: 75
ggggggagga gggggggggg gggggggggg 30

<210> SEQ ID NO 76
<211> LENGTH: 32

<212> TYPE: DNA
<213> ORGANISM: Glycine Max

<400> SEQUENCE: 76
acccccccac accccccca aaccaccaca cc 32

<210> SEQ ID NO 77
<211> LENGTH: 31
<212> TYPE: DNA
<213> ORGANISM: Glycine Max

<400> SEQUENCE: 77
aagagaaaaa aaaaagaaaa aaaaaaaaaa a 31

<210> SEQ ID NO 78
<211> LENGTH: 31
<212> TYPE: DNA
<213> ORGANISM: Glycine Max

<400> SEQUENCE: 78 tttttatta ttttttttt ttttttttt t 31

<210> SEQ ID NO 79
<211> LENGTH: 28
<212> TYPE: DNA
<213> ORGANISM: Glycine Max

<400> SEQUENCE: 79
agagaaaaaa aaaagaaaaa aaaaaaaa 28

<210> SEQ ID NO 80
<211> LENGTH: 29
<212> TYPE: DNA
<213> ORGANISM: Glycine Max

<400> SEQUENCE: 80
aaaaaaaaaa aaaaaaaaaa gggaaaaga 29

<210> SEQ ID NO 81
<211> LENGTH: 28
<212> TYPE: DNA
<213> ORGANISM: Glycine Max

<400> SEQUENCE: 81 cccaccccc cccaccccc cccccccc 28

<210> SEQ ID NO 82
<211> LENGTH: 29
<212> TYPE: DNA
<213> ORGANISM: Glycine Max

<400> SEQUENCE: 82
ccctctcctc cccctccccc ccccccccc 29

<210> SEQ ID NO 83
<211> LENGTH: 30
<212> TYPE: DNA
<213> ORGANISM: Glycine Max

<400> SEQUENCE: 83
aaragaaaaa aaaaagaaaa aaaaaaaaaa 30

<210> SEQ ID NO 84

<211> LENGTH: 30
<212> TYPE: DNA
<213> ORGANISM: Glycine Max

<400> SEQUENCE: 84
aaaaaaaaaa aaaaaaaaaa aggagaaaga 30

<210> SEQ ID NO 85
<211> LENGTH: 20
<212> TYPE: DNA
<213> ORGANISM: Glycine Max

<400> SEQUENCE: 85
cccccccccc cccaacccac 20

<210> SEQ ID NO 86
<211> LENGTH: 27
<212> TYPE: DNA
<213> ORGANISM: Glycine Max

<400> SEQUENCE: 86
cttctctctt ttttcccccc ccccccc 27

<210> SEQ ID NO 87
<211> LENGTH: 27
<212> TYPE: DNA
<213> ORGANISM: Glycine Max

<400> SEQUENCE: 87
ccctcccccc ccctcccccc ccccccc 27

<210> SEQ ID NO 88
<211> LENGTH: 20
<212> TYPE: DNA
<213> ORGANISM: Glycine Max

<400> SEQUENCE: 88
tttttaaaat tttttttttt 20

<210> SEQ ID NO 89
<211> LENGTH: 25
<212> TYPE: DNA
<213> ORGANISM: Glycine Max

<400> SEQUENCE: 89
aaaaaaaaaa aaaaaaggar aaaaa 25

<210> SEQ ID NO 90
<211> LENGTH: 26
<212> TYPE: DNA
<213> ORGANISM: Glycine Max

<400> SEQUENCE: 90
ttcttttttt ttcttttttt tttttt 26

<210> SEQ ID NO 91
<211> LENGTH: 30
<212> TYPE: DNA
<213> ORGANISM: Glycine Max

<400> SEQUENCE: 91
acgcaaaaca cccgccaaaa ccaaaaaaca 30

<210> SEQ ID NO 92
<211> LENGTH: 31
<212> TYPE: DNA
<213> ORGANISM: Glycine Max

<400> SEQUENCE: 92
ggagaggggg gggggagggg gggggggggg g 31

<210> SEQ ID NO 93
<211> LENGTH: 29
<212> TYPE: DNA
<213> ORGANISM: Glycine Max

<400> SEQUENCE: 93 cccaccccc ccccacccc ccccccccc 29

<210> SEQ ID NO 94
<211> LENGTH: 28
<212> TYPE: DNA
<213> ORGANISM: Glycine Max

<400> SEQUENCE: 94
ggggggggga rgrrgggggg gggggggg 28

<210> SEQ ID NO 95
<211> LENGTH: 30
<212> TYPE: DNA
<213> ORGANISM: Glycine Max

<400> SEQUENCE: 95
attataaaaa wwwatwaaaa aaaaaaaaaa 30

<210> SEQ ID NO 96
<211> LENGTH: 29
<212> TYPE: DNA
<213> ORGANISM: Glycine Max

<400> SEQUENCE: 96
ggggsggggg gggggggggs ggggggggg 29

<210> SEQ ID NO 97
<211> LENGTH: 31
<212> TYPE: DNA
<213> ORGANISM: Glycine Max

<400> SEQUENCE: 97
aatatataaw aaaataaaaa attawaaaat a 31

<210> SEQ ID NO 98
<211> LENGTH: 29
<212> TYPE: DNA
<213> ORGANISM: Glycine Max

<400> SEQUENCE: 98
cacaccccca aaacacccc ccccccccc 29

<210> SEQ ID NO 99
<211> LENGTH: 31
<212> TYPE: DNA
<213> ORGANISM: Glycine Max

<400> SEQUENCE: 99
ccccctctcy cccccctcc ccccttctcc t 31

<210> SEQ ID NO 100
<211> LENGTH: 27
<212> TYPE: DNA
<213> ORGANISM: Glycine Max

<400> SEQUENCE: 100
gggggcggcg gggcgggggg scgcggc 27

<210> SEQ ID NO 101
<211> LENGTH: 29
<212> TYPE: DNA
<213> ORGANISM: Glycine Max

<400> SEQUENCE: 101
attttttatt ttttttaaaa aawtataat 29

<210> SEQ ID NO 102
<211> LENGTH: 30
<212> TYPE: DNA
<213> ORGANISM: Glycine Max

<400> SEQUENCE: 102
gtgtgggggg ttttgtgggg gggggggggg 30

<210> SEQ ID NO 103
<211> LENGTH: 30
<212> TYPE: DNA
<213> ORGANISM: Glycine Max

<400> SEQUENCE: 103
ggsgcggggg ggggcggggg gggggggggg 30

<210> SEQ ID NO 104
<211> LENGTH: 28
<212> TYPE: DNA
<213> ORGANISM: Glycine Max

<400> SEQUENCE: 104
agggggagrg ggggggaaaa aargagaa 28

<210> SEQ ID NO 105
<211> LENGTH: 28
<212> TYPE: DNA
<213> ORGANISM: Glycine Max

<400> SEQUENCE: 105
aatawawaaa waaaaaaaaa aawaaaaa 28

<210> SEQ ID NO 106
<211> LENGTH: 29
<212> TYPE: DNA
<213> ORGANISM: Glycine Max

<400> SEQUENCE: 106
aaaagaagaa aaaaaaaaaa aaaaaaaaa 29

<210> SEQ ID NO 107
<211> LENGTH: 29
<212> TYPE: DNA
<213> ORGANISM: Glycine Max

<400> SEQUENCE: 107
tttttktttt tttttttttt ttttktktt 29

<210> SEQ ID NO 108
<211> LENGTH: 30
<212> TYPE: DNA
<213> ORGANISM: Glycine Max

<400> SEQUENCE: 108
gggggtgtgg ggggggggtg gggggkgtgg 30

<210> SEQ ID NO 109
<211> LENGTH: 30
<212> TYPE: DNA
<213> ORGANISM: Glycine Max

<400> SEQUENCE: 109
aggggggaag gggggggaaa aaargagaag 30

<210> SEQ ID NO 110
<211> LENGTH: 31
<212> TYPE: DNA
<213> ORGANISM: Glycine Max

<400> SEQUENCE: 110
aaaaacacaa aaaaaaacaa aaaamcacaa c 31

<210> SEQ ID NO 111
<211> LENGTH: 32
<212> TYPE: DNA
<213> ORGANISM: Glycine Max

<400> SEQUENCE: 111 gttttttgt kttttttttg gggggktgtg gt 32

<210> SEQ ID NO 112
<211> LENGTH: 31
<212> TYPE: DNA
<213> ORGANISM: Glycine Max

<400> SEQUENCE: 112
aaaaaataat aaaaaaaaaa aaaaaaaaaa a 31

<210> SEQ ID NO 113
<211> LENGTH: 32
<212> TYPE: DNA
<213> ORGANISM: Glycine Max

<400> SEQUENCE: 113
gtgtgggggg gttttgttgg gggggggggg gg 32

<210> SEQ ID NO 114
<211> LENGTH: 32
<212> TYPE: DNA
<213> ORGANISM: Glycine Max

<400> SEQUENCE: 114
ctctcccccc cttttcttcc cccccccccc cc 32

<210> SEQ ID NO 115
<211> LENGTH: 32
<212> TYPE: DNA
<213> ORGANISM: Glycine Max

<400> SEQUENCE: 115
aacaaaaaaa aaaaacaaaa aaaaaaaaaa aa 32

<210> SEQ ID NO 116
<211> LENGTH: 32
<212> TYPE: DNA
<213> ORGANISM: Glycine Max

<400> SEQUENCE: 116
ccmcaccccc mccccacmcc cccccccccc cc 32

<210> SEQ ID NO 117
<211> LENGTH: 31
<212> TYPE: DNA
<213> ORGANISM: Glycine Max

<400> SEQUENCE: 117
cctcttcccy cccctcctcc ccccytctcc t 31

<210> SEQ ID NO 118
<211> LENGTH: 31
<212> TYPE: DNA
<213> ORGANISM: Glycine Max

<400> SEQUENCE: 118
ttgtggtttk ttttgttgtt ttttkgtgtt g 31

<210> SEQ ID NO 119
<211> LENGTH: 32
<212> TYPE: DNA
<213> ORGANISM: Glycine Max

<400> SEQUENCE: 119
ggtgttgtgg tggggtggtg gggggktgtg gt 32

<210> SEQ ID NO 120
<211> LENGTH: 32
<212> TYPE: DNA
<213> ORGANISM: Glycine Max

<400> SEQUENCE: 120
ttttttgttg tttttttttt ttttttttttk tt 32

<210> SEQ ID NO 121
<211> LENGTH: 28
<212> TYPE: DNA
<213> ORGANISM: Glycine Max

<400> SEQUENCE: 121
ttataatwtt ttatattttt twatatta 28

<210> SEQ ID NO 122
<211> LENGTH: 18
<212> TYPE: DNA
<213> ORGANISM: Glycine Max

<400> SEQUENCE: 122
cttcctttcc cccccccc 18

<210> SEQ ID NO 123
<211> LENGTH: 17
<212> TYPE: DNA
<213> ORGANISM: Glycine Max

<400> SEQUENCE: 123 tcccccctc ccccccc 17

<210> SEQ ID NO 124
<211> LENGTH: 15
<212> TYPE: DNA
<213> ORGANISM: Glycine Max

<400> SEQUENCE: 124
aaaaggaaaa aaaaa 15

<210> SEQ ID NO 125
<211> LENGTH: 16
<212> TYPE: DNA
<213> ORGANISM: Glycine Max

<400> SEQUENCE: 125
tcttcctttt tttttt 16

<210> SEQ ID NO 126
<211> LENGTH: 23
<212> TYPE: DNA
<213> ORGANISM: Glycine Max

<400> SEQUENCE: 126
ccgccccccc cccccccscs ccs 23

<210> SEQ ID NO 127
<211> LENGTH: 23
<212> TYPE: DNA
<213> ORGANISM: Glycine Max

<400> SEQUENCE: 127
ggtgggtttt gggggggggk ggg 23

<210> SEQ ID NO 128
<211> LENGTH: 29
<212> TYPE: DNA
<213> ORGANISM: Glycine Max

<400> SEQUENCE: 128
cctctcccyc cctccccccc ccccccccc 29

<210> SEQ ID NO 129
<211> LENGTH: 32
<212> TYPE: DNA
<213> ORGANISM: Glycine Max

<400> SEQUENCE: 129
ggcgccgcgg sggggcggcg gggggscgcg gc 32

<210> SEQ ID NO 130
<211> LENGTH: 31
<212> TYPE: DNA
<213> ORGANISM: Glycine Max

<400> SEQUENCE: 130
ggkgtggtgg kggggtgggg gggggggggg g 31

<210> SEQ ID NO 131
<211> LENGTH: 31
<212> TYPE: DNA
<213> ORGANISM: Glycine Max

<400> SEQUENCE: 131
ttktgttttt kttttgtttt tttttttttt t 31

<210> SEQ ID NO 132
<211> LENGTH: 32
<212> TYPE: DNA
<213> ORGANISM: Glycine Max

<400> SEQUENCE: 132
ggtgttgtgg kggggtggtg gggggktgtg gt 32

<210> SEQ ID NO 133
<211> LENGTH: 31
<212> TYPE: DNA
<213> ORGANISM: Glycine Max

<400> SEQUENCE: 133
ttctcctctt yttttcttct tttttyctct c 31

<210> SEQ ID NO 134
<211> LENGTH: 31
<212> TYPE: DNA
<213> ORGANISM: Glycine Max

<400> SEQUENCE: 134
ttctctcttt ttttcttctt ttttyctctt c 31

<210> SEQ ID NO 135
<211> LENGTH: 25
<212> TYPE: DNA
<213> ORGANISM: Glycine Max

<400> SEQUENCE: 135
tcttcttttt ttctcttttt tcttc 25

<210> SEQ ID NO 136
<211> LENGTH: 25
<212> TYPE: DNA
<213> ORGANISM: Glycine Max

<400> SEQUENCE: 136
accccacacc cccccaaaaa acaac 25

<210> SEQ ID NO 137
<211> LENGTH: 22
<212> TYPE: DNA
<213> ORGANISM: Glycine Max

<400> SEQUENCE: 137
tctctttttt ttcttttttt tt 22

<210> SEQ ID NO 138
<211> LENGTH: 24
<212> TYPE: DNA
<213> ORGANISM: Glycine Max

<400> SEQUENCE: 138
cccctctccc cccccccccc cccc 24

<210> SEQ ID NO 139
<211> LENGTH: 26
<212> TYPE: DNA
<213> ORGANISM: Glycine Max

<400> SEQUENCE: 139
gagagggggg ggaggggggg gggagg 26

<210> SEQ ID NO 140
<211> LENGTH: 26
<212> TYPE: DNA
<213> ORGANISM: Glycine Max

<400> SEQUENCE: 140 cctcccctt ttcttccccc cccccc 26

<210> SEQ ID NO 141
<211> LENGTH: 28
<212> TYPE: DNA
<213> ORGANISM: Glycine Max

<400> SEQUENCE: 141 ttttytttt tttttttttt tttcyttc 28

<210> SEQ ID NO 142
<211> LENGTH: 25
<212> TYPE: DNA
<213> ORGANISM: Glycine Max

<400> SEQUENCE: 142
ggggagaggg gggggggggg ggggg 25

<210> SEQ ID NO 143
<211> LENGTH: 18
<212> TYPE: DNA
<213> ORGANISM: Glycine Max

<400> SEQUENCE: 143
tccttccctt tttttttt 18

<210> SEQ ID NO 144
<211> LENGTH: 18
<212> TYPE: DNA
<213> ORGANISM: Glycine Max

<400> SEQUENCE: 144
tccttccctt tttttttt 18

<210> SEQ ID NO 145
<211> LENGTH: 20
<212> TYPE: DNA
<213> ORGANISM: Glycine Max

<400> SEQUENCE: 145
tttctccccc tttttttttt 20

<210> SEQ ID NO 146
<211> LENGTH: 30
<212> TYPE: DNA
<213> ORGANISM: Glycine Max

<400> SEQUENCE: 146
ggaggagggg gggggggagg gggaagagga 30

<210> SEQ ID NO 147
<211> LENGTH: 29
<212> TYPE: DNA

<213> ORGANISM: Glycine Max

<400> SEQUENCE: 147
tatatttttt aaaataattt ttttttttt 29

<210> SEQ ID NO 148
<211> LENGTH: 30
<212> TYPE: DNA
<213> ORGANISM: Glycine Max

<400> SEQUENCE: 148
ggagagaggr ggggaggagg ggggragaga 30

<210> SEQ ID NO 149
<211> LENGTH: 31
<212> TYPE: DNA
<213> ORGANISM: Glycine Max

<400> SEQUENCE: 149
cctcttctcc yccccctctcc ccccttctcc t 31

<210> SEQ ID NO 150
<211> LENGTH: 29
<212> TYPE: DNA
<213> ORGANISM: Glycine Max

<400> SEQUENCE: 150
ttctcttctt tttcttttt ttttttttt 29

<210> SEQ ID NO 151
<211> LENGTH: 31
<212> TYPE: DNA
<213> ORGANISM: Glycine Max

<400> SEQUENCE: 151
ggagaagagg rgggaggagg ggggragagg a 31

<210> SEQ ID NO 152
<211> LENGTH: 30
<212> TYPE: DNA
<213> ORGANISM: Glycine Max

<400> SEQUENCE: 152 acccccacm cccccccaaa aaamcacaac 30

<210> SEQ ID NO 153
<211> LENGTH: 32
<212> TYPE: DNA
<213> ORGANISM: Glycine Max

<400> SEQUENCE: 153
acacaaaaaa accccaccaa aaaaaaaaaa aa 32

<210> SEQ ID NO 154
<211> LENGTH: 27
<212> TYPE: DNA
<213> ORGANISM: Glycine Max

<400> SEQUENCE: 154 ggggggggt kkggggggg gggggkg 27

<210> SEQ ID NO 155
<211> LENGTH: 26

<212> TYPE: DNA
<213> ORGANISM: Glycine Max

<400> SEQUENCE: 155
tttttktttg kkttttttttt ttttkt 26

<210> SEQ ID NO 156
<211> LENGTH: 24
<212> TYPE: DNA
<213> ORGANISM: Glycine Max

<400> SEQUENCE: 156 ttctctttt ttcttttttt tctt 24

<210> SEQ ID NO 157
<211> LENGTH: 23
<212> TYPE: DNA
<213> ORGANISM: Glycine Max

<400> SEQUENCE: 157
ttctcttytt yctttttytt cty 23

<210> SEQ ID NO 158
<211> LENGTH: 29
<212> TYPE: DNA
<213> ORGANISM: Glycine Max

<400> SEQUENCE: 158
ttgtggtttt tttttgtttt tttgtgttg 29

<210> SEQ ID NO 159
<211> LENGTH: 29
<212> TYPE: DNA
<213> ORGANISM: Glycine Max

<400> SEQUENCE: 159
ccacaacccc cccccacccc cccacacca 29

<210> SEQ ID NO 160
<211> LENGTH: 31
<212> TYPE: DNA
<213> ORGANISM: Glycine Max

<400> SEQUENCE: 160
gagagggggg aaaagaaggg gggggggggg g 31

<210> SEQ ID NO 161
<211> LENGTH: 29
<212> TYPE: DNA
<213> ORGANISM: Glycine Max

<400> SEQUENCE: 161
gggggagggg ggggggaggg gggagagga 29

<210> SEQ ID NO 162
<211> LENGTH: 28
<212> TYPE: DNA
<213> ORGANISM: Glycine Max

<400> SEQUENCE: 162
cctcttccyc ccctcccccc cctctcct 28

<210> SEQ ID NO 163

<211> LENGTH: 28
<212> TYPE: DNA
<213> ORGANISM: Glycine Max

<400> SEQUENCE: 163
tttttctttt tttttttttt tttctctt 28

<210> SEQ ID NO 164
<211> LENGTH: 31
<212> TYPE: DNA
<213> ORGANISM: Glycine Max

<400> SEQUENCE: 164 aggggggar ggggggggaa aaaargagaa g 31

<210> SEQ ID NO 165
<211> LENGTH: 32
<212> TYPE: DNA
<213> ORGANISM: Glycine Max

<400> SEQUENCE: 165
aagagaaaaa aaaaagaaaa aaaaaaaaaa aa 32

<210> SEQ ID NO 166
<211> LENGTH: 32
<212> TYPE: DNA
<213> ORGANISM: Glycine Max

<400> SEQUENCE: 166
tttttatttt ttttttttat tttttwatat ta 32

<210> SEQ ID NO 167
<211> LENGTH: 32
<212> TYPE: DNA
<213> ORGANISM: Glycine Max

<400> SEQUENCE: 167
aagaggaaaa aaaaagaaga aaaaargaga ag 32

<210> SEQ ID NO 168
<211> LENGTH: 32
<212> TYPE: DNA
<213> ORGANISM: Glycine Max

<400> SEQUENCE: 168
gggggagggg ggggggggag gggggragag ga 32

<210> SEQ ID NO 169
<211> LENGTH: 31
<212> TYPE: DNA
<213> ORGANISM: Glycine Max

<400> SEQUENCE: 169
cccccctcct cccccccccc cccccccccc c 31

<210> SEQ ID NO 170
<211> LENGTH: 30
<212> TYPE: DNA
<213> ORGANISM: Glycine Max

<400> SEQUENCE: 170 cccccctcctc cccccccccc cccccccccc 30

<210> SEQ ID NO 171
<211> LENGTH: 31
<212> TYPE: DNA
<213> ORGANISM: Glycine Max

<400> SEQUENCE: 171
gggagggggr ggggaggggg gggggggggg g 31

<210> SEQ ID NO 172
<211> LENGTH: 32
<212> TYPE: DNA
<213> ORGANISM: Glycine Max

<400> SEQUENCE: 172
ttctcctttt yttttcttct ttttttctct tc 32

<210> SEQ ID NO 173
<211> LENGTH: 32
<212> TYPE: DNA
<213> ORGANISM: Glycine Max

<400> SEQUENCE: 173
cccccctcct cccccccccc cccccccccc cc 32

<210> SEQ ID NO 174
<211> LENGTH: 32
<212> TYPE: DNA
<213> ORGANISM: Glycine Max

<400> SEQUENCE: 174
tttttgtttt ttttttttgt ttttttgtgt tg 32

<210> SEQ ID NO 175
<211> LENGTH: 31
<212> TYPE: DNA
<213> ORGANISM: Glycine Max

<400> SEQUENCE: 175
aaaaagaaaa aaaaaaaaar aaaaagagaa g 31

<210> SEQ ID NO 176
<211> LENGTH: 31
<212> TYPE: DNA
<213> ORGANISM: Glycine Max

<400> SEQUENCE: 176
ccccctcccc cccccccccc cccccctctcc t 31

<210> SEQ ID NO 177
<211> LENGTH: 29
<212> TYPE: DNA
<213> ORGANISM: Glycine Max

<400> SEQUENCE: 177
ttytcttttt ttttcttttt ttttctctt 29

<210> SEQ ID NO 178
<211> LENGTH: 30
<212> TYPE: DNA
<213> ORGANISM: Glycine Max

<400> SEQUENCE: 178
cctctccccc ccctcccccc cccccccccc 30

<210> SEQ ID NO 179
<211> LENGTH: 30
<212> TYPE: DNA
<213> ORGANISM: Glycine Max

<400> SEQUENCE: 179 cccccteccc cccccctccc cccytctcct 30

<210> SEQ ID NO 180
<211> LENGTH: 30
<212> TYPE: DNA
<213> ORGANISM: Glycine Max

<400> SEQUENCE: 180
ccccctcccc cccccctccc cccytctcct 30

<210> SEQ ID NO 181
<211> LENGTH: 31
<212> TYPE: DNA
<213> ORGANISM: Glycine Max

<400> SEQUENCE: 181
attttttatw tttttttaa aaaawtataa t 31

<210> SEQ ID NO 182
<211> LENGTH: 29
<212> TYPE: DNA
<213> ORGANISM: Glycine Max

<400> SEQUENCE: 182
aggggaaaar gggggggaa aaaaragag 29

<210> SEQ ID NO 183
<211> LENGTH: 29
<212> TYPE: DNA
<213> ORGANISM: Glycine Max

<400> SEQUENCE: 183
gggggggggg gggggggggg gggggagga 29

<210> SEQ ID NO 184
<211> LENGTH: 28
<212> TYPE: DNA
<213> ORGANISM: Glycine Max

<400> SEQUENCE: 184
aaaaaaaaaw aaaaaaaaaa aaaaataa 28

<210> SEQ ID NO 185
<211> LENGTH: 27
<212> TYPE: DNA
<213> ORGANISM: Glycine Max

<400> SEQUENCE: 185
ctctcccccc ttttcttccc ccccccc 27

<210> SEQ ID NO 186
<211> LENGTH: 27
<212> TYPE: DNA
<213> ORGANISM: Glycine Max

<400> SEQUENCE: 186
attttaaaaw tttttttaaa awaaaaa 27

<210> SEQ ID NO 187
<211> LENGTH: 27
<212> TYPE: DNA
<213> ORGANISM: Glycine Max

<400> SEQUENCE: 187
aagagaaaaa aaaagaaaaa aaaaaaa 27

<210> SEQ ID NO 188
<211> LENGTH: 27
<212> TYPE: DNA
<213> ORGANISM: Glycine Max

<400> SEQUENCE: 188
cctctccccs cccctccccc ccccccc 27

<210> SEQ ID NO 189
<211> LENGTH: 30
<212> TYPE: DNA
<213> ORGANISM: Glycine Max

<400> SEQUENCE: 189
aaaaaaaaaa aaaaaaaaaa aaaamacaac 30

<210> SEQ ID NO 190
<211> LENGTH: 31
<212> TYPE: DNA
<213> ORGANISM: Glycine Max

<400> SEQUENCE: 190
ggrgaggggg ggggaggggg gggggggggg g 31

<210> SEQ ID NO 191
<211> LENGTH: 32
<212> TYPE: DNA
<213> ORGANISM: Glycine Max

<400> SEQUENCE: 191
aaraagaaaa raaaaaaaga aaaaargaga ag 32

<210> SEQ ID NO 192
<211> LENGTH: 32
<212> TYPE: DNA
<213> ORGANISM: Glycine Max

<400> SEQUENCE: 192
gggggcgggg sgggggggcg gggggscgcg gc 32

<210> SEQ ID NO 193
<211> LENGTH: 32
<212> TYPE: DNA
<213> ORGANISM: Glycine Max

<400> SEQUENCE: 193
aaaaaacaac aaaaaaaaaa aaaaaaaaaa aa 32

<210> SEQ ID NO 194
<211> LENGTH: 31
<212> TYPE: DNA
<213> ORGANISM: Glycine Max

<400> SEQUENCE: 194
ttwttatttt tttttttatt ttttwatatt a 31

<210> SEQ ID NO 195
<211> LENGTH: 31
<212> TYPE: DNA
<213> ORGANISM: Glycine Max

<400> SEQUENCE: 195
tttttatttt tttttttat ttttttaatt a 31

<210> SEQ ID NO 196
<211> LENGTH: 32
<212> TYPE: DNA
<213> ORGANISM: Glycine Max

<400> SEQUENCE: 196
tttttgtttt tttttttgt ttttttgtgt tg 32

<210> SEQ ID NO 197
<211> LENGTH: 27
<212> TYPE: DNA
<213> ORGANISM: Glycine Max

<400> SEQUENCE: 197
cccccgcccc ccccccgccc ccccgcc 27

<210> SEQ ID NO 198
<211> LENGTH: 29
<212> TYPE: DNA
<213> ORGANISM: Glycine Max

<400> SEQUENCE: 198
gggggagggg ggggggaggg ggggagagg 29

<210> SEQ ID NO 199
<211> LENGTH: 29
<212> TYPE: DNA
<213> ORGANISM: Glycine Max

<400> SEQUENCE: 199
aaaaagaaaa aaaaaagaaa aaaagagaa 29

<210> SEQ ID NO 200
<211> LENGTH: 27
<212> TYPE: DNA
<213> ORGANISM: Glycine Max

<400> SEQUENCE: 200
cccccacccc ccccccaccc ccccaac 27

<210> SEQ ID NO 201
<211> LENGTH: 27
<212> TYPE: DNA
<213> ORGANISM: Glycine Max

<400> SEQUENCE: 201
tttttgtttt ttttttgttt ttttggt 27

<210> SEQ ID NO 202
<211> LENGTH: 18
<212> TYPE: DNA
<213> ORGANISM: Glycine Max

<400> SEQUENCE: 202
gggggggggg gaagggga 18

<210> SEQ ID NO 203
<211> LENGTH: 17
<212> TYPE: DNA
<213> ORGANISM: Glycine Max

<400> SEQUENCE: 203
gktggggggg ggggggg 17

<210> SEQ ID NO 204
<211> LENGTH: 21
<212> TYPE: DNA
<213> ORGANISM: Glycine Max

<400> SEQUENCE: 204
agagagaaaa gaaaaaaaaa a 21

<210> SEQ ID NO 205
<211> LENGTH: 22
<212> TYPE: DNA
<213> ORGANISM: Glycine Max

<400> SEQUENCE: 205
gggggggggg gggggggggg ga 22

<210> SEQ ID NO 206
<211> LENGTH: 25
<212> TYPE: DNA
<213> ORGANISM: Glycine Max

<400> SEQUENCE: 206 cctcccctt tctcccccc ccccc 25

<210> SEQ ID NO 207
<211> LENGTH: 25
<212> TYPE: DNA
<213> ORGANISM: Glycine Max

<400> SEQUENCE: 207
ggggagargg gggaggggg aggga 25

<210> SEQ ID NO 208
<211> LENGTH: 24
<212> TYPE: DNA
<213> ORGANISM: Glycine Max

<400> SEQUENCE: 208
gggttggtkg gggggggggg gggg 24

<210> SEQ ID NO 209
<211> LENGTH: 28
<212> TYPE: DNA
<213> ORGANISM: Glycine Max

<400> SEQUENCE: 209
ctctcccccc ttttctccyc cccccccc 28

<210> SEQ ID NO 210
<211> LENGTH: 30
<212> TYPE: DNA
<213> ORGANISM: Glycine Max

<400> SEQUENCE: 210
tttttctttt tttttttct ttttctcttc 30

<210> SEQ ID NO 211
<211> LENGTH: 31
<212> TYPE: DNA
<213> ORGANISM: Glycine Max

<400> SEQUENCE: 211
aaaaacaaaa aaaaaaaaca aaaaacacaa c 31

<210> SEQ ID NO 212
<211> LENGTH: 29
<212> TYPE: DNA
<213> ORGANISM: Glycine Max

<400> SEQUENCE: 212
ccccctcccc cccccccccc ccccctctcc 29

<210> SEQ ID NO 213
<211> LENGTH: 30
<212> TYPE: DNA
<213> ORGANISM: Glycine Max

<400> SEQUENCE: 213
tttttctttt tttttttttt tttttctctt 30

<210> SEQ ID NO 214
<211> LENGTH: 30
<212> TYPE: DNA
<213> ORGANISM: Glycine Max

<400> SEQUENCE: 214
ttctcttttt tttttctttt tttttttttt 30

<210> SEQ ID NO 215
<211> LENGTH: 30
<212> TYPE: DNA
<213> ORGANISM: Glycine Max

<400> SEQUENCE: 215
aaawataaaa aaaaaaaaaa aaaaatataa 30

<210> SEQ ID NO 216
<211> LENGTH: 30
<212> TYPE: DNA
<213> ORGANISM: Glycine Max

<400> SEQUENCE: 216
cccccctcct cccccccccc cccccccccc 30

<210> SEQ ID NO 217
<211> LENGTH: 27
<212> TYPE: DNA
<213> ORGANISM: Glycine Max

<400> SEQUENCE: 217
aggggagaar ggggggaaaa aaaagaa 27

<210> SEQ ID NO 218
<211> LENGTH: 25
<212> TYPE: DNA
<213> ORGANISM: Glycine Max

<400> SEQUENCE: 218
ggagaggggr ggggaggggg ggggg 25

<210> SEQ ID NO 219
<211> LENGTH: 23
<212> TYPE: DNA
<213> ORGANISM: Glycine Max

<400> SEQUENCE: 219
ctcttccctt ttctcccccc ccc 23

<210> SEQ ID NO 220
<211> LENGTH: 15
<212> TYPE: DNA
<213> ORGANISM: Glycine Max

<400> SEQUENCE: 220
caaccaaccc ccccc 15

<210> SEQ ID NO 221
<211> LENGTH: 23
<212> TYPE: DNA
<213> ORGANISM: Glycine Max

<400> SEQUENCE: 221 tccccccctcc cccccttttt ttt 23

<210> SEQ ID NO 222
<211> LENGTH: 27
<212> TYPE: DNA
<213> ORGANISM: Glycine Max

<400> SEQUENCE: 222
gggggagggg ggggggaggg ggggagg 27

<210> SEQ ID NO 223
<211> LENGTH: 27
<212> TYPE: DNA
<213> ORGANISM: Glycine Max

<400> SEQUENCE: 223
ggagaggggg gggagggggg ggggggg 27

<210> SEQ ID NO 224
<211> LENGTH: 29
<212> TYPE: DNA
<213> ORGANISM: Glycine Max

<400> SEQUENCE: 224
gggggtgggg ggggggtggg gggtgtggt 29

<210> SEQ ID NO 225
<211> LENGTH: 30
<212> TYPE: DNA
<213> ORGANISM: Glycine Max

<400> SEQUENCE: 225
tttttttttt tttttttttt tttttgtgtt 30

<210> SEQ ID NO 226
<211> LENGTH: 30
<212> TYPE: DNA

<213> ORGANISM: Glycine Max

<400> SEQUENCE: 226
gggggkgggg gggggggggg gggggtgtgg 30

<210> SEQ ID NO 227
<211> LENGTH: 28
<212> TYPE: DNA
<213> ORGANISM: Glycine Max

<400> SEQUENCE: 227
ttwtattttt tttttttttt ttwtttta 28

<210> SEQ ID NO 228
<211> LENGTH: 28
<212> TYPE: DNA
<213> ORGANISM: Glycine Max

<400> SEQUENCE: 228
aawaaaaaaa aaawataaaa aaawaaaa 28

<210> SEQ ID NO 229
<211> LENGTH: 31
<212> TYPE: DNA
<213> ORGANISM: Glycine Max

<400> SEQUENCE: 229
ttwtattttt tttttatttt tttttttttt t 31

<210> SEQ ID NO 230
<211> LENGTH: 30
<212> TYPE: DNA
<213> ORGANISM: Glycine Max

<400> SEQUENCE: 230
ccccgccccc cccccccgcc ccccgcgccg 30

<210> SEQ ID NO 231
<211> LENGTH: 28
<212> TYPE: DNA
<213> ORGANISM: Glycine Max

<400> SEQUENCE: 231
ggggtggggg gkkggggggg ggggtggt 28

<210> SEQ ID NO 232
<211> LENGTH: 30
<212> TYPE: DNA
<213> ORGANISM: Glycine Max

<400> SEQUENCE: 232
ttttwttttt ttttttttatt ttttattttt 30

<210> SEQ ID NO 233
<211> LENGTH: 30
<212> TYPE: DNA
<213> ORGANISM: Glycine Max

<400> SEQUENCE: 233
aaaataaaaa wwwaawagaa aaaaaataat 30

<210> SEQ ID NO 234
<211> LENGTH: 22

```
<212> TYPE: DNA
<213> ORGANISM: Glycine Max

<400> SEQUENCE: 234

aaaaaaaaaa aaaaaaaaaa at                                            22

<210> SEQ ID NO 235
<211> LENGTH: 28
<212> TYPE: DNA
<213> ORGANISM: Glycine Max

<400> SEQUENCE: 235

ggggcggggg ggggcggggg gscgcggc                                      28

<210> SEQ ID NO 236
<211> LENGTH: 32
<212> TYPE: DNA
<213> ORGANISM: Glycine Max

<400> SEQUENCE: 236

ggtgtggggg gggggtgggg gggggggggg gg                                 32

<210> SEQ ID NO 237
<211> LENGTH: 31
<212> TYPE: DNA
<213> ORGANISM: Glycine Max

<400> SEQUENCE: 237

tttttttcttc tttttttttt tttttttttt t                                 31

<210> SEQ ID NO 238
<211> LENGTH: 28
<212> TYPE: DNA
<213> ORGANISM: Glycine Max

<400> SEQUENCE: 238

tttwttttw wwatwwtttt tttttttt                                       28

<210> SEQ ID NO 239
<211> LENGTH: 29
<212> TYPE: DNA
<213> ORGANISM: Glycine Max

<400> SEQUENCE: 239

ttyttctttt ttttttcttt ttyctcttc                                     29

<210> SEQ ID NO 240
<211> LENGTH: 31
<212> TYPE: DNA
<213> ORGANISM: Glycine Max

<400> SEQUENCE: 240

tccccccctc yccccccctt ttttyctctt c                                  31

<210> SEQ ID NO 241
<211> LENGTH: 31
<212> TYPE: DNA
<213> ORGANISM: Glycine Max

<400> SEQUENCE: 241

aggggggggag gggggggaa aaargagaa g                                   31

<210> SEQ ID NO 242
```

<211> LENGTH: 31
<212> TYPE: DNA
<213> ORGANISM: Glycine Max

<400> SEQUENCE: 242
gaaaaaaaga raaaaaaagg ggggragagg a 31

<210> SEQ ID NO 243
<211> LENGTH: 26
<212> TYPE: DNA
<213> ORGANISM: Glycine Max

<400> SEQUENCE: 243
ttttcttttt tttttttttt yctctc 26

<210> SEQ ID NO 244
<211> LENGTH: 26
<212> TYPE: DNA
<213> ORGANISM: Glycine Max

<400> SEQUENCE: 244
ttgttttttt ttgttttttt tttttt 26

<210> SEQ ID NO 245
<211> LENGTH: 30
<212> TYPE: DNA
<213> ORGANISM: Glycine Max

<400> SEQUENCE: 245 acccccccm ccccccccaa aaaamcacac 30

<210> SEQ ID NO 246
<211> LENGTH: 32
<212> TYPE: DNA
<213> ORGANISM: Glycine Max

<400> SEQUENCE: 246
cgggggggcg gggggggggc cccccsgcgc cg 32

<210> SEQ ID NO 247
<211> LENGTH: 31
<212> TYPE: DNA
<213> ORGANISM: Glycine Max

<400> SEQUENCE: 247
acccccccac mccccccccaa aaaaacacaa c 31

<210> SEQ ID NO 248
<211> LENGTH: 30
<212> TYPE: DNA
<213> ORGANISM: Glycine Max

<400> SEQUENCE: 248
aamacaaaaa aaaacaaaaa aaaaaaaaaa 30

<210> SEQ ID NO 249
<211> LENGTH: 31
<212> TYPE: DNA
<213> ORGANISM: Glycine Max

<400> SEQUENCE: 249
ggcggcgggg gggggggcgg ggggccgcgg c 31

-continued

<210> SEQ ID NO 250
<211> LENGTH: 31
<212> TYPE: DNA
<213> ORGANISM: Glycine Max

<400> SEQUENCE: 250
cctctccccc cccctccccc cccccccccc c 31

<210> SEQ ID NO 251
<211> LENGTH: 32
<212> TYPE: DNA
<213> ORGANISM: Glycine Max

<400> SEQUENCE: 251
aataataaaa aaaaaaaata aaaaawtata at 32

<210> SEQ ID NO 252
<211> LENGTH: 32
<212> TYPE: DNA
<213> ORGANISM: Glycine Max

<400> SEQUENCE: 252
gggggtgggg gggggggtg gggggktgtg gt 32

<210> SEQ ID NO 253
<211> LENGTH: 31
<212> TYPE: DNA
<213> ORGANISM: Glycine Max

<400> SEQUENCE: 253
tctctttttt cccctccttt tttttytttt t 31

<210> SEQ ID NO 254
<211> LENGTH: 29
<212> TYPE: DNA
<213> ORGANISM: Glycine Max

<400> SEQUENCE: 254
cgcgcccccc cggggcgccc ccccccccc 29

<210> SEQ ID NO 255
<211> LENGTH: 21
<212> TYPE: DNA
<213> ORGANISM: Glycine Max

<400> SEQUENCE: 255
ggagggaaga gggggggggg g 21

<210> SEQ ID NO 256
<211> LENGTH: 21
<212> TYPE: DNA
<213> ORGANISM: Glycine Max

<400> SEQUENCE: 256
tgkgtttggt gttttttttt t 21

<210> SEQ ID NO 257
<211> LENGTH: 23
<212> TYPE: DNA
<213> ORGANISM: Glycine Max

<400> SEQUENCE: 257
cccscccccg cccccccccc ccc 23

<210> SEQ ID NO 258
<211> LENGTH: 25
<212> TYPE: DNA
<213> ORGANISM: Glycine Max

<400> SEQUENCE: 258
cccctccccc cccccccccc tctcc 25

<210> SEQ ID NO 259
<211> LENGTH: 12
<212> TYPE: DNA
<213> ORGANISM: Glycine Max

<400> SEQUENCE: 259
aaatwwaaaa aa 12

<210> SEQ ID NO 260
<211> LENGTH: 14
<212> TYPE: DNA
<213> ORGANISM: Glycine Max

<400> SEQUENCE: 260
aaatataaaa aaaa 14

<210> SEQ ID NO 261
<211> LENGTH: 26
<212> TYPE: DNA
<213> ORGANISM: Glycine Max

<400> SEQUENCE: 261
aacacaaaaa acaaaaaaaa aaaaaa 26

<210> SEQ ID NO 262
<211> LENGTH: 25
<212> TYPE: DNA
<213> ORGANISM: Glycine Max

<400> SEQUENCE: 262
atttaaawtt tttttaaaaa attat 25

<210> SEQ ID NO 263
<211> LENGTH: 21
<212> TYPE: DNA
<213> ORGANISM: Glycine Max

<400> SEQUENCE: 263 gggggggrg gaggggggg g 21

<210> SEQ ID NO 264
<211> LENGTH: 26
<212> TYPE: DNA
<213> ORGANISM: Glycine Max

<400> SEQUENCE: 264
gggggggggg ggggggaggg gggaar 26

<210> SEQ ID NO 265
<211> LENGTH: 30
<212> TYPE: DNA
<213> ORGANISM: Glycine Max

<400> SEQUENCE: 265
gtttttttgt gtttttttg gggggttggt 30

<210> SEQ ID NO 266
<211> LENGTH: 31
<212> TYPE: DNA
<213> ORGANISM: Glycine Max

<400> SEQUENCE: 266
ggrggagggg gggggggrgg gggggagagg a 31

<210> SEQ ID NO 267
<211> LENGTH: 22
<212> TYPE: DNA
<213> ORGANISM: Glycine Max

<400> SEQUENCE: 267
gagggaaaag gggggggggg gg 22

<210> SEQ ID NO 268
<211> LENGTH: 30
<212> TYPE: DNA
<213> ORGANISM: Glycine Max

<400> SEQUENCE: 268
acacaaaaaa ccccaccaaa aaaaaaaaaa 30

<210> SEQ ID NO 269
<211> LENGTH: 30
<212> TYPE: DNA
<213> ORGANISM: Glycine Max

<400> SEQUENCE: 269
ctctcccccc cttttcttcc cccccccccc 30

<210> SEQ ID NO 270
<211> LENGTH: 30
<212> TYPE: DNA
<213> ORGANISM: Glycine Max

<400> SEQUENCE: 270
cccctccccc cccccccctcc cccttytcct 30

<210> SEQ ID NO 271
<211> LENGTH: 29
<212> TYPE: DNA
<213> ORGANISM: Glycine Max

<400> SEQUENCE: 271
aaaaataata aaaaaaaaaa aaaaaaaaa 29

<210> SEQ ID NO 272
<211> LENGTH: 28
<212> TYPE: DNA
<213> ORGANISM: Glycine Max

<400> SEQUENCE: 272
aaaaataata aaaaaaaaaa aaaaaaaa 28

<210> SEQ ID NO 273
<211> LENGTH: 29
<212> TYPE: DNA
<213> ORGANISM: Glycine Max

<400> SEQUENCE: 273
aaaaataatt aaaaaaaaaa aaaaaaaaa 29

<210> SEQ ID NO 274
<211> LENGTH: 29
<212> TYPE: DNA
<213> ORGANISM: Glycine Max

<400> SEQUENCE: 274
accccccaca ccccccaaaa aamcacaac 29

<210> SEQ ID NO 275
<211> LENGTH: 21
<212> TYPE: DNA
<213> ORGANISM: Glycine Max

<400> SEQUENCE: 275
tatttttttt ttttttattt t 21

<210> SEQ ID NO 276
<211> LENGTH: 21
<212> TYPE: DNA
<213> ORGANISM: Glycine Max

<400> SEQUENCE: 276
tatttttttt ttttttattt a 21

<210> SEQ ID NO 277
<211> LENGTH: 21
<212> TYPE: DNA
<213> ORGANISM: Glycine Max

<400> SEQUENCE: 277
aaawttttta aaaaaaaaaa a 21

<210> SEQ ID NO 278
<211> LENGTH: 19
<212> TYPE: DNA
<213> ORGANISM: Glycine Max

<400> SEQUENCE: 278
ataaaaaaaa aaaaaaaat 19

<210> SEQ ID NO 279
<211> LENGTH: 19
<212> TYPE: DNA
<213> ORGANISM: Glycine Max

<400> SEQUENCE: 279
ataaaaaaaa aaaaaaaat 19

<210> SEQ ID NO 280
<211> LENGTH: 27
<212> TYPE: DNA
<213> ORGANISM: Glycine Max

<400> SEQUENCE: 280
ttttgtgttt tttttttttt ttttttt 27

<210> SEQ ID NO 281
<211> LENGTH: 26
<212> TYPE: DNA
<213> ORGANISM: Glycine Max

<400> SEQUENCE: 281
aggaaaaagg gggaaaaaaa aaaaaa 26

<210> SEQ ID NO 282
<211> LENGTH: 24
<212> TYPE: DNA
<213> ORGANISM: Glycine Max

<400> SEQUENCE: 282
tttctttttt ttttttttyc cttc 24

<210> SEQ ID NO 283
<211> LENGTH: 24
<212> TYPE: DNA
<213> ORGANISM: Glycine Max

<400> SEQUENCE: 283
tttgtttttt tttttttttg tttg 24

<210> SEQ ID NO 284
<211> LENGTH: 25
<212> TYPE: DNA
<213> ORGANISM: Glycine Max

<400> SEQUENCE: 284
cttccccttt tttccccccc ccccc 25

<210> SEQ ID NO 285
<211> LENGTH: 22
<212> TYPE: DNA
<213> ORGANISM: Glycine Max

<400> SEQUENCE: 285
tcctcycccc cctttttttt tt 22

<210> SEQ ID NO 286
<211> LENGTH: 21
<212> TYPE: DNA
<213> ORGANISM: Glycine Max

<400> SEQUENCE: 286
tcctctcccc ctttcttttt t 21

<210> SEQ ID NO 287
<211> LENGTH: 22
<212> TYPE: DNA
<213> ORGANISM: Glycine Max

<400> SEQUENCE: 287
gggcgcgggg gggggggcg gg 22

<210> SEQ ID NO 288
<211> LENGTH: 24
<212> TYPE: DNA
<213> ORGANISM: Glycine Max

<400> SEQUENCE: 288 tcccttttc cccttttttt tttt 24

<210> SEQ ID NO 289
<211> LENGTH: 29
<212> TYPE: DNA
<213> ORGANISM: Glycine Max

<400> SEQUENCE: 289
cccccacccc ccccccaccc ccccaacca 29

<210> SEQ ID NO 290
<211> LENGTH: 30
<212> TYPE: DNA
<213> ORGANISM: Glycine Max

<400> SEQUENCE: 290
ggrggagggg ggggggagg gggggaagga 30

<210> SEQ ID NO 291
<211> LENGTH: 30
<212> TYPE: DNA
<213> ORGANISM: Glycine Max

<400> SEQUENCE: 291
gcgcgggggg ccccgccggg gggggggggg 30

<210> SEQ ID NO 292
<211> LENGTH: 30
<212> TYPE: DNA
<213> ORGANISM: Glycine Max

<400> SEQUENCE: 292 gagaggggggg aaaagaaggg gggggggggg 30

<210> SEQ ID NO 293
<211> LENGTH: 30
<212> TYPE: DNA
<213> ORGANISM: Glycine Max

<400> SEQUENCE: 293
aawataaaaa aaaataaaaa aaaaaaaaaa 30

<210> SEQ ID NO 294
<211> LENGTH: 30
<212> TYPE: DNA
<213> ORGANISM: Glycine Max

<400> SEQUENCE: 294
ggtgtgggag gggtgggggg gggggggggg 30

<210> SEQ ID NO 295
<211> LENGTH: 30
<212> TYPE: DNA
<213> ORGANISM: Glycine Max

<400> SEQUENCE: 295
cgcgcccccg gggcggcccc cccccccccc 30

<210> SEQ ID NO 296
<211> LENGTH: 31
<212> TYPE: DNA
<213> ORGANISM: Glycine Max

<400> SEQUENCE: 296
twtttttttt ttatttwttt tttttttttt t 31

<210> SEQ ID NO 297
<211> LENGTH: 31
<212> TYPE: DNA
<213> ORGANISM: Glycine Max

<400> SEQUENCE: 297
ccctcccccc ccttcttccc cccccccccc c 31

<210> SEQ ID NO 298
<211> LENGTH: 32
<212> TYPE: DNA
<213> ORGANISM: Glycine Max

<400> SEQUENCE: 298
tttttttgtt kttttttttt tttttttttt tt 32

<210> SEQ ID NO 299
<211> LENGTH: 31
<212> TYPE: DNA
<213> ORGANISM: Glycine Max

<400> SEQUENCE: 299 tccccccctcy cccccccctt ttttyctctt c 31

<210> SEQ ID NO 300
<211> LENGTH: 26
<212> TYPE: DNA
<213> ORGANISM: Glycine Max

<400> SEQUENCE: 300
tatattttta aaaaattttt tttttt 26

<210> SEQ ID NO 301
<211> LENGTH: 31
<212> TYPE: DNA
<213> ORGANISM: Glycine Max

<400> SEQUENCE: 301
aaaaagaaaa aaaaaaagaa aaaargagaa g 31

<210> SEQ ID NO 302
<211> LENGTH: 31
<212> TYPE: DNA
<213> ORGANISM: Glycine Max

<400> SEQUENCE: 302
ttyttctttt tttttttctt ttttyctctt c 31

<210> SEQ ID NO 303
<211> LENGTH: 32
<212> TYPE: DNA
<213> ORGANISM: Glycine Max

<400> SEQUENCE: 303 gggggggtggt gggggggggg gggggggggg kg 32

<210> SEQ ID NO 304
<211> LENGTH: 32
<212> TYPE: DNA
<213> ORGANISM: Glycine Max

<400> SEQUENCE: 304
aaaaaaacaa maaaaaaaaa aaaaaaaaaa aa 32

<210> SEQ ID NO 305
<211> LENGTH: 31
<212> TYPE: DNA

<213> ORGANISM: Glycine Max

<400> SEQUENCE: 305
aaaaaagaag aaaaaaaaaa aaaaaaaaaa a 31

<210> SEQ ID NO 306
<211> LENGTH: 28
<212> TYPE: DNA
<213> ORGANISM: Glycine Max

<400> SEQUENCE: 306
tgkgtggtgk gggggtttt tttttttt 28

<210> SEQ ID NO 307
<211> LENGTH: 32
<212> TYPE: DNA
<213> ORGANISM: Glycine Max

<400> SEQUENCE: 307
ttttttgttg tttttttttt tttttttttt tt 32

<210> SEQ ID NO 308
<211> LENGTH: 32
<212> TYPE: DNA
<213> ORGANISM: Glycine Max

<400> SEQUENCE: 308
cccccctcct cccccccccc cccccccccc cc 32

<210> SEQ ID NO 309
<211> LENGTH: 31
<212> TYPE: DNA
<213> ORGANISM: Glycine Max

<400> SEQUENCE: 309
cttttttctt yttttttcc ccccyyctcc t 31

<210> SEQ ID NO 310
<211> LENGTH: 31
<212> TYPE: DNA
<213> ORGANISM: Glycine Max

<400> SEQUENCE: 310
ggrgaggggg gggggagggg gggggggggg g 31

<210> SEQ ID NO 311
<211> LENGTH: 32
<212> TYPE: DNA
<213> ORGANISM: Glycine Max

<400> SEQUENCE: 311 tcccccctc ycccccccct tttttcctct tc 32

<210> SEQ ID NO 312
<211> LENGTH: 32
<212> TYPE: DNA
<213> ORGANISM: Glycine Max

<400> SEQUENCE: 312
ttyttctctt tttttttct tttttctct tc 32

<210> SEQ ID NO 313
<211> LENGTH: 32

<212> TYPE: DNA
<213> ORGANISM: Glycine Max

<400> SEQUENCE: 313
tttttgttkt tttttttgt tttttkgtgt tg 32

<210> SEQ ID NO 314
<211> LENGTH: 32
<212> TYPE: DNA
<213> ORGANISM: Glycine Max

<400> SEQUENCE: 314 cttttttct yttttttttc ccttcytctc tt 32

<210> SEQ ID NO 315
<211> LENGTH: 30
<212> TYPE: DNA
<213> ORGANISM: Glycine Max

<400> SEQUENCE: 315 agggggaaa gggggggaa aaaaragaag 30

<210> SEQ ID NO 316
<211> LENGTH: 31
<212> TYPE: DNA
<213> ORGANISM: Glycine Max

<400> SEQUENCE: 316
gaaaaaaggg aaaaaaaagg ggggragagg a 31

<210> SEQ ID NO 317
<211> LENGTH: 31
<212> TYPE: DNA
<213> ORGANISM: Glycine Max

<400> SEQUENCE: 317
cttttttccc ttttttttcc ccccytctcc t 31

<210> SEQ ID NO 318
<211> LENGTH: 26
<212> TYPE: DNA
<213> ORGANISM: Glycine Max

<400> SEQUENCE: 318
agaaaaaaaa agaaaaaaaa aaaaaa 26

<210> SEQ ID NO 319
<211> LENGTH: 23
<212> TYPE: DNA
<213> ORGANISM: Glycine Max

<400> SEQUENCE: 319
aaaraaaaaa aaaaaaarag aaa 23

<210> SEQ ID NO 320
<211> LENGTH: 24
<212> TYPE: DNA
<213> ORGANISM: Glycine Max

<400> SEQUENCE: 320
tttwttttta tttttttwt attt 24

<210> SEQ ID NO 321

<211> LENGTH: 24
<212> TYPE: DNA
<213> ORGANISM: Glycine Max

<400> SEQUENCE: 321
tgtkttttgt gttttttttt tttg 24

<210> SEQ ID NO 322
<211> LENGTH: 32
<212> TYPE: DNA
<213> ORGANISM: Glycine Max

<400> SEQUENCE: 322
aaaaaaaaat taaaaaaaaa aaaaaaaaaa aa 32

<210> SEQ ID NO 323
<211> LENGTH: 32
<212> TYPE: DNA
<213> ORGANISM: Glycine Max

<400> SEQUENCE: 323 tcccccctt tcccccccct tttttyctct tc 32

<210> SEQ ID NO 324
<211> LENGTH: 17
<212> TYPE: DNA
<213> ORGANISM: Glycine Max

<400> SEQUENCE: 324
ggkgggktgg ggggkgg 17

<210> SEQ ID NO 325
<211> LENGTH: 18
<212> TYPE: DNA
<213> ORGANISM: Glycine Max

<400> SEQUENCE: 325
ggkgggktgg gggggggg 18

<210> SEQ ID NO 326
<211> LENGTH: 18
<212> TYPE: DNA
<213> ORGANISM: Glycine Max

<400> SEQUENCE: 326
tttatttttt tatttwtt 18

<210> SEQ ID NO 327
<211> LENGTH: 19
<212> TYPE: DNA
<213> ORGANISM: Glycine Max

<400> SEQUENCE: 327
tttgtttttt ttgtttktt 19

<210> SEQ ID NO 328
<211> LENGTH: 27
<212> TYPE: DNA
<213> ORGANISM: Glycine Max

<400> SEQUENCE: 328
cccccccccc ccccccccca cccccac 27

<210> SEQ ID NO 329
<211> LENGTH: 19
<212> TYPE: DNA
<213> ORGANISM: Glycine Max

<400> SEQUENCE: 329
gagggggaag ggrggaggg 19

<210> SEQ ID NO 330
<211> LENGTH: 19
<212> TYPE: DNA
<213> ORGANISM: Glycine Max

<400> SEQUENCE: 330
ataaaaaata aawaataaa 19

<210> SEQ ID NO 331
<211> LENGTH: 18
<212> TYPE: DNA
<213> ORGANISM: Glycine Max

<400> SEQUENCE: 331
gggggggggg ggagggga 18

<210> SEQ ID NO 332
<211> LENGTH: 19
<212> TYPE: DNA
<213> ORGANISM: Glycine Max

<400> SEQUENCE: 332
agaggaaaag aaaaaaaaa 19

<210> SEQ ID NO 333
<211> LENGTH: 21
<212> TYPE: DNA
<213> ORGANISM: Glycine Max

<400> SEQUENCE: 333
cttttccctt tccccccccc t 21

<210> SEQ ID NO 334
<211> LENGTH: 15
<212> TYPE: DNA
<213> ORGANISM: Glycine Max

<400> SEQUENCE: 334
agaaaaaaaa aaaag 15

<210> SEQ ID NO 335
<211> LENGTH: 15
<212> TYPE: DNA
<213> ORGANISM: Glycine Max

<400> SEQUENCE: 335
tgtttttttt ttttg 15

<210> SEQ ID NO 336
<211> LENGTH: 25
<212> TYPE: DNA
<213> ORGANISM: Glycine Max

<400> SEQUENCE: 336
gggggggggg gggggggagg gggag 25

<210> SEQ ID NO 337
<211> LENGTH: 26
<212> TYPE: DNA
<213> ORGANISM: Glycine Max

<400> SEQUENCE: 337
cccccccccc cccccccctc ccctc 26

<210> SEQ ID NO 338
<211> LENGTH: 31
<212> TYPE: DNA
<213> ORGANISM: Glycine Max

<400> SEQUENCE: 338 aggggggaa aggggggaa aaaargagaa g 31

<210> SEQ ID NO 339
<211> LENGTH: 31
<212> TYPE: DNA
<213> ORGANISM: Glycine Max

<400> SEQUENCE: 339
gaaaaaaagg gaaaaaaagg gggggagagg a 31

<210> SEQ ID NO 340
<211> LENGTH: 31
<212> TYPE: DNA
<213> ORGANISM: Glycine Max

<400> SEQUENCE: 340
cccccccccc cccccccccc ccttccccct c 31

<210> SEQ ID NO 341
<211> LENGTH: 32
<212> TYPE: DNA
<213> ORGANISM: Glycine Max

<400> SEQUENCE: 341
aaaaaaaaaa aaaaaaaaaa aaccaaaaaa ca 32

<210> SEQ ID NO 342
<211> LENGTH: 32
<212> TYPE: DNA
<213> ORGANISM: Glycine Max

<400> SEQUENCE: 342
taaaaatata waaaaaaaat ttaatwatat aa 32

<210> SEQ ID NO 343
<211> LENGTH: 32
<212> TYPE: DNA
<213> ORGANISM: Glycine Max

<400> SEQUENCE: 343
aaaaaaaaaa aaaaaaaaaa aargaaaaaa ga 32

<210> SEQ ID NO 344
<211> LENGTH: 32
<212> TYPE: DNA
<213> ORGANISM: Glycine Max

<400> SEQUENCE: 344
gcccccccgc scccccccg ggccgscgcg cc 32

<210> SEQ ID NO 345
<211> LENGTH: 31
<212> TYPE: DNA
<213> ORGANISM: Glycine Max

<400> SEQUENCE: 345
gagagggggg aaragaaggg gggggggggg g 31

<210> SEQ ID NO 346
<211> LENGTH: 24
<212> TYPE: DNA
<213> ORGANISM: Glycine Max

<400> SEQUENCE: 346
ttttttgttt tttttttttt tktt 24

<210> SEQ ID NO 347
<211> LENGTH: 31
<212> TYPE: DNA
<213> ORGANISM: Glycine Max

<400> SEQUENCE: 347
ccmccaaacc cccccmacc caacmacaca a 31

<210> SEQ ID NO 348
<211> LENGTH: 29
<212> TYPE: DNA
<213> ORGANISM: Glycine Max

<400> SEQUENCE: 348
gggggtttgg ggggggtgg gttgktgtg 29

<210> SEQ ID NO 349
<211> LENGTH: 26
<212> TYPE: DNA
<213> ORGANISM: Glycine Max

<400> SEQUENCE: 349
atwtattaaa ttataaatta tatatt 26

<210> SEQ ID NO 350
<211> LENGTH: 30
<212> TYPE: DNA
<213> ORGANISM: Glycine Max

<400> SEQUENCE: 350
tawataaata waaaataatt taatwatwaa 30

<210> SEQ ID NO 351
<211> LENGTH: 24
<212> TYPE: DNA
<213> ORGANISM: Glycine Max

<400> SEQUENCE: 351
tkttttkttt tttttttttt tttt 24

<210> SEQ ID NO 352
<211> LENGTH: 23
<212> TYPE: DNA
<213> ORGANISM: Glycine Max

<400> SEQUENCE: 352
grggggrggg ggggggrggg rgg 23

<210> SEQ ID NO 353
<211> LENGTH: 31
<212> TYPE: DNA
<213> ORGANISM: Glycine Max

<400> SEQUENCE: 353
aagagggaga aaaagaagaa aggargagag g 31

<210> SEQ ID NO 354
<211> LENGTH: 30
<212> TYPE: DNA
<213> ORGANISM: Glycine Max

<400> SEQUENCE: 354 agggggagg gggggrgaaa ggargagagg 30

<210> SEQ ID NO 355
<211> LENGTH: 31
<212> TYPE: DNA
<213> ORGANISM: Glycine Max

<400> SEQUENCE: 355
tttttaattt ttttttatt ttttwwtatt a 31

<210> SEQ ID NO 356
<211> LENGTH: 23
<212> TYPE: DNA
<213> ORGANISM: Glycine Max

<400> SEQUENCE: 356 tttttattt ttttttttt tta 23

<210> SEQ ID NO 357
<211> LENGTH: 18
<212> TYPE: DNA
<213> ORGANISM: Glycine Max

<400> SEQUENCE: 357
ttwttttwtt tttttttt 18

<210> SEQ ID NO 358
<211> LENGTH: 20
<212> TYPE: DNA
<213> ORGANISM: Glycine Max

<400> SEQUENCE: 358
tgggtgtggg ggttttktgg 20

<210> SEQ ID NO 359
<211> LENGTH: 31
<212> TYPE: DNA
<213> ORGANISM: Glycine Max

<400> SEQUENCE: 359
gaaaaaaaga aaaaaaaagg gaagragaga a 31

<210> SEQ ID NO 360
<211> LENGTH: 18
<212> TYPE: DNA
<213> ORGANISM: Glycine Max

<400> SEQUENCE: 360
taaaaataaa tataatat 18

<210> SEQ ID NO 361
<211> LENGTH: 23
<212> TYPE: DNA
<213> ORGANISM: Glycine Max

<400> SEQUENCE: 361
tatttttwtt ttttttttt ttt 23

<210> SEQ ID NO 362
<211> LENGTH: 22
<212> TYPE: DNA
<213> ORGANISM: Glycine Max

<400> SEQUENCE: 362
ataaaaawaa aaaaaaaaaa aa 22

<210> SEQ ID NO 363
<211> LENGTH: 22
<212> TYPE: DNA
<213> ORGANISM: Glycine Max

<400> SEQUENCE: 363
aaatwaaaaa aaaaaaaaaa aa 22

<210> SEQ ID NO 364
<211> LENGTH: 20
<212> TYPE: DNA
<213> ORGANISM: Glycine Max

<400> SEQUENCE: 364
ammaaaamca ccmaaaaaaa 20

<210> SEQ ID NO 365
<211> LENGTH: 20
<212> TYPE: DNA
<213> ORGANISM: Glycine Max

<400> SEQUENCE: 365
cmmcccccca amcccccccc 20

<210> SEQ ID NO 366
<211> LENGTH: 29
<212> TYPE: DNA
<213> ORGANISM: Glycine Max

<400> SEQUENCE: 366
attttttatw ttttttaaat tawtatatt 29

<210> SEQ ID NO 367
<211> LENGTH: 25
<212> TYPE: DNA
<213> ORGANISM: Glycine Max

<400> SEQUENCE: 367
tattaattta atattttttw tatta 25

<210> SEQ ID NO 368
<211> LENGTH: 25
<212> TYPE: DNA
<213> ORGANISM: Glycine Max

<400> SEQUENCE: 368
aaaaaaaaaa aaaaaaaaaw awaat 25

<210> SEQ ID NO 369
<211> LENGTH: 27
<212> TYPE: DNA
<213> ORGANISM: Glycine Max

<400> SEQUENCE: 369
accmcccacc ccccaaacca acacacc 27

<210> SEQ ID NO 370
<211> LENGTH: 28
<212> TYPE: DNA
<213> ORGANISM: Glycine Max

<400> SEQUENCE: 370
gtttttgttt ttttttgggt tggtgtgt 28

<210> SEQ ID NO 371
<211> LENGTH: 27
<212> TYPE: DNA
<213> ORGANISM: Glycine Max

<400> SEQUENCE: 371
taaaaataaa aaaaatttaa ttatata 27

<210> SEQ ID NO 372
<211> LENGTH: 27
<212> TYPE: DNA
<213> ORGANISM: Glycine Max

<400> SEQUENCE: 372
tgggggtggg ggggggtttg gttgttg 27

<210> SEQ ID NO 373
<211> LENGTH: 31
<212> TYPE: DNA
<213> ORGANISM: Glycine Max

<400> SEQUENCE: 373 gtttttttgtk tttttttttgg gttgktgtgt t 31

<210> SEQ ID NO 374
<211> LENGTH: 31
<212> TYPE: DNA
<213> ORGANISM: Glycine Max

<400> SEQUENCE: 374
cttttttctc tttttttttcc cttcytctct t 31

<210> SEQ ID NO 375
<211> LENGTH: 32
<212> TYPE: DNA
<213> ORGANISM: Glycine Max

<400> SEQUENCE: 375 cttttttttct yttttttttttc ycttcytctc tt 32

<210> SEQ ID NO 376
<211> LENGTH: 32
<212> TYPE: DNA
<213> ORGANISM: Glycine Max

<400> SEQUENCE: 376
gtktttttgt gtttttttttg ggttgktgtg tt 32

<210> SEQ ID NO 377
<211> LENGTH: 30
<212> TYPE: DNA
<213> ORGANISM: Glycine Max

<400> SEQUENCE: 377
aawataaaaa aaataaaaaa aaaaaaaaaa 30

<210> SEQ ID NO 378
<211> LENGTH: 32
<212> TYPE: DNA
<213> ORGANISM: Glycine Max

<400> SEQUENCE: 378
atatattaaa attttattta aaaaawtata at 32

<210> SEQ ID NO 379
<211> LENGTH: 22
<212> TYPE: DNA
<213> ORGANISM: Glycine Max

<400> SEQUENCE: 379
tttwttttww ttttatttwt ta 22

<210> SEQ ID NO 380
<211> LENGTH: 22
<212> TYPE: DNA
<213> ORGANISM: Glycine Max

<400> SEQUENCE: 380
ggagggrrgg gggggggggg gg 22

<210> SEQ ID NO 381
<211> LENGTH: 30
<212> TYPE: DNA
<213> ORGANISM: Glycine Max

<400> SEQUENCE: 381
ttatattttt tttttatttt tttttttttt 30

<210> SEQ ID NO 382
<211> LENGTH: 32
<212> TYPE: DNA
<213> ORGANISM: Glycine Max

<400> SEQUENCE: 382 gttttttttgt kttttttttg ggttgktgtg tt 32

<210> SEQ ID NO 383
<211> LENGTH: 29
<212> TYPE: DNA
<213> ORGANISM: Glycine Max

<400> SEQUENCE: 383
attttttatt ttttttaaat tawtatatt 29

<210> SEQ ID NO 384
<211> LENGTH: 32
<212> TYPE: DNA

<213> ORGANISM: Glycine Max

<400> SEQUENCE: 384
tttttttttt tttttttttt ttcctttttt ct 32

<210> SEQ ID NO 385
<211> LENGTH: 31
<212> TYPE: DNA
<213> ORGANISM: Glycine Max

<400> SEQUENCE: 385
ccgsgccccc cccccgcccc cccccccccc c 31

<210> SEQ ID NO 386
<211> LENGTH: 32
<212> TYPE: DNA
<213> ORGANISM: Glycine Max

<400> SEQUENCE: 386
gtgkgggggg gggggggggg gggggggggg gg 32

<210> SEQ ID NO 387
<211> LENGTH: 29
<212> TYPE: DNA
<213> ORGANISM: Glycine Max

<400> SEQUENCE: 387
ggagaggggg ggggaggggg ggggggggg 29

<210> SEQ ID NO 388
<211> LENGTH: 30
<212> TYPE: DNA
<213> ORGANISM: Glycine Max

<400> SEQUENCE: 388
tyyttttttt tttttttyt yttttttttt 30

<210> SEQ ID NO 389
<211> LENGTH: 31
<212> TYPE: DNA
<213> ORGANISM: Glycine Max

<400> SEQUENCE: 389
tyctttytyt ttttyyttty tycttyttyt y 31

<210> SEQ ID NO 390
<211> LENGTH: 31
<212> TYPE: DNA
<213> ORGANISM: Glycine Max

<400> SEQUENCE: 390
cyycccycyc ccccycccy cytccccccc y 31

<210> SEQ ID NO 391
<211> LENGTH: 31
<212> TYPE: DNA
<213> ORGANISM: Glycine Max

<400> SEQUENCE: 391
aaaaaaaaaa aaaaaaaaaa accaaaaaac a 31

<210> SEQ ID NO 392
<211> LENGTH: 30

<212> TYPE: DNA
<213> ORGANISM: Glycine Max

<400> SEQUENCE: 392
aawataaaaa aaataaaaaa ttaaaaaata 30

<210> SEQ ID NO 393
<211> LENGTH: 30
<212> TYPE: DNA
<213> ORGANISM: Glycine Max

<400> SEQUENCE: 393
ttwtattttt tttttatttt tttttttttt 30

<210> SEQ ID NO 394
<211> LENGTH: 32
<212> TYPE: DNA
<213> ORGANISM: Glycine Max

<400> SEQUENCE: 394
ggkgtggggg gggggtgggg gggggggggg gg 32

<210> SEQ ID NO 395
<211> LENGTH: 32
<212> TYPE: DNA
<213> ORGANISM: Glycine Max

<400> SEQUENCE: 395
ttytcttttt tytttctttt tttttttttt tt 32

<210> SEQ ID NO 396
<211> LENGTH: 29
<212> TYPE: DNA
<213> ORGANISM: Glycine Max

<400> SEQUENCE: 396
agggggagrg gggggggaaa ggrgagagg 29

<210> SEQ ID NO 397
<211> LENGTH: 30
<212> TYPE: DNA
<213> ORGANISM: Glycine Max

<400> SEQUENCE: 397
ttytcttttt cccctccttt tttyctcttc 30

<210> SEQ ID NO 398
<211> LENGTH: 30
<212> TYPE: DNA
<213> ORGANISM: Glycine Max

<400> SEQUENCE: 398
atataaaaaa aaaataaaaa aaaaaaaaaa 30

<210> SEQ ID NO 399
<211> LENGTH: 31
<212> TYPE: DNA
<213> ORGANISM: Glycine Max

<400> SEQUENCE: 399
gggkgtgggg ttttgtttgg ggggktgtgg t 31

<210> SEQ ID NO 400

<211> LENGTH: 32
<212> TYPE: DNA
<213> ORGANISM: Glycine Max

<400> SEQUENCE: 400
aawataaaaa aaaaataaaa aaaaaaaaaa aa 32

<210> SEQ ID NO 401
<211> LENGTH: 32
<212> TYPE: DNA
<213> ORGANISM: Glycine Max

<400> SEQUENCE: 401
ttttttttkt kttttttttt ttttkttttt tt 32

<210> SEQ ID NO 402
<211> LENGTH: 31
<212> TYPE: DNA
<213> ORGANISM: Glycine Max

<400> SEQUENCE: 402
aaaragaaaa ggggagggaa aaaaggagaa g 31

<210> SEQ ID NO 403
<211> LENGTH: 23
<212> TYPE: DNA
<213> ORGANISM: Glycine Max

<400> SEQUENCE: 403
gggggggggg argagggggg ggg 23

<210> SEQ ID NO 404
<211> LENGTH: 26
<212> TYPE: DNA
<213> ORGANISM: Glycine Max

<400> SEQUENCE: 404
ttctcttctt tttcttttt tttttt 26

<210> SEQ ID NO 405
<211> LENGTH: 27
<212> TYPE: DNA
<213> ORGANISM: Glycine Max

<400> SEQUENCE: 405
cctctcctcc cyctcccccc ccccccc 27

<210> SEQ ID NO 406
<211> LENGTH: 24
<212> TYPE: DNA
<213> ORGANISM: Glycine Max

<400> SEQUENCE: 406
ctycctcccc cccccccccc cccc 24

<210> SEQ ID NO 407
<211> LENGTH: 28
<212> TYPE: DNA
<213> ORGANISM: Glycine Max

<400> SEQUENCE: 407
ttctctctty tttttttttt tttttttt 28

<210> SEQ ID NO 408
<211> LENGTH: 30
<212> TYPE: DNA
<213> ORGANISM: Glycine Max

<400> SEQUENCE: 408
aagagaagaa aaaaagaaaa aaaaaaaaaa 30

<210> SEQ ID NO 409
<211> LENGTH: 28
<212> TYPE: DNA
<213> ORGANISM: Glycine Max

<400> SEQUENCE: 409
tttctttytt tttcttttt tttttttt 28

<210> SEQ ID NO 410
<211> LENGTH: 29
<212> TYPE: DNA
<213> ORGANISM: Glycine Max

<400> SEQUENCE: 410
ttctctttty tttcttttt ttttttttt 29

<210> SEQ ID NO 411
<211> LENGTH: 28
<212> TYPE: DNA
<213> ORGANISM: Glycine Max

<400> SEQUENCE: 411
aatataawta aaataaaaaa aaaaaaaa 28

<210> SEQ ID NO 412
<211> LENGTH: 27
<212> TYPE: DNA
<213> ORGANISM: Glycine Max

<400> SEQUENCE: 412
aatataawwa aaataaaaaa aaaaaaa 27

<210> SEQ ID NO 413
<211> LENGTH: 28
<212> TYPE: DNA
<213> ORGANISM: Glycine Max

<400> SEQUENCE: 413
caaaaaaama aaaaaaaccc cacacaca 28

<210> SEQ ID NO 414
<211> LENGTH: 32
<212> TYPE: DNA
<213> ORGANISM: Glycine Max

<400> SEQUENCE: 414
taaaaaatta taaaaaaaat tttattatat aa 32

<210> SEQ ID NO 415
<211> LENGTH: 29
<212> TYPE: DNA
<213> ORGANISM: Glycine Max

<400> SEQUENCE: 415
atwtttaatt ttttttaaaa tawtatatt 29

<210> SEQ ID NO 416
<211> LENGTH: 29
<212> TYPE: DNA
<213> ORGANISM: Glycine Max

<400> SEQUENCE: 416 cttttccct ttttttcccc tcttctctt 29

<210> SEQ ID NO 417
<211> LENGTH: 29
<212> TYPE: DNA
<213> ORGANISM: Glycine Max

<400> SEQUENCE: 417
tccccctttc ccccccttttt ctcctctcc 29

<210> SEQ ID NO 418
<211> LENGTH: 31
<212> TYPE: DNA
<213> ORGANISM: Glycine Max

<400> SEQUENCE: 418
ccccctcccc cttttctttc cccccyctcc t 31

<210> SEQ ID NO 419
<211> LENGTH: 18
<212> TYPE: DNA
<213> ORGANISM: Glycine Max

<400> SEQUENCE: 419
ggccggcgcc ggggggggc 18

<210> SEQ ID NO 420
<211> LENGTH: 18
<212> TYPE: DNA
<213> ORGANISM: Glycine Max

<400> SEQUENCE: 420
ggagggggag gggggga 18

<210> SEQ ID NO 421
<211> LENGTH: 28
<212> TYPE: DNA
<213> ORGANISM: Glycine Max

<400> SEQUENCE: 421
attttaatat ttttttaaat awtatatt 28

<210> SEQ ID NO 422
<211> LENGTH: 32
<212> TYPE: DNA
<213> ORGANISM: Glycine Max

<400> SEQUENCE: 422
tawaaaatta taaaaaaaat tttatwatat aa 32

<210> SEQ ID NO 423
<211> LENGTH: 31
<212> TYPE: DNA
<213> ORGANISM: Glycine Max

<400> SEQUENCE: 423
ccyctccccc ccccctcccc cccccccccc c 31

<210> SEQ ID NO 424
<211> LENGTH: 29
<212> TYPE: DNA
<213> ORGANISM: Glycine Max

<400> SEQUENCE: 424 tccccttct cccccccttt tctyctctc 29

<210> SEQ ID NO 425
<211> LENGTH: 25
<212> TYPE: DNA
<213> ORGANISM: Glycine Max

<400> SEQUENCE: 425
atttttaata tttttaaaaa ataat 25

<210> SEQ ID NO 426
<211> LENGTH: 22
<212> TYPE: DNA
<213> ORGANISM: Glycine Max

<400> SEQUENCE: 426
ataaaaaaaa waaaaaaaat aa 22

<210> SEQ ID NO 427
<211> LENGTH: 23
<212> TYPE: DNA
<213> ORGANISM: Glycine Max

<400> SEQUENCE: 427
gagrgggggg rgggggaggg agr 23

<210> SEQ ID NO 428
<211> LENGTH: 22
<212> TYPE: DNA
<213> ORGANISM: Glycine Max

<400> SEQUENCE: 428
aaawaaaaaa aaaaaaaata at 22

<210> SEQ ID NO 429
<211> LENGTH: 22
<212> TYPE: DNA
<213> ORGANISM: Glycine Max

<400> SEQUENCE: 429
cccmcccccc cccccccac ca 22

<210> SEQ ID NO 430
<211> LENGTH: 28
<212> TYPE: DNA
<213> ORGANISM: Glycine Max

<400> SEQUENCE: 430
gcgggggggg gggggggggg cggggggg 28

<210> SEQ ID NO 431
<211> LENGTH: 23
<212> TYPE: DNA
<213> ORGANISM: Glycine Max

<400> SEQUENCE: 431
gaaagggaaa aagggggggag aga 23

<210> SEQ ID NO 432
<211> LENGTH: 18
<212> TYPE: DNA
<213> ORGANISM: Glycine Max

<400> SEQUENCE: 432
ggtttgkgtt tgggggtg 18

<210> SEQ ID NO 433
<211> LENGTH: 32
<212> TYPE: DNA
<213> ORGANISM: Glycine Max

<400> SEQUENCE: 433
acmcccaaac acccccccca aaacamcaca cc 32

<210> SEQ ID NO 434
<211> LENGTH: 21
<212> TYPE: DNA
<213> ORGANISM: Glycine Max

<400> SEQUENCE: 434
aaaaaaaaat aaaaaaaaaa t 21

<210> SEQ ID NO 435
<211> LENGTH: 25
<212> TYPE: DNA
<213> ORGANISM: Glycine Max

<400> SEQUENCE: 435
tgtgkttkgt tgtttttttt tgtgg 25

<210> SEQ ID NO 436
<211> LENGTH: 24
<212> TYPE: DNA
<213> ORGANISM: Glycine Max

<400> SEQUENCE: 436
aaaaaaaaaa tataaaaaaa aaaa 24

<210> SEQ ID NO 437
<211> LENGTH: 26
<212> TYPE: DNA
<213> ORGANISM: Glycine Max

<400> SEQUENCE: 437
tttttttttt atwttttttt tttttt 26

<210> SEQ ID NO 438
<211> LENGTH: 29
<212> TYPE: DNA
<213> ORGANISM: Glycine Max

<400> SEQUENCE: 438
tgggggtttt gggggggttt gttgtgtgg 29

<210> SEQ ID NO 439
<211> LENGTH: 14
<212> TYPE: DNA
<213> ORGANISM: Glycine Max

<400> SEQUENCE: 439
twttwttttt tttt 14

<210> SEQ ID NO 440
<211> LENGTH: 26
<212> TYPE: DNA
<213> ORGANISM: Glycine Max

<400> SEQUENCE: 440
cgcgcccccc cccccccccc cccccc 26

<210> SEQ ID NO 441
<211> LENGTH: 30
<212> TYPE: DNA
<213> ORGANISM: Glycine Max

<400> SEQUENCE: 441
tccccctctc cccccccttt tctyctctcc 30

<210> SEQ ID NO 442
<211> LENGTH: 15
<212> TYPE: DNA
<213> ORGANISM: Glycine Max

<400> SEQUENCE: 442
ataaaaaaaa aaaat 15

<210> SEQ ID NO 443
<211> LENGTH: 18
<212> TYPE: DNA
<213> ORGANISM: Glycine Max

<400> SEQUENCE: 443
gaaggggagg ggagggga 18

<210> SEQ ID NO 444
<211> LENGTH: 20
<212> TYPE: DNA
<213> ORGANISM: Glycine Max

<400> SEQUENCE: 444
acccaaaacc aaaacaaaac 20

<210> SEQ ID NO 445
<211> LENGTH: 32
<212> TYPE: DNA
<213> ORGANISM: Glycine Max

<400> SEQUENCE: 445
ctytttccct cttttttttc ccctcytctc tt 32

<210> SEQ ID NO 446
<211> LENGTH: 29
<212> TYPE: DNA
<213> ORGANISM: Glycine Max

<400> SEQUENCE: 446
tgkgggttgt ggggggtttt tgtktgtgg 29

<210> SEQ ID NO 447
<211> LENGTH: 30
<212> TYPE: DNA
<213> ORGANISM: Glycine Max

<400> SEQUENCE: 447
tcycccttct cccccccctt ttctytctcc 30

<210> SEQ ID NO 448
<211> LENGTH: 28
<212> TYPE: DNA
<213> ORGANISM: Glycine Max

<400> SEQUENCE: 448
ggggaggggg ggaggggggg gggggggg 28

<210> SEQ ID NO 449
<211> LENGTH: 27
<212> TYPE: DNA
<213> ORGANISM: Glycine Max

<400> SEQUENCE: 449
gggggggggg ggggggggga gggggag 27

<210> SEQ ID NO 450
<211> LENGTH: 28
<212> TYPE: DNA
<213> ORGANISM: Glycine Max

<400> SEQUENCE: 450
cggggccgcg ggggggcccc gcscgcgg 28

<210> SEQ ID NO 451
<211> LENGTH: 23
<212> TYPE: DNA
<213> ORGANISM: Glycine Max

<400> SEQUENCE: 451
taagttttgg agttttgttt tgg 23

<210> SEQ ID NO 452
<211> LENGTH: 23
<212> TYPE: DNA
<213> ORGANISM: Glycine Max

<400> SEQUENCE: 452
ccctcccctt ctcccccccc cct 23

<210> SEQ ID NO 453
<211> LENGTH: 21
<212> TYPE: DNA
<213> ORGANISM: Glycine Max

<400> SEQUENCE: 453
graaggggaa aggggagggg a 21

<210> SEQ ID NO 454
<211> LENGTH: 20
<212> TYPE: DNA
<213> ORGANISM: Glycine Max

<400> SEQUENCE: 454
tkggttttgg ttttgtkttg 20

<210> SEQ ID NO 455
<211> LENGTH: 16
<212> TYPE: DNA
<213> ORGANISM: Glycine Max

<400> SEQUENCE: 455
ttctyctttt ctytct 16

<210> SEQ ID NO 456
<211> LENGTH: 15
<212> TYPE: DNA
<213> ORGANISM: Glycine Max

<400> SEQUENCE: 456
ggggagggga grgag 15

<210> SEQ ID NO 457
<211> LENGTH: 14
<212> TYPE: DNA
<213> ORGANISM: Glycine Max

<400> SEQUENCE: 457
gggggggggg gcgc 14

<210> SEQ ID NO 458
<211> LENGTH: 21
<212> TYPE: DNA
<213> ORGANISM: Glycine Max

<400> SEQUENCE: 458
agggargggg gaaaaaaaga g 21

<210> SEQ ID NO 459
<211> LENGTH: 26
<212> TYPE: DNA
<213> ORGANISM: Glycine Max

<400> SEQUENCE: 459
aaggaaaagg ggggaaaaga agaggg 26

<210> SEQ ID NO 460
<211> LENGTH: 23
<212> TYPE: DNA
<213> ORGANISM: Glycine Max

<400> SEQUENCE: 460
ccccccttct tcccccctct cct 23

<210> SEQ ID NO 461
<211> LENGTH: 16
<212> TYPE: DNA
<213> ORGANISM: Glycine Max

<400> SEQUENCE: 461 gggggaagg gggggg 16

<210> SEQ ID NO 462
<211> LENGTH: 16
<212> TYPE: DNA
<213> ORGANISM: Glycine Max

<400> SEQUENCE: 462
gggggaaggg gggaga 16

<210> SEQ ID NO 463
<211> LENGTH: 16
<212> TYPE: DNA

<213> ORGANISM: Glycine Max

<400> SEQUENCE: 463
gggggaaggg gggaga 16

<210> SEQ ID NO 464
<211> LENGTH: 19
<212> TYPE: DNA
<213> ORGANISM: Glycine Max

<400> SEQUENCE: 464
cgggaccggc ccccsgcgc 19

<210> SEQ ID NO 465
<211> LENGTH: 17
<212> TYPE: DNA
<213> ORGANISM: Glycine Max

<400> SEQUENCE: 465
gcggggccgg ggggcgg 17

<210> SEQ ID NO 466
<211> LENGTH: 17
<212> TYPE: DNA
<213> ORGANISM: Glycine Max

<400> SEQUENCE: 466
tcttttccct ttttttt 17

<210> SEQ ID NO 467
<211> LENGTH: 24
<212> TYPE: DNA
<213> ORGANISM: Glycine Max

<400> SEQUENCE: 467
cctccccccc ctcccccccc cccc 24

<210> SEQ ID NO 468
<211> LENGTH: 16
<212> TYPE: DNA
<213> ORGANISM: Glycine Max

<400> SEQUENCE: 468
ccccccggcc cccccc 16

<210> SEQ ID NO 469
<211> LENGTH: 23
<212> TYPE: DNA
<213> ORGANISM: Glycine Max

<400> SEQUENCE: 469
atttaaattt ttttaaaaaw aat 23

<210> SEQ ID NO 470
<211> LENGTH: 24
<212> TYPE: DNA
<213> ORGANISM: Glycine Max

<400> SEQUENCE: 470
tcccctttcc cccccttttt yttc 24

<210> SEQ ID NO 471
<211> LENGTH: 27

<212> TYPE: DNA
<213> ORGANISM: Glycine Max

<400> SEQUENCE: 471
gggggggggg gggggggggg gggcggc 27

<210> SEQ ID NO 472
<211> LENGTH: 29
<212> TYPE: DNA
<213> ORGANISM: Glycine Max

<400> SEQUENCE: 472
tcyccccttc tccccccttt tctccttcc 29

<210> SEQ ID NO 473
<211> LENGTH: 29
<212> TYPE: DNA
<213> ORGANISM: Glycine Max

<400> SEQUENCE: 473
ctyttttcct cttttttccc ctctctctt 29

<210> SEQ ID NO 474
<211> LENGTH: 29
<212> TYPE: DNA
<213> ORGANISM: Glycine Max

<400> SEQUENCE: 474
ctytttcctc tttttttccc ctctctctt 29

<210> SEQ ID NO 475
<211> LENGTH: 31
<212> TYPE: DNA
<213> ORGANISM: Glycine Max

<400> SEQUENCE: 475
ttwtattttt tttttatttt tttttttttt t 31

<210> SEQ ID NO 476
<211> LENGTH: 30
<212> TYPE: DNA
<213> ORGANISM: Glycine Max

<400> SEQUENCE: 476
aatataaaaa awaaataaaa aaaaaaaaaa 30

<210> SEQ ID NO 477
<211> LENGTH: 31
<212> TYPE: DNA
<213> ORGANISM: Glycine Max

<400> SEQUENCE: 477 attttttaw ttttttttaa aatawtattt t 31

<210> SEQ ID NO 478
<211> LENGTH: 32
<212> TYPE: DNA
<213> ORGANISM: Glycine Max

<400> SEQUENCE: 478
gggkgtgggg gttttgtttg gggggktgtg gt 32

<210> SEQ ID NO 479

<211> LENGTH: 32
<212> TYPE: DNA
<213> ORGANISM: Glycine Max

<400> SEQUENCE: 479
ccscgcggcc cccccgcccc cccccccccc cc 32

<210> SEQ ID NO 480
<211> LENGTH: 32
<212> TYPE: DNA
<213> ORGANISM: Glycine Max

<400> SEQUENCE: 480
atataaaaat aaaaaaaaaa aaataaaaaa ta 32

<210> SEQ ID NO 481
<211> LENGTH: 32
<212> TYPE: DNA
<213> ORGANISM: Glycine Max

<400> SEQUENCE: 481
acamaaaaac aaaaaaaaaa aaacaaaaaa ca 32

<210> SEQ ID NO 482
<211> LENGTH: 21
<212> TYPE: DNA
<213> ORGANISM: Glycine Max

<400> SEQUENCE: 482
gggggggggg tggkgggggg g 21

<210> SEQ ID NO 483
<211> LENGTH: 20
<212> TYPE: DNA
<213> ORGANISM: Glycine Max

<400> SEQUENCE: 483
atawttaaaa aataaaaaat 20

<210> SEQ ID NO 484
<211> LENGTH: 23
<212> TYPE: DNA
<213> ORGANISM: Glycine Max

<400> SEQUENCE: 484
ttttattttt attttttwa tta 23

<210> SEQ ID NO 485
<211> LENGTH: 19
<212> TYPE: DNA
<213> ORGANISM: Glycine Max

<400> SEQUENCE: 485
aaataaaaaa aaaaaaaaa 19

<210> SEQ ID NO 486
<211> LENGTH: 22
<212> TYPE: DNA
<213> ORGANISM: Glycine Max

<400> SEQUENCE: 486
agrgaaaagg gaaaagaaaa aa 22

<210> SEQ ID NO 487
<211> LENGTH: 20
<212> TYPE: DNA
<213> ORGANISM: Glycine Max

<400> SEQUENCE: 487
aaaaaaaaaa aaaaaawaat 20

<210> SEQ ID NO 488
<211> LENGTH: 29
<212> TYPE: DNA
<213> ORGANISM: Glycine Max

<400> SEQUENCE: 488
cccyctcccc ttttttccc ctcytctct 29

<210> SEQ ID NO 489
<211> LENGTH: 30
<212> TYPE: DNA
<213> ORGANISM: Glycine Max

<400> SEQUENCE: 489
cccyctcccc ttttctttcc cctcytctct 30

<210> SEQ ID NO 490
<211> LENGTH: 31
<212> TYPE: DNA
<213> ORGANISM: Glycine Max

<400> SEQUENCE: 490
ttytcttttt tttttctttt tttttttttt t 31

<210> SEQ ID NO 491
<211> LENGTH: 30
<212> TYPE: DNA
<213> ORGANISM: Glycine Max

<400> SEQUENCE: 491
ctttttccct cttttttttcc cctctctctt 30

<210> SEQ ID NO 492
<211> LENGTH: 22
<212> TYPE: DNA
<213> ORGANISM: Glycine Max

<400> SEQUENCE: 492 tttttttkt tgtttttttt tk 22

<210> SEQ ID NO 493
<211> LENGTH: 22
<212> TYPE: DNA
<213> ORGANISM: Glycine Max

<400> SEQUENCE: 493
gggggggggg gagggggggg gr 22

<210> SEQ ID NO 494
<211> LENGTH: 31
<212> TYPE: DNA
<213> ORGANISM: Glycine Max

<400> SEQUENCE: 494
aaaaagaaaa aggggaggaa aagargagag g 31

<210> SEQ ID NO 495
<211> LENGTH: 29
<212> TYPE: DNA
<213> ORGANISM: Glycine Max

<400> SEQUENCE: 495
aggggggagg gggggggaaa gargagagg 29

<210> SEQ ID NO 496
<211> LENGTH: 29
<212> TYPE: DNA
<213> ORGANISM: Glycine Max

<400> SEQUENCE: 496
ataaaaaata aaaaaaaaaa aaaaaaaaa 29

<210> SEQ ID NO 497
<211> LENGTH: 29
<212> TYPE: DNA
<213> ORGANISM: Glycine Max

<400> SEQUENCE: 497
ccccgccccg gggcggcccc gcsgcgcgg 29

<210> SEQ ID NO 498
<211> LENGTH: 24
<212> TYPE: DNA
<213> ORGANISM: Glycine Max

<400> SEQUENCE: 498
tttttttttc ctttttctyc ttcc 24

<210> SEQ ID NO 499
<211> LENGTH: 21
<212> TYPE: DNA
<213> ORGANISM: Glycine Max

<400> SEQUENCE: 499
tttttttttt tttttycttc c 21

<210> SEQ ID NO 500
<211> LENGTH: 20
<212> TYPE: DNA
<213> ORGANISM: Glycine Max

<400> SEQUENCE: 500
gggggggggc ggggggggcc 20

<210> SEQ ID NO 501
<211> LENGTH: 21
<212> TYPE: DNA
<213> ORGANISM: Glycine Max

<400> SEQUENCE: 501
cctctccccc ctcccccccc c 21

<210> SEQ ID NO 502
<211> LENGTH: 21
<212> TYPE: DNA
<213> ORGANISM: Glycine Max

<400> SEQUENCE: 502
tcccccccty cctttttttc c 21

```
<210> SEQ ID NO 503
<211> LENGTH: 28
<212> TYPE: DNA
<213> ORGANISM: Glycine Max

<400> SEQUENCE: 503

gggggagggg gaaagagggg aggagaaa                                          28

<210> SEQ ID NO 504
<211> LENGTH: 28
<212> TYPE: DNA
<213> ORGANISM: Glycine Max

<400> SEQUENCE: 504

tcccctcctc ytttcttttt tttttttt                                          28

<210> SEQ ID NO 505
<211> LENGTH: 28
<212> TYPE: DNA
<213> ORGANISM: Glycine Max

<400> SEQUENCE: 505

aaaaagaaaa agggagaaaa gaagaggg                                          28

<210> SEQ ID NO 506
<211> LENGTH: 29
<212> TYPE: DNA
<213> ORGANISM: Glycine Max

<400> SEQUENCE: 506

cgargagcgc aaaagaaccc caccaccaa                                         29

<210> SEQ ID NO 507
<211> LENGTH: 27
<212> TYPE: DNA
<213> ORGANISM: Glycine Max

<400> SEQUENCE: 507

ctctccccct yyycyccccc ccccccc                                           27

<210> SEQ ID NO 508
<211> LENGTH: 26
<212> TYPE: DNA
<213> ORGANISM: Glycine Max

<400> SEQUENCE: 508

aaaaaaawaa aaaaaaaaaa taaaww                                            26

<210> SEQ ID NO 509
<211> LENGTH: 29
<212> TYPE: DNA
<213> ORGANISM: Glycine Max

<400> SEQUENCE: 509

gggrgagggg gaaagaagg gagraagaa                                          29

<210> SEQ ID NO 510
<211> LENGTH: 30
<212> TYPE: DNA
<213> ORGANISM: Glycine Max

<400> SEQUENCE: 510
```

cccyctcccc ttttctttcc cctcytcttt 30

<210> SEQ ID NO 511
<211> LENGTH: 28
<212> TYPE: DNA
<213> ORGANISM: Glycine Max

<400> SEQUENCE: 511
tatattttat tttttttttt tttttttt 28

<210> SEQ ID NO 512
<211> LENGTH: 30
<212> TYPE: DNA
<213> ORGANISM: Glycine Max

<400> SEQUENCE: 512
ttytcttttt tttctttttt tttttttttt 30

<210> SEQ ID NO 513
<211> LENGTH: 30
<212> TYPE: DNA
<213> ORGANISM: Glycine Max

<400> SEQUENCE: 513
gggggagggg aaagaaaggg gagragagaa 30

<210> SEQ ID NO 514
<211> LENGTH: 31
<212> TYPE: DNA
<213> ORGANISM: Glycine Max

<400> SEQUENCE: 514
ccccctcccc ttttctttcc cctcytctct t 31

<210> SEQ ID NO 515
<211> LENGTH: 31
<212> TYPE: DNA
<213> ORGANISM: Glycine Max

<400> SEQUENCE: 515
cccyctcccc cttttctttc ccctcytctt t 31

<210> SEQ ID NO 516
<211> LENGTH: 32
<212> TYPE: DNA
<213> ORGANISM: Glycine Max

<400> SEQUENCE: 516
gggggagggg gaaaagaaag gggagragag aa 32

<210> SEQ ID NO 517
<211> LENGTH: 29
<212> TYPE: DNA
<213> ORGANISM: Glycine Max

<400> SEQUENCE: 517
ggagagggrg ggaggggggg ggggggggg 29

<210> SEQ ID NO 518
<211> LENGTH: 30
<212> TYPE: DNA
<213> ORGANISM: Glycine Max

<400> SEQUENCE: 518
gggggagggg aaagaaaggg gagragagaa 30

<210> SEQ ID NO 519
<211> LENGTH: 27
<212> TYPE: DNA
<213> ORGANISM: Glycine Max

<400> SEQUENCE: 519 ttttttttt tattatttt ttttatt 27

<210> SEQ ID NO 520
<211> LENGTH: 27
<212> TYPE: DNA
<213> ORGANISM: Glycine Max

<400> SEQUENCE: 520
cccccccccc caccaccccc ccccacc 27

<210> SEQ ID NO 521
<211> LENGTH: 26
<212> TYPE: DNA
<213> ORGANISM: Glycine Max

<400> SEQUENCE: 521
aaaaaaaaat ttattaaaaa atatat 26

<210> SEQ ID NO 522
<211> LENGTH: 25
<212> TYPE: DNA
<213> ORGANISM: Glycine Max

<400> SEQUENCE: 522
tttttttttc tttttttttt ctttc 25

<210> SEQ ID NO 523
<211> LENGTH: 30
<212> TYPE: DNA
<213> ORGANISM: Glycine Max

<400> SEQUENCE: 523
cctctccccc cccctccccc cccccccccc 30

<210> SEQ ID NO 524
<211> LENGTH: 31
<212> TYPE: DNA
<213> ORGANISM: Glycine Max

<400> SEQUENCE: 524
ccccctcccc cttttcttcc cctcytctct t 31

<210> SEQ ID NO 525
<211> LENGTH: 31
<212> TYPE: DNA
<213> ORGANISM: Glycine Max

<400> SEQUENCE: 525
tttttatttt taaaatawtt ttatwatata a 31

<210> SEQ ID NO 526
<211> LENGTH: 18
<212> TYPE: DNA
<213> ORGANISM: Glycine Max

<400> SEQUENCE: 526
tctttytttt tttttttt 18

<210> SEQ ID NO 527
<211> LENGTH: 17
<212> TYPE: DNA
<213> ORGANISM: Glycine Max

<400> SEQUENCE: 527
ttggtktttt tttttgt 17

<210> SEQ ID NO 528
<211> LENGTH: 17
<212> TYPE: DNA
<213> ORGANISM: Glycine Max

<400> SEQUENCE: 528
ggccgsgggg gggggcg 17

<210> SEQ ID NO 529
<211> LENGTH: 15
<212> TYPE: DNA
<213> ORGANISM: Glycine Max

<400> SEQUENCE: 529
ccacmccccc ccccc 15

<210> SEQ ID NO 530
<211> LENGTH: 22
<212> TYPE: DNA
<213> ORGANISM: Glycine Max

<400> SEQUENCE: 530 ttatatttt tattttttt tt 22

<210> SEQ ID NO 531
<211> LENGTH: 29
<212> TYPE: DNA
<213> ORGANISM: Glycine Max

<400> SEQUENCE: 531
cgggggggcg cggggggccc cgcsgccgg 29

<210> SEQ ID NO 532
<211> LENGTH: 23
<212> TYPE: DNA
<213> ORGANISM: Glycine Max

<400> SEQUENCE: 532
tttkttgttg tttttttttk ttt 23

<210> SEQ ID NO 533
<211> LENGTH: 22
<212> TYPE: DNA
<213> ORGANISM: Glycine Max

<400> SEQUENCE: 533
aaaaaaaaat waaaaaaawa aa 22

<210> SEQ ID NO 534
<211> LENGTH: 25
<212> TYPE: DNA
<213> ORGANISM: Glycine Max

<400> SEQUENCE: 534
cccyctcccc tttctycccc cytcc 25

<210> SEQ ID NO 535
<211> LENGTH: 21
<212> TYPE: DNA
<213> ORGANISM: Glycine Max

<400> SEQUENCE: 535
ttttttttta ttttatttta a 21

<210> SEQ ID NO 536
<211> LENGTH: 32
<212> TYPE: DNA
<213> ORGANISM: Glycine Max

<400> SEQUENCE: 536
aaamacaaaa accccamcca aaacamcaca cc 32

<210> SEQ ID NO 537
<211> LENGTH: 28
<212> TYPE: DNA
<213> ORGANISM: Glycine Max

<400> SEQUENCE: 537 ttycttttc ccctcctttt ctcctctc 28

<210> SEQ ID NO 538
<211> LENGTH: 28
<212> TYPE: DNA
<213> ORGANISM: Glycine Max

<400> SEQUENCE: 538
tgtktttttt tttttttttt tttttttt 28

<210> SEQ ID NO 539
<211> LENGTH: 30
<212> TYPE: DNA
<213> ORGANISM: Glycine Max

<400> SEQUENCE: 539
cccccacccc caamcaaacc ccacacacaa 30

<210> SEQ ID NO 540
<211> LENGTH: 26
<212> TYPE: DNA
<213> ORGANISM: Glycine Max

<400> SEQUENCE: 540
gggggagggg gggggggggg ggragg 26

<210> SEQ ID NO 541
<211> LENGTH: 24
<212> TYPE: DNA
<213> ORGANISM: Glycine Max

<400> SEQUENCE: 541
tttttttgtk gttttttttt gttg 24

<210> SEQ ID NO 542
<211> LENGTH: 22
<212> TYPE: DNA

<213> ORGANISM: Glycine Max

<400> SEQUENCE: 542
ttttattttt ttttttattt tt 22

<210> SEQ ID NO 543
<211> LENGTH: 20
<212> TYPE: DNA
<213> ORGANISM: Glycine Max

<400> SEQUENCE: 543
ttttcttttt tttttctttt 20

<210> SEQ ID NO 544
<211> LENGTH: 27
<212> TYPE: DNA
<213> ORGANISM: Glycine Max

<400> SEQUENCE: 544
ccccccccaa acaaacccca cmacaaa 27

<210> SEQ ID NO 545
<211> LENGTH: 23
<212> TYPE: DNA
<213> ORGANISM: Glycine Max

<400> SEQUENCE: 545
gggggggaaa gaaaggggggr gaa 23

<210> SEQ ID NO 546
<211> LENGTH: 19
<212> TYPE: DNA
<213> ORGANISM: Glycine Max

<400> SEQUENCE: 546
aaaataaata aaaaaaaaa 19

<210> SEQ ID NO 547
<211> LENGTH: 21
<212> TYPE: DNA
<213> ORGANISM: Glycine Max

<400> SEQUENCE: 547
gaaaaagaga ggggagrgag a 21

<210> SEQ ID NO 548
<211> LENGTH: 30
<212> TYPE: DNA
<213> ORGANISM: Glycine Max

<400> SEQUENCE: 548
gggggagggg aaagaaaggg gagragagaa 30

<210> SEQ ID NO 549
<211> LENGTH: 32
<212> TYPE: DNA
<213> ORGANISM: Glycine Max

<400> SEQUENCE: 549
ggrgaggggg gggggagggg gggggggggg gg 32

<210> SEQ ID NO 550
<211> LENGTH: 31

<212> TYPE: DNA
<213> ORGANISM: Glycine Max

<400> SEQUENCE: 550 aggggaaag ggggggggaa aagargagag g 31

<210> SEQ ID NO 551
<211> LENGTH: 31
<212> TYPE: DNA
<213> ORGANISM: Glycine Max

<400> SEQUENCE: 551
ccccctcccc cttttcttcc cctcytctct t 31

<210> SEQ ID NO 552
<211> LENGTH: 27
<212> TYPE: DNA
<213> ORGANISM: Glycine Max

<400> SEQUENCE: 552
cggggtgcgs ttttcccctc ytctctt 27

<210> SEQ ID NO 553
<211> LENGTH: 26
<212> TYPE: DNA
<213> ORGANISM: Glycine Max

<400> SEQUENCE: 553
gggggagggg gaaaaggggg gragaa 26

<210> SEQ ID NO 554
<211> LENGTH: 23
<212> TYPE: DNA
<213> ORGANISM: Glycine Max

<400> SEQUENCE: 554
gggggggggg gggggggggg gga 23

<210> SEQ ID NO 555
<211> LENGTH: 22
<212> TYPE: DNA
<213> ORGANISM: Glycine Max

<400> SEQUENCE: 555
aaaaagaaaa ggaaaaaaaa gg 22

<210> SEQ ID NO 556
<211> LENGTH: 22
<212> TYPE: DNA
<213> ORGANISM: Glycine Max

<400> SEQUENCE: 556
gaaaggggaa gggggggggg gg 22

<210> SEQ ID NO 557
<211> LENGTH: 23
<212> TYPE: DNA
<213> ORGANISM: Glycine Max

<400> SEQUENCE: 557 ggaggggga gggggggggg ggg 23

<210> SEQ ID NO 558

<211> LENGTH: 24
<212> TYPE: DNA
<213> ORGANISM: Glycine Max

<400> SEQUENCE: 558
gcgcgggcgg gggggggggg gggg 24

<210> SEQ ID NO 559
<211> LENGTH: 24
<212> TYPE: DNA
<213> ORGANISM: Glycine Max

<400> SEQUENCE: 559
cccctcccct tctccccccc tcct 24

<210> SEQ ID NO 560
<211> LENGTH: 22
<212> TYPE: DNA
<213> ORGANISM: Glycine Max

<400> SEQUENCE: 560
aaaaaaaaaa gaaaaaaaaa gg 22

<210> SEQ ID NO 561
<211> LENGTH: 21
<212> TYPE: DNA
<213> ORGANISM: Glycine Max

<400> SEQUENCE: 561
ccccccccct ccccccccct t 21

<210> SEQ ID NO 562
<211> LENGTH: 24
<212> TYPE: DNA
<213> ORGANISM: Glycine Max

<400> SEQUENCE: 562
gggggagggg gggggggggg gagg 24

<210> SEQ ID NO 563
<211> LENGTH: 29
<212> TYPE: DNA
<213> ORGANISM: Glycine Max

<400> SEQUENCE: 563
aaaaaaaaaa aataaataaa aaaaaaaaa 29

<210> SEQ ID NO 564
<211> LENGTH: 30
<212> TYPE: DNA
<213> ORGANISM: Glycine Max

<400> SEQUENCE: 564
gggggagggg gaaaagaagg ggagrgagaa 30

<210> SEQ ID NO 565
<211> LENGTH: 30
<212> TYPE: DNA
<213> ORGANISM: Glycine Max

<400> SEQUENCE: 565
cccyctcccc ttttcttccc ctcytytctt 30

<210> SEQ ID NO 566
<211> LENGTH: 30
<212> TYPE: DNA
<213> ORGANISM: Glycine Max

<400> SEQUENCE: 566 ctctcccty cccccccccc cccccccccc 30

<210> SEQ ID NO 567
<211> LENGTH: 25
<212> TYPE: DNA
<213> ORGANISM: Glycine Max

<400> SEQUENCE: 567
tctctcttcc ccctcctttt cyttc 25

<210> SEQ ID NO 568
<211> LENGTH: 25
<212> TYPE: DNA
<213> ORGANISM: Glycine Max

<400> SEQUENCE: 568
aaaaagaaaa agggagaaaa gaaag 25

<210> SEQ ID NO 569
<211> LENGTH: 21
<212> TYPE: DNA
<213> ORGANISM: Glycine Max

<400> SEQUENCE: 569
ccccccccct ctcccctccc c 21

<210> SEQ ID NO 570
<211> LENGTH: 21
<212> TYPE: DNA
<213> ORGANISM: Glycine Max

<400> SEQUENCE: 570
ccccccccct ctcccctccc c 21

<210> SEQ ID NO 571
<211> LENGTH: 22
<212> TYPE: DNA
<213> ORGANISM: Glycine Max

<400> SEQUENCE: 571
aaaacaaaaa acaaaacaac aa 22

<210> SEQ ID NO 572
<211> LENGTH: 23
<212> TYPE: DNA
<213> ORGANISM: Glycine Max

<400> SEQUENCE: 572
aaaagaaaaa gaaaaaraag rgg 23

<210> SEQ ID NO 573
<211> LENGTH: 25
<212> TYPE: DNA
<213> ORGANISM: Glycine Max

<400> SEQUENCE: 573
ggggaggggg agaggggrgg araaa 25

<210> SEQ ID NO 574
<211> LENGTH: 13
<212> TYPE: DNA
<213> ORGANISM: Glycine Max

<400> SEQUENCE: 574 ttttttttt wat 13

<210> SEQ ID NO 575
<211> LENGTH: 12
<212> TYPE: DNA
<213> ORGANISM: Glycine Max

<400> SEQUENCE: 575
gaaaaggggg gg 12

<210> SEQ ID NO 576
<211> LENGTH: 14
<212> TYPE: DNA
<213> ORGANISM: Glycine Max

<400> SEQUENCE: 576
aaaaargaaa aaaa 14

<210> SEQ ID NO 577
<211> LENGTH: 25
<212> TYPE: DNA
<213> ORGANISM: Glycine Max

<400> SEQUENCE: 577
ctycttcytt tcttcccccc tcttt 25

<210> SEQ ID NO 578
<211> LENGTH: 31
<212> TYPE: DNA
<213> ORGANISM: Glycine Max

<400> SEQUENCE: 578 gccccccccgs cccsccccgg ggcgscgcgc c 31

<210> SEQ ID NO 579
<211> LENGTH: 30
<212> TYPE: DNA
<213> ORGANISM: Glycine Max

<400> SEQUENCE: 579
agaraaaaaa aaaaaaaaaa aaaaaaaaaa 30

<210> SEQ ID NO 580
<211> LENGTH: 30
<212> TYPE: DNA
<213> ORGANISM: Glycine Max

<400> SEQUENCE: 580
ccyyctcccc ttttctttcc cctcytctct 30

<210> SEQ ID NO 581
<211> LENGTH: 24
<212> TYPE: DNA
<213> ORGANISM: Glycine Max

<400> SEQUENCE: 581
ggggggggga agaggggagg gaga 24

<210> SEQ ID NO 582
<211> LENGTH: 30
<212> TYPE: DNA
<213> ORGANISM: Glycine Max

<400> SEQUENCE: 582
tttytctttt tcccctcctt ttctcctccc 30

<210> SEQ ID NO 583
<211> LENGTH: 22
<212> TYPE: DNA
<213> ORGANISM: Glycine Max

<400> SEQUENCE: 583 ctttttcty tcaccccacc cc 22

<210> SEQ ID NO 584
<211> LENGTH: 23
<212> TYPE: DNA
<213> ORGANISM: Glycine Max

<400> SEQUENCE: 584
aaaaaaaaaa agaaaagaag aag 23

<210> SEQ ID NO 585
<211> LENGTH: 23
<212> TYPE: DNA
<213> ORGANISM: Glycine Max

<400> SEQUENCE: 585
gggggggggg gtggggtggt ggt 23

<210> SEQ ID NO 586
<211> LENGTH: 17
<212> TYPE: DNA
<213> ORGANISM: Glycine Max

<400> SEQUENCE: 586
caacccamcc ccccccc 17

<210> SEQ ID NO 587
<211> LENGTH: 24
<212> TYPE: DNA
<213> ORGANISM: Glycine Max

<400> SEQUENCE: 587
gggggggggt tgtgggggkt gtgt 24

<210> SEQ ID NO 588
<211> LENGTH: 32
<212> TYPE: DNA
<213> ORGANISM: Glycine Max

<400> SEQUENCE: 588
tawwttttta attttttttt tttttttttt tt 32

<210> SEQ ID NO 589
<211> LENGTH: 32
<212> TYPE: DNA
<213> ORGANISM: Glycine Max

<400> SEQUENCE: 589
gcssgggggc cggggggggg gggggggggg gg 32

<210> SEQ ID NO 590
<211> LENGTH: 32
<212> TYPE: DNA
<213> ORGANISM: Glycine Max

<400> SEQUENCE: 590
gtgkgggggt tggggggggg gggggggggg gg 32

<210> SEQ ID NO 591
<211> LENGTH: 32
<212> TYPE: DNA
<213> ORGANISM: Glycine Max

<400> SEQUENCE: 591
atawaaatat aaaaaaaaaa aaaaaaaaaa aa 32

<210> SEQ ID NO 592
<211> LENGTH: 32
<212> TYPE: DNA
<213> ORGANISM: Glycine Max

<400> SEQUENCE: 592
aarraggaaa rggggaggga aaagargaga gg 32

<210> SEQ ID NO 593
<211> LENGTH: 32
<212> TYPE: DNA
<213> ORGANISM: Glycine Max

<400> SEQUENCE: 593
cccccccccc cccccccccc cccaccccccc ac 32

<210> SEQ ID NO 594
<211> LENGTH: 32
<212> TYPE: DNA
<213> ORGANISM: Glycine Max

<400> SEQUENCE: 594
ccyycttccc yttttctttc ccctcttctc tt 32

<210> SEQ ID NO 595
<211> LENGTH: 31
<212> TYPE: DNA
<213> ORGANISM: Glycine Max

<400> SEQUENCE: 595
ttgtgttttt tttttgtttt tttttttttt t 31

<210> SEQ ID NO 596
<211> LENGTH: 32
<212> TYPE: DNA
<213> ORGANISM: Glycine Max

<400> SEQUENCE: 596
aaaaaaagaa raaaaaaaaa aaagaaaaaa ga 32

<210> SEQ ID NO 597
<211> LENGTH: 32
<212> TYPE: DNA
<213> ORGANISM: Glycine Max

<400> SEQUENCE: 597
gggkgtgggg gttttgtttg gggggktgtg gt 32

<210> SEQ ID NO 598
<211> LENGTH: 32
<212> TYPE: DNA
<213> ORGANISM: Glycine Max

<400> SEQUENCE: 598
aaaaaaccaa maaaaaaaaa aaacaaaaaa ca 32

<210> SEQ ID NO 599
<211> LENGTH: 29
<212> TYPE: DNA
<213> ORGANISM: Glycine Max

<400> SEQUENCE: 599
aaaaaaamaa maaaaaaaaa aaaaaaaaa 29

<210> SEQ ID NO 600
<211> LENGTH: 32
<212> TYPE: DNA
<213> ORGANISM: Glycine Max

<400> SEQUENCE: 600
ttttttttta tttttttttt tttatttttt at 32

<210> SEQ ID NO 601
<211> LENGTH: 30
<212> TYPE: DNA
<213> ORGANISM: Glycine Max

<400> SEQUENCE: 601
agagagaaaa aggggagaaa aaargagaag 30

<210> SEQ ID NO 602
<211> LENGTH: 31
<212> TYPE: DNA
<213> ORGANISM: Glycine Max

<400> SEQUENCE: 602
tggggggtgk gggggggttt ttttggtgtt g 31

<210> SEQ ID NO 603
<211> LENGTH: 32
<212> TYPE: DNA
<213> ORGANISM: Glycine Max

<400> SEQUENCE: 603
gggggcgggg gcggggggcg gggggscgcg gc 32

<210> SEQ ID NO 604
<211> LENGTH: 9
<212> TYPE: DNA
<213> ORGANISM: Glycine Max

<400> SEQUENCE: 604 tktgttgtg 9

<210> SEQ ID NO 605
<211> LENGTH: 11
<212> TYPE: DNA
<213> ORGANISM: Glycine Max

<400> SEQUENCE: 605
cccmcacacc c 11

<210> SEQ ID NO 606
<211> LENGTH: 11
<212> TYPE: DNA
<213> ORGANISM: Glycine Max

<400> SEQUENCE: 606
aaaaacacaa a 11

<210> SEQ ID NO 607
<211> LENGTH: 30
<212> TYPE: DNA
<213> ORGANISM: Glycine Max

<400> SEQUENCE: 607
gggggggggg gaaagaaggg gggggggggg 30

<210> SEQ ID NO 608
<211> LENGTH: 29
<212> TYPE: DNA
<213> ORGANISM: Glycine Max

<400> SEQUENCE: 608 gagaggggggg gggggggggg ggggggggg 29

<210> SEQ ID NO 609
<211> LENGTH: 27
<212> TYPE: DNA
<213> ORGANISM: Glycine Max

<400> SEQUENCE: 609 tcccttttt ytcccctttt ctttttt 27

<210> SEQ ID NO 610
<211> LENGTH: 16
<212> TYPE: DNA
<213> ORGANISM: Glycine Max

<400> SEQUENCE: 610
agaagaagaa aagaaa 16

<210> SEQ ID NO 611
<211> LENGTH: 16
<212> TYPE: DNA
<213> ORGANISM: Glycine Max

<400> SEQUENCE: 611
gaaaaaaagg ggagga 16

<210> SEQ ID NO 612
<211> LENGTH: 29
<212> TYPE: DNA
<213> ORGANISM: Glycine Max

<400> SEQUENCE: 612
ggkgkggggt gkgkkkgggg ggggggggt 29

<210> SEQ ID NO 613
<211> LENGTH: 28
<212> TYPE: DNA
<213> ORGANISM: Glycine Max

<400> SEQUENCE: 613
aaaggaaaga aaaaagaaaa aaaggaag 28

<210> SEQ ID NO 614
<211> LENGTH: 30
<212> TYPE: DNA
<213> ORGANISM: Glycine Max

<400> SEQUENCE: 614
gaaagaagar aaaaaaaagg ggagragagg 30

<210> SEQ ID NO 615
<211> LENGTH: 27
<212> TYPE: DNA
<213> ORGANISM: Glycine Max

<400> SEQUENCE: 615
tttttttttt taaaaatttt tatttttt 27

<210> SEQ ID NO 616
<211> LENGTH: 26
<212> TYPE: DNA
<213> ORGANISM: Glycine Max

<400> SEQUENCE: 616
tttttttttt taaaaatttt attttt 26

<210> SEQ ID NO 617
<211> LENGTH: 26
<212> TYPE: DNA
<213> ORGANISM: Glycine Max

<400> SEQUENCE: 617
tttttttttw taaaaatttt attttt 26

<210> SEQ ID NO 618
<211> LENGTH: 29
<212> TYPE: DNA
<213> ORGANISM: Glycine Max

<400> SEQUENCE: 618
agggagggag rgggggggaa aagagagaa 29

<210> SEQ ID NO 619
<211> LENGTH: 28
<212> TYPE: DNA
<213> ORGANISM: Glycine Max

<400> SEQUENCE: 619
gtttgtttgg kttttttttgg ggtgttgt 28

<210> SEQ ID NO 620
<211> LENGTH: 30
<212> TYPE: DNA
<213> ORGANISM: Glycine Max

<400> SEQUENCE: 620
ttkttttttt tttttttttt ttkttgtttt 30

<210> SEQ ID NO 621
<211> LENGTH: 31
<212> TYPE: DNA

<213> ORGANISM: Glycine Max

<400> SEQUENCE: 621
ctttctttcc cttttttttc ccctttctcc t 31

<210> SEQ ID NO 622
<211> LENGTH: 27
<212> TYPE: DNA
<213> ORGANISM: Glycine Max

<400> SEQUENCE: 622
aggaggagrg ggggggaaaa gargaag 27

<210> SEQ ID NO 623
<211> LENGTH: 25
<212> TYPE: DNA
<213> ORGANISM: Glycine Max

<400> SEQUENCE: 623
tggtggggkg gggggttttg tkttg 25

<210> SEQ ID NO 624
<211> LENGTH: 24
<212> TYPE: DNA
<213> ORGANISM: Glycine Max

<400> SEQUENCE: 624
aatatataaa aaaaaaaaaa awaa 24

<210> SEQ ID NO 625
<211> LENGTH: 29
<212> TYPE: DNA
<213> ORGANISM: Glycine Max

<400> SEQUENCE: 625
atawatataa ataaaaaata aaaawtata 29

<210> SEQ ID NO 626
<211> LENGTH: 32
<212> TYPE: DNA
<213> ORGANISM: Glycine Max

<400> SEQUENCE: 626
aaaaagaaaa agaaaaaaga aaaaargaga ag 32

<210> SEQ ID NO 627
<211> LENGTH: 31
<212> TYPE: DNA
<213> ORGANISM: Glycine Max

<400> SEQUENCE: 627
aaaaacaaaa acaaaaaaca aaaaaacaca c 31

<210> SEQ ID NO 628
<211> LENGTH: 28
<212> TYPE: DNA
<213> ORGANISM: Glycine Max

<400> SEQUENCE: 628
ttwtwwtttt ttttwttttt tttttttt 28

<210> SEQ ID NO 629
<211> LENGTH: 28

<212> TYPE: DNA
<213> ORGANISM: Glycine Max

<400> SEQUENCE: 629
ttytcytttt ttttyttttt tttttttt 28

<210> SEQ ID NO 630
<211> LENGTH: 25
<212> TYPE: DNA
<213> ORGANISM: Glycine Max

<400> SEQUENCE: 630
gcsggggcgg ssgggggggg sgggg 25

<210> SEQ ID NO 631
<211> LENGTH: 26
<212> TYPE: DNA
<213> ORGANISM: Glycine Max

<400> SEQUENCE: 631
cacmccccac cmmccccccc cmcccc 26

<210> SEQ ID NO 632
<211> LENGTH: 29
<212> TYPE: DNA
<213> ORGANISM: Glycine Max

<400> SEQUENCE: 632
taaataataw aaaaaatttt atwatatta 29

<210> SEQ ID NO 633
<211> LENGTH: 26
<212> TYPE: DNA
<213> ORGANISM: Glycine Max

<400> SEQUENCE: 633
cccccmcccc ccmcmccccc cccccc 26

<210> SEQ ID NO 634
<211> LENGTH: 27
<212> TYPE: DNA
<213> ORGANISM: Glycine Max

<400> SEQUENCE: 634
aaaaawaaaa aawawaaaaa aaaaaat 27

<210> SEQ ID NO 635
<211> LENGTH: 29
<212> TYPE: DNA
<213> ORGANISM: Glycine Max

<400> SEQUENCE: 635
aaawaaaaaa atwwaaaaaa aaaaataaa 29

<210> SEQ ID NO 636
<211> LENGTH: 27
<212> TYPE: DNA
<213> ORGANISM: Glycine Max

<400> SEQUENCE: 636
tttttttttt twtttttttt ttttttt 27

<210> SEQ ID NO 637

<211> LENGTH: 31
<212> TYPE: DNA
<213> ORGANISM: Glycine Max

<400> SEQUENCE: 637
gggrgggggg ggaagaaggg gggggggggg g 31

<210> SEQ ID NO 638
<211> LENGTH: 31
<212> TYPE: DNA
<213> ORGANISM: Glycine Max

<400> SEQUENCE: 638
gtgkgggggg gggggggggg gggggggggg g 31

<210> SEQ ID NO 639
<211> LENGTH: 30
<212> TYPE: DNA
<213> ORGANISM: Glycine Max

<400> SEQUENCE: 639
ctctcccccc cccccccccc cccccccccc 30

<210> SEQ ID NO 640
<211> LENGTH: 32
<212> TYPE: DNA
<213> ORGANISM: Glycine Max

<400> SEQUENCE: 640
tttttatwtt tattttttat tttttwttat tt 32

<210> SEQ ID NO 641
<211> LENGTH: 32
<212> TYPE: DNA
<213> ORGANISM: Glycine Max

<400> SEQUENCE: 641
cccmcccccc ccaaacaacc cccacccccc cc 32

<210> SEQ ID NO 642
<211> LENGTH: 31
<212> TYPE: DNA
<213> ORGANISM: Glycine Max

<400> SEQUENCE: 642
tgggttgggk tggggggttt ttgttgtttt g 31

<210> SEQ ID NO 643
<211> LENGTH: 31
<212> TYPE: DNA
<213> ORGANISM: Glycine Max

<400> SEQUENCE: 643
gggggtgggg gtggggggtg gggggkgggg g 31

<210> SEQ ID NO 644
<211> LENGTH: 28
<212> TYPE: DNA
<213> ORGANISM: Glycine Max

<400> SEQUENCE: 644
aaaaawaaaa aaaaaataaa aaaaaaaa 28

<210> SEQ ID NO 645
<211> LENGTH: 29
<212> TYPE: DNA
<213> ORGANISM: Glycine Max

<400> SEQUENCE: 645
twttttwttt twtttttttt attttttttt 29

<210> SEQ ID NO 646
<211> LENGTH: 32
<212> TYPE: DNA
<213> ORGANISM: Glycine Max

<400> SEQUENCE: 646
gcccgggcgc sgccccccgg ggggggcggg gc 32

<210> SEQ ID NO 647
<211> LENGTH: 29
<212> TYPE: DNA
<213> ORGANISM: Glycine Max

<400> SEQUENCE: 647
agggaagara gggggaaaaa gaagaaaag 29

<210> SEQ ID NO 648
<211> LENGTH: 32
<212> TYPE: DNA
<213> ORGANISM: Glycine Max

<400> SEQUENCE: 648
agggaagaag ragggggggaa aaaaaagaaa ag 32

<210> SEQ ID NO 649
<211> LENGTH: 19
<212> TYPE: DNA
<213> ORGANISM: Glycine Max

<400> SEQUENCE: 649
aaaarrrgaa aaaaaaaaa 19

<210> SEQ ID NO 650
<211> LENGTH: 19
<212> TYPE: DNA
<213> ORGANISM: Glycine Max

<400> SEQUENCE: 650
gagrgrragg gggaggggg 19

<210> SEQ ID NO 651
<211> LENGTH: 19
<212> TYPE: DNA
<213> ORGANISM: Glycine Max

<400> SEQUENCE: 651
agaaaaaaaa aaagaaaaa 19

<210> SEQ ID NO 652
<211> LENGTH: 20
<212> TYPE: DNA
<213> ORGANISM: Glycine Max

<400> SEQUENCE: 652
agaaaagaaa aaaagaaaaa 20

<210> SEQ ID NO 653
<211> LENGTH: 24
<212> TYPE: DNA
<213> ORGANISM: Glycine Max

<400> SEQUENCE: 653
tgtgtggttg ttttttttgt tttt 24

<210> SEQ ID NO 654
<211> LENGTH: 31
<212> TYPE: DNA
<213> ORGANISM: Glycine Max

<400> SEQUENCE: 654
agagaggaaa aggaaaaaga aaagaaaaaa a 31

<210> SEQ ID NO 655
<211> LENGTH: 31
<212> TYPE: DNA
<213> ORGANISM: Glycine Max

<400> SEQUENCE: 655
tctctccttt tcctttttct tttctttttt t 31

<210> SEQ ID NO 656
<211> LENGTH: 28
<212> TYPE: DNA
<213> ORGANISM: Glycine Max

<400> SEQUENCE: 656
ggaaagggga gggggagggg agrggggg 28

<210> SEQ ID NO 657
<211> LENGTH: 30
<212> TYPE: DNA
<213> ORGANISM: Glycine Max

<400> SEQUENCE: 657
agaraggaga ggaaaaagaa aagaaagaaa 30

<210> SEQ ID NO 658
<211> LENGTH: 29
<212> TYPE: DNA
<213> ORGANISM: Glycine Max

<400> SEQUENCE: 658
cttcttctyt tttttttccc ccctctcct 29

<210> SEQ ID NO 659
<211> LENGTH: 21
<212> TYPE: DNA
<213> ORGANISM: Glycine Max

<400> SEQUENCE: 659
tttcttcttt tttttttttt t 21

<210> SEQ ID NO 660
<211> LENGTH: 21
<212> TYPE: DNA
<213> ORGANISM: Glycine Max

<400> SEQUENCE: 660
tttattattt tttttttttt t 21

<210> SEQ ID NO 661
<211> LENGTH: 28
<212> TYPE: DNA
<213> ORGANISM: Glycine Max

<400> SEQUENCE: 661
ttttgttttt ggttttgttt tttttgtt 28

<210> SEQ ID NO 662
<211> LENGTH: 31
<212> TYPE: DNA
<213> ORGANISM: Glycine Max

<400> SEQUENCE: 662
tctcccctct cctttttctt ttctyttctt t 31

<210> SEQ ID NO 663
<211> LENGTH: 29
<212> TYPE: DNA
<213> ORGANISM: Glycine Max

<400> SEQUENCE: 663
ccaaacacaa cccccacccc acaccaccc 29

<210> SEQ ID NO 664
<211> LENGTH: 24
<212> TYPE: DNA
<213> ORGANISM: Glycine Max

<400> SEQUENCE: 664
ttctyttttt tttttttttt tctt 24

<210> SEQ ID NO 665
<211> LENGTH: 24
<212> TYPE: DNA
<213> ORGANISM: Glycine Max

<400> SEQUENCE: 665
aaaamaamca aaaaaaaaaa aaaa 24

<210> SEQ ID NO 666
<211> LENGTH: 32
<212> TYPE: DNA
<213> ORGANISM: Glycine Max

<400> SEQUENCE: 666
tctctccctc tcctttttct tttctyttct tt 32

<210> SEQ ID NO 667
<211> LENGTH: 29
<212> TYPE: DNA
<213> ORGANISM: Glycine Max

<400> SEQUENCE: 667
gaagaaagar aaaaaaaggg gagaagaga 29

<210> SEQ ID NO 668
<211> LENGTH: 29
<212> TYPE: DNA
<213> ORGANISM: Glycine Max

<400> SEQUENCE: 668
agggagggag rggggggga aargagaag 29

<210> SEQ ID NO 669
<211> LENGTH: 30
<212> TYPE: DNA
<213> ORGANISM: Glycine Max

<400> SEQUENCE: 669
agrraggaga ggaagaagaa aaaggagaag 30

<210> SEQ ID NO 670
<211> LENGTH: 32
<212> TYPE: DNA
<213> ORGANISM: Glycine Max

<400> SEQUENCE: 670
ctttctttct yttttttttc ccctcytctc ct 32

<210> SEQ ID NO 671
<211> LENGTH: 31
<212> TYPE: DNA
<213> ORGANISM: Glycine Max

<400> SEQUENCE: 671
atttatttat wtttttttta aaatawtata t 31

<210> SEQ ID NO 672
<211> LENGTH: 28
<212> TYPE: DNA
<213> ORGANISM: Glycine Max

<400> SEQUENCE: 672
aaawaawawa twaaaaaaaa ataaaaaa 28

<210> SEQ ID NO 673
<211> LENGTH: 29
<212> TYPE: DNA
<213> ORGANISM: Glycine Max

<400> SEQUENCE: 673
cgsgcccccc ccccgccccc ccgcgcccg 29

<210> SEQ ID NO 674
<211> LENGTH: 31
<212> TYPE: DNA
<213> ORGANISM: Glycine Max

<400> SEQUENCE: 674
awtaaaaaaa aaaataaaaa aataataaaa t 31

<210> SEQ ID NO 675
<211> LENGTH: 31
<212> TYPE: DNA
<213> ORGANISM: Glycine Max

<400> SEQUENCE: 675
tctctttttt tttttttttt tttttttttt t 31

<210> SEQ ID NO 676
<211> LENGTH: 24
<212> TYPE: DNA
<213> ORGANISM: Glycine Max

<400> SEQUENCE: 676 tttttttct tcttttttttt tttt 24

<210> SEQ ID NO 677
<211> LENGTH: 18
<212> TYPE: DNA
<213> ORGANISM: Glycine Max

<400> SEQUENCE: 677
ctccccctcc cccccyc 18

<210> SEQ ID NO 678
<211> LENGTH: 17
<212> TYPE: DNA
<213> ORGANISM: Glycine Max

<400> SEQUENCE: 678
tgttttgktt tttttkt 17

<210> SEQ ID NO 679
<211> LENGTH: 19
<212> TYPE: DNA
<213> ORGANISM: Glycine Max

<400> SEQUENCE: 679
aaraaaaaaa aaaaaaaag 19

<210> SEQ ID NO 680
<211> LENGTH: 28
<212> TYPE: DNA
<213> ORGANISM: Glycine Max

<400> SEQUENCE: 680
cttcttcttt ttttttcccc tcctctcc 28

<210> SEQ ID NO 681
<211> LENGTH: 26
<212> TYPE: DNA
<213> ORGANISM: Glycine Max

<400> SEQUENCE: 681
ctcccccccc cctccccccc cccccc 26

<210> SEQ ID NO 682
<211> LENGTH: 30
<212> TYPE: DNA
<213> ORGANISM: Glycine Max

<400> SEQUENCE: 682
cyycctcccc ccctcycccc ctcctcccct 30

<210> SEQ ID NO 683
<211> LENGTH: 31
<212> TYPE: DNA
<213> ORGANISM: Glycine Max

<400> SEQUENCE: 683
gggrgggggg ggaaggaggg gggggggggg g 31

<210> SEQ ID NO 684
<211> LENGTH: 31
<212> TYPE: DNA
<213> ORGANISM: Glycine Max

<400> SEQUENCE: 684
ccmccccccc ccccaccccc ccaccacccc a 31

<210> SEQ ID NO 685
<211> LENGTH: 31
<212> TYPE: DNA
<213> ORGANISM: Glycine Max

<400> SEQUENCE: 685
aawaaaaaaa aaaataaaaa aataataaaa t 31

<210> SEQ ID NO 686
<211> LENGTH: 30
<212> TYPE: DNA
<213> ORGANISM: Glycine Max

<400> SEQUENCE: 686
aagaaaggag raaaaggaaa agaagaaaag 30

<210> SEQ ID NO 687
<211> LENGTH: 13
<212> TYPE: DNA
<213> ORGANISM: Glycine Max

<400> SEQUENCE: 687
acaccaaaca aaa 13

<210> SEQ ID NO 688
<211> LENGTH: 16
<212> TYPE: DNA
<213> ORGANISM: Glycine Max

<400> SEQUENCE: 688
cgcgcgcccg gccgcc 16

<210> SEQ ID NO 689
<211> LENGTH: 28
<212> TYPE: DNA
<213> ORGANISM: Glycine Max

<400> SEQUENCE: 689
twtttttttt ttttattttt attatttt 28

<210> SEQ ID NO 690
<211> LENGTH: 32
<212> TYPE: DNA
<213> ORGANISM: Glycine Max

<400> SEQUENCE: 690
aawaaaatat waaaaataaa aaaaaaaaaa aa 32

<210> SEQ ID NO 691
<211> LENGTH: 32
<212> TYPE: DNA
<213> ORGANISM: Glycine Max

<400> SEQUENCE: 691 aggggggggag rggggggggga aaaggrgaga ag 32

<210> SEQ ID NO 692
<211> LENGTH: 25
<212> TYPE: DNA
<213> ORGANISM: Glycine Max

<400> SEQUENCE: 692
ccctcccycc ctccccccccc ccccc 25

<210> SEQ ID NO 693
<211> LENGTH: 22
<212> TYPE: DNA
<213> ORGANISM: Glycine Max

<400> SEQUENCE: 693
tttatttwtt attttttttt ta 22

<210> SEQ ID NO 694
<211> LENGTH: 20
<212> TYPE: DNA
<213> ORGANISM: Glycine Max

<400> SEQUENCE: 694
tattatttat tttttatttt 20

<210> SEQ ID NO 695
<211> LENGTH: 19
<212> TYPE: DNA
<213> ORGANISM: Glycine Max

<400> SEQUENCE: 695
ataawaaata aaaaaaaaa 19

<210> SEQ ID NO 696
<211> LENGTH: 27
<212> TYPE: DNA
<213> ORGANISM: Glycine Max

<400> SEQUENCE: 696
gggaaggggg aggggagggg gaagagg 27

<210> SEQ ID NO 697
<211> LENGTH: 27
<212> TYPE: DNA
<213> ORGANISM: Glycine Max

<400> SEQUENCE: 697
accccccaca ccccccaaaa cccacaa 27

<210> SEQ ID NO 698
<211> LENGTH: 26
<212> TYPE: DNA
<213> ORGANISM: Glycine Max

<400> SEQUENCE: 698
ccycccctcc cctccccccc cccccc 26

<210> SEQ ID NO 699
<211> LENGTH: 27
<212> TYPE: DNA
<213> ORGANISM: Glycine Max

<400> SEQUENCE: 699
ccccttccct tcccctcccc ctctccc 27

<210> SEQ ID NO 700
<211> LENGTH: 19
<212> TYPE: DNA

<213> ORGANISM: Glycine Max

<400> SEQUENCE: 700
tttttatwta tttttwttt 19

<210> SEQ ID NO 701
<211> LENGTH: 21
<212> TYPE: DNA
<213> ORGANISM: Glycine Max

<400> SEQUENCE: 701
aaatataaaw ttaaaaaaaa a 21

<210> SEQ ID NO 702
<211> LENGTH: 21
<212> TYPE: DNA
<213> ORGANISM: Glycine Max

<400> SEQUENCE: 702
attaaaaaaw aaaaaaaaaa a 21

<210> SEQ ID NO 703
<211> LENGTH: 21
<212> TYPE: DNA
<213> ORGANISM: Glycine Max

<400> SEQUENCE: 703
taatwtttww ttttttatwt t 21

<210> SEQ ID NO 704
<211> LENGTH: 30
<212> TYPE: DNA
<213> ORGANISM: Glycine Max

<400> SEQUENCE: 704
camaaaacmc caaaacaacc ccaaaacacc 30

<210> SEQ ID NO 705
<211> LENGTH: 29
<212> TYPE: DNA
<213> ORGANISM: Glycine Max

<400> SEQUENCE: 705
gcccccccgc cccccccggg gccsgcggc 29

<210> SEQ ID NO 706
<211> LENGTH: 30
<212> TYPE: DNA
<213> ORGANISM: Glycine Max

<400> SEQUENCE: 706
tttytttttt tttccttctt tttttttttt 30

<210> SEQ ID NO 707
<211> LENGTH: 30
<212> TYPE: DNA
<213> ORGANISM: Glycine Max

<400> SEQUENCE: 707
ccmccccacc mcccccaccc cccccccccc 30

<210> SEQ ID NO 708
<211> LENGTH: 30

<212> TYPE: DNA
<213> ORGANISM: Glycine Max

<400> SEQUENCE: 708 tccccccctcy ccccccccctt ttccyctctc 30

<210> SEQ ID NO 709
<211> LENGTH: 19
<212> TYPE: DNA
<213> ORGANISM: Glycine Max

<400> SEQUENCE: 709
tttttttgkt ttttttttt 19

<210> SEQ ID NO 710
<211> LENGTH: 18
<212> TYPE: DNA
<213> ORGANISM: Glycine Max

<400> SEQUENCE: 710
ttgggttttt tttgkttt 18

<210> SEQ ID NO 711
<211> LENGTH: 31
<212> TYPE: DNA
<213> ORGANISM: Glycine Max

<400> SEQUENCE: 711
tgtgttgttt tttttttttt tttttttttt t 31

<210> SEQ ID NO 712
<211> LENGTH: 22
<212> TYPE: DNA
<213> ORGANISM: Glycine Max

<400> SEQUENCE: 712
atttaaaaaw aaaaaaaaaa aa 22

<210> SEQ ID NO 713
<211> LENGTH: 24
<212> TYPE: DNA
<213> ORGANISM: Glycine Max

<400> SEQUENCE: 713
tawwataawt atatttttaw tttt 24

<210> SEQ ID NO 714
<211> LENGTH: 24
<212> TYPE: DNA
<213> ORGANISM: Glycine Max

<400> SEQUENCE: 714
taaaataawa atatttttaw ttta 24

<210> SEQ ID NO 715
<211> LENGTH: 14
<212> TYPE: DNA
<213> ORGANISM: Glycine Max

<400> SEQUENCE: 715 attttttat ttat 14

<210> SEQ ID NO 716

<211> LENGTH: 30
<212> TYPE: DNA
<213> ORGANISM: Glycine Max

<400> SEQUENCE: 716
gggkgggggg ggttgggggg gggggggggg 30

<210> SEQ ID NO 717
<211> LENGTH: 31
<212> TYPE: DNA
<213> ORGANISM: Glycine Max

<400> SEQUENCE: 717
ccacaacccc caaccaccac ccaamacacc a 31

<210> SEQ ID NO 718
<211> LENGTH: 28
<212> TYPE: DNA
<213> ORGANISM: Glycine Max

<400> SEQUENCE: 718
cccccccccc caccaccccc cccccccc 28

<210> SEQ ID NO 719
<211> LENGTH: 31
<212> TYPE: DNA
<213> ORGANISM: Glycine Max

<400> SEQUENCE: 719
aaaaaaaaaa aaataataaa aaaaaaaaaa a 31

<210> SEQ ID NO 720
<211> LENGTH: 31
<212> TYPE: DNA
<213> ORGANISM: Glycine Max

<400> SEQUENCE: 720
aaaaaaaaaa aaataataaa aaaaaaaaaa a 31

<210> SEQ ID NO 721
<211> LENGTH: 30
<212> TYPE: DNA
<213> ORGANISM: Glycine Max

<400> SEQUENCE: 721
cccccccccc cccaccaccc cccccccccc 30

<210> SEQ ID NO 722
<211> LENGTH: 30
<212> TYPE: DNA
<213> ORGANISM: Glycine Max

<400> SEQUENCE: 722
ttttcctttc ctttttcttt ttcyttcttt 30

<210> SEQ ID NO 723
<211> LENGTH: 22
<212> TYPE: DNA
<213> ORGANISM: Glycine Max

<400> SEQUENCE: 723
aawaaaaaaw aaaaaaaaaa aa 22

<210> SEQ ID NO 724
<211> LENGTH: 23
<212> TYPE: DNA
<213> ORGANISM: Glycine Max

<400> SEQUENCE: 724
atatatatta tataaaaata aat 23

<210> SEQ ID NO 725
<211> LENGTH: 28
<212> TYPE: DNA
<213> ORGANISM: Glycine Max

<400> SEQUENCE: 725
attttawttt tttttaaaat tttataat 28

<210> SEQ ID NO 726
<211> LENGTH: 27
<212> TYPE: DNA
<213> ORGANISM: Glycine Max

<400> SEQUENCE: 726
garaagraag gagaggggaa ragagga 27

<210> SEQ ID NO 727
<211> LENGTH: 26
<212> TYPE: DNA
<213> ORGANISM: Glycine Max

<400> SEQUENCE: 727
ctyttctytt ccctcccctt ytccct 26

<210> SEQ ID NO 728
<211> LENGTH: 27
<212> TYPE: DNA
<213> ORGANISM: Glycine Max

<400> SEQUENCE: 728
taawaaawaa ttatatttta awattta 27

<210> SEQ ID NO 729
<211> LENGTH: 29
<212> TYPE: DNA
<213> ORGANISM: Glycine Max

<400> SEQUENCE: 729
cctytttccc tttttttccc ctytctcct 29

<210> SEQ ID NO 730
<211> LENGTH: 31
<212> TYPE: DNA
<213> ORGANISM: Glycine Max

<400> SEQUENCE: 730
ttwttttttt ttaattattt tttttttttt t 31

<210> SEQ ID NO 731
<211> LENGTH: 31
<212> TYPE: DNA
<213> ORGANISM: Glycine Max

<400> SEQUENCE: 731
agrggagaaa ggggggggaa aaagagagaa g 31

<210> SEQ ID NO 732
<211> LENGTH: 31
<212> TYPE: DNA
<213> ORGANISM: Glycine Max

<400> SEQUENCE: 732 ttttttttt tttggtttt ttttttttt t 31

<210> SEQ ID NO 733
<211> LENGTH: 31
<212> TYPE: DNA
<213> ORGANISM: Glycine Max

<400> SEQUENCE: 733
ttawaatatt taaaaaaatt tttatatatt a 31

<210> SEQ ID NO 734
<211> LENGTH: 31
<212> TYPE: DNA
<213> ORGANISM: Glycine Max

<400> SEQUENCE: 734
atawaataat aaaaaaaaaa aataaaaaaa a 31

<210> SEQ ID NO 735
<211> LENGTH: 29
<212> TYPE: DNA
<213> ORGANISM: Glycine Max

<400> SEQUENCE: 735
ccacaacacc aaaaaacccc camacacca 29

<210> SEQ ID NO 736
<211> LENGTH: 31
<212> TYPE: DNA
<213> ORGANISM: Glycine Max

<400> SEQUENCE: 736
tatattattt tttttttttt tttttttttt t 31

<210> SEQ ID NO 737
<211> LENGTH: 31
<212> TYPE: DNA
<213> ORGANISM: Glycine Max

<400> SEQUENCE: 737
ggrggggggg gggggagggg gggggagggg a 31

<210> SEQ ID NO 738
<211> LENGTH: 31
<212> TYPE: DNA
<213> ORGANISM: Glycine Max

<400> SEQUENCE: 738
ttcttttttt tttttctttt tttttctttt c 31

<210> SEQ ID NO 739
<211> LENGTH: 31
<212> TYPE: DNA
<213> ORGANISM: Glycine Max

<400> SEQUENCE: 739 tcccccccctc yccttccctt ttccyctctt c 31

<210> SEQ ID NO 740
<211> LENGTH: 30
<212> TYPE: DNA
<213> ORGANISM: Glycine Max

<400> SEQUENCE: 740
gggggggggg ggkggtgggg gggggggggg 30

<210> SEQ ID NO 741
<211> LENGTH: 30
<212> TYPE: DNA
<213> ORGANISM: Glycine Max

<400> SEQUENCE: 741
tttttttttt ttttattttt tttttttttw 30

<210> SEQ ID NO 742
<211> LENGTH: 29
<212> TYPE: DNA
<213> ORGANISM: Glycine Max

<400> SEQUENCE: 742
taattattat tttttttttt tatttttt 29

<210> SEQ ID NO 743
<211> LENGTH: 31
<212> TYPE: DNA
<213> ORGANISM: Glycine Max

<400> SEQUENCE: 743
ctctcctcct cccccccccc cctccccccc c 31

<210> SEQ ID NO 744
<211> LENGTH: 30
<212> TYPE: DNA
<213> ORGANISM: Glycine Max

<400> SEQUENCE: 744
agaraaaaaa aaaaaaaaaa araaaaaaaa 30

<210> SEQ ID NO 745
<211> LENGTH: 32
<212> TYPE: DNA
<213> ORGANISM: Glycine Max

<400> SEQUENCE: 745
ctcycctcct cccccccccc ccctcccccc cc 32

<210> SEQ ID NO 746
<211> LENGTH: 31
<212> TYPE: DNA
<213> ORGANISM: Glycine Max

<400> SEQUENCE: 746
agaraagaag aaaaaaaaaa aaagaaaaaa a 31

<210> SEQ ID NO 747
<211> LENGTH: 29
<212> TYPE: DNA
<213> ORGANISM: Glycine Max

<400> SEQUENCE: 747
ggggtggggt tgggggtggg gggggtggg 29

<210> SEQ ID NO 748
<211> LENGTH: 28
<212> TYPE: DNA
<213> ORGANISM: Glycine Max

<400> SEQUENCE: 748
agarggagag gaaaaagaaa agaagaaa 28

<210> SEQ ID NO 749
<211> LENGTH: 28
<212> TYPE: DNA
<213> ORGANISM: Glycine Max

<400> SEQUENCE: 749
ctctaactca acccccaccc ctmccccc 28

<210> SEQ ID NO 750
<211> LENGTH: 31
<212> TYPE: DNA
<213> ORGANISM: Glycine Max

<400> SEQUENCE: 750
ttcttttcty ttttcctttt tttttctttt c 31

<210> SEQ ID NO 751
<211> LENGTH: 31
<212> TYPE: DNA
<213> ORGANISM: Glycine Max

<400> SEQUENCE: 751
tttycctttt tccttttctt tttcyttctt t 31

<210> SEQ ID NO 752
<211> LENGTH: 29
<212> TYPE: DNA
<213> ORGANISM: Glycine Max

<400> SEQUENCE: 752
gagagggagg gggggggggg ggggggggg 29

<210> SEQ ID NO 753
<211> LENGTH: 30
<212> TYPE: DNA
<213> ORGANISM: Glycine Max

<400> SEQUENCE: 753
tctyttcttt tttttttttt tttttttttt 30

<210> SEQ ID NO 754
<211> LENGTH: 31
<212> TYPE: DNA
<213> ORGANISM: Glycine Max

<400> SEQUENCE: 754
gtgkgttgtg ggggggtggg gggggggggg g 31

<210> SEQ ID NO 755
<211> LENGTH: 28
<212> TYPE: DNA
<213> ORGANISM: Glycine Max

<400> SEQUENCE: 755
gggggggggg gaagaggggg gggggggg 28

<210> SEQ ID NO 756
<211> LENGTH: 25
<212> TYPE: DNA
<213> ORGANISM: Glycine Max

<400> SEQUENCE: 756
aaaattaaaa taaataaaat ataaa 25

<210> SEQ ID NO 757
<211> LENGTH: 29
<212> TYPE: DNA
<213> ORGANISM: Glycine Max

<400> SEQUENCE: 757
tcccccctcy cccccccttt tccyctctt 29

<210> SEQ ID NO 758
<211> LENGTH: 20
<212> TYPE: DNA
<213> ORGANISM: Glycine Max

<400> SEQUENCE: 758
atataaatta aaaaataaaa 20

<210> SEQ ID NO 759
<211> LENGTH: 20
<212> TYPE: DNA
<213> ORGANISM: Glycine Max

<400> SEQUENCE: 759
atataaatta aaaaataaaa 20

<210> SEQ ID NO 760
<211> LENGTH: 14
<212> TYPE: DNA
<213> ORGANISM: Glycine Max

<400> SEQUENCE: 760
aaawtaaaat aaaa 14

<210> SEQ ID NO 761
<211> LENGTH: 13
<212> TYPE: DNA
<213> ORGANISM: Glycine Max

<400> SEQUENCE: 761
aaawaaaata aaa 13

<210> SEQ ID NO 762
<211> LENGTH: 17
<212> TYPE: DNA
<213> ORGANISM: Glycine Max

<400> SEQUENCE: 762
tctttccctt tcctttt 17

<210> SEQ ID NO 763
<211> LENGTH: 19
<212> TYPE: DNA
<213> ORGANISM: Glycine Max

<400> SEQUENCE: 763
ctttcctttc cccttcccc 19

<210> SEQ ID NO 764
<211> LENGTH: 16
<212> TYPE: DNA
<213> ORGANISM: Glycine Max

<400> SEQUENCE: 764
tggggttttt tgggtg 16

<210> SEQ ID NO 765
<211> LENGTH: 24
<212> TYPE: DNA
<213> ORGANISM: Glycine Max

<400> SEQUENCE: 765
tccccccttc ccttttctct cttc 24

<210> SEQ ID NO 766
<211> LENGTH: 26
<212> TYPE: DNA
<213> ORGANISM: Glycine Max

<400> SEQUENCE: 766
gagaggaagg agaggggggg gggggg 26

<210> SEQ ID NO 767
<211> LENGTH: 29
<212> TYPE: DNA
<213> ORGANISM: Glycine Max

<400> SEQUENCE: 767
ccyccccccc ccctcccccc ccctcccct 29

<210> SEQ ID NO 768
<211> LENGTH: 28
<212> TYPE: DNA
<213> ORGANISM: Glycine Max

<400> SEQUENCE: 768
gaaaaaagra aaaaagggga aragagga 28

<210> SEQ ID NO 769
<211> LENGTH: 27
<212> TYPE: DNA
<213> ORGANISM: Glycine Max

<400> SEQUENCE: 769
ggggaaggga agaggggggg aragagg 27

<210> SEQ ID NO 770
<211> LENGTH: 11
<212> TYPE: DNA
<213> ORGANISM: Glycine Max

<400> SEQUENCE: 770
ggaagggggg g 11

<210> SEQ ID NO 771
<211> LENGTH: 16
<212> TYPE: DNA
<213> ORGANISM: Glycine Max

<400> SEQUENCE: 771
gaaggggggg gggggg 16

<210> SEQ ID NO 772
<211> LENGTH: 16
<212> TYPE: DNA
<213> ORGANISM: Glycine Max

<400> SEQUENCE: 772
tggttttttt tttttt 16

<210> SEQ ID NO 773
<211> LENGTH: 16
<212> TYPE: DNA
<213> ORGANISM: Glycine Max

<400> SEQUENCE: 773
attaaaaaaa aaaaaa 16

<210> SEQ ID NO 774
<211> LENGTH: 17
<212> TYPE: DNA
<213> ORGANISM: Glycine Max

<400> SEQUENCE: 774
ccycccctcc ccccccc 17

<210> SEQ ID NO 775
<211> LENGTH: 28
<212> TYPE: DNA
<213> ORGANISM: Glycine Max

<400> SEQUENCE: 775
cytctctccc ttcttccccc tccccccc 28

<210> SEQ ID NO 776
<211> LENGTH: 28
<212> TYPE: DNA
<213> ORGANISM: Glycine Max

<400> SEQUENCE: 776
caaaacacaa aaaaaacccc aamaacca 28

<210> SEQ ID NO 777
<211> LENGTH: 28
<212> TYPE: DNA
<213> ORGANISM: Glycine Max

<400> SEQUENCE: 777
tccccctctc cccccctttt ccyccttc 28

<210> SEQ ID NO 778
<211> LENGTH: 28
<212> TYPE: DNA
<213> ORGANISM: Glycine Max

<400> SEQUENCE: 778
agggggagag ggggggaaaa ggrggaag 28

<210> SEQ ID NO 779
<211> LENGTH: 28
<212> TYPE: DNA

<213> ORGANISM: Glycine Max

<400> SEQUENCE: 779
cttctcctcc cccccccccc cccccccc 28

<210> SEQ ID NO 780
<211> LENGTH: 28
<212> TYPE: DNA
<213> ORGANISM: Glycine Max

<400> SEQUENCE: 780
ccacaccccc aacaccccccc cmacacca 28

<210> SEQ ID NO 781
<211> LENGTH: 21
<212> TYPE: DNA
<213> ORGANISM: Glycine Max

<400> SEQUENCE: 781
cttttctytt tttcccctcc c 21

<210> SEQ ID NO 782
<211> LENGTH: 22
<212> TYPE: DNA
<213> ORGANISM: Glycine Max

<400> SEQUENCE: 782
aawtaaaata waaaaawtaa at 22

<210> SEQ ID NO 783
<211> LENGTH: 27
<212> TYPE: DNA
<213> ORGANISM: Glycine Max

<400> SEQUENCE: 783
agagagagaa aggaggaaaa gaaaaaa 27

<210> SEQ ID NO 784
<211> LENGTH: 31
<212> TYPE: DNA
<213> ORGANISM: Glycine Max

<400> SEQUENCE: 784
agagaggaga aaaaaaaaaa aaaaaaaaaa a 31

<210> SEQ ID NO 785
<211> LENGTH: 31
<212> TYPE: DNA
<213> ORGANISM: Glycine Max

<400> SEQUENCE: 785
tctctcctct tttttttttt tttttttttt t 31

<210> SEQ ID NO 786
<211> LENGTH: 32
<212> TYPE: DNA
<213> ORGANISM: Glycine Max

<400> SEQUENCE: 786
ccacaacacc caaccaccac ccccamacac ca 32

<210> SEQ ID NO 787
<211> LENGTH: 18

<212> TYPE: DNA
<213> ORGANISM: Glycine Max

<400> SEQUENCE: 787 tcctttttttt tttttttt 18

<210> SEQ ID NO 788
<211> LENGTH: 16
<212> TYPE: DNA
<213> ORGANISM: Glycine Max

<400> SEQUENCE: 788
cttccccccc cccccc 16

<210> SEQ ID NO 789
<211> LENGTH: 16
<212> TYPE: DNA
<213> ORGANISM: Glycine Max

<400> SEQUENCE: 789
aaaaataaaa aaataa 16

<210> SEQ ID NO 790
<211> LENGTH: 17
<212> TYPE: DNA
<213> ORGANISM: Glycine Max

<400> SEQUENCE: 790
tttttatttt ttttatt 17

<210> SEQ ID NO 791
<211> LENGTH: 15
<212> TYPE: DNA
<213> ORGANISM: Glycine Max

<400> SEQUENCE: 791
ggggagaggg agggg 15

<210> SEQ ID NO 792
<211> LENGTH: 21
<212> TYPE: DNA
<213> ORGANISM: Glycine Max

<400> SEQUENCE: 792
ttgttttttt gttttttttt t 21

<210> SEQ ID NO 793
<211> LENGTH: 26
<212> TYPE: DNA
<213> ORGANISM: Glycine Max

<400> SEQUENCE: 793
gaggaggggg aaggaggggg gggggg 26

<210> SEQ ID NO 794
<211> LENGTH: 30
<212> TYPE: DNA
<213> ORGANISM: Glycine Max

<400> SEQUENCE: 794
cctcttcccc cttcctcctc cccctcctct 30

<210> SEQ ID NO 795

<211> LENGTH: 29
<212> TYPE: DNA
<213> ORGANISM: Glycine Max

<400> SEQUENCE: 795
acacaacaaa aaccaaaaaa aaaaaaaaa 29

<210> SEQ ID NO 796
<211> LENGTH: 29
<212> TYPE: DNA
<213> ORGANISM: Glycine Max

<400> SEQUENCE: 796 ccycccccc cccctccccc cccctccct 29

<210> SEQ ID NO 797
<211> LENGTH: 31
<212> TYPE: DNA
<213> ORGANISM: Glycine Max

<400> SEQUENCE: 797
aaaaaaataa aaaaataaaa aaaaaaaaaa a 31

<210> SEQ ID NO 798
<211> LENGTH: 32
<212> TYPE: DNA
<213> ORGANISM: Glycine Max

<400> SEQUENCE: 798
tcyycccctc tccttcctct ttttctctct tc 32

<210> SEQ ID NO 799
<211> LENGTH: 30
<212> TYPE: DNA
<213> ORGANISM: Glycine Max

<400> SEQUENCE: 799
ggggggaggr gggggggggg gggggggggg 30

<210> SEQ ID NO 800
<211> LENGTH: 32
<212> TYPE: DNA
<213> ORGANISM: Glycine Max

<400> SEQUENCE: 800
attwttttat attaattata aaaatwtata at 32

<210> SEQ ID NO 801
<211> LENGTH: 29
<212> TYPE: DNA
<213> ORGANISM: Glycine Max

<400> SEQUENCE: 801
tatwaattat atttaatttt tatttattt 29

<210> SEQ ID NO 802
<211> LENGTH: 31
<212> TYPE: DNA
<213> ORGANISM: Glycine Max

<400> SEQUENCE: 802
aaaaawaaaa twaaaaawaa aaawwaaaaa a 31

<210> SEQ ID NO 803
<211> LENGTH: 28
<212> TYPE: DNA
<213> ORGANISM: Glycine Max

<400> SEQUENCE: 803
gtgtggtgtg gggggggggg gggggggg 28

<210> SEQ ID NO 804
<211> LENGTH: 26
<212> TYPE: DNA
<213> ORGANISM: Glycine Max

<400> SEQUENCE: 804
tttttytttt tttttttttt tytytt 26

<210> SEQ ID NO 805
<211> LENGTH: 22
<212> TYPE: DNA
<213> ORGANISM: Glycine Max

<400> SEQUENCE: 805
gggggggccg gggggggggg gg 22

<210> SEQ ID NO 806
<211> LENGTH: 21
<212> TYPE: DNA
<213> ORGANISM: Glycine Max

<400> SEQUENCE: 806
tttttttctt tttttttttt t 21

<210> SEQ ID NO 807
<211> LENGTH: 14
<212> TYPE: DNA
<213> ORGANISM: Glycine Max

<400> SEQUENCE: 807
aaaaaaataa aaat 14

<210> SEQ ID NO 808
<211> LENGTH: 13
<212> TYPE: DNA
<213> ORGANISM: Glycine Max

<400> SEQUENCE: 808
ttttttattt tta 13

<210> SEQ ID NO 809
<211> LENGTH: 29
<212> TYPE: DNA
<213> ORGANISM: Glycine Max

<400> SEQUENCE: 809
ttatatattt tttatttttt atttttttt 29

<210> SEQ ID NO 810
<211> LENGTH: 21
<212> TYPE: DNA
<213> ORGANISM: Glycine Max

<400> SEQUENCE: 810
taaaatawaa ttattttata t 21

<210> SEQ ID NO 811
<211> LENGTH: 29
<212> TYPE: DNA
<213> ORGANISM: Glycine Max

<400> SEQUENCE: 811
accmcccacc ccaacacaaa accmcacaa 29

<210> SEQ ID NO 812
<211> LENGTH: 29
<212> TYPE: DNA
<213> ORGANISM: Glycine Max

<400> SEQUENCE: 812
ttgttttttt ttttgttttt ttttgtttt 29

<210> SEQ ID NO 813
<211> LENGTH: 29
<212> TYPE: DNA
<213> ORGANISM: Glycine Max

<400> SEQUENCE: 813
agaraaaaga aaaaaaaaaa gaaaaaaaa 29

<210> SEQ ID NO 814
<211> LENGTH: 31
<212> TYPE: DNA
<213> ORGANISM: Glycine Max

<400> SEQUENCE: 814
cctccccccc ccccctcccc ccccctcccc t 31

<210> SEQ ID NO 815
<211> LENGTH: 27
<212> TYPE: DNA
<213> ORGANISM: Glycine Max

<400> SEQUENCE: 815
ggcggggggg ggggcggggg gcggggc 27

<210> SEQ ID NO 816
<211> LENGTH: 24
<212> TYPE: DNA
<213> ORGANISM: Glycine Max

<400> SEQUENCE: 816
aaaaataaaa aaaaaaaata aawa 24

<210> SEQ ID NO 817
<211> LENGTH: 24
<212> TYPE: DNA
<213> ORGANISM: Glycine Max

<400> SEQUENCE: 817
tttttatttt ttttttttat ttwt 24

<210> SEQ ID NO 818
<211> LENGTH: 24
<212> TYPE: DNA
<213> ORGANISM: Glycine Max

<400> SEQUENCE: 818
aaaaataaaa aaaaaaaata aawa 24

<210> SEQ ID NO 819
<211> LENGTH: 30
<212> TYPE: DNA
<213> ORGANISM: Glycine Max

<400> SEQUENCE: 819
tggkgggtgk ggttggtgtt ttgggtgttg 30

<210> SEQ ID NO 820
<211> LENGTH: 28
<212> TYPE: DNA
<213> ORGANISM: Glycine Max

<400> SEQUENCE: 820
ccccaacccc aaccccaccc ccccaccc 28

<210> SEQ ID NO 821
<211> LENGTH: 27
<212> TYPE: DNA
<213> ORGANISM: Glycine Max

<400> SEQUENCE: 821
gaaraaagar aaggaagggg aagagga 27

<210> SEQ ID NO 822
<211> LENGTH: 30
<212> TYPE: DNA
<213> ORGANISM: Glycine Max

<400> SEQUENCE: 822
gagagggggg gggggggggg gggggggggg 30

<210> SEQ ID NO 823
<211> LENGTH: 23
<212> TYPE: DNA
<213> ORGANISM: Glycine Max

<400> SEQUENCE: 823
tttttttttt ttcttttttt ttt 23

<210> SEQ ID NO 824
<211> LENGTH: 28
<212> TYPE: DNA
<213> ORGANISM: Glycine Max

<400> SEQUENCE: 824
aatatttaat ttatataaaa ttwtatat 28

<210> SEQ ID NO 825
<211> LENGTH: 30
<212> TYPE: DNA
<213> ORGANISM: Glycine Max

<400> SEQUENCE: 825
tttttctctt ttttcttttt tctttttttt 30

<210> SEQ ID NO 826
<211> LENGTH: 30
<212> TYPE: DNA
<213> ORGANISM: Glycine Max

<400> SEQUENCE: 826
ggggccgggc cgggggcggg ggcsggcggg 30

<210> SEQ ID NO 827
<211> LENGTH: 27
<212> TYPE: DNA
<213> ORGANISM: Glycine Max

<400> SEQUENCE: 827
aaaaccmaaa accaaaaaca acaaaac 27

<210> SEQ ID NO 828
<211> LENGTH: 27
<212> TYPE: DNA
<213> ORGANISM: Glycine Max

<400> SEQUENCE: 828
ttttaawttt taatttttat tatttta 27

<210> SEQ ID NO 829
<211> LENGTH: 28
<212> TYPE: DNA
<213> ORGANISM: Glycine Max

<400> SEQUENCE: 829
ttctttctyt tttcttttt ctcttttc 28

<210> SEQ ID NO 830
<211> LENGTH: 24
<212> TYPE: DNA
<213> ORGANISM: Glycine Max

<400> SEQUENCE: 830
aaaawaawaa aaaaaaaata aaaa 24

<210> SEQ ID NO 831
<211> LENGTH: 20
<212> TYPE: DNA
<213> ORGANISM: Glycine Max

<400> SEQUENCE: 831
tttttttttt attttttatw 20

<210> SEQ ID NO 832
<211> LENGTH: 23
<212> TYPE: DNA
<213> ORGANISM: Glycine Max

<400> SEQUENCE: 832
ttgttttttt ggtttttktt ttt 23

<210> SEQ ID NO 833
<211> LENGTH: 24
<212> TYPE: DNA
<213> ORGANISM: Glycine Max

<400> SEQUENCE: 833
tttttttttt ttttttktt kttt 24

<210> SEQ ID NO 834
<211> LENGTH: 24
<212> TYPE: DNA
<213> ORGANISM: Glycine Max

<400> SEQUENCE: 834 gggggtkgg gggggggggg kggg 24

<210> SEQ ID NO 835
<211> LENGTH: 22
<212> TYPE: DNA
<213> ORGANISM: Glycine Max

<400> SEQUENCE: 835
ctcccccccc ccccctcccc ct 22

<210> SEQ ID NO 836
<211> LENGTH: 20
<212> TYPE: DNA
<213> ORGANISM: Glycine Max

<400> SEQUENCE: 836
tatttttttt ttttttttat 20

<210> SEQ ID NO 837
<211> LENGTH: 24
<212> TYPE: DNA
<213> ORGANISM: Glycine Max

<400> SEQUENCE: 837
cccccccccc acccccaaca ccca 24

<210> SEQ ID NO 838
<211> LENGTH: 30
<212> TYPE: DNA
<213> ORGANISM: Glycine Max

<400> SEQUENCE: 838
cctccctctc ccccttcccc cttcctcctt 30

<210> SEQ ID NO 839
<211> LENGTH: 29
<212> TYPE: DNA
<213> ORGANISM: Glycine Max

<400> SEQUENCE: 839
agaaaagaar aaagaaaaaa ggaaaaagg 29

<210> SEQ ID NO 840
<211> LENGTH: 27
<212> TYPE: DNA
<213> ORGANISM: Glycine Max

<400> SEQUENCE: 840
ttgttttttt tttgtttttt ttgtttg 27

<210> SEQ ID NO 841
<211> LENGTH: 28
<212> TYPE: DNA
<213> ORGANISM: Glycine Max

<400> SEQUENCE: 841
ttwttttttt ttttattttt tttttttt 28

<210> SEQ ID NO 842
<211> LENGTH: 24
<212> TYPE: DNA
<213> ORGANISM: Glycine Max

<400> SEQUENCE: 842
ggagggggrg gagggggagg ggaa 24

<210> SEQ ID NO 843
<211> LENGTH: 25
<212> TYPE: DNA
<213> ORGANISM: Glycine Max

<400> SEQUENCE: 843
cccccccccc ctccccccctc ccctt 25

<210> SEQ ID NO 844
<211> LENGTH: 26
<212> TYPE: DNA
<213> ORGANISM: Glycine Max

<400> SEQUENCE: 844
gggggagggg ggaggggggg ggggaa 26

<210> SEQ ID NO 845
<211> LENGTH: 25
<212> TYPE: DNA
<213> ORGANISM: Glycine Max

<400> SEQUENCE: 845
agaaaaaaaa aaagaaaaaa aaaaa 25

<210> SEQ ID NO 846
<211> LENGTH: 30
<212> TYPE: DNA
<213> ORGANISM: Glycine Max

<400> SEQUENCE: 846
aaaaagaaga aaaaagaaaa aaaaaaaaaa 30

<210> SEQ ID NO 847
<211> LENGTH: 29
<212> TYPE: DNA
<213> ORGANISM: Glycine Max

<400> SEQUENCE: 847
tttttcttyt tttcttttttt cttctttcc 29

<210> SEQ ID NO 848
<211> LENGTH: 30
<212> TYPE: DNA
<213> ORGANISM: Glycine Max

<400> SEQUENCE: 848
ttttttctty ttttcttttt tcttctttcc 30

<210> SEQ ID NO 849
<211> LENGTH: 28
<212> TYPE: DNA
<213> ORGANISM: Glycine Max

<400> SEQUENCE: 849
gggggaggag gggaggggga ggagggaa 28

<210> SEQ ID NO 850
<211> LENGTH: 27
<212> TYPE: DNA
<213> ORGANISM: Glycine Max

<400> SEQUENCE: 850
aaaattaaat taaaaaaaat taataaa 27

<210> SEQ ID NO 851
<211> LENGTH: 27
<212> TYPE: DNA
<213> ORGANISM: Glycine Max

<400> SEQUENCE: 851
ggagggagrg gggaggggag gagggaa 27

<210> SEQ ID NO 852
<211> LENGTH: 27
<212> TYPE: DNA
<213> ORGANISM: Glycine Max

<400> SEQUENCE: 852
ttcttttttt tttctttttc ttcttcc 27

<210> SEQ ID NO 853
<211> LENGTH: 25
<212> TYPE: DNA
<213> ORGANISM: Glycine Max

<400> SEQUENCE: 853
ttttttttyt tttttttct ttttc 25

<210> SEQ ID NO 854
<211> LENGTH: 25
<212> TYPE: DNA
<213> ORGANISM: Glycine Max

<400> SEQUENCE: 854 gggggggrg gggggggag gggga 25

<210> SEQ ID NO 855
<211> LENGTH: 25
<212> TYPE: DNA
<213> ORGANISM: Glycine Max

<400> SEQUENCE: 855
ccccccccyc cccccccctc cccct 25

<210> SEQ ID NO 856
<211> LENGTH: 26
<212> TYPE: DNA
<213> ORGANISM: Glycine Max

<400> SEQUENCE: 856 ggagggggr gggggggag gaggga 26

<210> SEQ ID NO 857
<211> LENGTH: 27
<212> TYPE: DNA
<213> ORGANISM: Glycine Max

<400> SEQUENCE: 857
acaaaaaaaa aaacaaaaaa caaaaac 27

<210> SEQ ID NO 858
<211> LENGTH: 27
<212> TYPE: DNA

<213> ORGANISM: Glycine Max

<400> SEQUENCE: 858 tattttttttt tttatttttt attttta 27

<210> SEQ ID NO 859
<211> LENGTH: 28
<212> TYPE: DNA
<213> ORGANISM: Glycine Max

<400> SEQUENCE: 859
cctccccccc cccctccccc ctcccccct 28

<210> SEQ ID NO 860
<211> LENGTH: 26
<212> TYPE: DNA
<213> ORGANISM: Glycine Max

<400> SEQUENCE: 860
aaaaaaaaaa aaagaaaaag aaaaag 26

<210> SEQ ID NO 861
<211> LENGTH: 26
<212> TYPE: DNA
<213> ORGANISM: Glycine Max

<400> SEQUENCE: 861
cccccccccc ccctccccct cccccct 26

<210> SEQ ID NO 862
<211> LENGTH: 27
<212> TYPE: DNA
<213> ORGANISM: Glycine Max

<400> SEQUENCE: 862
ttattttata ttttattttt atattaa 27

<210> SEQ ID NO 863
<211> LENGTH: 25
<212> TYPE: DNA
<213> ORGANISM: Glycine Max

<400> SEQUENCE: 863
aaaaawaaaw aaaaaaaaaa aaaaa 25

<210> SEQ ID NO 864
<211> LENGTH: 23
<212> TYPE: DNA
<213> ORGANISM: Glycine Max

<400> SEQUENCE: 864
aaaamaaaaa aaaaaaamaa aaa 23

<210> SEQ ID NO 865
<211> LENGTH: 27
<212> TYPE: DNA
<213> ORGANISM: Glycine Max

<400> SEQUENCE: 865
tttttatttt tttttttttt tttattt 27

<210> SEQ ID NO 866
<211> LENGTH: 30

<212> TYPE: DNA
<213> ORGANISM: Glycine Max

<400> SEQUENCE: 866
ctccccccyc ccctcccccc ttcctccctt 30

<210> SEQ ID NO 867
<211> LENGTH: 31
<212> TYPE: DNA
<213> ORGANISM: Glycine Max

<400> SEQUENCE: 867 ccgcccccs ccccgccccc cggccgcccg g 31

<210> SEQ ID NO 868
<211> LENGTH: 16
<212> TYPE: DNA
<213> ORGANISM: Glycine Max

<400> SEQUENCE: 868
ttgttggttg tttttt 16

<210> SEQ ID NO 869
<211> LENGTH: 23
<212> TYPE: DNA
<213> ORGANISM: Glycine Max

<400> SEQUENCE: 869
cccaaaacam aaaaacccmc aca 23

<210> SEQ ID NO 870
<211> LENGTH: 25
<212> TYPE: DNA
<213> ORGANISM: Glycine Max

<400> SEQUENCE: 870
aaaaaaaraa aaaaaaaaga aaaag 25

<210> SEQ ID NO 871
<211> LENGTH: 25
<212> TYPE: DNA
<213> ORGANISM: Glycine Max

<400> SEQUENCE: 871 ccccccycc ccccccctc cccct 25

<210> SEQ ID NO 872
<211> LENGTH: 26
<212> TYPE: DNA
<213> ORGANISM: Glycine Max

<400> SEQUENCE: 872 tttttattt ttttattttt ttttta 26

<210> SEQ ID NO 873
<211> LENGTH: 28
<212> TYPE: DNA
<213> ORGANISM: Glycine Max

<400> SEQUENCE: 873
ttwtttttat tttttttttt awttattt 28

<210> SEQ ID NO 874

<211> LENGTH: 28
<212> TYPE: DNA
<213> ORGANISM: Glycine Max

<400> SEQUENCE: 874
ttatttatta ttttaatttt taattttt 28

<210> SEQ ID NO 875
<211> LENGTH: 29
<212> TYPE: DNA
<213> ORGANISM: Glycine Max

<400> SEQUENCE: 875
ccaccccaca cccaaccccc aaccaccca 29

<210> SEQ ID NO 876
<211> LENGTH: 30
<212> TYPE: DNA
<213> ORGANISM: Glycine Max

<400> SEQUENCE: 876
gggggggggg gggggggggg aagggggggag 30

<210> SEQ ID NO 877
<211> LENGTH: 32
<212> TYPE: DNA
<213> ORGANISM: Glycine Max

<400> SEQUENCE: 877
ggcgggccgc sggggccggg ggccggcggg cc 32

<210> SEQ ID NO 878
<211> LENGTH: 27
<212> TYPE: DNA
<213> ORGANISM: Glycine Max

<400> SEQUENCE: 878
aawaaaataa aaaaaaawaa taawaaa 27

<210> SEQ ID NO 879
<211> LENGTH: 26
<212> TYPE: DNA
<213> ORGANISM: Glycine Max

<400> SEQUENCE: 879
ccmccccacc cccccccccc ccmccc 26

<210> SEQ ID NO 880
<211> LENGTH: 30
<212> TYPE: DNA
<213> ORGANISM: Glycine Max

<400> SEQUENCE: 880
ttattttatt wtttaatttt taatatttaa 30

<210> SEQ ID NO 881
<211> LENGTH: 32
<212> TYPE: DNA
<213> ORGANISM: Glycine Max

<400> SEQUENCE: 881 ccccccctcct cccccccccc cccccccccc cc 32

<210> SEQ ID NO 882
<211> LENGTH: 32
<212> TYPE: DNA
<213> ORGANISM: Glycine Max

<400> SEQUENCE: 882
ggtgggttgt gggggttggg ggttggtggg tt 32

<210> SEQ ID NO 883
<211> LENGTH: 32
<212> TYPE: DNA
<213> ORGANISM: Glycine Max

<400> SEQUENCE: 883
aataaaataa aaaaattaaa aattaataaa tt 32

<210> SEQ ID NO 884
<211> LENGTH: 32
<212> TYPE: DNA
<213> ORGANISM: Glycine Max

<400> SEQUENCE: 884
ttcttttctt yttttctttt ttccttcttt cc 32

<210> SEQ ID NO 885
<211> LENGTH: 32
<212> TYPE: DNA
<213> ORGANISM: Glycine Max

<400> SEQUENCE: 885
ttcttttctt yttttccttt ttccttcttt cc 32

<210> SEQ ID NO 886
<211> LENGTH: 31
<212> TYPE: DNA
<213> ORGANISM: Glycine Max

<400> SEQUENCE: 886
aagaaaagaa raaaagaaaa aggaaraaag g 31

<210> SEQ ID NO 887
<211> LENGTH: 31
<212> TYPE: DNA
<213> ORGANISM: Glycine Max

<400> SEQUENCE: 887 tttttatat ttttttttt ttttttttt t 31

<210> SEQ ID NO 888
<211> LENGTH: 32
<212> TYPE: DNA
<213> ORGANISM: Glycine Max

<400> SEQUENCE: 888
ggggggagga gggggggggg gggggggggg gg 32

<210> SEQ ID NO 889
<211> LENGTH: 30
<212> TYPE: DNA
<213> ORGANISM: Glycine Max

<400> SEQUENCE: 889
ggagggaagr ggggaagggg gaaggaggga 30

<210> SEQ ID NO 890
<211> LENGTH: 29
<212> TYPE: DNA
<213> ORGANISM: Glycine Max

<400> SEQUENCE: 890
ttctttccty ttttcttttc cttctttcc 29

<210> SEQ ID NO 891
<211> LENGTH: 31
<212> TYPE: DNA
<213> ORGANISM: Glycine Max

<400> SEQUENCE: 891
ggagggaaga rggggaaggg ggaaggagga a 31

<210> SEQ ID NO 892
<211> LENGTH: 26
<212> TYPE: DNA
<213> ORGANISM: Glycine Max

<400> SEQUENCE: 892
ttttttgttt tttttttttt ttttgg 26

<210> SEQ ID NO 893
<211> LENGTH: 23
<212> TYPE: DNA
<213> ORGANISM: Glycine Max

<400> SEQUENCE: 893
gggggggggg gkgggggggg gtt 23

<210> SEQ ID NO 894
<211> LENGTH: 31
<212> TYPE: DNA
<213> ORGANISM: Glycine Max

<400> SEQUENCE: 894
cctcccttct yccccttccc cttcctccct t 31

<210> SEQ ID NO 895
<211> LENGTH: 31
<212> TYPE: DNA
<213> ORGANISM: Glycine Max

<400> SEQUENCE: 895
ttttcccttt ccccttcctt tttcyttctt t 31

<210> SEQ ID NO 896
<211> LENGTH: 31
<212> TYPE: DNA
<213> ORGANISM: Glycine Max

<400> SEQUENCE: 896
ggggaaaggg aaaagaaagg gggarggagg g 31

<210> SEQ ID NO 897
<211> LENGTH: 18
<212> TYPE: DNA
<213> ORGANISM: Glycine Max

<400> SEQUENCE: 897
ttwatwtatt taatttat 18

<210> SEQ ID NO 898
<211> LENGTH: 23
<212> TYPE: DNA
<213> ORGANISM: Glycine Max

<400> SEQUENCE: 898
tttyctttcc ttctttttyt ttt 23

<210> SEQ ID NO 899
<211> LENGTH: 24
<212> TYPE: DNA
<213> ORGANISM: Glycine Max

<400> SEQUENCE: 899
aaawtaaatt ataaaaatwa aaaa 24

<210> SEQ ID NO 900
<211> LENGTH: 24
<212> TYPE: DNA
<213> ORGANISM: Glycine Max

<400> SEQUENCE: 900
tttwatttaa tatttttawt tttt 24

<210> SEQ ID NO 901
<211> LENGTH: 22
<212> TYPE: DNA
<213> ORGANISM: Glycine Max

<400> SEQUENCE: 901
ccccttcccc tccccccccc cc 22

<210> SEQ ID NO 902
<211> LENGTH: 25
<212> TYPE: DNA
<213> ORGANISM: Glycine Max

<400> SEQUENCE: 902
cccctcccct tcttcccccc ccccc 25

<210> SEQ ID NO 903
<211> LENGTH: 31
<212> TYPE: DNA
<213> ORGANISM: Glycine Max

<400> SEQUENCE: 903
aaarggaaaa ggggaaggaa aaagraagaa a 31

<210> SEQ ID NO 904
<211> LENGTH: 29
<212> TYPE: DNA
<213> ORGANISM: Glycine Max

<400> SEQUENCE: 904
aaaatttata ttttttaaaa atwaataaa 29

<210> SEQ ID NO 905
<211> LENGTH: 29
<212> TYPE: DNA
<213> ORGANISM: Glycine Max

<400> SEQUENCE: 905
aaagggagag gggagggaaa aagragaaa 29

<210> SEQ ID NO 906
<211> LENGTH: 31
<212> TYPE: DNA
<213> ORGANISM: Glycine Max

<400> SEQUENCE: 906
cccccctcct cccccctccc cccccccccc c 31

<210> SEQ ID NO 907
<211> LENGTH: 28
<212> TYPE: DNA
<213> ORGANISM: Glycine Max

<400> SEQUENCE: 907
aaaaagagaa aaaaaaaaaa aaaaaaaa 28

<210> SEQ ID NO 908
<211> LENGTH: 26
<212> TYPE: DNA
<213> ORGANISM: Glycine Max

<400> SEQUENCE: 908
cccttccttt tctttccccy cctccc 26

<210> SEQ ID NO 909
<211> LENGTH: 29
<212> TYPE: DNA
<213> ORGANISM: Glycine Max

<400> SEQUENCE: 909
tttccttttc ccttcctttt tcyttcttt 29

<210> SEQ ID NO 910
<211> LENGTH: 27
<212> TYPE: DNA
<213> ORGANISM: Glycine Max

<400> SEQUENCE: 910
tttattttta ttaatttttt tttattt 27

<210> SEQ ID NO 911
<211> LENGTH: 25
<212> TYPE: DNA
<213> ORGANISM: Glycine Max

<400> SEQUENCE: 911
aaataaaatt taaaaaaatw aaaaa 25

<210> SEQ ID NO 912
<211> LENGTH: 28
<212> TYPE: DNA
<213> ORGANISM: Glycine Max

<400> SEQUENCE: 912
ggkttggggt tttgttgggg ttggtggg 28

<210> SEQ ID NO 913
<211> LENGTH: 21
<212> TYPE: DNA
<213> ORGANISM: Glycine Max

<400> SEQUENCE: 913
ccctcctttc tcccttcctc c 21

<210> SEQ ID NO 914
<211> LENGTH: 15
<212> TYPE: DNA
<213> ORGANISM: Glycine Max

<400> SEQUENCE: 914
aaaaaacaaa aaaaa 15

<210> SEQ ID NO 915
<211> LENGTH: 31
<212> TYPE: DNA
<213> ORGANISM: Glycine Max

<400> SEQUENCE: 915
cccsgggccg cggggcgggc cccgsccgcc c 31

<210> SEQ ID NO 916
<211> LENGTH: 29
<212> TYPE: DNA
<213> ORGANISM: Glycine Max

<400> SEQUENCE: 916
aaaaatataa aaaataaaaa aaaaaaaaa 29

<210> SEQ ID NO 917
<211> LENGTH: 30
<212> TYPE: DNA
<213> ORGANISM: Glycine Max

<400> SEQUENCE: 917
aaaccmaaaa ccccaaccaa aaaccaacaa 30

<210> SEQ ID NO 918
<211> LENGTH: 30
<212> TYPE: DNA
<213> ORGANISM: Glycine Max

<400> SEQUENCE: 918
tttggttttt ggggttggtt tttggttgtt 30

<210> SEQ ID NO 919
<211> LENGTH: 24
<212> TYPE: DNA
<213> ORGANISM: Glycine Max

<400> SEQUENCE: 919
aaaaaaaaat taaaaaaawa aaaa 24

<210> SEQ ID NO 920
<211> LENGTH: 24
<212> TYPE: DNA
<213> ORGANISM: Glycine Max

<400> SEQUENCE: 920 cccccccyy cyctcccycc cccc 24

<210> SEQ ID NO 921
<211> LENGTH: 22
<212> TYPE: DNA
<213> ORGANISM: Glycine Max

<400> SEQUENCE: 921
ttttwttawt tattttttt wt 22

<210> SEQ ID NO 922
<211> LENGTH: 22
<212> TYPE: DNA
<213> ORGANISM: Glycine Max

<400> SEQUENCE: 922
ttttwtttww tttttattt wt 22

<210> SEQ ID NO 923
<211> LENGTH: 21
<212> TYPE: DNA
<213> ORGANISM: Glycine Max

<400> SEQUENCE: 923
awaawaaata aaaaawataa a 21

<210> SEQ ID NO 924
<211> LENGTH: 32
<212> TYPE: DNA
<213> ORGANISM: Glycine Max

<400> SEQUENCE: 924
ttcycctctc ycccccccct ttcccyctct cc 32

<210> SEQ ID NO 925
<211> LENGTH: 31
<212> TYPE: DNA
<213> ORGANISM: Glycine Max

<400> SEQUENCE: 925
cccccctccc cccccccccc cccccccccc c 31

<210> SEQ ID NO 926
<211> LENGTH: 32
<212> TYPE: DNA
<213> ORGANISM: Glycine Max

<400> SEQUENCE: 926
tttytttttt tttccttctt tttttttttt tt 32

<210> SEQ ID NO 927
<211> LENGTH: 29
<212> TYPE: DNA
<213> ORGANISM: Glycine Max

<400> SEQUENCE: 927
ccccctcccc cctccccccc cccccyccc 29

<210> SEQ ID NO 928
<211> LENGTH: 25
<212> TYPE: DNA
<213> ORGANISM: Glycine Max

<400> SEQUENCE: 928
aaaaaaaaaa waawaaaawa waaaa 25

<210> SEQ ID NO 929
<211> LENGTH: 24
<212> TYPE: DNA
<213> ORGANISM: Glycine Max

<400> SEQUENCE: 929
cctccyccyc yctccccycc yccc 24

<210> SEQ ID NO 930
<211> LENGTH: 23
<212> TYPE: DNA
<213> ORGANISM: Glycine Max

<400> SEQUENCE: 930
ttcttytttt tttttytty ttt 23

<210> SEQ ID NO 931
<211> LENGTH: 29
<212> TYPE: DNA
<213> ORGANISM: Glycine Max

<400> SEQUENCE: 931
ccyctccccy ttttcttccc ctycctccc 29

<210> SEQ ID NO 932
<211> LENGTH: 31
<212> TYPE: DNA
<213> ORGANISM: Glycine Max

<400> SEQUENCE: 932
aaaaaataaa aataaataaa aaaaaaaaaa a 31

<210> SEQ ID NO 933
<211> LENGTH: 31
<212> TYPE: DNA
<213> ORGANISM: Glycine Max

<400> SEQUENCE: 933
ttwtttaatt tttttatttt ttaattatta a 31

<210> SEQ ID NO 934
<211> LENGTH: 30
<212> TYPE: DNA
<213> ORGANISM: Glycine Max

<400> SEQUENCE: 934
cctyttttct yttttttttc ccttytcctt 30

<210> SEQ ID NO 935
<211> LENGTH: 25
<212> TYPE: DNA
<213> ORGANISM: Glycine Max

<400> SEQUENCE: 935
tataaataaa aaaaatttaa watta 25

<210> SEQ ID NO 936
<211> LENGTH: 11
<212> TYPE: DNA
<213> ORGANISM: Glycine Max

<400> SEQUENCE: 936
tttawtttaw t 11

<210> SEQ ID NO 937
<211> LENGTH: 10
<212> TYPE: DNA

<213> ORGANISM: Glycine Max

<400> SEQUENCE: 937 ttttttttawt 10

<210> SEQ ID NO 938
<211> LENGTH: 12
<212> TYPE: DNA
<213> ORGANISM: Glycine Max

<400> SEQUENCE: 938
ttataatttt tt 12

<210> SEQ ID NO 939
<211> LENGTH: 31
<212> TYPE: DNA
<213> ORGANISM: Glycine Max

<400> SEQUENCE: 939
ccgcggggcg ggcgggcggc ccggsgcgcg g 31

<210> SEQ ID NO 940
<211> LENGTH: 16
<212> TYPE: DNA
<213> ORGANISM: Glycine Max

<400> SEQUENCE: 940
ttataaaatt tattat 16

<210> SEQ ID NO 941
<211> LENGTH: 16
<212> TYPE: DNA
<213> ORGANISM: Glycine Max

<400> SEQUENCE: 941
ttctctcttt tcttct 16

<210> SEQ ID NO 942
<211> LENGTH: 20
<212> TYPE: DNA
<213> ORGANISM: Glycine Max

<400> SEQUENCE: 942
ggaagagaag agggggagaa 20

<210> SEQ ID NO 943
<211> LENGTH: 21
<212> TYPE: DNA
<213> ORGANISM: Glycine Max

<400> SEQUENCE: 943
ttccctctcc tctttttctc c 21

<210> SEQ ID NO 944
<211> LENGTH: 32
<212> TYPE: DNA
<213> ORGANISM: Glycine Max

<400> SEQUENCE: 944
aawaaaataa aaaaataaaa aattaataaa tt 32

<210> SEQ ID NO 945
<211> LENGTH: 31

<212> TYPE: DNA
<213> ORGANISM: Glycine Max

<400> SEQUENCE: 945
cccccccccc ccgcccgccc cccccccccc c 31

<210> SEQ ID NO 946
<211> LENGTH: 29
<212> TYPE: DNA
<213> ORGANISM: Glycine Max

<400> SEQUENCE: 946
ttttaatata waaatatttt tatttattt 29

<210> SEQ ID NO 947
<211> LENGTH: 29
<212> TYPE: DNA
<213> ORGANISM: Glycine Max

<400> SEQUENCE: 947
aaaaccccac acccaccaaa aacaacaaa 29

<210> SEQ ID NO 948
<211> LENGTH: 30
<212> TYPE: DNA
<213> ORGANISM: Glycine Max

<400> SEQUENCE: 948
ccccttctct ytttcttccc ccttcctccc 30

<210> SEQ ID NO 949
<211> LENGTH: 32
<212> TYPE: DNA
<213> ORGANISM: Glycine Max

<400> SEQUENCE: 949
ccccaacaca maaaacaaac ccccamccac cc 32

<210> SEQ ID NO 950
<211> LENGTH: 32
<212> TYPE: DNA
<213> ORGANISM: Glycine Max

<400> SEQUENCE: 950
ccmmaaaaca maaaacaaac ccccamccac cc 32

<210> SEQ ID NO 951
<211> LENGTH: 30
<212> TYPE: DNA
<213> ORGANISM: Glycine Max

<400> SEQUENCE: 951
tttkgggtgk tggtgggttt ttgkttgttt 30

<210> SEQ ID NO 952
<211> LENGTH: 31
<212> TYPE: DNA
<213> ORGANISM: Glycine Max

<400> SEQUENCE: 952
tttwaaataw ttaattaatt tttawttatt t 31

<210> SEQ ID NO 953

<211> LENGTH: 29
<212> TYPE: DNA
<213> ORGANISM: Glycine Max

<400> SEQUENCE: 953
aaaaggggaa aagaagaaaa agraagaaa 29

<210> SEQ ID NO 954
<211> LENGTH: 28
<212> TYPE: DNA
<213> ORGANISM: Glycine Max

<400> SEQUENCE: 954
cccccccccc cacccccccc mcccaccc 28

<210> SEQ ID NO 955
<211> LENGTH: 29
<212> TYPE: DNA
<213> ORGANISM: Glycine Max

<400> SEQUENCE: 955
ttttaatttt tttttttttt ttwtttttt 29

<210> SEQ ID NO 956
<211> LENGTH: 32
<212> TYPE: DNA
<213> ORGANISM: Glycine Max

<400> SEQUENCE: 956
ccyyttctct tccytccttc cccctccctc cc 32

<210> SEQ ID NO 957
<211> LENGTH: 30
<212> TYPE: DNA
<213> ORGANISM: Glycine Max

<400> SEQUENCE: 957
ttttcccctc ytccttcttt ttcyttcttt 30

<210> SEQ ID NO 958
<211> LENGTH: 31
<212> TYPE: DNA
<213> ORGANISM: Glycine Max

<400> SEQUENCE: 958
ccyyttttct yccttcctcc ccctccctcc c 31

<210> SEQ ID NO 959
<211> LENGTH: 31
<212> TYPE: DNA
<213> ORGANISM: Glycine Max

<400> SEQUENCE: 959
ccyyttttct yccttcctcc ccctycctcc c 31

<210> SEQ ID NO 960
<211> LENGTH: 30
<212> TYPE: DNA
<213> ORGANISM: Glycine Max

<400> SEQUENCE: 960
ttttgktktg ktggttggtt ttgkttgttt 30

-continued

<210> SEQ ID NO 961
<211> LENGTH: 30
<212> TYPE: DNA
<213> ORGANISM: Glycine Max

<400> SEQUENCE: 961
ccyctttctt ccttcctccc cctycctccc 30

<210> SEQ ID NO 962
<211> LENGTH: 31
<212> TYPE: DNA
<213> ORGANISM: Glycine Max

<400> SEQUENCE: 962
tyttttttyt tttyttyttt tttttttttt t 31

<210> SEQ ID NO 963
<211> LENGTH: 32
<212> TYPE: DNA
<213> ORGANISM: Glycine Max

<400> SEQUENCE: 963
gggraagggg gggaaggaag ggggaaggag gg 32

<210> SEQ ID NO 964
<211> LENGTH: 32
<212> TYPE: DNA
<213> ORGANISM: Glycine Max

<400> SEQUENCE: 964
cctyttttct tttttttttc cctttytctc tt 32

<210> SEQ ID NO 965
<211> LENGTH: 31
<212> TYPE: DNA
<213> ORGANISM: Glycine Max

<400> SEQUENCE: 965
gggsccccgc sggccggccg ggggcsggcg g 31

<210> SEQ ID NO 966
<211> LENGTH: 29
<212> TYPE: DNA
<213> ORGANISM: Glycine Max

<400> SEQUENCE: 966
tttycctctc yttcttcctt tcyttcttt 29

<210> SEQ ID NO 967
<211> LENGTH: 23
<212> TYPE: DNA
<213> ORGANISM: Glycine Max

<400> SEQUENCE: 967
tttttttctt cttttttttt ttt 23

<210> SEQ ID NO 968
<211> LENGTH: 25
<212> TYPE: DNA
<213> ORGANISM: Glycine Max

<400> SEQUENCE: 968
ggggtggkgg tggtgggggg ggtgg 25

<210> SEQ ID NO 969
<211> LENGTH: 28
<212> TYPE: DNA
<213> ORGANISM: Glycine Max

<400> SEQUENCE: 969 tttttttcttt tttttttttt tttttttt                                28

<210> SEQ ID NO 970
<211> LENGTH: 31
<212> TYPE: DNA
<213> ORGANISM: Glycine Max

<400> SEQUENCE: 970
aawaaaataw aaaaaaaaaa aaaaaaaaaa a                             31

<210> SEQ ID NO 971
<211> LENGTH: 32
<212> TYPE: DNA
<213> ORGANISM: Glycine Max

<400> SEQUENCE: 971
gggggggggg gttggttggg gggggggtggg gt                           32

<210> SEQ ID NO 972
<211> LENGTH: 29
<212> TYPE: DNA
<213> ORGANISM: Glycine Max

<400> SEQUENCE: 972
aataaataaa ttaattaaaa ataaaaaat                                29

<210> SEQ ID NO 973
<211> LENGTH: 29
<212> TYPE: DNA
<213> ORGANISM: Glycine Max

<400> SEQUENCE: 973
gggkttgggg ggttggtggg gttggtggg                                29

<210> SEQ ID NO 974
<211> LENGTH: 30
<212> TYPE: DNA
<213> ORGANISM: Glycine Max

<400> SEQUENCE: 974
cyccttcccc cccttcctcc ccctyctccc                               30

<210> SEQ ID NO 975
<211> LENGTH: 31
<212> TYPE: DNA
<213> ORGANISM: Glycine Max

<400> SEQUENCE: 975
ggcgggcggg gccggccggg gggggcggsc c                             31

<210> SEQ ID NO 976
<211> LENGTH: 30
<212> TYPE: DNA
<213> ORGANISM: Glycine Max

<400> SEQUENCE: 976
aagaaaaaag gaaggaaaaa aaaagaaaag                               30

<210> SEQ ID NO 977
<211> LENGTH: 29
<212> TYPE: DNA
<213> ORGANISM: Glycine Max

<400> SEQUENCE: 977
aacmccccma ccccccaaaa acmcacaac 29

<210> SEQ ID NO 978
<211> LENGTH: 24
<212> TYPE: DNA
<213> ORGANISM: Glycine Max

<400> SEQUENCE: 978
aaaaaamaaa acaaaaaaaa aaaa 24

<210> SEQ ID NO 979
<211> LENGTH: 23
<212> TYPE: DNA
<213> ORGANISM: Glycine Max

<400> SEQUENCE: 979
cccccccccy yccccccccc ccc 23

<210> SEQ ID NO 980
<211> LENGTH: 31
<212> TYPE: DNA
<213> ORGANISM: Glycine Max

<400> SEQUENCE: 980 tttyttttttt tttcttcttt tttttttttt t 31

<210> SEQ ID NO 981
<211> LENGTH: 28
<212> TYPE: DNA
<213> ORGANISM: Glycine Max

<400> SEQUENCE: 981
aawwataaat atawataaaa aaataaaa 28

<210> SEQ ID NO 982
<211> LENGTH: 27
<212> TYPE: DNA
<213> ORGANISM: Glycine Max

<400> SEQUENCE: 982
ggrrgaggga ggrgaggggg ggagggg 27

<210> SEQ ID NO 983
<211> LENGTH: 30
<212> TYPE: DNA
<213> ORGANISM: Glycine Max

<400> SEQUENCE: 983
aawaaaataa waaaaaaaaa aaaaaaaaaa 30

<210> SEQ ID NO 984
<211> LENGTH: 29
<212> TYPE: DNA
<213> ORGANISM: Glycine Max

<400> SEQUENCE: 984
gggsgsgggg ggsgsggggg gsgsgsggc 29

<210> SEQ ID NO 985
<211> LENGTH: 31
<212> TYPE: DNA
<213> ORGANISM: Glycine Max

<400> SEQUENCE: 985
aamaccaaaa acccccccaa aaccccacaa c 31

<210> SEQ ID NO 986
<211> LENGTH: 29
<212> TYPE: DNA
<213> ORGANISM: Glycine Max

<400> SEQUENCE: 986
ggggggtggg gkgggggggg ggtgggggg 29

<210> SEQ ID NO 987
<211> LENGTH: 31
<212> TYPE: DNA
<213> ORGANISM: Glycine Max

<400> SEQUENCE: 987
aatwttttat wtttttttaa aattatataa t 31

<210> SEQ ID NO 988
<211> LENGTH: 31
<212> TYPE: DNA
<213> ORGANISM: Glycine Max

<400> SEQUENCE: 988
ttawaaaata waaaaaaawt ttaatatatt a 31

<210> SEQ ID NO 989
<211> LENGTH: 31
<212> TYPE: DNA
<213> ORGANISM: Glycine Max

<400> SEQUENCE: 989
aaaaaacaaa aaaaaaaaaa aacaaaaaaa a 31

<210> SEQ ID NO 990
<211> LENGTH: 28
<212> TYPE: DNA
<213> ORGANISM: Glycine Max

<400> SEQUENCE: 990
agaaaaaaaa ggagaaaaaa aagaaaag 28

<210> SEQ ID NO 991
<211> LENGTH: 22
<212> TYPE: DNA
<213> ORGANISM: Glycine Max

<400> SEQUENCE: 991
tttwttttwt tttttttatt tt 22

<210> SEQ ID NO 992
<211> LENGTH: 26
<212> TYPE: DNA
<213> ORGANISM: Glycine Max

<400> SEQUENCE: 992
aaaaaaaaaw wawaaaaaaa aaaaaa 26

<210> SEQ ID NO 993
<211> LENGTH: 29
<212> TYPE: DNA
<213> ORGANISM: Glycine Max

<400> SEQUENCE: 993
aaaaagaaaa aaaaaaaaaa gaaaaaaaa 29

<210> SEQ ID NO 994
<211> LENGTH: 32
<212> TYPE: DNA
<213> ORGANISM: Glycine Max

<400> SEQUENCE: 994
ttatttattt waattaattt ttttttattt ta 32

<210> SEQ ID NO 995
<211> LENGTH: 31
<212> TYPE: DNA
<213> ORGANISM: Glycine Max

<400> SEQUENCE: 995
aagaaaaaaa rggaaggaaa aaraagaaaa g 31

<210> SEQ ID NO 996
<211> LENGTH: 31
<212> TYPE: DNA
<213> ORGANISM: Glycine Max

<400> SEQUENCE: 996
aagaaaaaaa agaaggaaaa aaaaagaaaa g 31

<210> SEQ ID NO 997
<211> LENGTH: 31
<212> TYPE: DNA
<213> ORGANISM: Glycine Max

<400> SEQUENCE: 997
ttcttttttt yccttccttt ttttttcttt t 31

<210> SEQ ID NO 998
<211> LENGTH: 30
<212> TYPE: DNA
<213> ORGANISM: Glycine Max

<400> SEQUENCE: 998
ttyttttttt tccttctttt tttttctttt 30

<210> SEQ ID NO 999
<211> LENGTH: 31
<212> TYPE: DNA
<213> ORGANISM: Glycine Max

<400> SEQUENCE: 999
aaraaaaaaa rggaaggaaa aaaaaagaaa a 31

<210> SEQ ID NO 1000
<211> LENGTH: 31
<212> TYPE: DNA
<213> ORGANISM: Glycine Max

<400> SEQUENCE: 1000
aaraaaaaaa rggaaggaaa aaaaaagaaa a 31

<210> SEQ ID NO 1001
<211> LENGTH: 31
<212> TYPE: DNA
<213> ORGANISM: Glycine Max

<400> SEQUENCE: 1001
ggtgggtggg kttggttggg gggggtggg t 31

<210> SEQ ID NO 1002
<211> LENGTH: 31
<212> TYPE: DNA
<213> ORGANISM: Glycine Max

<400> SEQUENCE: 1002
tttttttttt tttttttttt twttttttta t 31

<210> SEQ ID NO 1003
<211> LENGTH: 29
<212> TYPE: DNA
<213> ORGANISM: Glycine Max

<400> SEQUENCE: 1003
gggggagggg gggggggggg ggggggggg 29

<210> SEQ ID NO 1004
<211> LENGTH: 30
<212> TYPE: DNA
<213> ORGANISM: Glycine Max

<400> SEQUENCE: 1004
ggaraaaggg raaaaaaaag gggargagga 30

<210> SEQ ID NO 1005
<211> LENGTH: 32
<212> TYPE: DNA
<213> ORGANISM: Glycine Max

<400> SEQUENCE: 1005
ttttttattt attttttttt tttttttttt tt 32

<210> SEQ ID NO 1006
<211> LENGTH: 20
<212> TYPE: DNA
<213> ORGANISM: Glycine Max

<400> SEQUENCE: 1006
ttttattttt attttttttwt 20

<210> SEQ ID NO 1007
<211> LENGTH: 25
<212> TYPE: DNA
<213> ORGANISM: Glycine Max

<400> SEQUENCE: 1007 ttytttttttc tttctttttt ctttc 25

<210> SEQ ID NO 1008
<211> LENGTH: 23
<212> TYPE: DNA
<213> ORGANISM: Glycine Max

<400> SEQUENCE: 1008
ttwtattata aatattttta tta 23

<210> SEQ ID NO 1009
<211> LENGTH: 31
<212> TYPE: DNA
<213> ORGANISM: Glycine Max

<400> SEQUENCE: 1009
aaaaggaaaa aaggaaggaa aaagraagaa a 31

<210> SEQ ID NO 1010
<211> LENGTH: 31
<212> TYPE: DNA
<213> ORGANISM: Glycine Max

<400> SEQUENCE: 1010
cccccccccc aacccacccc cccccccccc c 31

<210> SEQ ID NO 1011
<211> LENGTH: 30
<212> TYPE: DNA
<213> ORGANISM: Glycine Max

<400> SEQUENCE: 1011
tttttttctt tttttttttt tytttttttct 30

<210> SEQ ID NO 1012
<211> LENGTH: 29
<212> TYPE: DNA
<213> ORGANISM: Glycine Max

<400> SEQUENCE: 1012
aawaaaatat waaataaaaa aaataaatt 29

<210> SEQ ID NO 1013
<211> LENGTH: 29
<212> TYPE: DNA
<213> ORGANISM: Glycine Max

<400> SEQUENCE: 1013
aaaaaaaaaa ggaaagaaaa aaaaaaaaa 29

<210> SEQ ID NO 1014
<211> LENGTH: 26
<212> TYPE: DNA
<213> ORGANISM: Glycine Max

<400> SEQUENCE: 1014
aaaaaaaaaw taataaaaaa aaaaaa 26

<210> SEQ ID NO 1015
<211> LENGTH: 25
<212> TYPE: DNA
<213> ORGANISM: Glycine Max

<400> SEQUENCE: 1015
tttttttatw tttttttttt ttwtt 25

<210> SEQ ID NO 1016
<211> LENGTH: 27
<212> TYPE: DNA

<213> ORGANISM: Glycine Max

<400> SEQUENCE: 1016
aaaaaaaaar gaaaaaaaaa aaaaaaa 27

<210> SEQ ID NO 1017
<211> LENGTH: 27
<212> TYPE: DNA
<213> ORGANISM: Glycine Max

<400> SEQUENCE: 1017
aaaaaaaagg aaaaaaaaaa aaaaaaa 27

<210> SEQ ID NO 1018
<211> LENGTH: 28
<212> TYPE: DNA
<213> ORGANISM: Glycine Max

<400> SEQUENCE: 1018
aamccmaama ccaacaaaca ccaacaca 28

<210> SEQ ID NO 1019
<211> LENGTH: 28
<212> TYPE: DNA
<213> ORGANISM: Glycine Max

<400> SEQUENCE: 1019
aaawtttaaw tttattaaat atwaataa 28

<210> SEQ ID NO 1020
<211> LENGTH: 27
<212> TYPE: DNA
<213> ORGANISM: Glycine Max

<400> SEQUENCE: 1020
aawwtttatt atttataaaa twtatat 27

<210> SEQ ID NO 1021
<211> LENGTH: 27
<212> TYPE: DNA
<213> ORGANISM: Glycine Max

<400> SEQUENCE: 1021 ttttttttt atttattttt ttttttt 27

<210> SEQ ID NO 1022
<211> LENGTH: 26
<212> TYPE: DNA
<213> ORGANISM: Glycine Max

<400> SEQUENCE: 1022
tttwaattwt aattatttta wttatt 26

<210> SEQ ID NO 1023
<211> LENGTH: 31
<212> TYPE: DNA
<213> ORGANISM: Glycine Max

<400> SEQUENCE: 1023
cccmaaaccc aaaacaaacc cacamccaca c 31

<210> SEQ ID NO 1024
<211> LENGTH: 32

<212> TYPE: DNA
<213> ORGANISM: Glycine Max

<400> SEQUENCE: 1024
aaaaaaaaaa accaaacaaa aaaaaaaaaa aa 32

<210> SEQ ID NO 1025
<211> LENGTH: 32
<212> TYPE: DNA
<213> ORGANISM: Glycine Max

<400> SEQUENCE: 1025
aacaaaaaac aaaaacaaaa aaaaaacaaa ac 32

<210> SEQ ID NO 1026
<211> LENGTH: 31
<212> TYPE: DNA
<213> ORGANISM: Glycine Max

<400> SEQUENCE: 1026
ggcgccccgc gcccccccgg gcgcscgcgc c 31

<210> SEQ ID NO 1027
<211> LENGTH: 30
<212> TYPE: DNA
<213> ORGANISM: Glycine Max

<400> SEQUENCE: 1027
aaaaccccaa accccaccaa acacmaacaa 30

<210> SEQ ID NO 1028
<211> LENGTH: 32
<212> TYPE: DNA
<213> ORGANISM: Glycine Max

<400> SEQUENCE: 1028
tttttttttt tttttctttt ttttttcttt tc 32

<210> SEQ ID NO 1029
<211> LENGTH: 32
<212> TYPE: DNA
<213> ORGANISM: Glycine Max

<400> SEQUENCE: 1029
cccyttcccc cttttctctc cccctycctc cc 32

<210> SEQ ID NO 1030
<211> LENGTH: 32
<212> TYPE: DNA
<213> ORGANISM: Glycine Max

<400> SEQUENCE: 1030
tttttycctt yttttttctt ttcttttttt ct 32

<210> SEQ ID NO 1031
<211> LENGTH: 30
<212> TYPE: DNA
<213> ORGANISM: Glycine Max

<400> SEQUENCE: 1031
aagrggggag rggggggaaa gagrgagagg 30

<210> SEQ ID NO 1032

<211> LENGTH: 22
<212> TYPE: DNA
<213> ORGANISM: Glycine Max

<400> SEQUENCE: 1032
gcgggggsgs gggcgsgggs gg 22

<210> SEQ ID NO 1033
<211> LENGTH: 22
<212> TYPE: DNA
<213> ORGANISM: Glycine Max

<400> SEQUENCE: 1033
ttttcctttt tttttttctt tc 22

<210> SEQ ID NO 1034
<211> LENGTH: 28
<212> TYPE: DNA
<213> ORGANISM: Glycine Max

<400> SEQUENCE: 1034 ggggggagg gggggggga ggggggag 28

<210> SEQ ID NO 1035
<211> LENGTH: 31
<212> TYPE: DNA
<213> ORGANISM: Glycine Max

<400> SEQUENCE: 1035
aaaaaaaaaa aggaaagaaa aaaaaaaaaa a 31

<210> SEQ ID NO 1036
<211> LENGTH: 31
<212> TYPE: DNA
<213> ORGANISM: Glycine Max

<400> SEQUENCE: 1036
ccmccccccc accccacacc cccccacccc a 31

<210> SEQ ID NO 1037
<211> LENGTH: 30
<212> TYPE: DNA
<213> ORGANISM: Glycine Max

<400> SEQUENCE: 1037 ggggggagg gggggggggg ggagggggag 30

<210> SEQ ID NO 1038
<211> LENGTH: 32
<212> TYPE: DNA
<213> ORGANISM: Glycine Max

<400> SEQUENCE: 1038
cccccccccc sccccccgcc cccccccccc cc 32

<210> SEQ ID NO 1039
<211> LENGTH: 32
<212> TYPE: DNA
<213> ORGANISM: Glycine Max

<400> SEQUENCE: 1039
aaaaaaagaa aaaaaaaaaa aagaaaaaaa ga 32

```
<210> SEQ ID NO 1040
<211> LENGTH: 30
<212> TYPE: DNA
<213> ORGANISM: Glycine Max

<400> SEQUENCE: 1040

gggggggtgg gttggggggg tgggggggtg                                    30

<210> SEQ ID NO 1041
<211> LENGTH: 29
<212> TYPE: DNA
<213> ORGANISM: Glycine Max

<400> SEQUENCE: 1041

aaaaaaaaaa attaaaaaaa aaaaaaaaa                                     29

<210> SEQ ID NO 1042
<211> LENGTH: 32
<212> TYPE: DNA
<213> ORGANISM: Glycine Max

<400> SEQUENCE: 1042

tttttttttt tggtttgttt tttttttttt tt                                 32

<210> SEQ ID NO 1043
<211> LENGTH: 31
<212> TYPE: DNA
<213> ORGANISM: Glycine Max

<400> SEQUENCE: 1043

cccccccccc cgcccgcccc cccccccccc c                                  31

<210> SEQ ID NO 1044
<211> LENGTH: 30
<212> TYPE: DNA
<213> ORGANISM: Glycine Max

<400> SEQUENCE: 1044

ggagaaaaga raaaaaaagg agaragagaa                                    30

<210> SEQ ID NO 1045
<211> LENGTH: 30
<212> TYPE: DNA
<213> ORGANISM: Glycine Max

<400> SEQUENCE: 1045

gggggggtgg gggggggggg gggggggggtg                                   30

<210> SEQ ID NO 1046
<211> LENGTH: 30
<212> TYPE: DNA
<213> ORGANISM: Glycine Max

<400> SEQUENCE: 1046

ttttttctt tttttttttt tttttttttct                                    30

<210> SEQ ID NO 1047
<211> LENGTH: 29
<212> TYPE: DNA
<213> ORGANISM: Glycine Max

<400> SEQUENCE: 1047

aaaaaaaaaa agaaaaraaa aaaaaaaag                                     29
```

<210> SEQ ID NO 1048
<211> LENGTH: 26
<212> TYPE: DNA
<213> ORGANISM: Glycine Max

<400> SEQUENCE: 1048
aaaaaacaaa aaaaamaaaa aaaaaa 26

<210> SEQ ID NO 1049
<211> LENGTH: 24
<212> TYPE: DNA
<213> ORGANISM: Glycine Max

<400> SEQUENCE: 1049
aaaaaataaa aataaaaaaa aaat 24

<210> SEQ ID NO 1050
<211> LENGTH: 30
<212> TYPE: DNA
<213> ORGANISM: Glycine Max

<400> SEQUENCE: 1050
tttttttctt tttttttttt tcttttttct 30

<210> SEQ ID NO 1051
<211> LENGTH: 31
<212> TYPE: DNA
<213> ORGANISM: Glycine Max

<400> SEQUENCE: 1051
ggaggggagg gaaggaaggg ggaggaggga a 31

<210> SEQ ID NO 1052
<211> LENGTH: 30
<212> TYPE: DNA
<213> ORGANISM: Glycine Max

<400> SEQUENCE: 1052
ttkttttttt tggttggttt ttttgttttg 30

<210> SEQ ID NO 1053
<211> LENGTH: 31
<212> TYPE: DNA
<213> ORGANISM: Glycine Max

<400> SEQUENCE: 1053
aagaaaggaa aggaaggaaa aagaagaaag g 31

<210> SEQ ID NO 1054
<211> LENGTH: 32
<212> TYPE: DNA
<213> ORGANISM: Glycine Max

<400> SEQUENCE: 1054
ttattttttt taattaattt ttttttattt ta 32

<210> SEQ ID NO 1055
<211> LENGTH: 26
<212> TYPE: DNA
<213> ORGANISM: Glycine Max

<400> SEQUENCE: 1055
cccccccccc cccccccccc gccccg 26

<210> SEQ ID NO 1056
<211> LENGTH: 26
<212> TYPE: DNA
<213> ORGANISM: Glycine Max

<400> SEQUENCE: 1056
tttttatttt ttttttattt ttttat 26

<210> SEQ ID NO 1057
<211> LENGTH: 31
<212> TYPE: DNA
<213> ORGANISM: Glycine Max

<400> SEQUENCE: 1057
gggggggggg aagggagggg gggggggggg g 31

<210> SEQ ID NO 1058
<211> LENGTH: 32
<212> TYPE: DNA
<213> ORGANISM: Glycine Max

<400> SEQUENCE: 1058
gggggggggg gaagggaggg gggggggggg gg 32

<210> SEQ ID NO 1059
<211> LENGTH: 31
<212> TYPE: DNA
<213> ORGANISM: Glycine Max

<400> SEQUENCE: 1059
ttttttaatt aaattaattt tattttttta t 31

<210> SEQ ID NO 1060
<211> LENGTH: 32
<212> TYPE: DNA
<213> ORGANISM: Glycine Max

<400> SEQUENCE: 1060
ccycccttcc yttcctttcc cctccctccc tt 32

<210> SEQ ID NO 1061
<211> LENGTH: 31
<212> TYPE: DNA
<213> ORGANISM: Glycine Max

<400> SEQUENCE: 1061
ccccccaacc mcccccaccc cmcccccccca c 31

<210> SEQ ID NO 1062
<211> LENGTH: 29
<212> TYPE: DNA
<213> ORGANISM: Glycine Max

<400> SEQUENCE: 1062
ccccccaccc ccccccccca cccccccac 29

<210> SEQ ID NO 1063
<211> LENGTH: 31
<212> TYPE: DNA
<213> ORGANISM: Glycine Max

<400> SEQUENCE: 1063
gggggggggg gccggcgggg gggggggggg g 31

<210> SEQ ID NO 1064
<211> LENGTH: 30
<212> TYPE: DNA
<213> ORGANISM: Glycine Max

<400> SEQUENCE: 1064 cccccttcc yccccccccc cccccccccc 30

<210> SEQ ID NO 1065
<211> LENGTH: 26
<212> TYPE: DNA
<213> ORGANISM: Glycine Max

<400> SEQUENCE: 1065
ttttttttta tttttttttt attttt 26

<210> SEQ ID NO 1066
<211> LENGTH: 27
<212> TYPE: DNA
<213> ORGANISM: Glycine Max

<400> SEQUENCE: 1066
gggggaaggr aggaaggggg ggaggg 27

<210> SEQ ID NO 1067
<211> LENGTH: 31
<212> TYPE: DNA
<213> ORGANISM: Glycine Max

<400> SEQUENCE: 1067
ggggggaagg gggggggggg gggggggggg g 31

<210> SEQ ID NO 1068
<211> LENGTH: 30
<212> TYPE: DNA
<213> ORGANISM: Glycine Max

<400> SEQUENCE: 1068
ttgttttttt ttttgttttt ttttgttttg 30

<210> SEQ ID NO 1069
<211> LENGTH: 32
<212> TYPE: DNA
<213> ORGANISM: Glycine Max

<400> SEQUENCE: 1069
ggggggaggg gaagggaggg gggggggggg gg 32

<210> SEQ ID NO 1070
<211> LENGTH: 28
<212> TYPE: DNA
<213> ORGANISM: Glycine Max

<400> SEQUENCE: 1070
aaraaagaaa aaaaaraaaa aaraaaaa 28

<210> SEQ ID NO 1071
<211> LENGTH: 28
<212> TYPE: DNA
<213> ORGANISM: Glycine Max

<400> SEQUENCE: 1071
ggsgggcggg gggggggggg ggsggggg 28

<210> SEQ ID NO 1072
<211> LENGTH: 31
<212> TYPE: DNA
<213> ORGANISM: Glycine Max

<400> SEQUENCE: 1072
gggggccggg gggggggggg gggggggggg g 31

<210> SEQ ID NO 1073
<211> LENGTH: 31
<212> TYPE: DNA
<213> ORGANISM: Glycine Max

<400> SEQUENCE: 1073
ttataaaata aaaaaaaatt tatatatata a 31

<210> SEQ ID NO 1074
<211> LENGTH: 31
<212> TYPE: DNA
<213> ORGANISM: Glycine Max

<400> SEQUENCE: 1074
ccyccctccc ttcctttccc ccccctcccc t 31

<210> SEQ ID NO 1075
<211> LENGTH: 32
<212> TYPE: DNA
<213> ORGANISM: Glycine Max

<400> SEQUENCE: 1075
ttyttttttt tttttctttt tttttctttt tc 32

<210> SEQ ID NO 1076
<211> LENGTH: 31
<212> TYPE: DNA
<213> ORGANISM: Glycine Max

<400> SEQUENCE: 1076
tttttttttt tcctttcttt tttttttttt t 31

<210> SEQ ID NO 1077
<211> LENGTH: 28
<212> TYPE: DNA
<213> ORGANISM: Glycine Max

<400> SEQUENCE: 1077 ccccctttccc cccccccccc cccccccc 28

<210> SEQ ID NO 1078
<211> LENGTH: 32
<212> TYPE: DNA
<213> ORGANISM: Glycine Max

<400> SEQUENCE: 1078
ggggggaggg gggggggggg gggggggggg gg 32

<210> SEQ ID NO 1079
<211> LENGTH: 29
<212> TYPE: DNA
<213> ORGANISM: Glycine Max

<400> SEQUENCE: 1079
aawaaattaw twaattaaaa aaaataaaa 29

<210> SEQ ID NO 1080
<211> LENGTH: 31
<212> TYPE: DNA
<213> ORGANISM: Glycine Max

<400> SEQUENCE: 1080 cccccttcc cccccccccc cccccccccc c 31

<210> SEQ ID NO 1081
<211> LENGTH: 27
<212> TYPE: DNA
<213> ORGANISM: Glycine Max

<400> SEQUENCE: 1081
gggggggggg gccggggggg ggggsg 27

<210> SEQ ID NO 1082
<211> LENGTH: 30
<212> TYPE: DNA
<213> ORGANISM: Glycine Max

<400> SEQUENCE: 1082
aaaaaaataa ataaaaaaaa aaaaaaaaaa 30

<210> SEQ ID NO 1083
<211> LENGTH: 31
<212> TYPE: DNA
<213> ORGANISM: Glycine Max

<400> SEQUENCE: 1083
aaaaaaataa attaaataaa aaaaaaaaaa a 31

<210> SEQ ID NO 1084
<211> LENGTH: 27
<212> TYPE: DNA
<213> ORGANISM: Glycine Max

<400> SEQUENCE: 1084
ttttttttaa attatttttt ttttttt 27

<210> SEQ ID NO 1085
<211> LENGTH: 26
<212> TYPE: DNA
<213> ORGANISM: Glycine Max

<400> SEQUENCE: 1085
aaaattaatt tataaaaaww aataaa 26

<210> SEQ ID NO 1086
<211> LENGTH: 29
<212> TYPE: DNA
<213> ORGANISM: Glycine Max

<400> SEQUENCE: 1086
tttttttctt cctttttttt ttttttttt 29

<210> SEQ ID NO 1087
<211> LENGTH: 31
<212> TYPE: DNA
<213> ORGANISM: Glycine Max

<400> SEQUENCE: 1087
aaaaaaagaa aggaaaaaaa aaaaaaaaaa a 31

<210> SEQ ID NO 1088
<211> LENGTH: 29
<212> TYPE: DNA
<213> ORGANISM: Glycine Max

<400> SEQUENCE: 1088
cccccccccc tcccttcccc ccccccccc 29

<210> SEQ ID NO 1089
<211> LENGTH: 30
<212> TYPE: DNA
<213> ORGANISM: Glycine Max

<400> SEQUENCE: 1089
gggggggggg tkgggttggg gggggggggg 30

<210> SEQ ID NO 1090
<211> LENGTH: 28
<212> TYPE: DNA
<213> ORGANISM: Glycine Max

<400> SEQUENCE: 1090
cccccccccc aaccaccccc cccccccc 28

<210> SEQ ID NO 1091
<211> LENGTH: 29
<212> TYPE: DNA
<213> ORGANISM: Glycine Max

<400> SEQUENCE: 1091
ccccccccct ttcccttccc ccccccccc 29

<210> SEQ ID NO 1092
<211> LENGTH: 28
<212> TYPE: DNA
<213> ORGANISM: Glycine Max

<400> SEQUENCE: 1092
ttttttttyc ctttcctttt tttttttt 28

<210> SEQ ID NO 1093
<211> LENGTH: 29
<212> TYPE: DNA
<213> ORGANISM: Glycine Max

<400> SEQUENCE: 1093
aaaaaaaaaa aaaattaaaa aaaaaaaat 29

<210> SEQ ID NO 1094
<211> LENGTH: 28
<212> TYPE: DNA
<213> ORGANISM: Glycine Max

<400> SEQUENCE: 1094
aaaaaaacaa caaaaccaaa aaaaaaaa 28

<210> SEQ ID NO 1095
<211> LENGTH: 27
<212> TYPE: DNA

<213> ORGANISM: Glycine Max

<400> SEQUENCE: 1095
ccccaacccc cccccccaac ccccacc 27

<210> SEQ ID NO 1096
<211> LENGTH: 30
<212> TYPE: DNA
<213> ORGANISM: Glycine Max

<400> SEQUENCE: 1096
aaaaagaaaa ggaaagaaaa aaaaaaaaaa 30

<210> SEQ ID NO 1097
<211> LENGTH: 30
<212> TYPE: DNA
<213> ORGANISM: Glycine Max

<400> SEQUENCE: 1097
cccccccccc ttccctcccc cccccccccc 30

<210> SEQ ID NO 1098
<211> LENGTH: 27
<212> TYPE: DNA
<213> ORGANISM: Glycine Max

<400> SEQUENCE: 1098
ggagggaggg aggaaggggg ggagggg 27

<210> SEQ ID NO 1099
<211> LENGTH: 29
<212> TYPE: DNA
<213> ORGANISM: Glycine Max

<400> SEQUENCE: 1099
gggggggggg ttgggtgggg ggggggggg 29

<210> SEQ ID NO 1100
<211> LENGTH: 32
<212> TYPE: DNA
<213> ORGANISM: Glycine Max

<400> SEQUENCE: 1100
aaaaaaaaaa aggaaagaaa aaaaaaaaaa aa 32

<210> SEQ ID NO 1101
<211> LENGTH: 32
<212> TYPE: DNA
<213> ORGANISM: Glycine Max

<400> SEQUENCE: 1101
aaaaaaaaaa aggaaagaaa aaaaaaaaaa aa 32

<210> SEQ ID NO 1102
<211> LENGTH: 25
<212> TYPE: DNA
<213> ORGANISM: Glycine Max

<400> SEQUENCE: 1102
tttttwtttt tttttttttt wtttt 25

<210> SEQ ID NO 1103
<211> LENGTH: 25

<212> TYPE: DNA
<213> ORGANISM: Glycine Max

<400> SEQUENCE: 1103
awwaaaataa waataaaaaa taaaa 25

<210> SEQ ID NO 1104
<211> LENGTH: 32
<212> TYPE: DNA
<213> ORGANISM: Glycine Max

<400> SEQUENCE: 1104
ccmccccacc maaccaaacc ccccccaccc ca 32

<210> SEQ ID NO 1105
<211> LENGTH: 20
<212> TYPE: DNA
<213> ORGANISM: Glycine Max

<400> SEQUENCE: 1105
aawaaaaatw taaaaaaaaa 20

<210> SEQ ID NO 1106
<211> LENGTH: 20
<212> TYPE: DNA
<213> ORGANISM: Glycine Max

<400> SEQUENCE: 1106
tttttttaat attttttttt 20

<210> SEQ ID NO 1107
<211> LENGTH: 22
<212> TYPE: DNA
<213> ORGANISM: Glycine Max

<400> SEQUENCE: 1107
ggggtgggtg gggggggggg gg 22

<210> SEQ ID NO 1108
<211> LENGTH: 24
<212> TYPE: DNA
<213> ORGANISM: Glycine Max

<400> SEQUENCE: 1108
aaaagaaaga gaaaaaaaaa aaaa 24

<210> SEQ ID NO 1109
<211> LENGTH: 29
<212> TYPE: DNA
<213> ORGANISM: Glycine Max

<400> SEQUENCE: 1109
aaaaggaaaa aagaaagaaa aaraagaaa 29

<210> SEQ ID NO 1110
<211> LENGTH: 28
<212> TYPE: DNA
<213> ORGANISM: Glycine Max

<400> SEQUENCE: 1110
ttataaattt taaataattt twatatta 28

<210> SEQ ID NO 1111

<211> LENGTH: 27
<212> TYPE: DNA
<213> ORGANISM: Glycine Max

<400> SEQUENCE: 1111
tttttttttt tcttcttttt tttcttt 27

<210> SEQ ID NO 1112
<211> LENGTH: 25
<212> TYPE: DNA
<213> ORGANISM: Glycine Max

<400> SEQUENCE: 1112 cccccwccc ccycccccccc tcccc 25

<210> SEQ ID NO 1113
<211> LENGTH: 25
<212> TYPE: DNA
<213> ORGANISM: Glycine Max

<400> SEQUENCE: 1113
tttttttttt ttyttttttt ctttt 25

<210> SEQ ID NO 1114
<211> LENGTH: 27
<212> TYPE: DNA
<213> ORGANISM: Glycine Max

<400> SEQUENCE: 1114 tyttttttttt ttctcttttt ttctttc 27

<210> SEQ ID NO 1115
<211> LENGTH: 29
<212> TYPE: DNA
<213> ORGANISM: Glycine Max

<400> SEQUENCE: 1115
ccmccccccc ccacaccccc cccacccca 29

<210> SEQ ID NO 1116
<211> LENGTH: 29
<212> TYPE: DNA
<213> ORGANISM: Glycine Max

<400> SEQUENCE: 1116
ttcttttttt ttctcttttt tttcttttc 29

<210> SEQ ID NO 1117
<211> LENGTH: 28
<212> TYPE: DNA
<213> ORGANISM: Glycine Max

<400> SEQUENCE: 1117
ccccccccct tccttccccc ccctcccc 28

<210> SEQ ID NO 1118
<211> LENGTH: 27
<212> TYPE: DNA
<213> ORGANISM: Glycine Max

<400> SEQUENCE: 1118
tttttttttt cttctttttt tttcttt 27

```
<210> SEQ ID NO 1119
<211> LENGTH: 26
<212> TYPE: DNA
<213> ORGANISM: Glycine Max

<400> SEQUENCE: 1119

ggraaggagg gaaggagggg gagggg                                            26

<210> SEQ ID NO 1120
<211> LENGTH: 26
<212> TYPE: DNA
<213> ORGANISM: Glycine Max

<400> SEQUENCE: 1120

ccsggcccgc cggccgcccc cgcccc                                            26

<210> SEQ ID NO 1121
<211> LENGTH: 27
<212> TYPE: DNA
<213> ORGANISM: Glycine Max

<400> SEQUENCE: 1121

aaaaaaaaaa aawaaaaaaa aaaaaaa                                           27

<210> SEQ ID NO 1122
<211> LENGTH: 26
<212> TYPE: DNA
<213> ORGANISM: Glycine Max

<400> SEQUENCE: 1122

tcttttttcc tccctttttt tctttc                                            26

<210> SEQ ID NO 1123
<211> LENGTH: 24
<212> TYPE: DNA
<213> ORGANISM: Glycine Max

<400> SEQUENCE: 1123

agaggaaagg ggggaaaaga gaag                                              24

<210> SEQ ID NO 1124
<211> LENGTH: 24
<212> TYPE: DNA
<213> ORGANISM: Glycine Max

<400> SEQUENCE: 1124

tctcctttcc cccttttct cttc                                               24

<210> SEQ ID NO 1125
<211> LENGTH: 25
<212> TYPE: DNA
<213> ORGANISM: Glycine Max

<400> SEQUENCE: 1125

agaggaaggg gggaaaaaga gaaag                                             25

<210> SEQ ID NO 1126
<211> LENGTH: 24
<212> TYPE: DNA
<213> ORGANISM: Glycine Max

<400> SEQUENCE: 1126

ccctcccctt ccccccctcc cccc                                              24
```

<210> SEQ ID NO 1127
<211> LENGTH: 23
<212> TYPE: DNA
<213> ORGANISM: Glycine Max

<400> SEQUENCE: 1127 ggggggggc cggggggcg ggc 23

<210> SEQ ID NO 1128
<211> LENGTH: 20
<212> TYPE: DNA
<213> ORGANISM: Glycine Max

<400> SEQUENCE: 1128
cccccccttc ccccccccct 20

<210> SEQ ID NO 1129
<211> LENGTH: 19
<212> TYPE: DNA
<213> ORGANISM: Glycine Max

<400> SEQUENCE: 1129
tttttccctt ttttctttc 19

<210> SEQ ID NO 1130
<211> LENGTH: 28
<212> TYPE: DNA
<213> ORGANISM: Glycine Max

<400> SEQUENCE: 1130
tgtttttttk ggttggtttt ttgttttg 28

<210> SEQ ID NO 1131
<211> LENGTH: 29
<212> TYPE: DNA
<213> ORGANISM: Glycine Max

<400> SEQUENCE: 1131 ttcyccctte cccccccttt tttctcttc 29

<210> SEQ ID NO 1132
<211> LENGTH: 32
<212> TYPE: DNA
<213> ORGANISM: Glycine Max

<400> SEQUENCE: 1132
ccssgggccg cccggcccgc ccccgcccgc cc 32

<210> SEQ ID NO 1133
<211> LENGTH: 31
<212> TYPE: DNA
<213> ORGANISM: Glycine Max

<400> SEQUENCE: 1133
ccyccccccy ctcctctccc ccccctcccc t 31

<210> SEQ ID NO 1134
<211> LENGTH: 29
<212> TYPE: DNA
<213> ORGANISM: Glycine Max

<400> SEQUENCE: 1134
tcycccttcc cccccccttt tctctcttc 29

<210> SEQ ID NO 1135
<211> LENGTH: 28
<212> TYPE: DNA
<213> ORGANISM: Glycine Max

<400> SEQUENCE: 1135
aragggaaga aaggaaagaa aagagaaa 28

<210> SEQ ID NO 1136
<211> LENGTH: 17
<212> TYPE: DNA
<213> ORGANISM: Glycine Max

<400> SEQUENCE: 1136
ttaatatatt ttttatt 17

<210> SEQ ID NO 1137
<211> LENGTH: 18
<212> TYPE: DNA
<213> ORGANISM: Glycine Max

<400> SEQUENCE: 1137
aaaaaaagga aaaaagaa 18

<210> SEQ ID NO 1138
<211> LENGTH: 27
<212> TYPE: DNA
<213> ORGANISM: Glycine Max

<400> SEQUENCE: 1138
tttttttctc tttctttttt tcttttc 27

<210> SEQ ID NO 1139
<211> LENGTH: 22
<212> TYPE: DNA
<213> ORGANISM: Glycine Max

<400> SEQUENCE: 1139
tatttttttt attttttttt tt 22

<210> SEQ ID NO 1140
<211> LENGTH: 31
<212> TYPE: DNA
<213> ORGANISM: Glycine Max

<400> SEQUENCE: 1140
ccyccccccc yctcctctcc cccccctccc t 31

<210> SEQ ID NO 1141
<211> LENGTH: 31
<212> TYPE: DNA
<213> ORGANISM: Glycine Max

<400> SEQUENCE: 1141
ggrggggggg raaggaaggg gggggagggg a 31

<210> SEQ ID NO 1142
<211> LENGTH: 29
<212> TYPE: DNA
<213> ORGANISM: Glycine Max

<400> SEQUENCE: 1142
aawaaaaaaw ataatataaa aaaataaat 29

<210> SEQ ID NO 1143
<211> LENGTH: 25
<212> TYPE: DNA
<213> ORGANISM: Glycine Max

<400> SEQUENCE: 1143
ccmccccccc accaccccca ccccc 25

<210> SEQ ID NO 1144
<211> LENGTH: 23
<212> TYPE: DNA
<213> ORGANISM: Glycine Max

<400> SEQUENCE: 1144
tttttttttt ttttttata ttt 23

<210> SEQ ID NO 1145
<211> LENGTH: 25
<212> TYPE: DNA
<213> ORGANISM: Glycine Max

<400> SEQUENCE: 1145
aatattaata aaaaaaaawa aaaaa 25

<210> SEQ ID NO 1146
<211> LENGTH: 32
<212> TYPE: DNA
<213> ORGANISM: Glycine Max

<400> SEQUENCE: 1146
ccyccccccc yctcctctcc cccccctccc ct 32

<210> SEQ ID NO 1147
<211> LENGTH: 32
<212> TYPE: DNA
<213> ORGANISM: Glycine Max

<400> SEQUENCE: 1147
ccaccccccc mcaccacacc ccccccaccc ca 32

<210> SEQ ID NO 1148
<211> LENGTH: 31
<212> TYPE: DNA
<213> ORGANISM: Glycine Max

<400> SEQUENCE: 1148
cccccccgcc cgccccgccc cccccccccc c 31

<210> SEQ ID NO 1149
<211> LENGTH: 29
<212> TYPE: DNA
<213> ORGANISM: Glycine Max

<400> SEQUENCE: 1149
tttttgkttt gktttttttt tttkttttt 29

<210> SEQ ID NO 1150
<211> LENGTH: 30
<212> TYPE: DNA
<213> ORGANISM: Glycine Max

<400> SEQUENCE: 1150
tttttttttk ttttgttttt ttttkttttt 30

<210> SEQ ID NO 1151
<211> LENGTH: 31
<212> TYPE: DNA
<213> ORGANISM: Glycine Max

<400> SEQUENCE: 1151
ggggaaggga gggaagggag ggggagggag g 31

<210> SEQ ID NO 1152
<211> LENGTH: 31
<212> TYPE: DNA
<213> ORGANISM: Glycine Max

<400> SEQUENCE: 1152
aaraaaaaaa agaagagaaa aaaaagaaaa g 31

<210> SEQ ID NO 1153
<211> LENGTH: 30
<212> TYPE: DNA
<213> ORGANISM: Glycine Max

<400> SEQUENCE: 1153
aacaaaaaaa acaacacaaa aaaaacaaac 30

<210> SEQ ID NO 1154
<211> LENGTH: 29
<212> TYPE: DNA
<213> ORGANISM: Glycine Max

<400> SEQUENCE: 1154
ggkggggggk gtggtggggg gggtggggt 29

<210> SEQ ID NO 1155
<211> LENGTH: 29
<212> TYPE: DNA
<213> ORGANISM: Glycine Max

<400> SEQUENCE: 1155
ccsccccccs cgccgccccc cccgccccg 29

<210> SEQ ID NO 1156
<211> LENGTH: 28
<212> TYPE: DNA
<213> ORGANISM: Glycine Max

<400> SEQUENCE: 1156 gggggggsg cggcgggggg ggcggggc 28

<210> SEQ ID NO 1157
<211> LENGTH: 28
<212> TYPE: DNA
<213> ORGANISM: Glycine Max

<400> SEQUENCE: 1157
ttkggttgtt tggttttttt gkttgttt 28

<210> SEQ ID NO 1158
<211> LENGTH: 28
<212> TYPE: DNA
<213> ORGANISM: Glycine Max

<400> SEQUENCE: 1158 ccccccccyct cctctccccc cctcccct 28

<210> SEQ ID NO 1159
<211> LENGTH: 29
<212> TYPE: DNA
<213> ORGANISM: Glycine Max

<400> SEQUENCE: 1159
ttctggttyc cggccctttt tgtctgttc 29

<210> SEQ ID NO 1160
<211> LENGTH: 26
<212> TYPE: DNA
<213> ORGANISM: Glycine Max

<400> SEQUENCE: 1160
ccccttcctc tttccccct yccccc 26

<210> SEQ ID NO 1161
<211> LENGTH: 21
<212> TYPE: DNA
<213> ORGANISM: Glycine Max

<400> SEQUENCE: 1161
ggcggggcgg gcgggggggg c 21

<210> SEQ ID NO 1162
<211> LENGTH: 18
<212> TYPE: DNA
<213> ORGANISM: Glycine Max

<400> SEQUENCE: 1162
gggggrgaag gggggggg 18

<210> SEQ ID NO 1163
<211> LENGTH: 24
<212> TYPE: DNA
<213> ORGANISM: Glycine Max

<400> SEQUENCE: 1163
ttctccctyc ccccttttc yttt 24

<210> SEQ ID NO 1164
<211> LENGTH: 22
<212> TYPE: DNA
<213> ORGANISM: Glycine Max

<400> SEQUENCE: 1164
cctcttccct cccccctyct cc 22

<210> SEQ ID NO 1165
<211> LENGTH: 20
<212> TYPE: DNA
<213> ORGANISM: Glycine Max

<400> SEQUENCE: 1165
cccttccttc ccccty ctcc 20

<210> SEQ ID NO 1166
<211> LENGTH: 20
<212> TYPE: DNA
<213> ORGANISM: Glycine Max

<400> SEQUENCE: 1166
tttgtttggt tttttttktt 20

<210> SEQ ID NO 1167
<211> LENGTH: 18
<212> TYPE: DNA
<213> ORGANISM: Glycine Max

<400> SEQUENCE: 1167
ggrggggggg ggargagg 18

<210> SEQ ID NO 1168
<211> LENGTH: 22
<212> TYPE: DNA
<213> ORGANISM: Glycine Max

<400> SEQUENCE: 1168
ggragaggga ggggggarga gg 22

<210> SEQ ID NO 1169
<211> LENGTH: 22
<212> TYPE: DNA
<213> ORGANISM: Glycine Max

<400> SEQUENCE: 1169
ggggggggtg tgggkggggg gg 22

<210> SEQ ID NO 1170
<211> LENGTH: 24
<212> TYPE: DNA
<213> ORGANISM: Glycine Max

<400> SEQUENCE: 1170
aagrggaaag gggaaaaagg agaa 24

<210> SEQ ID NO 1171
<211> LENGTH: 31
<212> TYPE: DNA
<213> ORGANISM: Glycine Max

<400> SEQUENCE: 1171
ggkggggggg kgtggtgggg gggggtgggg t 31

<210> SEQ ID NO 1172
<211> LENGTH: 32
<212> TYPE: DNA
<213> ORGANISM: Glycine Max

<400> SEQUENCE: 1172
ttctcccctc yccccccccct ttttcyctct tc 32

<210> SEQ ID NO 1173
<211> LENGTH: 30
<212> TYPE: DNA
<213> ORGANISM: Glycine Max

<400> SEQUENCE: 1173
ggaggggggg raggargggg ggggrgggga 30

<210> SEQ ID NO 1174
<211> LENGTH: 31
<212> TYPE: DNA

<213> ORGANISM: Glycine Max

<400> SEQUENCE: 1174
cccccmcccc ccccccmccc cccccmcccc c 31

<210> SEQ ID NO 1175
<211> LENGTH: 30
<212> TYPE: DNA
<213> ORGANISM: Glycine Max

<400> SEQUENCE: 1175
tttttctttt cttttttttt tttttttttt 30

<210> SEQ ID NO 1176
<211> LENGTH: 30
<212> TYPE: DNA
<213> ORGANISM: Glycine Max

<400> SEQUENCE: 1176
ggggrtgggg gggggrgggg ggggrggggg 30

<210> SEQ ID NO 1177
<211> LENGTH: 28
<212> TYPE: DNA
<213> ORGANISM: Glycine Max

<400> SEQUENCE: 1177
ggggragggg gaggaggggg gggagggg 28

<210> SEQ ID NO 1178
<211> LENGTH: 28
<212> TYPE: DNA
<213> ORGANISM: Glycine Max

<400> SEQUENCE: 1178
ccccyccccc cccctccccc ccctcccc 28

<210> SEQ ID NO 1179
<211> LENGTH: 26
<212> TYPE: DNA
<213> ORGANISM: Glycine Max

<400> SEQUENCE: 1179
ggaraaagga gaaaaggggg argagg 26

<210> SEQ ID NO 1180
<211> LENGTH: 28
<212> TYPE: DNA
<213> ORGANISM: Glycine Max

<400> SEQUENCE: 1180
aagaaagaaa aggaggaaaa aaaraaaa 28

<210> SEQ ID NO 1181
<211> LENGTH: 26
<212> TYPE: DNA
<213> ORGANISM: Glycine Max

<400> SEQUENCE: 1181
gggggggagg gggagggggg gggggg 26

<210> SEQ ID NO 1182
<211> LENGTH: 28

<212> TYPE: DNA
<213> ORGANISM: Glycine Max

<400> SEQUENCE: 1182
aagaggggag agggggaaaa agragaag 28

<210> SEQ ID NO 1183
<211> LENGTH: 31
<212> TYPE: DNA
<213> ORGANISM: Glycine Max

<400> SEQUENCE: 1183
cctytttcct cattttatcc ccctytctcc t 31

<210> SEQ ID NO 1184
<211> LENGTH: 31
<212> TYPE: DNA
<213> ORGANISM: Glycine Max

<400> SEQUENCE: 1184
gggggggggg gaggggaggg gggggggggg g 31

<210> SEQ ID NO 1185
<211> LENGTH: 31
<212> TYPE: DNA
<213> ORGANISM: Glycine Max

<400> SEQUENCE: 1185
aagaaaaaaa aagaagaaaa aaaaagaaaa g 31

<210> SEQ ID NO 1186
<211> LENGTH: 22
<212> TYPE: DNA
<213> ORGANISM: Glycine Max

<400> SEQUENCE: 1186
ccccccccca cacccccccc cc 22

<210> SEQ ID NO 1187
<211> LENGTH: 21
<212> TYPE: DNA
<213> ORGANISM: Glycine Max

<400> SEQUENCE: 1187
ccctttccct tccccctccc c 21

<210> SEQ ID NO 1188
<211> LENGTH: 23
<212> TYPE: DNA
<213> ORGANISM: Glycine Max

<400> SEQUENCE: 1188
cccccccamc accccccccc ccc 23

<210> SEQ ID NO 1189
<211> LENGTH: 27
<212> TYPE: DNA
<213> ORGANISM: Glycine Max

<400> SEQUENCE: 1189
ggagggaggg aggaggggggg ggagggg 27

<210> SEQ ID NO 1190

<211> LENGTH: 27
<212> TYPE: DNA
<213> ORGANISM: Glycine Max

<400> SEQUENCE: 1190
cctccccccc cccccccccc cctcccc 27

<210> SEQ ID NO 1191
<211> LENGTH: 32
<212> TYPE: DNA
<213> ORGANISM: Glycine Max

<400> SEQUENCE: 1191
ccsccccccc ccgccgcgcc ccccccgccc cg 32

<210> SEQ ID NO 1192
<211> LENGTH: 30
<212> TYPE: DNA
<213> ORGANISM: Glycine Max

<400> SEQUENCE: 1192
aagrgggaag gggggggaaa aagagagaag 30

<210> SEQ ID NO 1193
<211> LENGTH: 31
<212> TYPE: DNA
<213> ORGANISM: Glycine Max

<400> SEQUENCE: 1193
gggggggggg aggggagggg gggggggggg g 31

<210> SEQ ID NO 1194
<211> LENGTH: 31
<212> TYPE: DNA
<213> ORGANISM: Glycine Max

<400> SEQUENCE: 1194
cccccccccc tcccctcccc cccccccccc c 31

<210> SEQ ID NO 1195
<211> LENGTH: 29
<212> TYPE: DNA
<213> ORGANISM: Glycine Max

<400> SEQUENCE: 1195
aagrggaaag gggggggaaa aagragaag 29

<210> SEQ ID NO 1196
<211> LENGTH: 25
<212> TYPE: DNA
<213> ORGANISM: Glycine Max

<400> SEQUENCE: 1196
ggaraagggg aggggggar gaggg 25

<210> SEQ ID NO 1197
<211> LENGTH: 19
<212> TYPE: DNA
<213> ORGANISM: Glycine Max

<400> SEQUENCE: 1197
ccycccctcc ccccdyccc 19

<210> SEQ ID NO 1198
<211> LENGTH: 20
<212> TYPE: DNA
<213> ORGANISM: Glycine Max

<400> SEQUENCE: 1198
cccacccmcc cccccccccc 20

<210> SEQ ID NO 1199
<211> LENGTH: 26
<212> TYPE: DNA
<213> ORGANISM: Glycine Max

<400> SEQUENCE: 1199
cccccccccc tcctcccccc cccccc 26

<210> SEQ ID NO 1200
<211> LENGTH: 28
<212> TYPE: DNA
<213> ORGANISM: Glycine Max

<400> SEQUENCE: 1200
ggrraaggga gggaaggggg ggggaggr 28

<210> SEQ ID NO 1201
<211> LENGTH: 28
<212> TYPE: DNA
<213> ORGANISM: Glycine Max

<400> SEQUENCE: 1201
ttttttcttt tctttctttt tttttttt 28

<210> SEQ ID NO 1202
<211> LENGTH: 24
<212> TYPE: DNA
<213> ORGANISM: Glycine Max

<400> SEQUENCE: 1202
ttyttttttt cctcttttttt tttc 24

<210> SEQ ID NO 1203
<211> LENGTH: 27
<212> TYPE: DNA
<213> ORGANISM: Glycine Max

<400> SEQUENCE: 1203
ccmccccccc cacaccccccc ccacccc 27

<210> SEQ ID NO 1204
<211> LENGTH: 27
<212> TYPE: DNA
<213> ORGANISM: Glycine Max

<400> SEQUENCE: 1204
aaraaaaaaa ggagaaaaaa aagaaaa 27

<210> SEQ ID NO 1205
<211> LENGTH: 28
<212> TYPE: DNA
<213> ORGANISM: Glycine Max

<400> SEQUENCE: 1205
aarrggaaga gagaagaaaa agraagaa 28

<210> SEQ ID NO 1206
<211> LENGTH: 28
<212> TYPE: DNA
<213> ORGANISM: Glycine Max

<400> SEQUENCE: 1206
aaarggaaaa aagaagaaaa agraagaa 28

<210> SEQ ID NO 1207
<211> LENGTH: 20
<212> TYPE: DNA
<213> ORGANISM: Glycine Max

<400> SEQUENCE: 1207
ttctctttcc tttttcttt 20

<210> SEQ ID NO 1208
<211> LENGTH: 23
<212> TYPE: DNA
<213> ORGANISM: Glycine Max

<400> SEQUENCE: 1208
tttgttttgg tgtttttgtt ttt 23

<210> SEQ ID NO 1209
<211> LENGTH: 31
<212> TYPE: DNA
<213> ORGANISM: Glycine Max

<400> SEQUENCE: 1209
ccyccccccy ctcctctccc ccccctcccc t 31

<210> SEQ ID NO 1210
<211> LENGTH: 30
<212> TYPE: DNA
<213> ORGANISM: Glycine Max

<400> SEQUENCE: 1210 ccyccccccyc tcctctcccc cccctcccct 30

<210> SEQ ID NO 1211
<211> LENGTH: 28
<212> TYPE: DNA
<213> ORGANISM: Glycine Max

<400> SEQUENCE: 1211
ggrgaagagg gaaggagggg gaggaggg 28

<210> SEQ ID NO 1212
<211> LENGTH: 29
<212> TYPE: DNA
<213> ORGANISM: Glycine Max

<400> SEQUENCE: 1212
ccacaaccam aaaaaaaccc ccaccacca 29

<210> SEQ ID NO 1213
<211> LENGTH: 27
<212> TYPE: DNA
<213> ORGANISM: Glycine Max

<400> SEQUENCE: 1213
ttkttttttk ttttgttttt ttgtttg 27

<210> SEQ ID NO 1214
<211> LENGTH: 29
<212> TYPE: DNA
<213> ORGANISM: Glycine Max

<400> SEQUENCE: 1214 ggrgggggg raggaaaggg ggggaggga 29

<210> SEQ ID NO 1215
<211> LENGTH: 21
<212> TYPE: DNA
<213> ORGANISM: Glycine Max

<400> SEQUENCE: 1215
ggggggkgtg gggggggtgg t 21

<210> SEQ ID NO 1216
<211> LENGTH: 26
<212> TYPE: DNA
<213> ORGANISM: Glycine Max

<400> SEQUENCE: 1216
ccgsggcccg ggggcccccg sgcgcc 26

<210> SEQ ID NO 1217
<211> LENGTH: 24
<212> TYPE: DNA
<213> ORGANISM: Glycine Max

<400> SEQUENCE: 1217
aaagaaaaag aaaaaaaaaa aaaa 24

<210> SEQ ID NO 1218
<211> LENGTH: 25
<212> TYPE: DNA
<213> ORGANISM: Glycine Max

<400> SEQUENCE: 1218
aaattaataa ataaataaaa twaaa 25

<210> SEQ ID NO 1219
<211> LENGTH: 29
<212> TYPE: DNA
<213> ORGANISM: Glycine Max

<400> SEQUENCE: 1219
aagaaaaaar ggaagggaaa aaaagaaag 29

<210> SEQ ID NO 1220
<211> LENGTH: 31
<212> TYPE: DNA
<213> ORGANISM: Glycine Max

<400> SEQUENCE: 1220
ggaraaagga raaaaaaagg gggaragagg a 31

<210> SEQ ID NO 1221
<211> LENGTH: 25
<212> TYPE: DNA
<213> ORGANISM: Glycine Max

<400> SEQUENCE: 1221
aaaataaaat taawaaaaaa aaaaa 25

<210> SEQ ID NO 1222
<211> LENGTH: 24
<212> TYPE: DNA
<213> ORGANISM: Glycine Max

<400> SEQUENCE: 1222
ttttawtwta tttttttttt tttt 24

<210> SEQ ID NO 1223
<211> LENGTH: 21
<212> TYPE: DNA
<213> ORGANISM: Glycine Max

<400> SEQUENCE: 1223
aawaaaatta aaaaaaaaaa a 21

<210> SEQ ID NO 1224
<211> LENGTH: 23
<212> TYPE: DNA
<213> ORGANISM: Glycine Max

<400> SEQUENCE: 1224
ttwtttttaa tttttttttt ttt 23

<210> SEQ ID NO 1225
<211> LENGTH: 32
<212> TYPE: DNA
<213> ORGANISM: Glycine Max

<400> SEQUENCE: 1225
aatattttat tattttatta aaaatwtata at 32

<210> SEQ ID NO 1226
<211> LENGTH: 29
<212> TYPE: DNA
<213> ORGANISM: Glycine Max

<400> SEQUENCE: 1226
aaaaaaaaaa caaacaaaaa aaaaaaaaa 29

<210> SEQ ID NO 1227
<211> LENGTH: 30
<212> TYPE: DNA
<213> ORGANISM: Glycine Max

<400> SEQUENCE: 1227
gggggggggg gtgggtgggg gggggggggg 30

<210> SEQ ID NO 1228
<211> LENGTH: 29
<212> TYPE: DNA
<213> ORGANISM: Glycine Max

<400> SEQUENCE: 1228
ccccccccca ccccaccccc ccccccccc 29

<210> SEQ ID NO 1229
<211> LENGTH: 29
<212> TYPE: DNA
<213> ORGANISM: Glycine Max

<400> SEQUENCE: 1229
tawaaaataw aaaaaaaatt ttawatatt 29

<210> SEQ ID NO 1230
<211> LENGTH: 30
<212> TYPE: DNA
<213> ORGANISM: Glycine Max

<400> SEQUENCE: 1230
aaaaaaaaaa ataaaatawa aaaaaaaaaa 30

<210> SEQ ID NO 1231
<211> LENGTH: 31
<212> TYPE: DNA
<213> ORGANISM: Glycine Max

<400> SEQUENCE: 1231
aatattatat wttttttta aaaatatata a 31

<210> SEQ ID NO 1232
<211> LENGTH: 32
<212> TYPE: DNA
<213> ORGANISM: Glycine Max

<400> SEQUENCE: 1232
aaaaaaaaaa agaaaagaaa aaaaaaaaaa aa 32

<210> SEQ ID NO 1233
<211> LENGTH: 31
<212> TYPE: DNA
<213> ORGANISM: Glycine Max

<400> SEQUENCE: 1233
tttttttttt attttatttt tttttttttt t 31

<210> SEQ ID NO 1234
<211> LENGTH: 31
<212> TYPE: DNA
<213> ORGANISM: Glycine Max

<400> SEQUENCE: 1234
aawaaaaaaw ataatataaa aaaaataaaa t 31

<210> SEQ ID NO 1235
<211> LENGTH: 28
<212> TYPE: DNA
<213> ORGANISM: Glycine Max

<400> SEQUENCE: 1235
ttattttttt tttwtttttt tttttta 28

<210> SEQ ID NO 1236
<211> LENGTH: 32
<212> TYPE: DNA
<213> ORGANISM: Glycine Max

<400> SEQUENCE: 1236
ttttttattt tattttattt tttttttttt tt 32

<210> SEQ ID NO 1237
<211> LENGTH: 32
<212> TYPE: DNA
<213> ORGANISM: Glycine Max

<400> SEQUENCE: 1237
ttctttcttt yccttccctt ttttttcttt tc 32

<210> SEQ ID NO 1238
<211> LENGTH: 30
<212> TYPE: DNA
<213> ORGANISM: Glycine Max

<400> SEQUENCE: 1238
aaaaaaaaaa agaaagaaaa aaaaaaaaaa 30

<210> SEQ ID NO 1239
<211> LENGTH: 28
<212> TYPE: DNA
<213> ORGANISM: Glycine Max

<400> SEQUENCE: 1239
tttttctttt cttttctttt tttttttt 28

<210> SEQ ID NO 1240
<211> LENGTH: 29
<212> TYPE: DNA
<213> ORGANISM: Glycine Max

<400> SEQUENCE: 1240
ttttttattt tawttatttt ttttttttt 29

<210> SEQ ID NO 1241
<211> LENGTH: 30
<212> TYPE: DNA
<213> ORGANISM: Glycine Max

<400> SEQUENCE: 1241
ggsggggggg ggsggggggg ggggcggggg 30

<210> SEQ ID NO 1242
<211> LENGTH: 31
<212> TYPE: DNA
<213> ORGANISM: Glycine Max

<400> SEQUENCE: 1242
cccccccccc ctcccctccc cccccccccc c 31

<210> SEQ ID NO 1243
<211> LENGTH: 31
<212> TYPE: DNA
<213> ORGANISM: Glycine Max

<400> SEQUENCE: 1243
aaawttataa aaattaataa aaatwaataa a 31

<210> SEQ ID NO 1244
<211> LENGTH: 31
<212> TYPE: DNA
<213> ORGANISM: Glycine Max

<400> SEQUENCE: 1244
aagaaagaaa rggaagggaa aaaaagaaaa g 31

<210> SEQ ID NO 1245
<211> LENGTH: 30
<212> TYPE: DNA
<213> ORGANISM: Glycine Max

<400> SEQUENCE: 1245
ggrgggaggr aaggaagggg ggggagggga 30

<210> SEQ ID NO 1246
<211> LENGTH: 30
<212> TYPE: DNA
<213> ORGANISM: Glycine Max

<400> SEQUENCE: 1246
ccyccccccy ctcctccccc cccctcccct 30

<210> SEQ ID NO 1247
<211> LENGTH: 30
<212> TYPE: DNA
<213> ORGANISM: Glycine Max

<400> SEQUENCE: 1247
ttgttttttt kttttgtttt tttttgtttg 30

<210> SEQ ID NO 1248
<211> LENGTH: 22
<212> TYPE: DNA
<213> ORGANISM: Glycine Max

<400> SEQUENCE: 1248
aaaaawwaaa aaaaaaawaa aa 22

<210> SEQ ID NO 1249
<211> LENGTH: 27
<212> TYPE: DNA
<213> ORGANISM: Glycine Max

<400> SEQUENCE: 1249
aaaattaaaa attaataaaa ataaaaa 27

<210> SEQ ID NO 1250
<211> LENGTH: 26
<212> TYPE: DNA
<213> ORGANISM: Glycine Max

<400> SEQUENCE: 1250
ttatttattt attatttttt ttatta 26

<210> SEQ ID NO 1251
<211> LENGTH: 32
<212> TYPE: DNA
<213> ORGANISM: Glycine Max

<400> SEQUENCE: 1251
ggrgggaggg raaggaaagg ggggggaggg ga 32

<210> SEQ ID NO 1252
<211> LENGTH: 31
<212> TYPE: DNA
<213> ORGANISM: Glycine Max

<400> SEQUENCE: 1252
cctytttcty ttttttttcc ccctytctcc t 31

<210> SEQ ID NO 1253
<211> LENGTH: 29
<212> TYPE: DNA

<213> ORGANISM: Glycine Max

<400> SEQUENCE: 1253
ttyttttttt cttctctttt tttcttttc 29

<210> SEQ ID NO 1254
<211> LENGTH: 27
<212> TYPE: DNA
<213> ORGANISM: Glycine Max

<400> SEQUENCE: 1254
gggggggggg aggggggggg gagggga 27

<210> SEQ ID NO 1255
<211> LENGTH: 27
<212> TYPE: DNA
<213> ORGANISM: Glycine Max

<400> SEQUENCE: 1255
aaaaaaaaaa aataaaaaaa ataaaat 27

<210> SEQ ID NO 1256
<211> LENGTH: 31
<212> TYPE: DNA
<213> ORGANISM: Glycine Max

<400> SEQUENCE: 1256
ccmccccccc caccacaccc cccacacccc a 31

<210> SEQ ID NO 1257
<211> LENGTH: 31
<212> TYPE: DNA
<213> ORGANISM: Glycine Max

<400> SEQUENCE: 1257
ggaraaagag aaaaaaaagg gggaaagagg a 31

<210> SEQ ID NO 1258
<211> LENGTH: 31
<212> TYPE: DNA
<213> ORGANISM: Glycine Max

<400> SEQUENCE: 1258
tttttttttt cttttctttt tttttttttt t 31

<210> SEQ ID NO 1259
<211> LENGTH: 31
<212> TYPE: DNA
<213> ORGANISM: Glycine Max

<400> SEQUENCE: 1259
ttcttttttt tcttctcttt tttttctttt c 31

<210> SEQ ID NO 1260
<211> LENGTH: 29
<212> TYPE: DNA
<213> ORGANISM: Glycine Max

<400> SEQUENCE: 1260
ttgtttgttt ttgttttttt ttttttttg 29

<210> SEQ ID NO 1261
<211> LENGTH: 28

<212> TYPE: DNA
<213> ORGANISM: Glycine Max

<400> SEQUENCE: 1261
ttctcctctc ccctcctttt tcctcttc 28

<210> SEQ ID NO 1262
<211> LENGTH: 31
<212> TYPE: DNA
<213> ORGANISM: Glycine Max

<400> SEQUENCE: 1262
ttcycctctc cttcccttct ttttcyctct c 31

<210> SEQ ID NO 1263
<211> LENGTH: 32
<212> TYPE: DNA
<213> ORGANISM: Glycine Max

<400> SEQUENCE: 1263
aagaggagag raagggaaga aaaagrgagg ag 32

<210> SEQ ID NO 1264
<211> LENGTH: 20
<212> TYPE: DNA
<213> ORGANISM: Glycine Max

<400> SEQUENCE: 1264
ttttatttat tttttttttt 20

<210> SEQ ID NO 1265
<211> LENGTH: 24
<212> TYPE: DNA
<213> ORGANISM: Glycine Max

<400> SEQUENCE: 1265
gggggrgggg grgggggggr ggrg 24

<210> SEQ ID NO 1266
<211> LENGTH: 26
<212> TYPE: DNA
<213> ORGANISM: Glycine Max

<400> SEQUENCE: 1266
ttkttktttt tktttttttk tgtktk 26

<210> SEQ ID NO 1267
<211> LENGTH: 27
<212> TYPE: DNA
<213> ORGANISM: Glycine Max

<400> SEQUENCE: 1267
tttttttttt tctctttttt ttttttt 27

<210> SEQ ID NO 1268
<211> LENGTH: 32
<212> TYPE: DNA
<213> ORGANISM: Glycine Max

<400> SEQUENCE: 1268
cccccccccc ccaccccacc cccccccccc cc 32

<210> SEQ ID NO 1269

-continued

<211> LENGTH: 32
<212> TYPE: DNA
<213> ORGANISM: Glycine Max

<400> SEQUENCE: 1269
ttgkggggtg kggggggggt ttttgkgtgg tg 32

<210> SEQ ID NO 1270
<211> LENGTH: 30
<212> TYPE: DNA
<213> ORGANISM: Glycine Max

<400> SEQUENCE: 1270
aawwtttwta atttaataaa aatwaataaa 30

<210> SEQ ID NO 1271
<211> LENGTH: 32
<212> TYPE: DNA
<213> ORGANISM: Glycine Max

<400> SEQUENCE: 1271
aaaaaaaaaa aagaaaagaa aaaaaaaaaa aa 32

<210> SEQ ID NO 1272
<211> LENGTH: 32
<212> TYPE: DNA
<213> ORGANISM: Glycine Max

<400> SEQUENCE: 1272
cccyttctcc cctttccttc cccctycctc cc 32

<210> SEQ ID NO 1273
<211> LENGTH: 28
<212> TYPE: DNA
<213> ORGANISM: Glycine Max

<400> SEQUENCE: 1273
aaaggagaaa aaggaaagaa aaagraga 28

<210> SEQ ID NO 1274
<211> LENGTH: 31
<212> TYPE: DNA
<213> ORGANISM: Glycine Max

<400> SEQUENCE: 1274
cccyttctcc cctttccttc cccctyctcc c 31

<210> SEQ ID NO 1275
<211> LENGTH: 30
<212> TYPE: DNA
<213> ORGANISM: Glycine Max

<400> SEQUENCE: 1275 ggrggggga gggggggggg ggrgggggg 30

<210> SEQ ID NO 1276
<211> LENGTH: 31
<212> TYPE: DNA
<213> ORGANISM: Glycine Max

<400> SEQUENCE: 1276
ggaggggggg aggggagggg gggggagggg a 31

<210> SEQ ID NO 1277
<211> LENGTH: 30
<212> TYPE: DNA
<213> ORGANISM: Glycine Max

<400> SEQUENCE: 1277
cccccccccs cccccccccc ccccccgcc 30

<210> SEQ ID NO 1278
<211> LENGTH: 31
<212> TYPE: DNA
<213> ORGANISM: Glycine Max

<400> SEQUENCE: 1278 tttttattt ttttttttt tttttttat t 31

<210> SEQ ID NO 1279
<211> LENGTH: 31
<212> TYPE: DNA
<213> ORGANISM: Glycine Max

<400> SEQUENCE: 1279
cccccctccc cccccycccc ccccccccctc c 31

<210> SEQ ID NO 1280
<211> LENGTH: 31
<212> TYPE: DNA
<213> ORGANISM: Glycine Max

<400> SEQUENCE: 1280
cccyttttcc ctttccttcc ccctyccttc c 31

<210> SEQ ID NO 1281
<211> LENGTH: 30
<212> TYPE: DNA
<213> ORGANISM: Glycine Max

<400> SEQUENCE: 1281
ggraaagggg aaaggaaggg ggarggaagg 30

<210> SEQ ID NO 1282
<211> LENGTH: 30
<212> TYPE: DNA
<213> ORGANISM: Glycine Max

<400> SEQUENCE: 1282
ggraaagggg aaaggaaggg ggarggaagg 30

<210> SEQ ID NO 1283
<211> LENGTH: 31
<212> TYPE: DNA
<213> ORGANISM: Glycine Max

<400> SEQUENCE: 1283
cccccccccc tcccctcccc cccccccccc c 31

<210> SEQ ID NO 1284
<211> LENGTH: 19
<212> TYPE: DNA
<213> ORGANISM: Glycine Max

<400> SEQUENCE: 1284
aaataaataa aaaaaaaaa 19

<210> SEQ ID NO 1285
<211> LENGTH: 21
<212> TYPE: DNA
<213> ORGANISM: Glycine Max

<400> SEQUENCE: 1285
aaaaggaaag aaaaaaaaaa a 21

<210> SEQ ID NO 1286
<211> LENGTH: 23
<212> TYPE: DNA
<213> ORGANISM: Glycine Max

<400> SEQUENCE: 1286
ggggaaggga gggggggga agg 23

<210> SEQ ID NO 1287
<211> LENGTH: 27
<212> TYPE: DNA
<213> ORGANISM: Glycine Max

<400> SEQUENCE: 1287
tttttttttt tttttttttt ttttttt 27

<210> SEQ ID NO 1288
<211> LENGTH: 30
<212> TYPE: DNA
<213> ORGANISM: Glycine Max

<400> SEQUENCE: 1288
aagaaaaaag aaaaagaaaa aaaagaaaag 30

<210> SEQ ID NO 1289
<211> LENGTH: 32
<212> TYPE: DNA
<213> ORGANISM: Glycine Max

<400> SEQUENCE: 1289
ggagggggga gggggagggg ggggggaggg ga 32

<210> SEQ ID NO 1290
<211> LENGTH: 30
<212> TYPE: DNA
<213> ORGANISM: Glycine Max

<400> SEQUENCE: 1290
aaamccacaa aacccaacaa aaacmacaaa 30

<210> SEQ ID NO 1291
<211> LENGTH: 32
<212> TYPE: DNA
<213> ORGANISM: Glycine Max

<400> SEQUENCE: 1291 cctccccccct cccccccccc cccccccccc cc 32

<210> SEQ ID NO 1292
<211> LENGTH: 30
<212> TYPE: DNA
<213> ORGANISM: Glycine Max

<400> SEQUENCE: 1292
aacmccccac mcccaccaaa aacmaaccaa 30

<210> SEQ ID NO 1293
<211> LENGTH: 29
<212> TYPE: DNA
<213> ORGANISM: Glycine Max

<400> SEQUENCE: 1293
aaaaaamaaa aaaaaaaaaa aaacaacaa 29

<210> SEQ ID NO 1294
<211> LENGTH: 25
<212> TYPE: DNA
<213> ORGANISM: Glycine Max

<400> SEQUENCE: 1294
aattttttaw ttttttaata attat 25

<210> SEQ ID NO 1295
<211> LENGTH: 23
<212> TYPE: DNA
<213> ORGANISM: Glycine Max

<400> SEQUENCE: 1295
aatattaaaa tttaaaaaaa tta 23

<210> SEQ ID NO 1296
<211> LENGTH: 23
<212> TYPE: DNA
<213> ORGANISM: Glycine Max

<400> SEQUENCE: 1296
ttgtggtttt gggttttttt ggt 23

<210> SEQ ID NO 1297
<211> LENGTH: 28
<212> TYPE: DNA
<213> ORGANISM: Glycine Max

<400> SEQUENCE: 1297
cctccccccc ccctcccccc ccctcccc 28

<210> SEQ ID NO 1298
<211> LENGTH: 25
<212> TYPE: DNA
<213> ORGANISM: Glycine Max

<400> SEQUENCE: 1298
ttgttgtgkg gkggtttttk gtktg 25

<210> SEQ ID NO 1299
<211> LENGTH: 15
<212> TYPE: DNA
<213> ORGANISM: Glycine Max

<400> SEQUENCE: 1299
ggagaggagg ggggg 15

<210> SEQ ID NO 1300
<211> LENGTH: 15
<212> TYPE: DNA
<213> ORGANISM: Glycine Max

<400> SEQUENCE: 1300
aacacaacaa aaaaa 15

<210> SEQ ID NO 1301
<211> LENGTH: 17
<212> TYPE: DNA
<213> ORGANISM: Glycine Max

<400> SEQUENCE: 1301
tttaaataat tttttat 17

<210> SEQ ID NO 1302
<211> LENGTH: 19
<212> TYPE: DNA
<213> ORGANISM: Glycine Max

<400> SEQUENCE: 1302
tttatttatt ttttttwtt 19

<210> SEQ ID NO 1303
<211> LENGTH: 23
<212> TYPE: DNA
<213> ORGANISM: Glycine Max

<400> SEQUENCE: 1303
ttawaataaa aaattttaat aat 23

<210> SEQ ID NO 1304
<211> LENGTH: 11
<212> TYPE: DNA
<213> ORGANISM: Glycine Max

<400> SEQUENCE: 1304
ttctcccctt t 11

<210> SEQ ID NO 1305
<211> LENGTH: 9
<212> TYPE: DNA
<213> ORGANISM: Glycine Max

<400> SEQUENCE: 1305 cycttccct 9

<210> SEQ ID NO 1306
<211> LENGTH: 11
<212> TYPE: DNA
<213> ORGANISM: Glycine Max

<400> SEQUENCE: 1306
gkggttgggg t 11

<210> SEQ ID NO 1307
<211> LENGTH: 15
<212> TYPE: DNA
<213> ORGANISM: Glycine Max

<400> SEQUENCE: 1307
agaggaggga aaaga 15

<210> SEQ ID NO 1308
<211> LENGTH: 25
<212> TYPE: DNA
<213> ORGANISM: Glycine Max

<400> SEQUENCE: 1308

-continued

```
ttcyccccty cccccttttt ctcct                                              25


<210> SEQ ID NO 1309
<211> LENGTH: 31
<212> TYPE: DNA
<213> ORGANISM: Glycine Max

<400> SEQUENCE: 1309

ttgkggggtg kggggggggt ttttgkgtgg t                                       31


<210> SEQ ID NO 1310
<211> LENGTH: 26
<212> TYPE: DNA
<213> ORGANISM: Glycine Max

<400> SEQUENCE: 1310

agagaggaag ggagagaaga aaaaga                                             26
```